US012410449B2

(12) United States Patent
Thomas et al.

(10) Patent No.: US 12,410,449 B2
(45) Date of Patent: Sep. 9, 2025

(54) ENDONUCLEASE SYSTEMS

(71) Applicant: Metagenomi, Inc., Emeryville, CA (US)

(72) Inventors: Brian C. Thomas, Berkeley, CA (US); Christopher Brown, Albany, CA (US); Cristina Butterfield, Oakland, CA (US); Lisa Alexander, Albany, CA (US); Daniela S. A. Goltsman, Oakland, CA (US); Rebecca Lamothe, Albany, CA (US); Isabel Nocedal, Oakland, CA (US)

(73) Assignee: Metagenomi, Inc., Emeryville, CA (US)

( * ) Notice: Subject to any disclaimer, the term of this patent is extended or adjusted under 35 U.S.C. 154(b) by 0 days.

(21) Appl. No.: 18/669,712

(22) Filed: May 21, 2024

(65) Prior Publication Data

US 2024/0294948 A1 Sep. 5, 2024

Related U.S. Application Data

(63) Continuation of application No. PCT/US2022/080437, filed on Nov. 23, 2022.

(60) Provisional application No. 63/356,908, filed on Jun. 29, 2022, provisional application No. 63/289,981, filed on Dec. 15, 2021, provisional application No. 63/282,999, filed on Nov. 24, 2021.

(51) Int. Cl.
*C12N 9/22* (2006.01)
*C12N 15/11* (2006.01)
*C12N 15/90* (2006.01)

(52) U.S. Cl.
CPC ............ *C12N 15/907* (2013.01); *C12N 9/22* (2013.01); *C12N 15/11* (2013.01); *C12N 15/902* (2013.01); *C12N 2310/20* (2017.05); *C12N 2310/531* (2013.01); *C12N 2800/80* (2013.01)

(58) Field of Classification Search
None
See application file for complete search history.

(56) References Cited

U.S. PATENT DOCUMENTS

| 5,858,988 | A | 1/1999 | Wang |
| 6,291,438 | B1 | 9/2001 | Wang |
| 8,889,418 | B2 | 11/2014 | Zhang et al. |
| 10,011,849 | B1 | 7/2018 | Gill et al. |
| 10,253,365 | B1 | 4/2019 | Doudna et al. |
| 10,392,607 | B2 | 8/2019 | Sternberg et al. |
| 10,913,941 | B2 | 2/2021 | Thomas et al. |
| 10,982,200 | B2 | 4/2021 | Thomas et al. |
| 11,946,039 | B2 | 4/2024 | Thomas et al. |
| 12,024,727 | B2 | 7/2024 | Thomas et al. |
| 2014/0186919 | A1 | 7/2014 | Zhang et al. |
| 2014/0186958 | A1 | 7/2014 | Zhang et al. |
| 2015/0045546 | A1 | 2/2015 | Siksnys et al. |
| 2016/0289700 | A1 | 10/2016 | Barrangou et al. |
| 2016/0362667 | A1 | 12/2016 | Donohoue et al. |
| 2018/0312824 | A1 | 11/2018 | Zhang et al. |
| 2018/0371498 | A1 | 12/2018 | Gill et al. |
| 2019/0010471 | A1 | 1/2019 | Zhang et al. |
| 2019/0062735 | A1 | 2/2019 | Welstead et al. |
| 2019/0249200 | A1 | 8/2019 | Seebeck et al. |
| 2019/0264232 | A1 | 8/2019 | Hou et al. |
| 2020/0032240 | A1 | 1/2020 | Wang et al. |
| 2020/0080067 | A1 | 3/2020 | Zhang et al. |
| 2020/0263165 | A1 | 8/2020 | Bendezu et al. |
| 2020/0302240 | A1 | 9/2020 | Murata et al. |
| 2020/0332273 | A1 | 10/2020 | Thomas et al. |
| 2022/0033791 | A1 | 2/2022 | Thomas et al. |
| 2022/0220460 | A1 | 7/2022 | Thomas et al. |
| 2022/0298494 | A1 | 9/2022 | Thomas et al. |
| 2022/0364067 | A1 | 11/2022 | Lin et al. |
| 2022/0403357 | A1 | 12/2022 | Zhang et al. |
| 2024/0110167 | A1 | 4/2024 | Thomas et al. |
| 2024/0117330 | A1 | 4/2024 | Thomas et al. |
| 2024/0209332 | A1 | 6/2024 | Thomas et al. |
| 2024/0309356 | A1 | 9/2024 | Thomas et al. |
| 2024/0344045 | A1 | 10/2024 | Thomas et al. |
| 2024/0409962 | A1 | 12/2024 | Thomas et al. |

FOREIGN PATENT DOCUMENTS

| CA | 3091267 | A1 | 8/2019 |
| CN | 104520429 | A | 4/2015 |
| CN | 105142669 | A | 12/2015 |
| CN | 105209621 | A | 12/2015 |
| CN | 112126661 | A | 12/2020 |
| EP | 3141604 | A1 | 3/2017 |
| EP | 3617311 | A1 | 3/2020 |
| EP | 3854877 | A1 | 7/2021 |
| EP | 4308699 | A1 | 1/2024 |

(Continued)

OTHER PUBLICATIONS

Kapitonov, V. V., Makarova, K. S., & Koonin, E. V. ISC, a novel group of bacterial and archaeal DNA transposons that encode Cas9 homologs. Journal of bacteriology, 198(5), 797-807. posted online Dec. 28, 2015. (Year: 2015).*
Andronescu et al. Efficient Parameter Estimation for RNA Secondary Structure Prediction. Bioinformatics 23(13):119-128 (2007).
Altae-Tran et al.: The widespread IS200/IS605 transposon family encodes diverse programmable RNA-guided endonucleases. Science. 374(6563):57-65 doi:10.1126/science.abj6856 (2021).
Bitard-Feildel, T. et al., Order in Disorder as Observed by the Hydrophobic Cluster Analysis of Protein Sequences, Proteomics, 2018, vol. 18, E1800054, pp. 1-12.

(Continued)

*Primary Examiner* — Brian Whiteman
*Assistant Examiner* — Khaleda B Hasan
(74) *Attorney, Agent, or Firm* — Wilson Sonsini Goodrich & Rosati

(57) ABSTRACT

The present disclosure provides for endonuclease enzymes as well as methods of using such enzymes or variants thereof.

29 Claims, 54 Drawing Sheets

Specification includes a Sequence Listing.

(56) References Cited

FOREIGN PATENT DOCUMENTS

| | | |
|---|---|---|
| JP | 2019507599 A | 3/2019 |
| JP | 2019534695 A | 12/2019 |
| JP | 2022520428 A | 3/2022 |
| WO | WO-2015066119 A1 | 5/2015 |
| WO | WO-2016073990 A2 | 5/2016 |
| WO | WO-2016141224 A1 | 9/2016 |
| WO | WO-2016183041 A2 | 11/2016 |
| WO | WO-2016186953 A1 | 11/2016 |
| WO | WO-2016196655 A1 | 12/2016 |
| WO | WO-2017152015 A1 | 9/2017 |
| WO | WO-2017155714 A1 | 9/2017 |
| WO | WO-2018035250 A1 | 2/2018 |
| WO | WO-2018041120 A1 | 3/2018 |
| WO | WO-2018064352 A1 | 4/2018 |
| WO | WO-2018073393 A2 | 4/2018 |
| WO | WO-2018074979 A1 | 4/2018 |
| WO | WO-2018129346 A1 | 7/2018 |
| WO | WO-2018172556 A1 | 9/2018 |
| WO | WO-2018209712 A1 | 11/2018 |
| WO | WO-2019097305 A2 | 5/2019 |
| WO | WO-2019161290 A1 | 8/2019 |
| WO | WO-2019178421 A1 | 9/2019 |
| WO | WO-2019200306 A1 | 10/2019 |
| WO | WO-2020041120 A1 | 2/2020 |
| WO | WO-2020055941 A1 | 3/2020 |
| WO | WO-2020057486 A1 | 3/2020 |
| WO | WO-2020081613 A1 | 4/2020 |
| WO | WO-2020150534 A2 | 7/2020 |
| WO | WO-2020168122 A1 | 8/2020 |
| WO | WO-2020168234 A1 | 8/2020 |
| WO | WO-2020168291 A1 | 8/2020 |
| WO | WO-2020236967 A1 | 11/2020 |
| WO | WO-2021097118 A1 * | 5/2021 ............ C12N 15/11 |
| WO | WO-2021202559 A1 | 10/2021 |
| WO | WO-2021202568 A1 | 10/2021 |
| WO | WO-2021226363 A1 | 11/2021 |
| WO | WO-2021226369 A1 | 11/2021 |
| WO | WO-2022056324 A1 | 3/2022 |
| WO | WO-2022087494 A1 | 4/2022 |
| WO | WO-2023097262 A1 | 6/2023 |
| WO | WO-2023097282 A1 | 6/2023 |

OTHER PUBLICATIONS

Burstein, David et al. New CRISPR-Cas systems from uncultivated microbes. Nature vol. 542,7640: 237-241 (2017).
Carugo, O., Amino Acid Composition and Protein Dimension, Protein Science, Oct. 2008, vol. 17, No. 12, pp. 2187-2191.
Co-pending U.S. Appl. No. 18/053,232, inventors Thomas; Brian et al., filed Nov. 7, 2022.
Co-pending U.S. Appl. No. 18/435,779, inventors Thomas; Brian et al., filed Feb. 7, 2024.
Co-pending U.S. Appl. No. 18/668,543, inventors Thomas; Brian C et al., filed May 20, 2024.
Co-pending U.S. Appl. No. 18/660,722, inventors Thomas; Brian C et al., filed May 10, 2021.
Corley, et al. How RNA-Binding Proteins Interact with RNA: Molecules and Mechanisms. Molecular Cell. 78(1):9-29 (2020).
CtSKENNERTON: Mining CRISPRs in Environmental Datasets: Minced. GitHub URL:www.github.com/ctSkennerton/minced [1-4](2019).
Ding et al.: Recent Advances in Genome Editing Using CRISPR/Cas9. Front Plant Sci. 7:703:1-12 doi:10.3389/fpls.2016.00703 (2016).
Dyson, H.J., Roles of intrinsic disorder in protein—nucleic acid interactions, Mol Biosyst, 2011, vol. 8, No. 1, pp. 97-104.
Fang et al.: CRISPR/Cas9-mediated Genome Editing Technology. Progress in Biochemistry and Biophysics, 40(8):691-702 [with English Machine Translation] (2013).
Gasiunas et al., A catalogue of biochemically diverse CRISPR-Cas9 orthologs. Nat Commun. 11: 5512, pp. 1-10 (2020).

Gasiunas, Giedrius. et al. Cas9-crRNA Ribonucleoprotein complex Mediates specific DNA cleavage for Adaptive Immunity in Bacteria. Proceedings of the National Academy of Sciences of the United States of America 109(39):E2579-E2586 (2012).
GenPept Accession No. CAH11307. Version No. CAH11307.1. hypothetical protein Ipp0160 [Legionella pneumophila str. Paris]. Record created Oct. 3, 2004. pp. 1-2. Retrieved Jun. 10, 2024 at URL: https://www.ncbi.nlm.nih.gov/protein/CAH11307.1.
GenPept Accession No. WP_127108862. Version No. WP_127108862.1. type II-B CRISPR-associated RNA-guided endonuclease Cas9/Csx12 [Legionella sp. km535]. Record created Jan. 6, 2019. pp. 1-2. Retrieved Jun. 10, 2024 at URL: https://www.ncbi.nlm.nih.gov/protein/WP_127108862.1.
Goltsman et al.: Compact Cas9d and HEARO enzymes for genome editing discovered from uncultivated microbes. Nat Commun. 13(1):7602:1-11. doi:10.1038/s41467-022-35257-7 (2022).
Guo et al.: Off-target effects and optimization strategies of CRISPR/Cas9 technology. Progress in Biochemistry and Biophysics, 45(8):798-807 [with English Machine Translation] (2018).
Harms, M. et al., Analyzing protein structure and function using ancestral gene reconstruction, Current Opinion in Structural Biology, 2010, vol. 20, No. 6, pp. 360-366.
Harrington, Lucas B. et al. Programmed DNA Destruction by Miniature CRISPR-Cas14 Enzymes. Science 362(6416):839-842 (2018).
Harris, K.A. et al., Large Noncoding RNAs in Bacteria, Microbiol Spectr, 2018, vol. 6, No. 4, pp. 1-18.
Herdewijn: Heterocyclic modifications of oligonucleotides and antisense technology. Antisense & Nucleic Acid Drug Dev 10:297-310 (2000).
Huber et al. Orchestrating High-Throughput Genomic Analysis With Bioconductor. Nat Methods 12(2):115-21 (2015).
Jiang, F., et al., CRISPR—Cas9 Structures and Mechanisms, Annual Reviews Biophys., (2017), 46:505-529.
Jinek, Martin. et al. A Programmable dual-RNA-guided DNA Endonuclease in adaptive Bacterial Immunity. Science 337(6096):816-821 (2012).
Kapitonov et al.: ISC, a Novel Group of Bacterial and Archaeal DNA Transposons That Encode Cas9 Homologs. J Bacteriol. 198(5):797-807 doi:10.1128/JB.00783-15 (2015).
Karvelis et al. Methods for Decoding Cas9 Protospacer Adjacent Motif (PAM) Sequences: a Brief Overview. Methods 121-122:3-8 (2017).
Katoh, K. et al., MAFFT Multiple Sequence Alignment Software Version 7: Improvements in Performance and Usability, Molecular Biology and Evolution, 2013, vol. 30, No. 4, pp. 772-780.
Koonin et al. (2017) Diversity, classification and evolution of CRISPR-Cas systems. Current Opinion in Microbiology, 37:67-78 (Year : 2017).
Madshus, I.H.. Regulation of intracellular pH in eukaryotic cells, Biochemical Journal, 1988, vol. 250, No. 1, pp. 1-8.
Makarova et al. Evolutionary classification of CRISPR-Cas systems: a burst of class 2 and derived variants. Nat Rev Microbiol. 18(2):67-83 (2020).
Mali, Prashant. et al. RNA-Guided Human Genome Engineering via Cas9. Science 339(6121):823-826 (2013).
Mir et al.: Type II-C CRISPR-Cas9 Biology, Mechanism, and Application. ACS Chem Biol. 13(2):357-365 (2018).
Moon et al.: Recent advances in the CRISPR genome editing tool set. Exp Mol Med. 51(130):1-11 (2019).
Murthy, A.C. et al., "Molecular interactions underlying liquid-liquid phase separation of the FUS low complexity domain", Nat Struct Mol Biol, 2019, vol. 26, No. 7, pp. 637-648.
NCBI GenBank Accession No. HHR99113.1, TPA: type II Crispr RNA-guided endonuclease Cas9 [Acidobacteria bacterium] [1-2](2020).
NCBI GenBank Accession No. WP_061212298.1, HNH endonuclease [Dermabacter hominis] [1-2](2016).
NCBI GenBank: GBR72910.1—CRISPR-associated protein Csn1 family [Candidatus Termititenax aidoneus], pp. 1-3 (Oct. 31, 2019).
NCBI GenBank: OGP48943.1—MAG: hypothetical protein A2022_01700 [Deltaproteobacteria bacterium GWF2_42_12], pp. 1-2 (Oct. 20, 2016).

(56) References Cited

OTHER PUBLICATIONS

NCBI GenBank: WP_070675185.1—Multispecies: HNH endonuclease [unclassified Rothia (in: high G+C Gram-positive bacteria)], pp. 1-2 (Jan. 20, 2023).
NCBI GenBank: WP_070690139.1—HNH endonuclease [*Rothia* sp. HMSC076D04], pp. 1-3 (Jan. 20, 2023).
NCBI GenBank: WP_070847477.1—HNH endonuclease [*Rothia* sp. HMSC065C03], pp. 1-2 (May 16, 2022).
NCBI Reference Sequence: RMH36335.1, hypothetical protein D66910_06140 [Nitrospirae bacterium], https://www.ncbi.nlm.nih.gov/protein/RMH36335.1/ [1-2](Published on Oct. 29, 2018).
Nowak et al. Guide RNA engineering for versatile Cas9 functionality. Nucleic Acids Res. 44(20):9555-9564 (2016).
Osorio, D. et al., Peptides: A Package for Data Mining of Antimicrobial Peptides, The R. Journal, 2015, 7(1), 4-14, pp. 1-11.
Paix, et al. Precision genome editing using synthesis-dependent repair of Cas9-induced DNA breaks. Proceedings of the National Academy of Sciences of the United States of America 114,50:E10745-E10754 (2017).
PCT/US2020/018353 International Search Report and Written Opinion dated Jun. 30, 2020.
PCT/US2020/018432 International Search Report and Written Opinion dated Jun. 30, 2020.
PCT/US2021/024927 International Search Report and Written Opinion dated Jul. 21, 2021.
PCT/US2021/024945 International Search Report and Written Opinion mailed Jul. 20, 2021.
PCT/US2021/031136 International Search Report and Written Opinion dated Aug. 25, 2021.
PCT/US2021/031143 International Search Report and Written Opinion dated Aug. 25, 2021.
PCT/US2022/080411 International Preliminary Report on Patentability dated Jun. 6, 2024.
PCT/US2022/080411 International Search Report and Written Opinion dated Apr. 19, 2023.
PCT/US2022/080437 International Preliminary Report on Patentability dated Jun. 6, 2024.
PCT/US2022/080437 International Search Report and Written Opinion dated Feb. 28, 2023.
Price, M.N. et al., Fast Tree2—Approximately Maximum-Likelihood Trees for Large Alignments, PLOS One, 2010, vol. 5, No. 3, e9490, pp. 1-10.
Ran, F. et al., In vivo genome editing using Staphylococcus aureus Cas 9, Nature, 2015, vol. 520, pp. 1-18.
Rautela et al.: Efficient genome editing of human natural killer cells by CRISPR RNP. bioRxiv prePrint doi: https://doi.org/10.1101/406934 [1-24] (2018).
Schneider et al. Sequence logos: a new way to display consensus sequences. Nucleic acids research 18(20):6097-6100 (1990).
Shmakov, et al. Diversity and evolution of class 2 CRISPR-Cas systems. Nat Rev Microbiol 15(3):169-182 (2017).
Shmakov, Sergey. et al. Discovery and Functional Characterization of Diverse Class 2 CRISPR-Cas Systems. Molecular Cell 60(3):385-397 (2015).
Singh, et al. Protein Engineering Approaches in the Post-Genomic Era. Current Protein and Peptide Science 18:1-11 (2017).
Stamatakis, A., RAxML Version 8: a tool for phylogenetic analysis and post-analysis of large phylogenies, Bioinformatics, 2014, vol. 30, No. 9, pp. 1312-1313.
Tang et al.: Class 2 CRISPR/Cas: an expanding biotechnology toolbox for and beyond genome editing. Cell Biosci. 8:59 doi:10.1186/s13578-018-0255-x [1-13](2018).
Tareen et al.: Logomaker: beautiful sequence logos in Python. Bioinformatics 6(7):2272-2274 (2020).
UniProtKB Accession No. A0A3B9GP868. CRISPR-associated endonuclease Cas9. Record created Jan. 16, 2019. p. 1, Retrieved Jun. 10, 2024 at URL: https://www.uniprot.org/uniprotkb/A0A3B9GP86/entry.
UniProtKB, [online] Accession No. A0A1F8ZSN4, HNH nuclease domain-containing protein, Dec. 11, 2019, p. 1 [retrieved online Apr. 24, 2024], URL: https://rest.uniprot.org/unisave/A0A1F8ZSN4?format=txt&versions=11.
UniProtKB, [online] Accession No. AA0A3D 5Y812 and HNHc domain-containingprotein, Dec. 11, 2019, p. 1 [retrieved online Apr. 24, 2024], URL: https://rest.uniprot.org/unisave/A0A3D5Y812?format=txt&versions=6.
Uniprotkb/trembl: A0A1F0KNW4 • A0A1F0KNW4_9MICC HNHc domain-containing protein. *Rothia* sp. HMSC066H02, pp. 1-5 [retrieved online Dec. 1, 2022] URL: https://www.uniprot.org/uniprotkb/A0A1F0KNW4/entry (Feb. 15, 2017).
Uniprotkb/trembl: A0A1S1DAD0 • A0A1S1DAD0_9MICC HNH Cas9-type domain-containing protein. *Rothia* sp. HMSC065C03, pp. 1-5 [retrieved online Dec. 1, 2022] URL: https://www.uniprot.org/uniprotkb/A0A1S1DAD0/entry (Apr. 12, 2017).
Uniprotkb/trembl: A1F0PN46 • A0A1F0PN46_9MICC HNH Cas9-type domain-containing protein. *Rothia* sp. HMSC076D04, pp. 1-5 [retrieved online Dec. 1, 2022] URL: https://www.uniprot.org/uniprotkb/A0A1F0PN46/entry (Feb. 15, 2017).
U.S. Appl. No. 17/193,173 Final Office Action dated Apr. 17, 2023.
U.S. Appl. No. 17/193,173 Non-Final Office Action dated Oct. 7, 2022.
U.S. Appl. No. 17/857,923 Advisory Action dated Aug. 8, 2023.
U.S. Appl. No. 17/857,923 Final Office Action dated Jun. 13, 2023.
U.S. Appl. No. 17/857,923 Non-Final Office Action dated Feb. 28, 2023.
U.S. Appl. No. 16/917,837 Office Action dated Aug. 26, 2020.
U.S. Appl. No. 16/917,838 Office Action dated Jul. 28, 2020.
U.S. Appl. No. 17/431,135 Office Action dated Feb. 16, 2024.
U.S. Appl. No. 17/431,135 Office Action dated Jun. 4, 2024.
Weinberg, Z. et al., Extraordinary Structured Noncoding RNAs Revealed by Bacterial Metagenome Analysis, Nature 2009, vol. 462, No. 7273, pp. 656-659.
Xiao, N. et la., protr/ProtrWeb: R package and web server for generating various numerical representation schemes of protein sequences, Bioinformatics, 2015, vol. 31, No. 11, pp. 1857-1859.
Xu, Daohua. Tigit Cas9-KO Strategy. GenPharmatech Co, Ltd., Retrieved at URL: https://oss.gempharmatech.com/upload/file/20240324/T012735.Tigit%20Cas9-KO%20%20Strategy-EN.pdf, 11 pages (2019).
Xu, et al. Efficient genome engineering in eukaryotes using Cas9 from *Streptococcus thermophilus*. Cellular and Molecular Life Sciences 72(2):383-399 (2014).
Yan et al., Functionally diverse type V CRISPR-Cas systems. Science 363: 88-91 (2019).
Yang et al.: New CRISPR-Cas systems discovered. Cell Res. 27(3):313-314 doi:10.1038/cr.2017.21 (2017).
Yang, Z., "PAML 4: Phylogenetic Analysis by Maximum Likelihood", Molecular Biology and Evolution, 2007, vol. 24, No. 8, pp. 1586-1591.
Zhang et al. Propagated Perturbations from a Peripheral Mutation Show Interactions Supporting WW Domain Thermostability. Structure 26(11):1474-1485 (2018).
Zhou, X.M. et al. Intrinsic Expression of Immune Checkpoint Molecule TIGIT Could Help Tumor Growth in vivo by Suppressing the Function of NK and CD8+ T Cells. Front. Immunol. Vol. 9, Article 2821: 1-11 (2018).
Kortleve, D. et al. Orthotopic editing of T-cell receptors. Cell Therapy vol. 3: 949-950 (2019).

\* cited by examiner

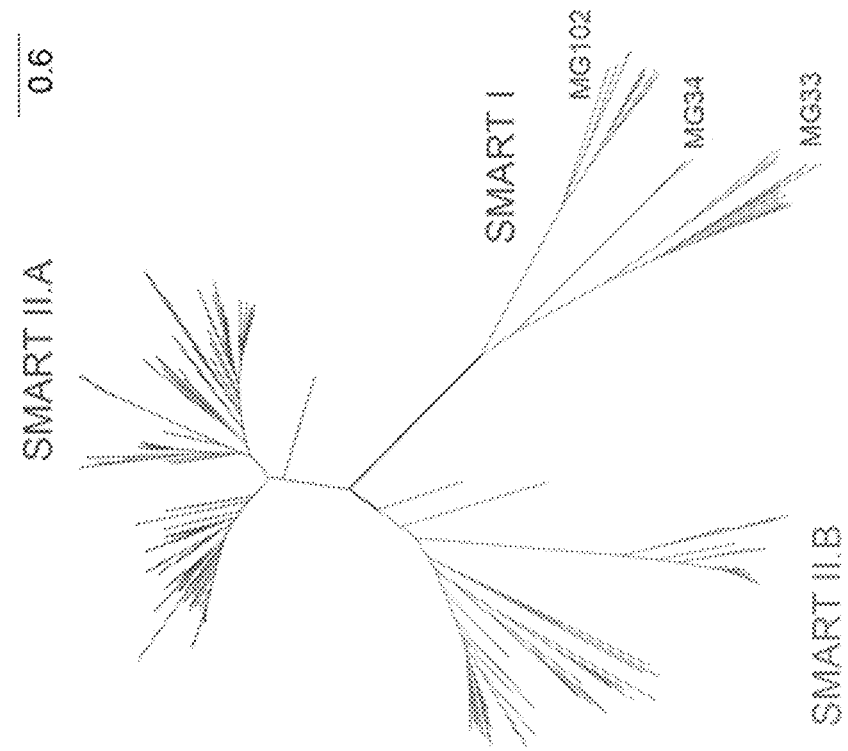
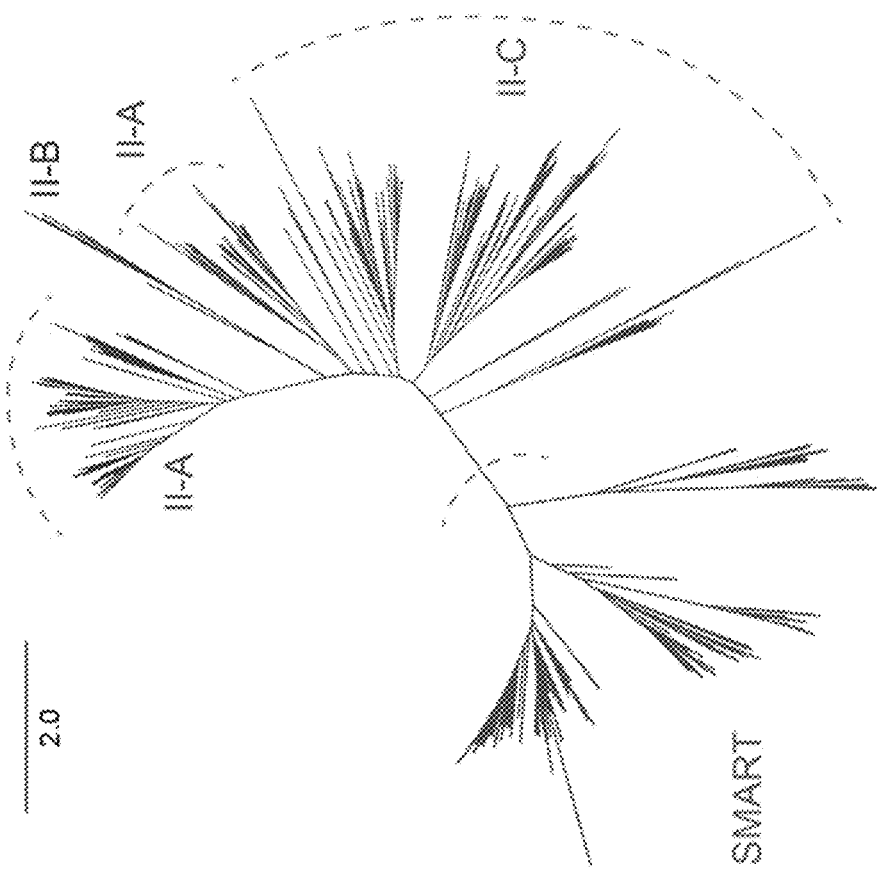

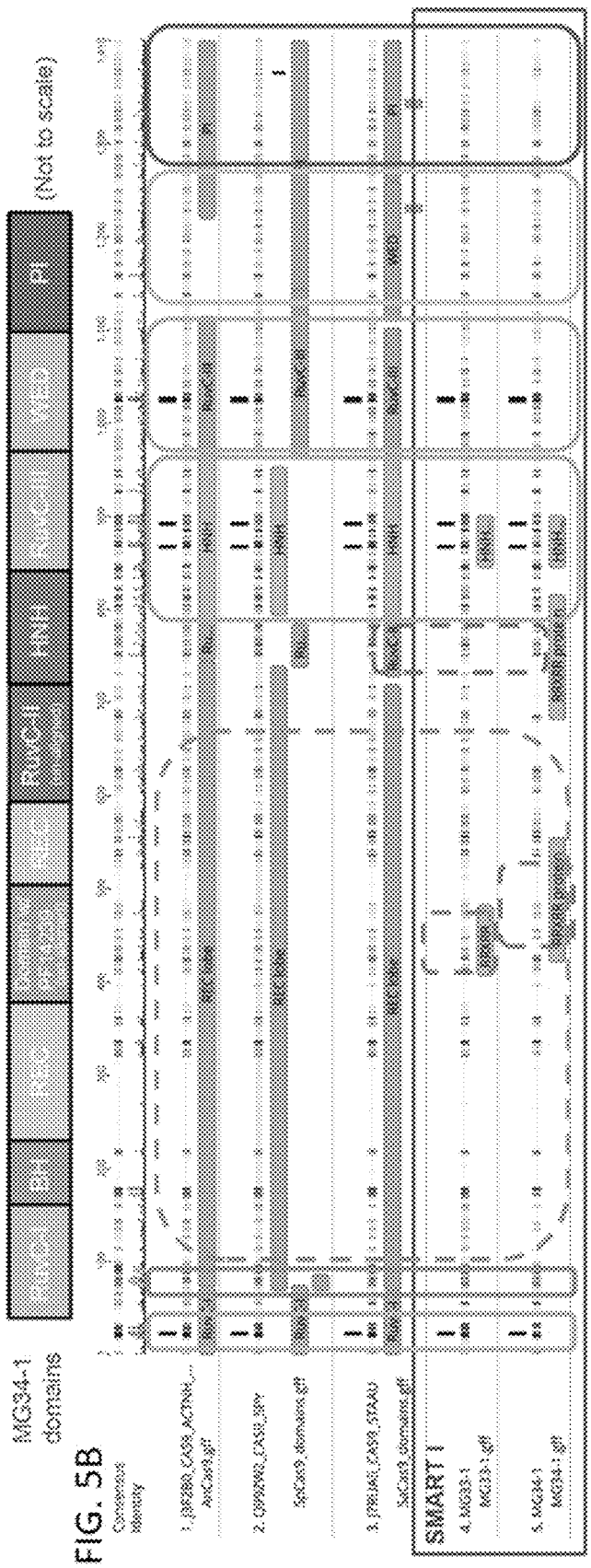
SEQ ID NO: 1361;
RRXRR motif

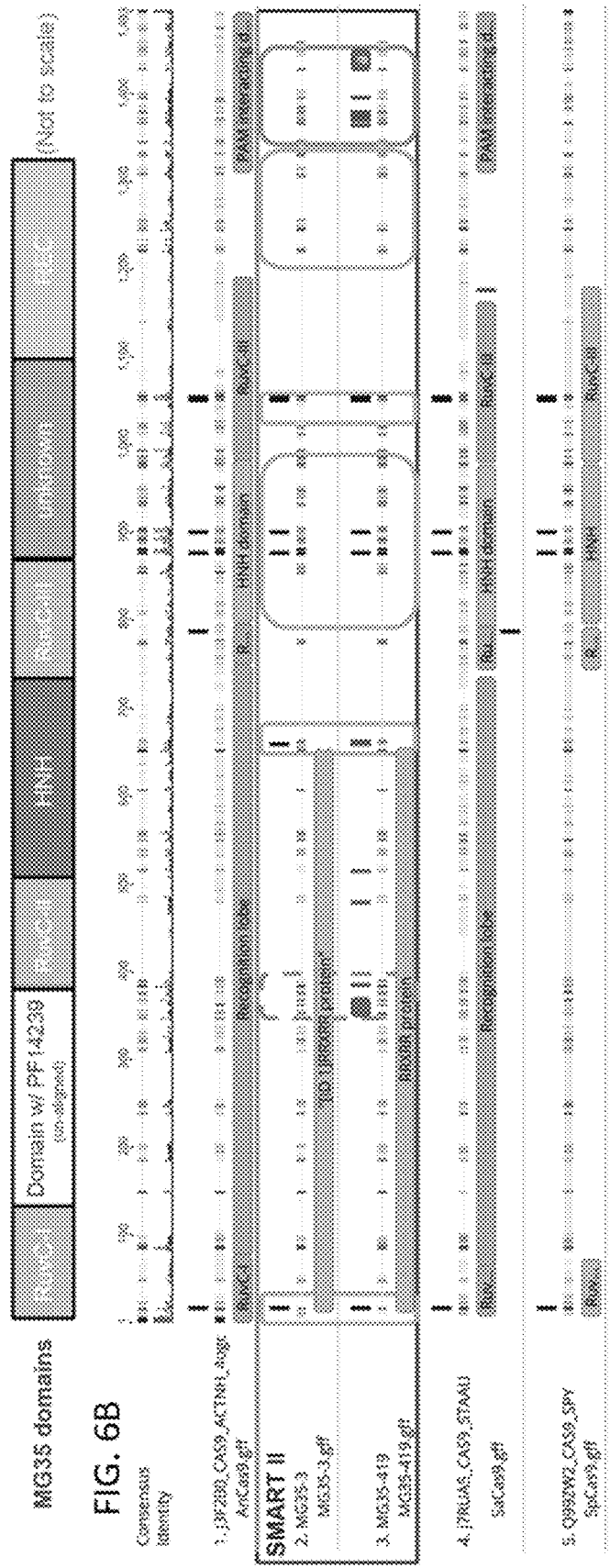

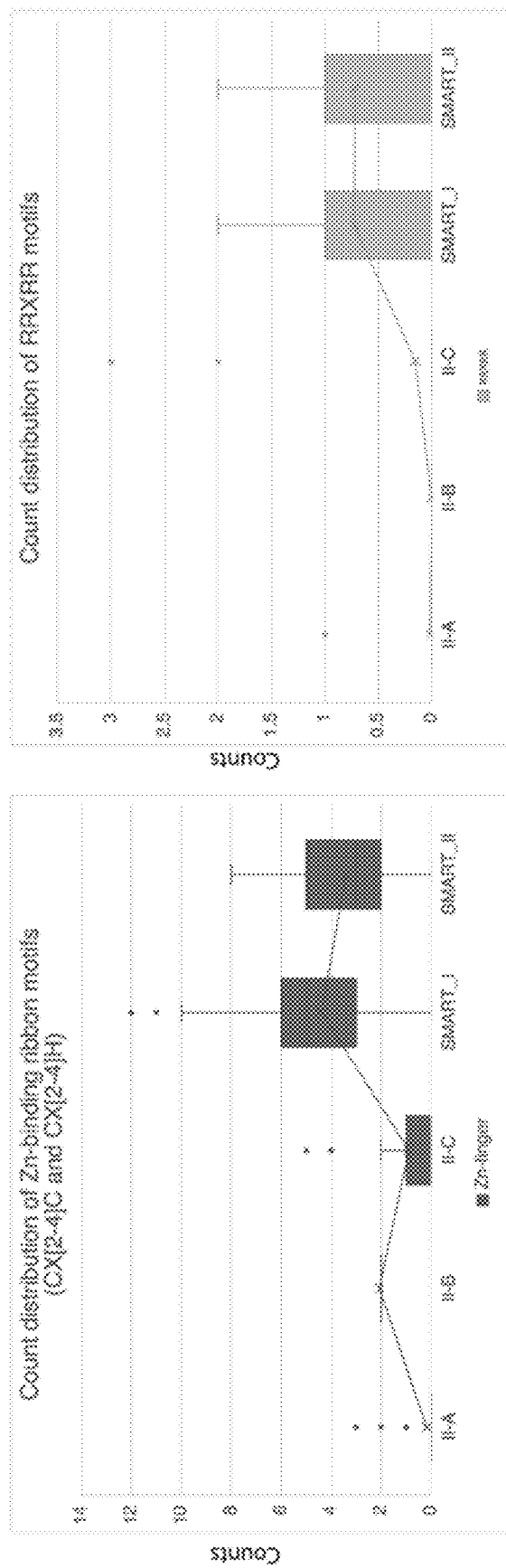

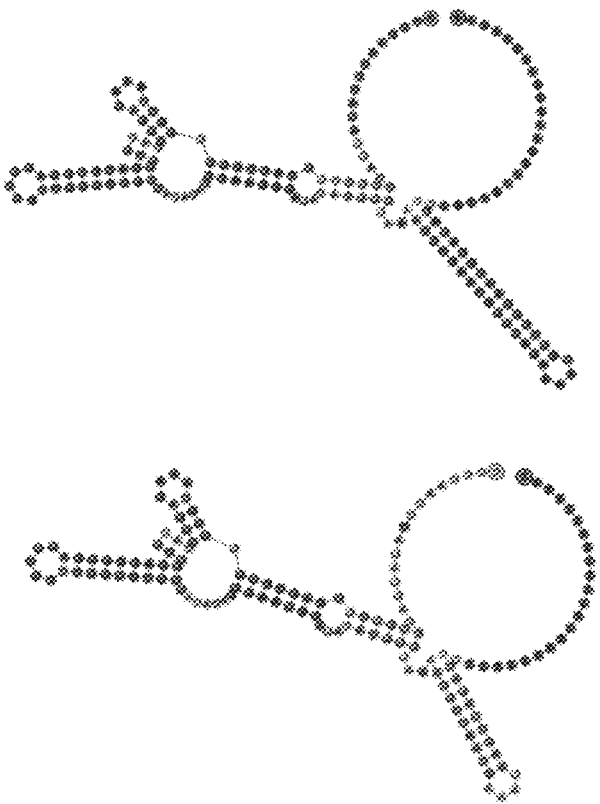
FIG. 9A  SEQ ID NO: 1323
FIG. 9B  SEQ ID NO: 1324
FIG. 9C  SEQ ID NO: 1325
FIG. 9D  SEQ ID NO: 1326

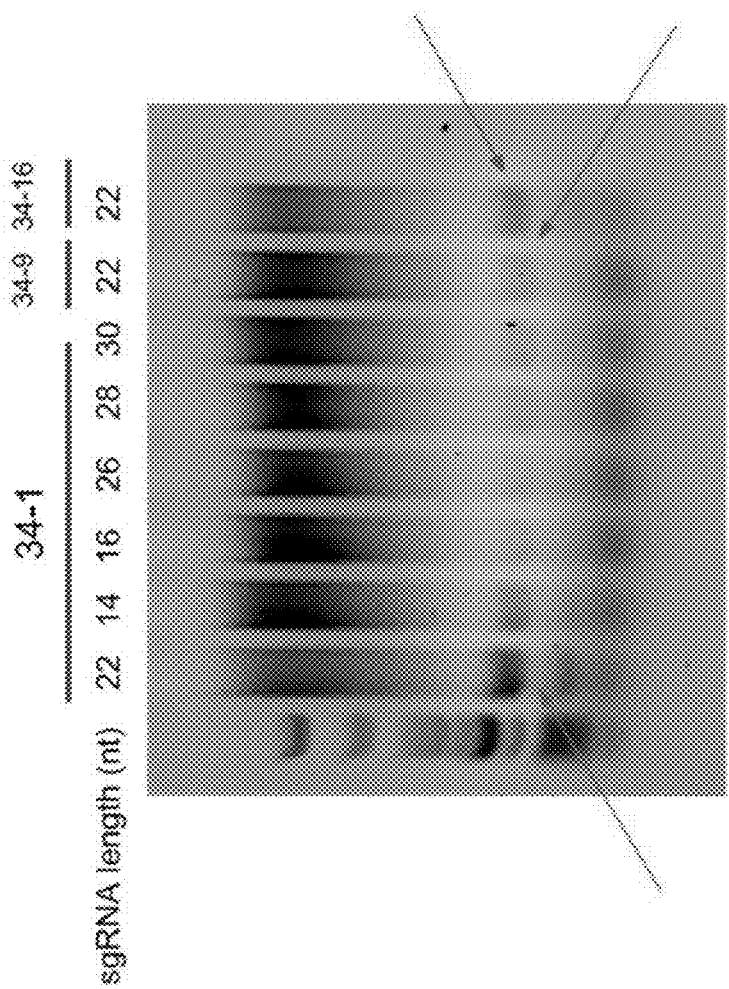
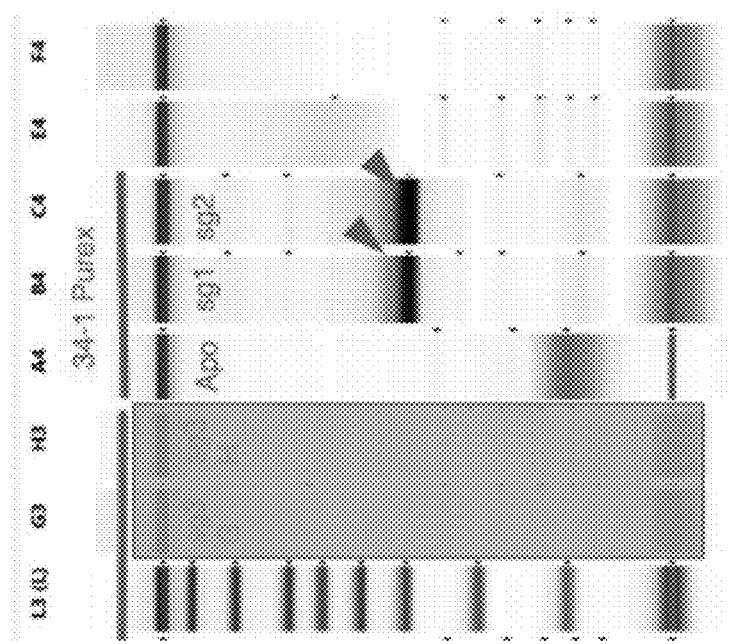
FIG. 10B
FIG. 10A

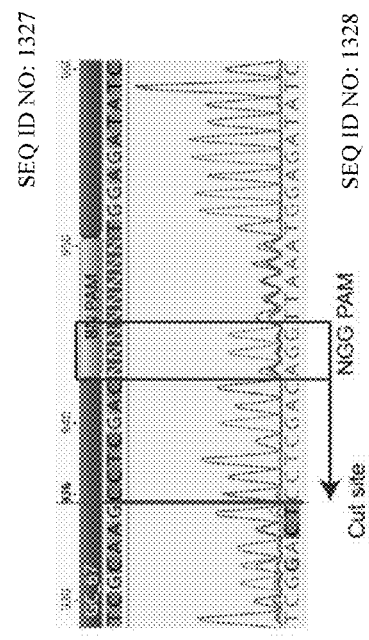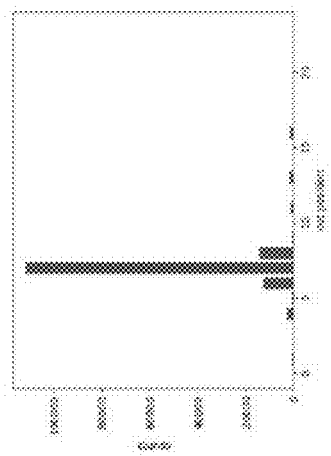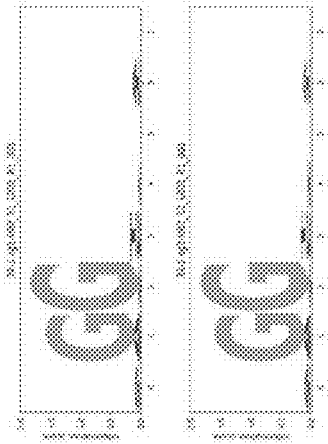

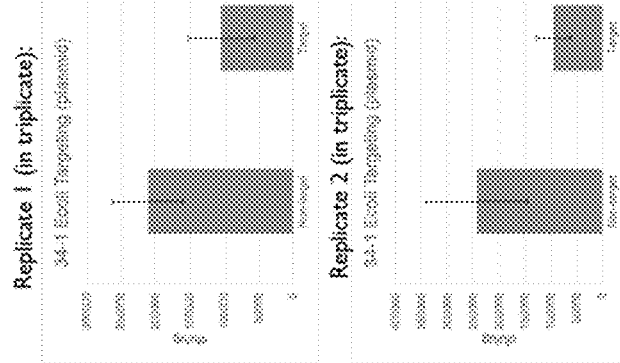
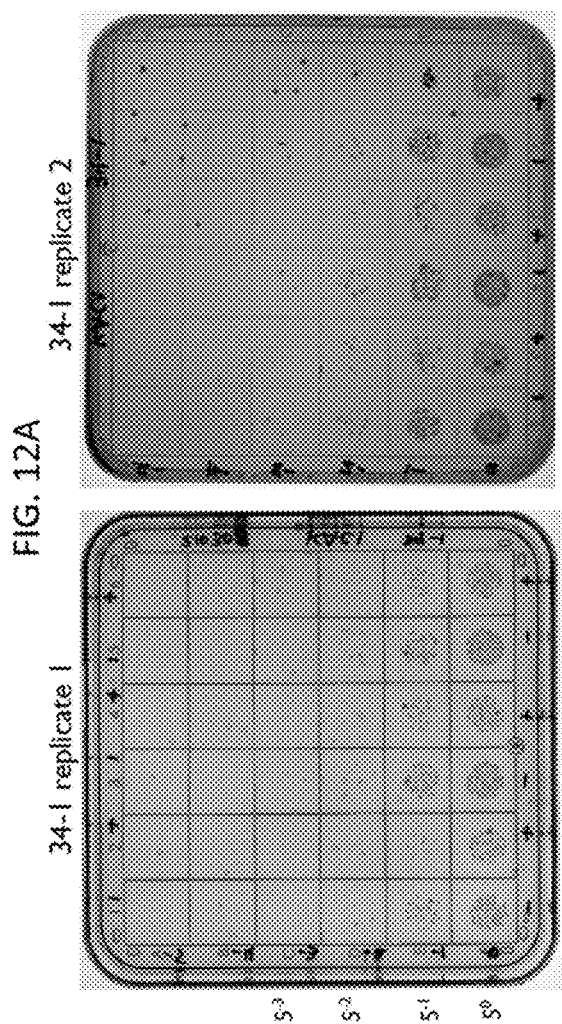
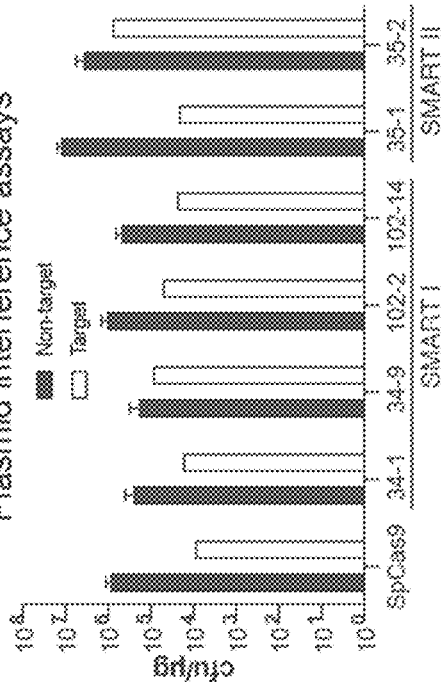
FIG. 12A
FIG. 12B
FIG. 12C

SEQ ID NO: 1361;
RRXRR motif

SEQ ID NO: 1361;
RRXRR motif

| Candidate | Protein size (aa) | gRNA size (nt) | 3' TAM (Sanger) | cut site |
|---|---|---|---|---|
| 35-1 | 429 | 270 | AaGG | 5 and 7 |
| 35-2 | 495 | 234 | nARAA | 7 |
| 35-3 | 424 | 278 | ATGAnA | 7 |
| 35-4 | 429 | 277 | ATGA | 7 and 13 |
| 35-5 | 494 | 287 | ATGG | 5 and 7 |
| 35-6 | 428 | 277 | A-rich, need NGS | 13 |
| 35-102 | 424 | 292 | nTGA | 7 |

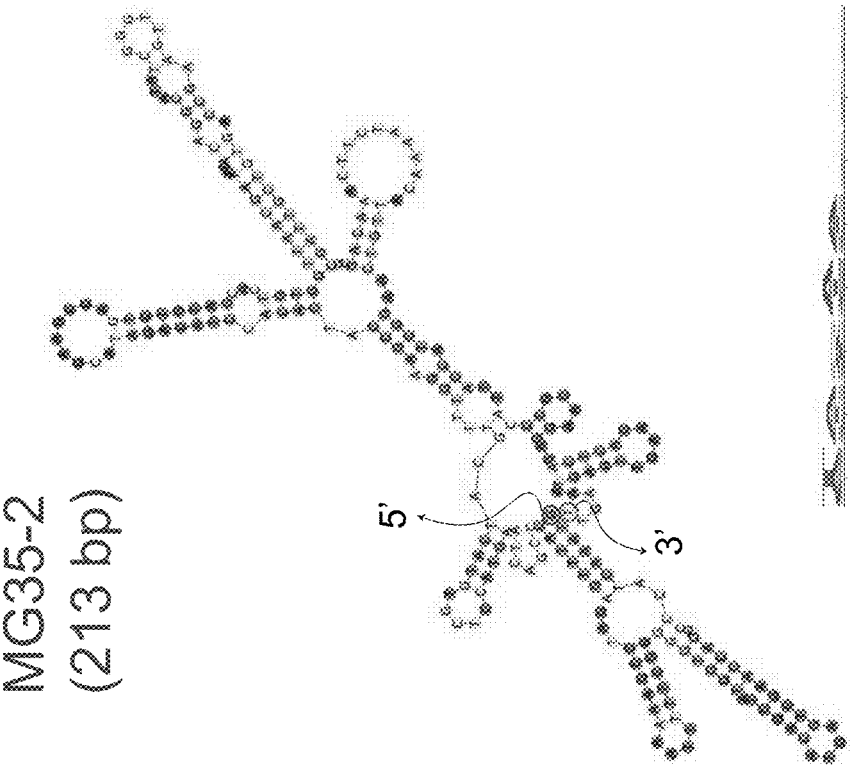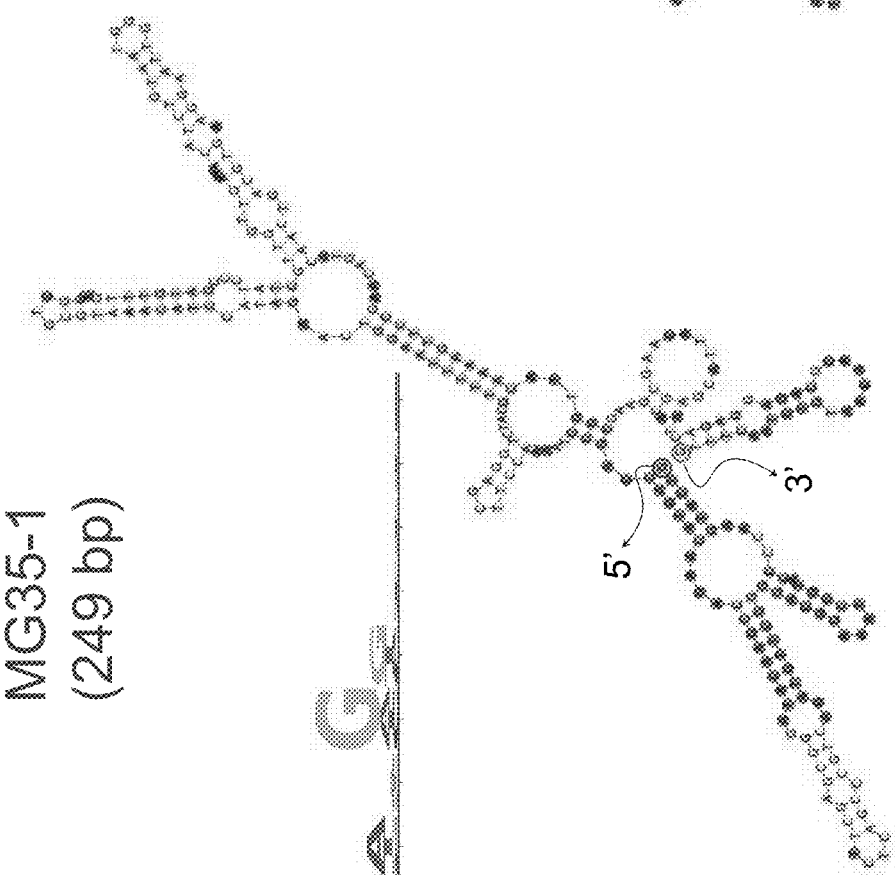
FIG. 21D

| | A | R | N | D | C | E | Q | G | H | I | L | K | M | F | P | S | T | W | Y | V |
|---|---|---|---|---|---|---|---|---|---|---|---|---|---|---|---|---|---|---|---|---|
| MG35-1 | 7.2 | 9.8 | 4.2 | 3.7 | 2.1 | 3.7 | 4.7 | 8.9 | 1.9 | 6.3 | 7.5 | 10.9 | 6.0 | 3.0 | 4.4 | 5.1 | 5.9 | 1.2 | 3.5 | 5.9 |
| MG35-2 | 8.4 | 8.0 | 5.0 | 4.6 | 2.1 | 4.8 | 3.6 | 6.1 | 4.4 | 4.8 | 8.4 | 7.9 | 2.7 | 3.1 | 4.6 | 4.6 | 6.5 | 0.8 | 3.2 | 6.5 |
| MG35-3 | 7.6 | 8.5 | 4.5 | 3.5 | 2.1 | 4.3 | 4.5 | 7.1 | 2.8 | 5.7 | 9.7 | 8.7 | 1.2 | 4.3 | 4.3 | 5.2 | 6.9 | 0.9 | 3.1 | 5.2 |
| MG35-8 | 6.9 | 9.3 | 4.7 | 3.7 | 2.3 | 4.0 | 4.7 | 7.7 | 2.3 | 5.4 | 9.6 | 8.6 | 1.2 | 3.0 | 4.7 | 4.9 | 7.0 | 1.4 | 2.8 | 6.1 |
| MG35-102 | 8.0 | 8.0 | 4.5 | 3.3 | 2.4 | 4.0 | 5.4 | 8.0 | 2.6 | 5.7 | 9.7 | 8.5 | 6.3 | 3.6 | 5.0 | 4.7 | 6.4 | 1.2 | 2.8 | 5.4 |
| lacB (Altae-Tran, 2021) | 10.0 | 8.0 | 3.2 | 2.1 | 1.6 | 4.6 | 6.2 | 7.7 | 3.4 | 5.0 | 10.0 | 5.9 | 0.7 | 2.5 | 4.3 | 4.6 | 5.5 | 1.4 | 2.3 | 6.2 |
| MG34-1 | 5.5 | 9.6 | 5.4 | 5.8 | 1.6 | 9.4 | 1.7 | 6.2 | 2.4 | 6.2 | 6.6 | 12.0 | 1.4 | 3.5 | 3.2 | 4.4 | 5.2 | 0.7 | 3.1 | 5.9 |
| MG102-2 | 6.9 | 8.7 | 3.0 | 6.9 | 1.7 | 6.0 | 4.3 | 6.7 | 2.4 | 5.8 | 9.3 | 7.4 | 4.7 | 3.4 | 5.1 | 7.3 | 5.0 | 1.1 | 3.7 | 4.9 |
| MG102-14 | 8.1 | 11.1 | 3.7 | 5.0 | 1.9 | 7.7 | 2.8 | 6.0 | 2.3 | 5.6 | 9.0 | 7.0 | 5.2 | 3.2 | 5.0 | 6.7 | 4.8 | 1.1 | 3.8 | 4.6 |
| MG102-35 | 8.0 | 9.0 | 4.4 | 6.1 | 1.8 | 7.3 | 2.8 | 6.4 | 1.7 | 4.9 | 9.4 | 8.5 | 0.9 | 3.2 | 4.7 | 6.9 | 4.5 | 0.9 | 3.4 | 4.4 |
| MG102-45 | 8.1 | 9.6 | 4.2 | 5.5 | 1.8 | 7.4 | 3.0 | 7.0 | 1.9 | 5.5 | 9.1 | 7.0 | 5.8 | 3.3 | 5.0 | 6.7 | 3.7 | 1.1 | 3.4 | 4.3 |
| Typical | 8.7 | 8.2 | 3.9 | 5.7 | 1.5 | 6.2 | 3.9 | 6.9 | 2.2 | 5.7 | 9.8 | 5.9 | 2.3 | 4.0 | 5.0 | 7.0 | 5.3 | 1.3 | 2.9 | 6.5 |

FIG. 23

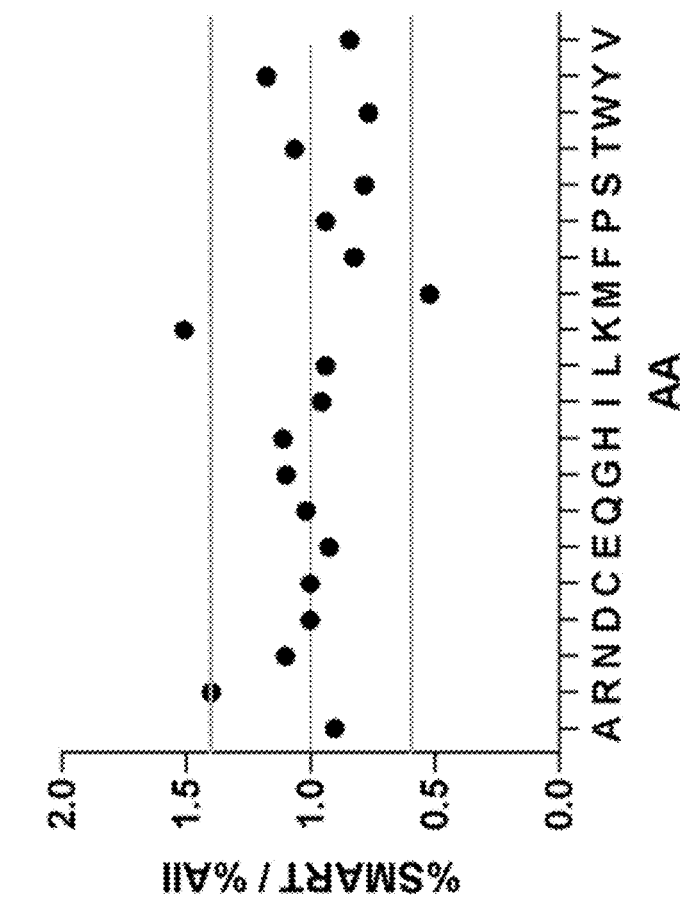
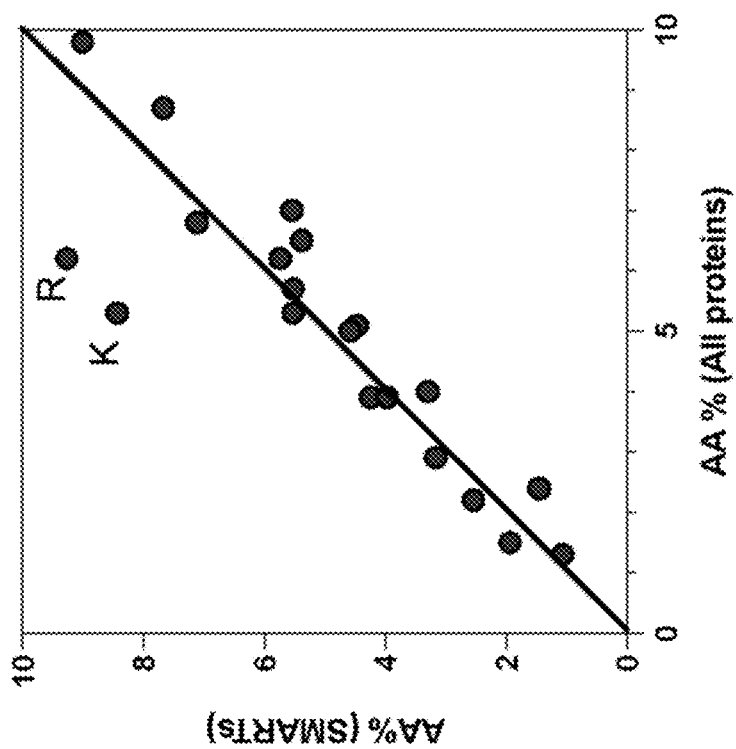
FIG. 24A
FIG. 24B

SEQ ID NO: 1361; RRXRR motif

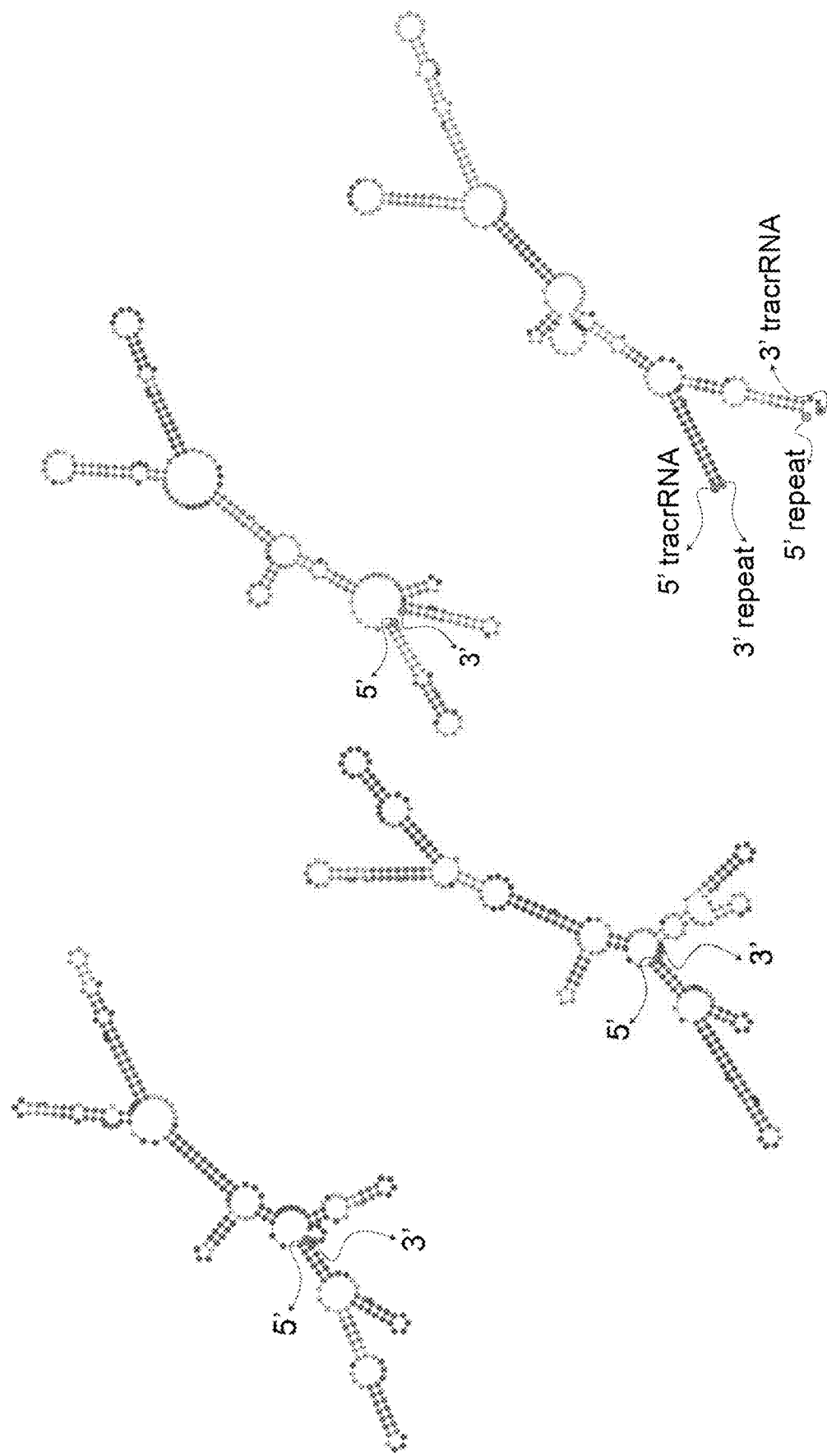
FIG. 32D SEQ ID NO: 1353
FIG. 32E SEQ ID NO: 1354
FIG. 32F SEQ ID NO: 1355
FIG. 32G SEQ ID NO: 1356

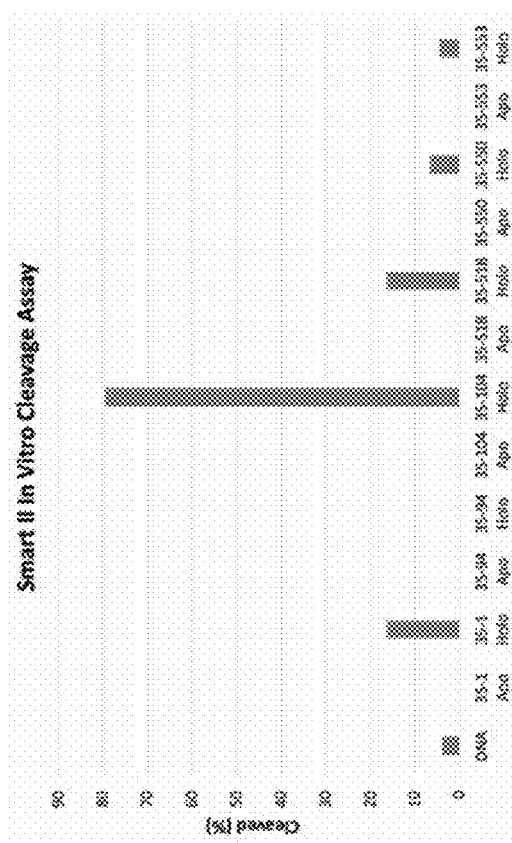
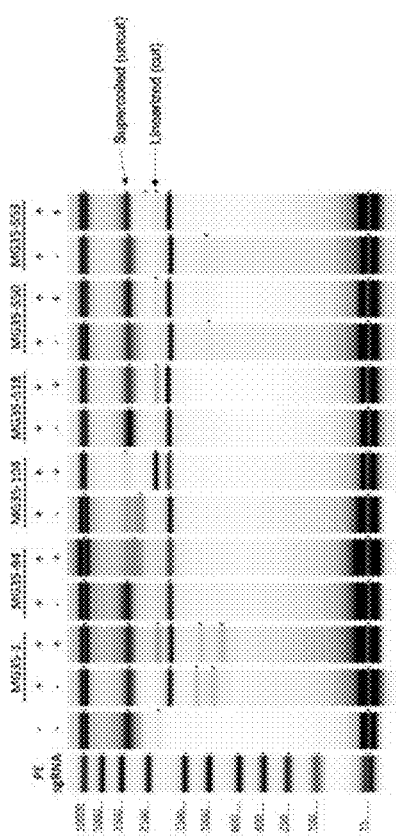
FIG. 35A
FIG. 35B

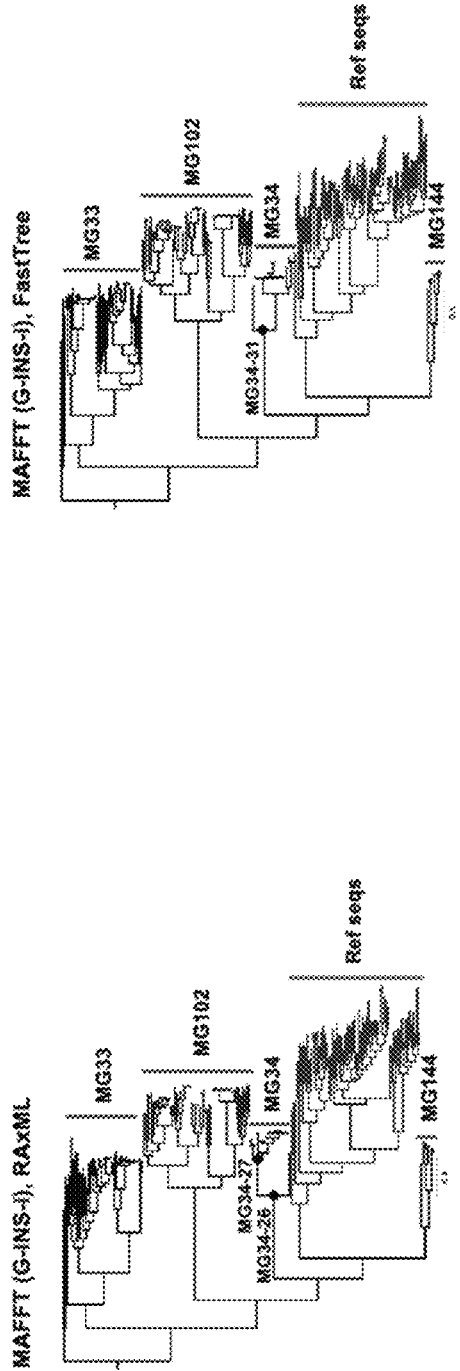
FIG. 37A
FIG. 37B
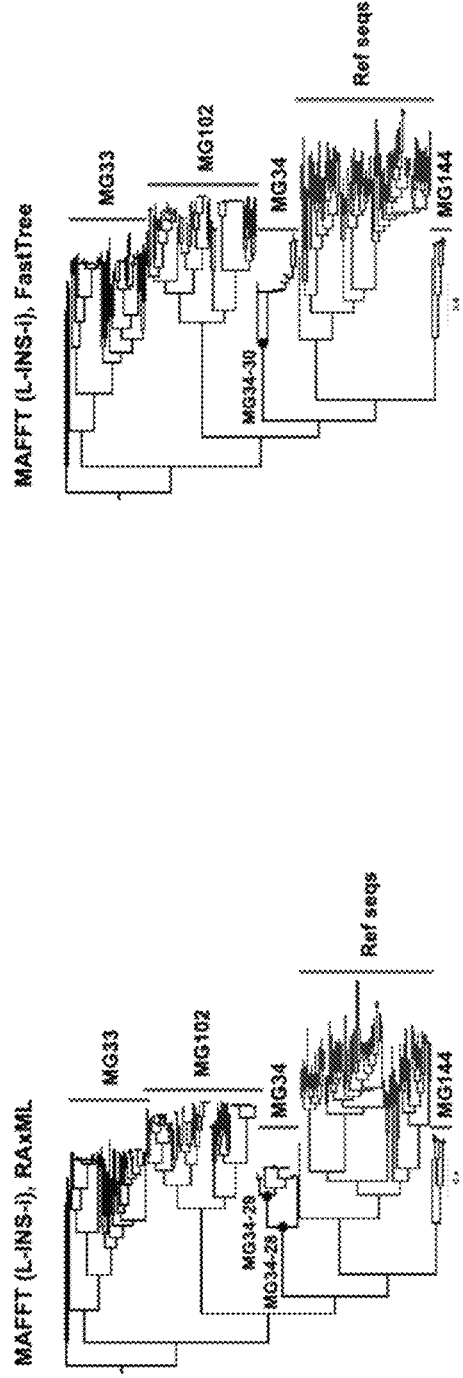
FIG. 37C
FIG. 37D

US 12,410,449 B2

ENDONUCLEASE SYSTEMS

CROSS-REFERENCE

This application is a continuation of International Application No. PCT/US2022/080437, filed on Nov. 23, 2022, entitled "ENDONUCLEASE SYSTEMS", which application claims the benefit of U.S. Provisional Application No. 63/282,999, filed on Nov. 24, 2021; 63/289,981, filed on Dec. 15, 2021; and 63/356,908, filed on Jun. 29, 2022; each of which is incorporated by reference herein in its entirety.

This application is related to PCT Application No. PCT/US21/24945, which is incorporated by reference herein in its entirety.

SEQUENCE LISTING

The instant application contains a Sequence Listing which has been submitted electronically in XML format and is hereby incorporated by reference in its entirety. Said XML copy, created on Mar. 28, 2025, is named 55921-741_301_SL.xml and is 1,976,586 bytes in size.

BACKGROUND

Cas enzymes along with their associated Clustered Regularly Interspaced Short Palindromic Repeats (CRISPR) guide ribonucleic acids (RNAs) appear to be a pervasive (~45% of bacteria, ~84% of archaea) component of prokaryotic immune systems, serving to protect such microorganisms against non-self nucleic acids, such as infectious viruses and plasmids by CRISPR-RNA guided nucleic acid cleavage. While the deoxyribonucleic acid (DNA) elements encoding CRISPR RNA elements may be relatively conserved in structure and length, their CRISPR-associated (Cas) proteins are highly diverse, containing a wide variety of nucleic acid-interacting domains. While CRISPR DNA elements have been observed as early as 1987, the programmable endonuclease cleavage ability of CRISPR/Cas complexes has only been recognized relatively recently, leading to the use of recombinant CRISPR/Cas systems in diverse DNA manipulation and gene editing applications. Owing to the utility of these enzymes, they are being repurposed for a wide variety of biotechnology, gene editing, and therapeutic applications. Due to their single-effector architecture, the majority of systems currently being repurposed for genome engineering belong to the CRISPR Class 2 category.

SUMMARY

The large size (greater than ca. 1200 amino acids) of many class 2 Cas effectors makes delivery for therapeutic applications challenging. Accordingly, described herein are methods, compositions, and systems relating to novel putative guided dsDNA nucleases referred to as SMART (SMall ARchaeal-associaTed) nuclease systems. These endonuclease effectors are defined by their small size (about 400 aa to about 1050 aa), the presence of RuvC and HNH catalytic domains, and other predicted protein features that together suggest novel biochemical mechanisms.

In some aspects, the present disclosure provides for an engineered nuclease system, comprising: (a) an endonuclease comprising a RuvC domain and an HNH domain, wherein the endonuclease is derived from an uncultivated microorganism; and (b) an engineered guide ribonucleic acid structure configured to form a complex with the endonuclease comprising: (i) a guide ribonucleic acid sequence configured to hybridize to a target deoxyribonucleic acid sequence; and (ii) a ribonucleic acid sequence configured to bind to the endonuclease; wherein the endonuclease has a molecular weight of about 96 kDa or less, about 80 kDa or less, about 70 kDa or less, or about 60 kDa or less, and wherein: (1) the endonuclease comprises an arginine rich region or a domain with PF14239 homology with at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to an arginine rich region or a domain with PF14239 homology from any one of SEQ ID NOs: 1-198, 221-459, 463-612, 617-668, 674-675, 975-1002, 1260-1321, or a variant thereof; (2) the endonuclease comprises a REC domain with at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a REC domain from any one of SEQ ID NOs: 1-198, 221-459, 463-612, 617-668, 674-675, 975-1002, 1260-1321, or a variant thereof; or (3) the endonuclease comprises a sequence with at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1-198, 221-459, 463-612, 617-668, 674-675, 975-1002, 1260-1321, or a variant thereof. In some embodiments, (1) the endonuclease comprises an arginine rich region or a domain with PF14239 homology with at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to an arginine rich region or a domain with PF14239 homology from any one of SEQ ID NOs: 674-675, 975-1002, or 1260-1321, or a variant thereof; (2) the endonuclease comprises a REC domain with at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a REC domain from any one of SEQ ID NOs: 674-675, 975-1002, or 1260-1321, or a variant thereof; or (3) the endonuclease comprises a sequence with at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity sequence identity to any one of SEQ ID NOs: 674-675, 975-1002, or 1260-1321, or a variant thereof. In some embodiments, the endonuclease is an Archaeal endonuclease. In some embodiments, the endonuclease comprises a sequence with at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1-198, 221-459, 463-612, 617-668, 674-675, 975-1002, 1260-1321. In some embodiments, the endonuclease further comprises an arginine-rich region comprising an RRxRR motif (SEQ ID NO: 1361) or a domain with PF14239 homology. In some embodiments, the arginine rich region or the domain with PF14239 homology has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the arginine rich region or the domain with PF14239 homology of any one of SEQ ID NOs: 1-198, 221-459, 463-612, 617-668, 674-675, 975-1002, 1260-1321. In some embodiments, the endonuclease further comprises a REC (recognition) domain. In some embodiments, the REC domain has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a REC domain of any one of SEQ ID NOs: 1-198, 221-459, 463-612, 617-668, 674-675, 975-1002, 1260-1321. In some embodiments, the endonuclease further comprises a BH (bridge helix) domain, a WED (wedge) domain, or a PI (PAM interacting) or TI (TAM interacting) domain. In some embodiments, the WED domain, or the PI domain has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a BH domain, a WED domain, or a PI domain of any one of SEQ ID NOs: 1-198, 221-459, 463-612, 617-668, 674-675, 975-1002, 1260-1321.

In some aspects, the present disclosure provides for an engineered nuclease system comprising: (a) an endonuclease comprising a RuvC-I domain and an HNH domain; and (b) an engineered guide ribonucleic acid structure configured to form a complex with the endonuclease comprising: (i) a guide ribonucleic acid sequence configured to hybridize to a target deoxyribonucleic acid sequence; and (ii) a ribonucleic acid sequence configured to bind to the endonuclease, wherein the endonuclease comprises a sequence with at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 674-675, 975-1002, 1260-1321, or a variant thereof. In some embodiments, the endonuclease is an archaeal endonuclease. In some embodiments, the endonuclease further comprises an arginine-rich region comprising an RRxRR motif (SEQ ID NO: 1361) or a domain with PF14239 homology. In some embodiments, the arginine rich region or the domain with PF14239 homology has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to an arginine rich region of any one of SEQ ID NOs: 674-675, 975-1002, 1260-1321. In some embodiments, the endonuclease further comprises a REC (recognition) domain. In some embodiments, the REC domain having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a REC domain of any one of SEQ ID NOs: 674-675, 975-1002, 1260-1321. In some embodiments, the endonuclease further comprises a BH domain, a WED domain, and a PI domain. In some embodiments, the BH domain, the WED domain, or the PI domain has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a BH domain, a WED domain, or a PI domain of any one of SEQ ID NOs: 674-675, 975-1002, 1260-1321. In some embodiments, the endonuclease is derived from an uncultivated microorganism. In some embodiments, the ribonucleic acid sequence configured to bind the endonuclease comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 199-200, 460-461, or 669-673, or a sequence with at least 80% sequence identity to the non-degenerate nucleotides of any one of SEQ ID NOs: 201-203, 613-616, 677-686, 1003-1022, or 1231-1259. In some embodiments, the guide nucleic acid structure comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the non-degenerate nucleotides of any one of SEQ ID NOs: 201-203, 613-616, 677-686, 1003-1022, or 1231-1259.

In some aspects, the present disclosure provides for an engineered nuclease system comprising, (a) an engineered guide ribonucleic acid structure comprising: (i) a guide ribonucleic acid sequence configured to hybridize to a target deoxyribonucleic acid sequence; and (ii) a ribonucleic acid sequence configured to bind to an endonuclease, wherein the ribonucleic acid sequence comprises a sequence with at least 80% sequence identity to any one of SEQ ID NOs: 199-200, 460-461, or 669-673, or a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to nonvariable nucleotides of any one of SEQ ID NOs: 677-686, 1006-1012, or 1231-1259; and (b) an RNA-guided endonuclease configured to bind to the engineered guide ribonucleic acid. In some embodiments, the RNA-guided endonuclease is an Archaeal endonuclease. In some embodiments, the endonuclease has a molecular weight of about 120 kDa or less, 100 kDa or less, 90 kDa or less, or 60 kDa or less. In some embodiments, the engineered guide ribonucleic acid structure comprises at least two ribonucleic acid polynucleotides. In some embodiments, the engineered guide ribonucleic acid structure comprises a single ribonucleic acid polynucleotide comprising the guide ribonucleic acid sequence and the ribonucleic acid sequence configured to bind the endonuclease. In some embodiments, the guide ribonucleic acid sequence is complementary to a prokaryotic, bacterial, archaeal, eukaryotic, fungal, plant, mammalian, or human genomic sequence. In some embodiments, the guide ribonucleic acid sequence is from about 14 to about 28 nucleotides in length, from about 18 to about 26 nucleotides in length, from about 22 to about 26 nucleotides in length, or from about 24 nucleotides in length. In some embodiments, the guide ribonuclease acid sequence comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 462, 676, or 1229-1230. In some embodiments, the endonuclease comprises one or more nuclear localization sequences (NLSs) proximal to an N- or C-terminus of the endonuclease. In some embodiments, the NLS comprises a sequence selected from any one of SEQ ID NOs: 205-220. In some embodiments, the system further comprises a single- or double-stranded DNA repair template comprising from 5' to 3': a first homology arm comprising a sequence of at least 20 nucleotides 5' to the target deoxyribonucleic acid sequence, a synthetic DNA sequence of at least 10 nucleotides, and a second homology arm comprising a sequence of at least 20 nucleotides 3' to the target sequence. In some embodiments, the first or second homology arm comprises a sequence of at least 40, 80, 120, 150, 200, 300, 500, or 1,000 nucleotides. In some embodiments, the system further comprises a source of $Mg^{2+}$. In some embodiments, the endonuclease and the ribonucleic acid sequence configured to bind the endonuclease are derived from distinct species within a same phylum. In some embodiments, the endonuclease comprises a sequence with at least 70% sequence identity to any one of SEQ ID NOs: 2-24 and the guide RNA structure comprises an RNA sequence predicted to comprise a hairpin comprising a stem and a loop, wherein the stem comprises at least 10 pairs of ribonucleotides and an intervening multiloop. In some embodiments, the guide RNA structure further comprises a second stem and a second loop, wherein the second stem comprises at least 5 pairs of ribonucleotides. In some embodiments, the guide RNA structure further comprises an RNA structure comprising at least two hairpins. In some embodiments, a) the endonuclease comprises a sequence having at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1-198, 221-459, 463-612, 617-668, 674-675, 975-1002, 1260-1321, or a variant thereof; and b) the guide RNA structure comprises a sequence having at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 199-200, 460-461, or 669-673, or the nonvariable nucleotides of any one of SEQ ID NOs: 201-203, 613-616, 677-686, 1006-1012, or 1231-1259. In some embodiments, a) the endonuclease comprises a sequence at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1-198, 221-459, 463-612, 617-668, 674-675, 975-1002, 1260-1321; and b) the guide RNA structure comprises a sequence at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a class 2, type II sgRNA or tracr sequence. In some embodiments, the sequence identity is determined by a BLASTP, CLUSTALW, MUSCLE, MAFFT, or CLUSTALW with parameters of the Smith-Waterman homology search algorithm. In some embodiments, the sequence identity is determined by the BLASTP homology search algorithm using parameters of a wordlength (W) of 3, an expectation (E) of 10, and a BLOSUM62 scoring matrix setting gap costs at existence of 11, extension of 1, and using a conditional compositional score matrix adjustment. In some embodiments, the endonuclease is not a Cas9 endonuclease, a Cas14 endonuclease, a Cas12a endonuclease, a Cas12b endonuclease, a Cas 12c endonuclease, a Cas12d endonuclease, a Cas12e endonuclease, a Cas13a endonuclease, a Cas13b endonuclease, a Cas 13c endonuclease, or a Cas 13d endonuclease. In some embodiments, the endonuclease has less than 80% identity to a Cas9 endonuclease.

In some aspects, the present disclosure provides for an engineered nuclease system comprising: (a) an endonuclease configured to be selective for a target adjacent motif (TAM) sequence comprising any one of ANGG (SEQ ID NO: 1029), NARAA (SEQ ID NO: 1030), ATGAAA (SEQ ID NO: 1031), ATGA (SEQ ID NO: 1032), or WTGG (SEQ ID NO: 1033), wherein the endonuclease comprises a TAM interacting domain having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a TAM interacting domain of any one of SEQ ID NOs: 1-198, 221-459, 463-612, 617-668, 674-675, 975-1002, 1260-1321; and (b) an engineered guide RNA, wherein the engineered guide RNA is configured to form a complex with the endonuclease and the engineered guide RNA comprises a spacer sequence configured to hybridize to a target nucleic acid sequence. In some embodiments, the TAM-interacting domain comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a TAM-interacting domain of SEQ ID NO: 674 or a variant thereof or at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a TAM-interacting domain of SEQ ID NO: 675 or a variant thereof. In some embodiments, the endonuclease system comprises a sequence complementary to a eukaryotic, fungal, plant, mammalian, or human genomic polynucleotide sequence. In some embodiments, the guide RNA is 30-280 nucleotides in length. In some embodiments, the system further comprises a single- or double-stranded DNA repair template comprising from 5' to 3': a first homology arm comprising a sequence of at least 20 nucleotides 5' to the target deoxyribonucleic acid sequence, a synthetic DNA sequence of at least 10 nucleotides, and a second homology arm comprising a sequence of at least 20 nucleotides 3' to the target sequence. In some embodiments, the first or second homology arm comprises a sequence of at least 40 nucleotides. In some embodiments, the first and second homology arms are homologous to a genomic sequence of a eukaryote. In some embodiments, the single- or double-stranded DNA repair template comprises a transgene donor. In some embodiments, the system further comprises a DNA repair template comprising a double-stranded DNA segment flanked by one or two single-stranded DNA segments. In some embodiments, the single-stranded DNA segments are conjugated to the 5' ends of the double-stranded DNA segment. In some embodiments, the single stranded DNA segments are conjugated to the 3' ends of the double-stranded DNA segment. In some embodiments, the single-stranded DNA segments have a length from 4 to 10 nucleotide bases. In some embodiments, the single-stranded DNA segments have a nucleotide sequence complementary to a sequence within the spacer sequence. In some embodiments, the double-stranded DNA sequence comprises a barcode, an open reading frame, an enhancer, a promoter, a protein-coding sequence, a miRNA coding sequence, an RNA coding sequence, or a transgene. In some embodiments, the double-stranded DNA sequence is flanked by a nuclease cut site.

In some aspects, the present disclosure provides for an engineered nuclease system comprising: (a) an endonuclease configured to be selective for a protospacer adjacent motif (PAM) sequence comprising NRR, wherein the endonuclease comprises a PAM interacting domain having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a PAM interacting domain of any one of SEQ ID NOS: 1313-1318; and (b) an engineered guide RNA, wherein the engineered guide RNA is configured to form a complex with the endonuclease and the engineered guide RNA comprises a spacer sequence configured to hybridize to a target nucleic acid sequence. In some embodiments, the TAM-interacting domain comprises a sequence having at least 80% sequence identity to a TAM-interacting domain of SEQ ID NO: 674 or a variant thereof or at least 80% sequence identity to a TAM-interacting domain of SEQ ID NO: 675 or a variant thereof. In some embodiments, the endonuclease system comprises a sequence complementary to a eukaryotic, fungal, plant, mammalian, or human genomic polynucleotide sequence. In some embodiments, the guide RNA is 30-280 nucleotides in length. In some embodiments, the system further comprises a single- or double-stranded DNA repair template comprising from 5' to 3': a first homology arm comprising a sequence of at least 20 nucleotides 5' to the target deoxyribonucleic acid sequence, a synthetic DNA sequence of at least 10 nucleotides, and a second homology arm comprising a sequence of at least 20 nucleotides 3' to the target sequence. In some embodiments, the first or second homology arm comprises a sequence of at least 40 nucleotides. In some embodiments, the first and second homology arms are homologous to a genomic sequence of a eukaryote. In some embodiments, the single- or double-stranded DNA repair template comprises a transgene donor. In some embodiments, the system further comprises a DNA repair template comprising a double-stranded DNA segment flanked by one or two single-stranded DNA segments. In some embodiments, the single-stranded DNA segments are conjugated to the 5' ends of the double-stranded DNA segment. In some embodiments, the single stranded DNA segments are conjugated to the 3' ends of the double-stranded DNA segment. In some embodiments, the single-stranded DNA segments have a length from 4 to 10 nucleotide bases. In some embodiments, the single-stranded DNA segments have a nucleotide sequence complementary to a sequence within the spacer sequence. In some embodiments, the double-stranded DNA sequence comprises a barcode, an open reading frame, an enhancer, a promoter, a protein-coding sequence, a miRNA coding sequence, an RNA coding sequence, or a transgene. In some embodiments, the double-stranded DNA sequence is flanked by a nuclease cut site.

In some aspects, the present disclosure provides for an engineered single guide ribonucleic acid polynucleotide comprising: a) a DNA-targeting segment comprising a nucleotide sequence that is complementary to a target sequence in a target DNA molecule; and b) a protein-binding segment comprising two complementary stretches of nucleotides that hybridize to form a double-stranded RNA (dsRNA) duplex, wherein the two complementary stretches of nucleotides are covalently linked to one another with intervening nucleotides, and wherein the engineered guide ribonucleic acid polynucleotide is configured to form a complex with an endonuclease comprising a variant having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 674-675, 975-1002, 1260-1321, or a variant thereof. In some embodiments, the DNA-targeting segment is positioned 5' of both of the two complementary stretches of nucleotides. In some embodiments: a) the protein binding segment comprises a sequence having at least at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 199-200, 460-461, or 669-673; or b) the protein binding segment comprises a sequence having at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the non-variable nucleotides of any one of SEQ ID NOs: 201-203, 613-616, 677-686, 1003-1022, or 1231-1259. In some embodiments, a) the endonuclease comprises a sequence having at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 674-675, 975-1002, 1260-1321, or a variant thereof; and b) the guide RNA structure comprises a sequence having at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a class 2, type II sgRNA. In some embodiments, the endonuclease further comprises a base editor or a histone editor coupled to the endonuclease. In some embodiments, the base editor is an adenosine deaminase. In some embodiments, the adenosine deaminase comprises ADAR1 or ADAR2. In some embodiments, the base editor is a cytosine deaminase. In some embodiments, the cytosine deaminase comprises APOBEC1, APOBEC2, APOBEC3A, APOBEC3B, APOBEC3C, APOBEC3D, APOBEC3F, APOBEC3G, APOBEC3H, or APOBEC4.

In some aspects, the present disclosure provides for a deoxyribonucleic acid polynucleotide encoding any of the engineered guide ribonucleic acid polynucleotides described herein.

In some aspects, the present disclosure provides for a nucleic acid comprising an engineered nucleic acid sequence optimized for expression in an organism, wherein the nucleic acid encodes an endonuclease comprising a RuvC domain and an HNH domain, wherein the endonuclease is derived from an uncultivated microorganism, and wherein the endonuclease has a molecular weight of about 120 kDa or less, 100 kDa or less, 90 kDa or less, 60 kDa or less, or 30 kDa or less, and wherein the endonuclease comprises SEQ ID NO: 674-675, 975-1002, 1260-1321, or a variant thereof having at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity thereto. In some embodiments, the endonuclease further comprises a sequence encoding one or more nuclear localization sequences (NLSs) proximal to an N- or C-terminus of the endonuclease. In some embodiments, the NLS comprises a sequence selected from SEQ ID NOs: 205-220. In some embodiments, the organism is prokaryotic, bacterial, eukaryotic, fungal, plant, mammalian, rodent, or human. In some embodiments, the organism is prokaryotic or bacterial, and the organism is a different organism from an organism from which the endonuclease is derived. In some embodiments, the organism is not the uncultivated microorganism.

In some aspects, the present disclosure provides for a vector comprising a nucleic acid sequence encoding an RNA-guided endonuclease comprising a RuvC-I domain and an HNH domain, wherein the endonuclease is derived from an uncultivated microorganism, and wherein the endonuclease has a molecular weight of about 120 kDa or less, 100 kDa or less, 90 kDa or less, or 60 kDa or less, wherein the RNA-guided endonuclease is optionally archaeal, and wherein the RNA-guided endonuclease comprises SEQ ID NO: 674-675, 975-1002, 1260-1321, or a variant thereof having at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity thereto. In some embodiments, the endonuclease further comprises an arginine-rich region comprising an RRxRR motif (SEQ ID NO: 1361) or a domain with PF14239 homology. In some embodiments, the endonuclease further comprises a REC (recognition) domain. In some embodiments, the endonuclease further comprises a BH domain, a WED domain, and a target adjacent motif (TAM)-interacting (TI) domain. In some embodiments, the TI domain comprises a TI domain of any one of SEQ ID NO: 1-198, 221-459, 463-612, 617-668, 674-675, 975-1002, 1260-1321.

In some aspects, the present disclosure provides for a vector comprising any of the nucleic acids described herein. In some embodiments, the vector further comprises a nucleic acid encoding an engineered guide ribonucleic acid structure configured to form a complex with the endonuclease, the engineered guide ribonucleic acid structure comprising: a) a guide ribonucleic acid sequence configured to hybridize to a target deoxyribonucleic acid sequence; and b) a ribonucleic acid sequence configured to bind to the endonuclease. In some embodiments, vector is a plasmid, a minicircle, a CELiD, an adeno-associated virus (AAV) derived virion, or a lentivirus.

In some aspects, the present disclosure provides for a cell comprising any of the vectors described herein. In some embodiments, the cell is a bacterial, archaeal, fungal, eukaryotic, mammalian, or plant cell. In some embodiments, the cell is a bacterial cell.

In some aspects, the present disclosure provides for a method of manufacturing an endonuclease, comprising cultivating any of the cells described herein.

In some aspects, the present disclosure provides for a method for binding, cleaving, marking, or modifying a double-stranded deoxyribonucleic acid polynucleotide, comprising: (a) contacting the double-stranded deoxyribonucleic acid polynucleotide with an endonuclease in complex with an engineered guide ribonucleic acid structure configured to bind to the endonuclease and the double-stranded deoxyribonucleic acid polynucleotide; (b) wherein the double-stranded deoxyribonucleic acid polynucleotide comprises a target adjacent motif (TAM); wherein the endonuclease has a molecular weight of about 120 kDa or less, 100 kDa or less, 90 kDa or less, or 60 kDa or less. In some embodiments, the endonuclease cleaves the double-stranded deoxyribonucleic acid polynucleotide, wherein the TAM comprises any one of SEQ ID NOs: 1023-1044. In some embodiments, the endonuclease cleaves the double-stranded deoxyribonucleic acid polynucleotide 5-7 nucleotides, 5 nucleotides, 6 nucleotides, or 7 nucleotides from the TAM. In some embodiments, the endonuclease comprises a variant with at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1-198, 221-459, 463-612, 617-668, 674-675, 975-1002, 1260-1321.

In some aspects, the present disclosure provides for a method for binding, cleaving, marking, or modifying a double-stranded deoxyribonucleic acid polynucleotide, comprising: (a) contacting the double-stranded deoxyribonucleic acid polynucleotide with an RNA-guided archaeal endonuclease in complex with an engineered guide ribonucleic acid structure configured to bind to the endonuclease and the double-stranded deoxyribonucleic acid polynucleotide; (b) wherein the double-stranded deoxyribonucleic acid polynucleotide comprises a protospacer adjacent motif (PAM); and wherein the endonuclease comprises a variant with at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 674-675, 975-1002, 1260-1321. In some embodiments, the endonuclease cleaves the double-stranded deoxyribonucleic acid polynucleotide, wherein the PAM comprises NGG. In some embodiments, the endonuclease cleaves the double-stranded deoxyribonucleic acid polynucleotide 6-9 or 7 nucleotides from the PAM. In some embodiments, the endonuclease is not a Cas9 endonuclease, a Cas14 endonuclease, a Cas 12a endonuclease, a Cas 12b endonuclease, a Cas 12c endonuclease, a Cas12d endonuclease, a Cas12e endonuclease, a Cas13a endonuclease, a Cas13b endonuclease, a Cas13c endonuclease, or a Cas 13d endonuclease. In some embodiments, the endonuclease is derived from an uncultivated microorganism. In some embodiments, the double-stranded deoxyribonucleic acid polynucleotide is a prokaryotic, archaeal, bacterial, eukaryotic, plant, fungal, mammalian, rodent, or human double-stranded deoxyribonucleic acid polynucleotide. In some embodiments, the double-stranded deoxyribonucleic acid polynucleotide is a prokaryotic, archaeal, or bacterial double-stranded deoxyribonucleic acid polynucleotide from a species other than a species from which the endonuclease was derived.

In some aspects, the present disclosure provides for a method of modifying a target nucleic acid locus, the method comprising delivering to the target nucleic acid locus any of the engineered nuclease systems described herein, wherein the endonuclease is configured to form a complex with the engineered guide ribonucleic acid structure, and wherein the complex is configured such that upon binding of the complex to the target nucleic acid locus, the complex modifies the target nucleic locus. In some embodiments, the target nucleic acid locus comprises binding, nicking, cleaving, or marking the target nucleic acid locus. In some embodiments, the target nucleic acid locus comprises deoxyribonucleic acid (DNA) or ribonucleic acid (RNA). In some embodiments, the target nucleic acid comprises genomic eukaryotic DNA, archaeal DNA, viral DNA, or bacterial DNA. In some embodiments, the target nucleic acid comprises bacterial DNA wherein the bacterial DNA is derived from a bacterial or archaeal species different from a species from which the endonuclease was derived. In some embodiments, the target nucleic acid locus is in vitro. In some embodiments, the target nucleic acid locus is within a cell. In some embodiments, endonuclease and the engineered guide nucleic acid structure are encoded by separate nucleic acid molecules. In some embodiments, the cell is a prokaryotic cell, a bacterial cell, an archaeal cell, a eukaryotic cell, a fungal cell, a plant cell, an animal cell, a mammalian cell, a rodent cell, a primate cell, or a human cell. In some embodiments, the cell is derived from a species different from a species from which the endonuclease was derived. In some embodiments, delivering the engineered nuclease system to the target nucleic acid locus comprises delivering any of the nucleic acids described herein or any of the vectors described herein. In some embodiments, delivering the engineered nuclease system to the target nucleic acid locus comprises delivering a nucleic acid comprising an open reading frame encoding the endonuclease. In some embodiments, the nucleic acid comprises a promoter to which the open reading frame encoding the endonuclease is operably linked. In some embodiments, delivering the engineered nuclease system to the target nucleic acid locus comprises delivering a capped mRNA containing the open reading frame encoding the endonuclease. In some embodiments, delivering the engineered nuclease system to the target nucleic acid locus comprises delivering a translated polypeptide. In some embodiments, delivering the engineered nuclease system to the target nucleic acid locus comprises delivering a deoxyribonucleic acid (DNA) encoding the engineered guide ribonucleic acid structure operably linked to a ribonucleic acid (RNA) pol III promoter. In some embodiments, the endonuclease induces a single-stranded break or a double-stranded break at or proximal to the target locus. In some embodiments, the endonuclease induces a double stranded break proximal to the target locus 5' from a protospacer adjacent motif (PAM). In some embodiments, the endonuclease induces a double-stranded break 6-8 nucleotides or 7 nucleotides 5' from the PAM. In some embodiments, the engineered nuclease system induces a chemical modification of a nucleotide base within or proximal to the target locus. In some embodiments, the chemical modification is deamination of an adenosine or a cytosine nucleotide. In some embodiments, the endonuclease further comprises a base editor coupled to the endonuclease. In some embodiments, the base editor is an adenosine deaminase. In some embodiments, the adenosine deaminase comprises ADAR1 or ADAR2. In some embodiments, the base editor is a cytosine deaminase. In some embodiments, the cytosine deaminase comprises APOBEC1, APOBEC2, APOBEC3A, APOBEC3B, APOBEC3C, APOBEC3D, APOBEC3F, APOBEC3G, APOBEC3H, or APOBEC4.

In some aspects, the present disclosure provides for a method of disrupting a TRAC locus in a cell, comprising contacting to the cell a composition comprising: (a) an endonuclease having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1-198, 221-459, 463-612, 617-668, 674-675, 975-1002, 1260-1321, or a variant thereof, and (b) an engineered guide RNA, wherein the engineered guide RNA is configured to form a complex with the endonuclease and the engineered guide RNA comprises a spacer sequence configured to hybridize to a region of the locus, wherein the engineered guide RNA is configured to hybridize to any one of SEQ ID NOS: 1079-1082, 1145-1166, and 1169-1170. In some embodiments, the engineered guide RNA comprises a sequence having at least about at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1123-1144 or 1167-1168. In some embodiments, the engineered guide RNA comprises the modified nucleotides of any one of SEQ ID NOs: 1123-1144 or 1167-1168. In some embodiments, the engineered guide RNA comprises a sequence having at least about at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence complementary to any one of SEQ ID NOs: 1145-1166 or 1169-1170. In some embodiments, the endonuclease has at least about 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 582, 988, 990, 993, 996, 999, or 1002. In some embodiments, the region is 5' to a protospacer adjacent motif (PAM) comprising any one of SEQ ID NOs: SEQ ID NOs: 1023-1044.

In some aspects, the present disclosure provides for an isolated RNA molecule comprising a sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to any one of SEQ ID NOs: 1123-1144 or 1167-1168. In some embodiments, the isolated RNA molecule comprises the pattern of chemical modifications recited in any one of SEQ ID NOs: 1123-1144 or 1167-1168.

In some aspects, the present disclosure provides for use of any of the isolated RNA molecules described herein for modifying a TRAC locus of a cell.

In some aspects, the present disclosure provides for a method of disrupting an AAVS1 locus in a cell, comprising contacting to the cell a composition comprising: (a) an endonuclease having at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1-198, 221-459, 463-612, 617-668, 674-675, 975-1002, 1260-1321, or a variant thereof, and (b) an engineered guide RNA, wherein the engineered guide RNA is configured to form a complex with the endonuclease and the engineered guide RNA comprises a spacer sequence configured to hybridize to a region of the locus, wherein the engineered guide RNA is configured to hybridize to any one of SEQ ID NOs: 1105-1122. In some embodiments, the engineered guide RNA comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1087-1104. In some embodiments, the engineered guide RNA comprises the modified nucleotides of any one of SEQ ID NOs: 1087-1104. In some embodiments, the engineered guide RNA comprises a sequence having at least about 80% identity to a sequence complementary to any one of SEQ ID NOs: 1105-1122. In some embodiments, the endonuclease has at least about 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 582, 988, 990, 993, 996, 999, or 1002. In some embodiments, the endonuclease has at least about 75%, 80%, or 90% sequence identity to SEQ ID NO: 582. In some embodiments, the region is 5' to a protospacer adjacent motif (PAM) comprising any one of SEQ ID NOs: 1023-1044.

In some aspects, the present disclosure provides for an isolated RNA molecule comprising a sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to any one of SEQ ID NOs: 1087-1104. In some embodiments, the RNA molecule comprises the pattern of chemical modifications recited in any one of SEQ ID NOs: 1087-1104.

In some aspects, the present disclosure provides for an engineered nuclease system, comprising: (a) an endonuclease comprising a RuvC domain and an HNH domain; wherein the endonuclease comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 25-27, 30, 126, 582, 594, 118, 128, 396, 530, 618, 620, 621, 653, 656, 657, 656, or a variant thereof, and (b) an engineered guide ribonucleic acid structure configured to form a complex with the endonuclease comprising: (i) a guide ribonucleic acid sequence configured to hybridize to a target deoxyribonucleic acid sequence; and (ii) a ribonucleic acid sequence configured to bind to the endonuclease; wherein the ribonucleic acid sequence configured to bind the endonuclease comprises a sequence with at least at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the non-degenerate nucleotides of any one of SEQ ID NOs: 677-681, 686, 1006-1008, 1011-1014, or 1231-1259.

In some embodiments, the engineered guide ribonucleic acid structure comprises a single ribonucleic acid polynucleotide comprising the guide ribonucleic acid sequence and the ribonucleic acid sequence configured to bind the endonuclease. In some embodiments, the guide ribonucleic acid sequence is complementary to a prokaryotic, bacterial, archaeal, eukaryotic, fungal, plant, mammalian, or human genomic sequence. In some embodiments, the endonuclease comprises one or more nuclear localization sequences (NLSs) proximal to an N- or C-terminus of the endonuclease. In some embodiments, the NLS comprises a sequence selected from any one SEQ ID NOs: 205-220. In some embodiments, the system further comprises a single- or double-stranded DNA repair template comprising from 5' to 3': a first homology arm comprising a sequence of at least 20 nucleotides 5' to the target deoxyribonucleic acid sequence, a synthetic DNA sequence of at least 10 nucleotides, and a second homology arm comprising a sequence of at least 20 nucleotides 3' to the target sequence. In some embodiments, the endonuclease and the ribonucleic acid sequence configured to bind the endonuclease are derived from distinct species within a same phylum. In some embodiments, the endonuclease is not a Cas9 endonuclease, a Cas14 endonuclease, a Cas12a endonuclease, a Cas12b endonuclease, a Cas 12c endonuclease, a Cas12d endonuclease, a Cas12e endonuclease, a Cas13a endonuclease, a Cas13b endonuclease, a Cas13c endonuclease, or a Cas 13d endonuclease. In some embodiments, the endonuclease does not exhibit collateral ssDNA cleavage activity.

In some aspects, the present disclosure provides for an engineered nuclease system, comprising: (a) an endonuclease comprising a RuvC domain and an HNH domain; wherein the endonuclease comprises a sequence having at least 80% sequence identity to any one of the endonuclease effectors sequences described herein, or a variant thereof, and (b) an engineered guide ribonucleic acid structure configured to form a complex with the endonuclease comprising: (i) a guide ribonucleic acid sequence configured to hybridize to a target deoxyribonucleic acid sequence; and (ii) a ribonucleic acid sequence configured to bind to the endonuclease; wherein the endonuclease comprises a sequence having at least 80% sequence identity to non-degenerate nucleotides of any of the sgRNA sequences described herein, or a variant thereof.

In some aspects, the present disclosure provides for an isolated RNA molecule comprising a sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to non-degenerate nucleotides of any of the sgRNA sequences described herein.

In some aspects, the present disclosure provides for a nucleic acid comprising any of the sequences described herein.

In some aspects, the present disclosure provides for a vector comprising any of the nucleic acid sequences described herein.

In some aspects, the present disclosure provides for an engineered nuclease system, comprising: (a) an endonuclease comprising a RuvC domain and an HNH domain, wherein said endonuclease is derived from an uncultivated microorganism; and (b) an engineered guide ribonucleic acid structure configured to form a complex with said endonuclease comprising: (i) a guide ribonucleic acid sequence configured to hybridize to a target deoxyribonucleic acid sequence; and (ii) a tracr ribonucleic acid sequence configured to bind to said endonuclease; wherein said endonuclease has a molecular weight of about 96 kDa or less. In some embodiments, said endonuclease is an archaeal endonuclease. In some embodiments, said endonuclease is a Class 2, Type II Cas endonuclease. In some embodiments, said endonuclease comprises a sequence with at least 70%, at least 75%, at least 80% or at least 90% sequence identity to any one of SEQ ID NOs: 1-198, 221-459, 463-612, 617-668, 674-675, 975-1002, 1260-1321, or a variant thereof. In some embodiments, said endonuclease further comprises an arginine-rich region comprising an RRxRR motif (SEQ ID NO: 1361) or a domain with PF14239 homology. In some embodiments, said arginine rich region or said domain with PF14239 homology has at least 85%, at least 90%, or at least 95% identity to an arginine rich region or a domain with PF14239 homology of any one of SEQ ID NOs: 1-198, 221-459, 463-612, 617-668, 674-675, 975-1002, 1260-1321, or a variant thereof. In some embodiments, said endonuclease further comprises a REC (recognition) domain. In some embodiments, said REC domain has at least 85%, at least 90%, or at least 95% identity to a REC domain of any one of SEQ ID NOs: 1-198, 221-459, 463-612, 617-668, 674-675, 975-1002, 1260-1321, or a variant thereof. In some embodiments, said endonuclease further comprises a BH (bridge helix) domain, a WED (wedge) domain, and a PI (PAM interacting) domain. In some embodiments, said BH domain, said WED domain, or said PI domain has at least 85%, at least 90%, or at least 95% identity to a BH domain, a WED domain, or a PI domain of any one of SEQ ID NOs: 1-198, 221-459, 463-612, 617-668, 674-675, 975-1002, 1260-1321, or a variant thereof.

In some aspects, the present disclosure provides for an engineered nuclease system comprising: (a) an endonuclease comprising a RuvC-I domain and an HNH domain; and (b) an engineered guide ribonucleic acid structure configured to form a complex with said endonuclease comprising: (i) a guide ribonucleic acid sequence configured to hybridize to a target deoxyribonucleic acid sequence; and (ii) a ribonucleic acid sequence configured to bind to said endonuclease, wherein said endonuclease comprises a sequence with at least 70%, at least 75%, at least 80% or at least 90% sequence identity to any one of SEQ ID NOs: 1-198, 221-459, 463-612, 617-668, 674-675, 975-1002, 1260-1321, or a variant thereof. In some embodiments, said endonuclease is an archaeal endonuclease. In some embodiments, said endonuclease is a class 2, type II Cas endonuclease. In some embodiments, said endonuclease further comprises an arginine-rich region comprising an RRxRR motif (SEQ ID NO: 1361) or a domain with PF14239 homology. In some embodiments, said arginine rich region or said domain with PF14239 homology has at least 85%, at least 90%, or at least 95% identity to an arginine rich region of any one of SEQ ID NOs: 1-198, 221-459, 463-612, 617-668, 674-675, 975-1002, 1260-1321, or a variant thereof. In some embodiments, said endonuclease further comprises a REC (recognition) domain. In some embodiments, said REC domain having at least 85%, at least 90%, or at least 95% identity to a REC domain of any one of SEQ ID NOs: 1-198, 221-459, 463-612, 617-668, 674-675, 975- 1002, 1260-1321, or a variant thereof. In some embodiments, said endonuclease further comprises a BH domain, a WED domain, and a PI domain. In some embodiments, said BH domain, said WED domain, or said PI domain has at least 85%, at least 90%, or at least 95% identity to a BH domain, a WED domain, or a PI domain of any one of SEQ ID NOs: 1-198, 221-459, 463-612, 617-668, 674-675, 975-1002, 1260-1321, or a variant thereof. In some embodiments, said endonuclease is derived from an uncultivated microorganism. In some embodiments, said ribonucleic acid sequence configured to bind said endonuclease comprises a sequence with at least 80% sequence identity to any one of SEQ ID NOs: 199-200, 460-461, or 669-673, or a sequence with at least 80% sequence identity to the non-degenerate nucleotides of any one of SEQ ID NOs: 201-203, 613-616, 677-686, 1003-1022, or 1231-1259. In some embodiments, said guide nucleic acid structure comprises a sequence with at least 80% identity to the non-degenerate nucleotides of any one of SEQ ID NOs: 201-203, 613-616, 677-686, 1003-1022, or 1231-1259.

In some aspects, the present disclosure provides for an engineered nuclease system comprising: (a) an engineered guide ribonucleic acid structure comprising: (i) a guide ribonucleic acid sequence configured to hybridize to a target deoxyribonucleic acid sequence; and (ii) a ribonucleic acid sequence configured to bind to an endonuclease, wherein said ribonucleic acid sequence comprises a sequence with at least 80% sequence identity to any one of SEQ ID NOs: 199-200, 460-461, or 669-673, or a sequence with at least 80% sequence identity to nonvariable nucleotides of any one of SEQ ID NOs: 201-203, 613-616, 677-686, 1003-1022, or 1231-1259; and (b) an RNA-guided endonuclease configured to bind to said engineered guide ribonucleic acid. In some embodiments, said RNA-guided endonuclease is an archaeal endonuclease. In some embodiments, said endonuclease has a molecular weight of about 120 kDa or less, 100 kDa or less, 90 kDa or less, or 60 kDa or less. In some embodiments, said engineered guide ribonucleic acid structure comprises at least two ribonucleic acid polynucleotides. In some embodiments, said engineered guide ribonucleic acid structure comprises a single ribonucleic acid polynucleotide comprising said guide ribonucleic acid sequence and said tracr ribonucleic acid sequence. In some embodiments, said guide ribonucleic acid sequence is complementary to a prokaryotic, bacterial, archaeal, eukaryotic, fungal, plant, mammalian, or human genomic sequence. In some embodiments, said guide ribonucleic acid sequence is 15-24 nucleotides in length. In some embodiments, said endonuclease comprises one or more nuclear localization sequences (NLSs) proximal to an N- or C-terminus of said endonuclease. In some embodiments, said NLS comprises a sequence selected from SEQ ID NOs: 205-220. In some embodiments, the system further comprises a single- or double-stranded DNA repair template comprising from 5' to 3': a first homology arm comprising a sequence of at least 20 nucleotides 5' to said target deoxyribonucleic acid sequence, a synthetic DNA sequence of at least 10 nucleotides, and a second homology arm comprising a sequence of at least 20 nucleotides 3' to said target sequence. In some embodiments, said first or second homology arm comprises a sequence of at least 40, 80, 120, 150, 200, 300, 500, or 1,000 nucleotides. In some embodiments, said system further comprises a source of $Mg^{2+}$. In some embodiments, said endonuclease and said tracr ribonucleic acid sequence are derived from distinct bacterial species within a same phylum. In some embodiments, said endonuclease comprises a sequence with at least 70% sequence identity to any one of SEQ ID NOs:

2-24 and said guide RNA structure comprises an RNA sequence predicted to comprise a hairpin comprising a stem and a loop, wherein said stem comprises at least 12 pairs of ribonucleotides. In some embodiments, said guide RNA structure further comprises a second stem and a second loop, wherein the second stem comprises at least 5 pairs of ribonucleotides. In some embodiments, said guide RNA structure further comprises an RNA structure comprising at least two hairpins. In some embodiments, said endonuclease comprises a sequence with at least 70% sequence identity to SEQ ID NO: 1 and said guide RNA structure comprises an RNA sequence predicted to comprise at least four hairpins comprising a stem and a loop. In some embodiments, a) said endonuclease comprises a sequence at least 70%, at least 80%, or at least 90% identical to any one of SEQ ID NOs: 1, 2, 10, 17, or 613-616; and b) said guide RNA structure comprises a sequence at least 70%, at least 80%, or at least 90% identical to any one of SEQ ID NOs: 199-200 or 669-673 or the nonvariable nucleotides of any one of SEQ ID NOs: 201-203, 613-616. In some embodiments, a) said endonuclease comprises a sequence at least 70%, at least 80%, or at least 90% identical to any one of SEQ ID NOs: 1-24, 462-488, or 501-612; and b) said guide RNA structure comprises a sequence at least 70%, at least 80%, or at least 90% identical to any one of SEQ ID NOs: 199-200 or 669-673 or the nonvariable nucleotides of any one of SEQ ID NOS: 201-203 or 613-616. In some embodiments, a) said endonuclease comprises a sequence at least 70%, at least 80%, or at least 90% identical to any one of SEQ ID NOs: 2, 10, or 17; and b) said guide RNA structure comprises a sequence at least 70%, at least 80%, or at least 90% identical to the nonvariable nucleotides of any one of SEQ ID NOs: 202-203 or 613-614. In some embodiments: a) said endonuclease comprises a sequence at least 70%, at least 80%, or at least 90% identical to any one of SEQ ID NOs: 25-198, 221-459, or 489-580; and b) said guide RNA structure comprises a sequence at least 70%, at least 80%, or at least 90% identical to a class 2, type II sgRNA or tracr sequence. In some embodiments, said sequence identity is determined by a BLASTP, CLUSTALW, MUSCLE, MAFFT, or CLUSTALW with parameters of the Smith-Waterman homology search algorithm. In some embodiments, said sequence identity is determined by said BLASTP homology search algorithm using parameters of a wordlength (W) of 3, an expectation (E) of 10, and a BLOSUM62 scoring matrix setting gap costs at existence of 11, extension of 1, and using a conditional compositional score matrix adjustment. In some embodiments, said endonuclease is not a Cas9 endonuclease, a Cas14 endonuclease, a Cas 12a endonuclease, a Cas12b endonuclease, a Cas 12c endonuclease, a Cas12d endonuclease, a Cas 12e endonuclease, a Cas13a endonuclease, a Cas13b endonuclease, a Cas13c endonuclease, or a Cas 13d endonuclease. In some embodiments, said endonuclease has less than 80% identity to a Cas9 endonuclease.

In some aspects, the present disclosure provides for an engineered single guide ribonucleic acid polynucleotide comprising: a) a DNA-targeting segment comprising a nucleotide sequence that is complementary to a target sequence in a target DNA molecule; and b) a protein-binding segment comprising two complementary stretches of nucleotides that hybridize to form a double-stranded RNA (dsRNA) duplex, wherein said two complementary stretches of nucleotides are covalently linked to one another with intervening nucleotides, and wherein said engineered guide ribonucleic acid polynucleotide is configured to form a complex with an endonuclease comprising a variant having at least 75% sequence identity to any one of SEQ ID NOs: 1-198, 221-459, 463-612, 617-668, 674-675, 975-1002, 1260-1321, or a variant thereof. In some embodiments, said DNA-targeting segment is positioned 5' of both of said two complementary stretches of nucleotides. In some embodiments, a) said protein binding segment comprises a sequence having at least at least 70%, at least 80%, or at least 90% identical to any one of SEQ ID NOs: 199-200 or 669-673; b) said protein binding segment comprises a sequence having at least 70%, at least 80%, or at least 90% identical to the nonvariable nucleotides of any one of SEQ ID NOs: 201-203 or 613-616. In some embodiments, a) said endonuclease comprises a sequence at least 70%, at least 80%, or at least 90% identical to any one of SEQ ID NOs: 2, 10, or 17; and b) said guide RNA structure comprises a sequence at least 70%, at least 80%, or at least 90% identical to at least one of SEQ ID NO: 200 or the nonvariable nucleotides of SEQ ID NO: 202-203 or 613-614. In some embodiments, a) said endonuclease comprises a sequence at least 70%, at least 80%, or at least 90% identical to any one of SEQ ID NOs: 25-198, 221-459, or 489-580; and b) said guide RNA structure comprises a sequence at least 70%, at least 80%, or at least 90% identical to a class 2, type II sgRNA. In some embodiments, said endonuclease further comprises a base editor or a histone editor coupled to said endonuclease. In some embodiments, said base editor is an adenosine deaminase. In some embodiments, said adenosine deaminase comprises ADAR1 or ADAR2. In some embodiments, said base editor is a cytosine deaminase. In some embodiments, said cytosine deaminase comprises APOBEC1, APOBEC2, APOBEC3A, APOBEC3B, APOBEC3C, APOBEC3D, APOBEC3F, APOBEC3G, APOBEC3H, or APOBEC4.

In some aspects, the present disclosure provides for a deoxyribonucleic acid polynucleotide encoding any of the engineered guide ribonucleic acid polynucleotides described herein.

In some aspects, the present disclosure provides for a nucleic acid comprising an engineered nucleic acid sequence optimized for expression in an organism, wherein said nucleic acid encodes a class 2, type II Cas endonuclease comprising a RuvC domain and an HNH domain, wherein said endonuclease is derived from an uncultivated microorganism, and wherein said endonuclease has a molecular weight of about 120 kDa or less, 100 kDa or less, 90 kDa or less, 60 kDa or less, or 30 kDa or less. In some embodiments, said endonuclease comprises SEQ ID NOs: 1-198, 221-459, 463-612, 617-668, 674-675, 975-1002, 1260-1321, or a variant thereof having at least 70% sequence identity thereto. In some embodiments, said endonuclease further comprises a sequence encoding one or more nuclear localization sequences (NLSs) proximal to an N- or C-terminus of said endonuclease. In some embodiments, said NLS comprises a sequence selected from SEQ ID NOs: 205-220. In some embodiments, said organism is prokaryotic, bacterial, eukaryotic, fungal, plant, mammalian, rodent, or human. In some embodiments, said organism is prokaryotic or bacterial, and said organism is a different organism from an organism from which said endonuclease is derived. In some embodiments, said organism is not said uncultivated microorganism.

In some aspects, the present disclosure provides for a vector comprising a nucleic acid sequence encoding an RNA-guided endonuclease comprising a RuvC-I domain and an HNH domain, wherein said endonuclease is derived from an uncultivated microorganism, and wherein said endonuclease has a molecular weight of about 120 kDa or less, 100 kDa or less, 90 kDa or less, or 60 kDa or less, wherein the RNA-guided endonuclease is optionally archaeal. In some embodiments, said endonuclease further comprises an arginine-rich region comprising an RRxRR motif (SEQ ID NO: 1361) or a domain with PF14239 homology. In some embodiments, said endonuclease further comprises a REC (recognition) domain. In some embodiments, said endonuclease further comprises a BH domain, a WED domain, and a PI domain.

In some aspects, the present disclosure provides for a vector comprising any of the nucleic acids described herein. In some embodiments, the vector further comprising a nucleic acid encoding an engineered guide ribonucleic acid structure configured to form a complex with said endonuclease, said engineered guide ribonucleic acid structure comprising: a) a guide ribonucleic acid sequence configured to hybridize to a target deoxyribonucleic acid sequence; and b) a tracr ribonucleic acid sequence configured to binding to said endonuclease. In some embodiments, the vector is a plasmid, a minicircle, a CELiD, an adeno-associated virus (AAV) derived virion, or a lentivirus.

In some aspects, the present disclosure provides for a cell comprising any of the vectors described herein. In some embodiments, said cell is a bacterial, archaeal, fungal, eukaryotic, mammalian, or plant cell. In some embodiments, said cell is a bacterial cell.

In some aspects, the present disclosure provides for a method of manufacturing an endonuclease, comprising cultivating any of the cells described herein.

In some aspects, the present disclosure provides for a method for binding, cleaving, marking, or modifying a double-stranded deoxyribonucleic acid polynucleotide, comprising: (a) contacting said double-stranded deoxyribonucleic acid polynucleotide with a class 2, type II Cas endonuclease in complex with an engineered guide ribonucleic acid structure configured to bind to said endonuclease and said double-stranded deoxyribonucleic acid polynucleotide; (b) wherein said double-stranded deoxyribonucleic acid polynucleotide comprises a protospacer adjacent motif (PAM); wherein said endonuclease has a molecular weight of about 120 kDa or less, 100 kDa or less, 90 kDa or less, or 60 kDa or less. In some embodiments, said endonuclease cleaves said double-stranded deoxyribonucleic acid polynucleotide, wherein said PAM comprises NGG. In some embodiments, said endonuclease cleaves said double-stranded deoxyribonucleic acid polynucleotide 6-8 nucleotides or 7 nucleotides from said PAM. In some embodiments, said endonuclease comprises a variant with at least 70%, at least 75%, at least 80% or at least 90% sequence identity to any one of SEQ ID NOs: 1-198, 221-459, 463-612, 617-668, 674-675, 975-1002, 1260-1321, or a variant thereof.

In some aspects, the present disclosure provides for a method for binding, cleaving, marking, or modifying a double-stranded deoxyribonucleic acid polynucleotide, comprising: (a) contacting said double-stranded deoxyribonucleic acid polynucleotide with an RNA-guided archaeal endonuclease in complex with an engineered guide ribonucleic acid structure configured to bind to said endonuclease and said double-stranded deoxyribonucleic acid polynucleotide; wherein said double-stranded deoxyribonucleic acid polynucleotide comprises a protospacer adjacent motif (PAM); and wherein said endonuclease comprises a variant with at least 70%, at least 75%, at least 80% or at least 90% sequence identity to any one of SEQ ID NOs: 1-198, 221-459, 463-612, 617-668, 674-675, 975-1002, 1260-1321, or a variant thereof. In some embodiments, said endonuclease cleaves said double-stranded deoxyribonucleic acid polynucleotide, wherein said PAM comprises NGG. In some embodiments, said endonuclease cleaves said double-stranded deoxyribonucleic acid polynucleotide 6-8 or 7 nucleotides from said PAM. In some embodiments, said class 2, type II Cas endonuclease is not a Cas9 endonuclease, a Cas 14 endonuclease, a Cas 12a endonuclease, a Cas 12b endonuclease, a Cas 12c endonuclease, a Cas12d endonuclease, a Cas12e endonuclease, a Cas13a endonuclease, a Cas13b endonuclease, a Cas13c endonuclease, or a Cas 13d endonuclease. In some embodiments, said class 2, type II Cas endonuclease is derived from an uncultivated microorganism. In some embodiments, said double-stranded deoxyribonucleic acid polynucleotide is a prokaryotic, archaeal, bacterial, eukaryotic, plant, fungal, mammalian, rodent, or human double-stranded deoxyribonucleic acid polynucleotide. In some embodiments, said double-stranded deoxyribonucleic acid polynucleotide is a prokaryotic, archaeal, or bacterial double-stranded deoxyribonucleic acid polynucleotide from a species other than a species from which said endonuclease was derived.

In some aspects, the present disclosure provides for a method of modifying a target nucleic acid locus, said method comprising delivering to said target nucleic acid locus any of the engineered nuclease systems described herein, wherein said endonuclease is configured to form a complex with said engineered guide ribonucleic acid structure, and wherein said complex is configured such that upon binding of said complex to said target nucleic acid locus, said complex modifies said target nucleic locus. In some embodiments, modifying said target nucleic acid locus comprises binding, nicking, cleaving, or marking said target nucleic acid locus. In some embodiments, said target nucleic acid locus comprises deoxyribonucleic acid (DNA) or ribonucleic acid (RNA). In some embodiments, said target nucleic acid comprises genomic eukaryotic DNA, archaeal DNA, viral DNA, or bacterial DNA. In some embodiments, said target nucleic acid comprises bacterial DNA wherein said bacterial DNA is derived from a bacterial or archaeal species different from a species from which said endonuclease was derived. In some embodiments, said target nucleic acid locus is in vitro. In some embodiments, said target nucleic acid locus is within a cell. In some embodiments, said endonuclease and said engineered guide nucleic acid structure are encoded by separate nucleic acid molecules. In some embodiments, said cell is a prokaryotic cell, a bacterial cell, an archaeal cell, a eukaryotic cell, a fungal cell, a plant cell, an animal cell, a mammalian cell, a rodent cell, a primate cell, or a human cell. In some embodiments, said cell is derived from a species different from a species from which said endonuclease was derived. In some embodiments, delivering said engineered nuclease system to said target nucleic acid locus comprises delivering any of the nucleic acids described herein or any of the vectors described herein. In some embodiments, delivering said engineered nuclease system to said target nucleic acid locus comprises delivering a nucleic acid comprising an open reading frame encoding said endonuclease. In some embodiments, said nucleic acid comprises a promoter to which said open reading frame encoding said endonuclease is operably linked. In some embodiments, delivering said engineered nuclease system to said target nucleic acid locus comprises delivering a capped mRNA containing said open reading frame encoding said endonuclease. In some embodiments, delivering said engineered nuclease system to said target nucleic acid locus comprises delivering a translated polypeptide. In some embodiments, delivering said engineered nuclease system to said target nucleic acid locus comprises delivering a deoxyribonucleic acid (DNA) encoding said engineered guide ribonucleic acid structure operably linked to a ribonucleic acid (RNA) pol III promoter. In some embodiments, said endonuclease induces a single-stranded break or a double-stranded break at or proximal to said target locus. In some embodiments, said endonuclease induces a double stranded break proximal to said target locus 5' from a protospacer adjacent motif (PAM). In some embodiments, said endonuclease induces a double-stranded break 6-8 nucleotides or 7 nucleotides 5' from said PAM. In some embodiments, said engineered nuclease system induces a chemical modification of a nucleotide base within or proximal to said target locus or a chemical modification of a histone within or proximal to said target locus. In some embodiments, said chemical modification is deamination of an adenosine or a cytosine nucleotide. In some embodiments, said endonuclease further comprises a base editor coupled to said endonuclease. In some embodiments, said base editor is an adenosine deaminase. In some embodiments, said adenosine deaminase comprises ADAR1 or ADAR2. In some embodiments, said base editor is a cytosine deaminase. In some embodiments, said cytosine deaminase comprises APOBEC1, APOBEC2, APOBEC3A, APOBEC3B, APOBEC3C, APOBEC3D, APOBEC3F, APOBEC3G, APOBEC3H, or APOBEC4.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 1A-FIG. 1B depicts a dendrogram showing homology relationships of CRISPR/Cas loci of different classes and types. Shown are SMART I and II Cas enzyme classes described herein relative to Class 2, Type II-A, II-B, and II-C Cas systems, demonstrating that these systems group into separate classes than II-A, II-B, and II-C. (FIG. 1A) shows a SMART phylogenetic tree in context of Cas9 reference sequences, where SMART effectors are distantly clustered away from Cas9 reference sequences (Type II-A, II-B, and II-C); (FIG. 1B) shows a SMART phylogenetic tree illustrating subgroups of SMART enzymes.

(FIG. 3A) genomic context of the SMART I MG33-1 nuclease and CRISPR loci encoded upstream from a SMART II nuclease MG35-236, showing downstream from the SMART II a predicted insertion sequence carrying transposases TnpA and TnpB; (FIG. 3B): genomic context of the SMART I nuclease MG34-1, where environmental expression sequencing reads are shown aligned under the CRISPR array and the predicted tracrRNA, and the transcriptomic coverage for the regions is illustrated above the contig sequence; (FIG. 3C) genomic context of the SMART I nuclease MG34-16, wherein environmental expression sequencing reads are shown aligned under the CRISPR array and the predicted tracrRNA, and the transcriptomic coverage for the regions is illustrated above the contig sequence; and (FIG. 3D) a genomic fragment targeted by spacer 7 from the MG34-16 CRISPR array in (FIG. 3D), where the genomic fragment was identified as being derived from phage based on virus-specific gene annotations terminase and portal; the inset shows the location of the MG34-16 spacer 7 targeting the C-terminus of a viral gene of unknown function—the putative NGG PAM for MG34-16 is highlighted by a grey box downstream from the spacer match. Figure discloses SEQ ID NO: 1322.

(FIG. 4A) an alignment of the endonuclease region containing the RuvC-I and bridge helix domains; (FIG. 4B) an alignment of the region containing the RuvC-III domain; and (FIG. 4C) an alignment of the region containing the RuvC-II and HNH domains FIG. 5A -FIG. 5B depicts an example domain organization for SMART I endonucleases, using MG34-1 as an example. Shown are (FIG. 5A) a diagram showing the predicted domain architecture of SMART I nucleases comprising three RuvC domains, a bridge helix ("BH"), a domain with homology to a Pfam PF14239 which interrupts a recognition domain ("REC"), an HNH endonuclease domain ("HNH"), a wedge domain ("WED"), and a PAM interacting domain (PI); and (FIG. 5B) a multiple sequence alignment overview of two SMART I nucleases relative to reference Cas9 nuclease sequences, wherein RuvC and HNH catalytic residues are shown as black bars above each sequence, regions that align in 3D space with the crystal structure of SaCas are represented by rounded boxes, and dashed lines represent regions with poor or no alignment in 3D space between the 3D structure prediction of the SMART and SaCas9. Figure discloses "RRXRR" motif as SEQ ID NO: 1361.

FIG. 6A-FIG. 6B depicts an example domain organization for SMART II endonucleases, using MG35 family enzymes (MG35-3, MG35-4) as an example. Shown are (FIG. 6A) a diagram showing the predicted domain architecture of SMART II nucleases comprising three RuvC domains, a domain with homology to a Pfam PF14239, an HNH endonuclease domain, an unknown domain, and a recognition domain (REC); and (FIG. 6B) a multiple sequence alignment overview of two SMART II nucleases relative to reference Cas9 nuclease sequences, where RuvC and HNH catalytic residues are shown as black bars above each sequence, regions that align in 3D space with the crystal structure of SaCas are represented by rounded boxes, and residues identified from 3D structure prediction which may be involved in recognizing a guide/target/PAM sequence are represented by dark grey boxes above the MG35-419 sequence (within the RRXRR ("RRXRR" motif is SEQ ID NO: 1361) and REC domains).

(FIG. 7B) a dot plot of length of individual SMART I domains of enzymes described herein.

FIG. 8A-FIG. 8B illustrates count distribution of various SMART-specific motifs versus motifs predicted in Cas9 nuclease sequences showing that these motifs occur more commonly in SMART enzymes; motifs were predicted on 803 reference Cas9 sequences (Type II-A, II-B, and II-C), 84 SMART I sequences, and 471 SMART II sequences. Shown are (FIG. 8A) a box plot of count frequency of Zn-binding ribbon motifs ($CX_{[2-4]}C$ and $CX_{[2-4]}H$) in various types of class 2 Cas enzymes; and (B) a histogram of count frequency of RRXRR motifs (SEQ ID NO: 1361) in various types of class 2 Cas enzymes. In (FIG. 8A) and (FIG. 8B) lines track the mean count value, while outliers are represented by dots.

FIG. 9A-FIG. 9D illustrates predicted guide RNA structures of designed single-guide RNAs (sgRNAs) for cleavage activity with SMART I endonucleases. Shown are (FIG. 9A) MG34-1 sgRNA 1 (SEQ ID NO: 1323); (FIG. 9B) MG34-1 sgRNA 2 (SEQ ID NO: 1324); (FIG. 9C) MG34-9 sgRNA 1 (SEQ ID NO: 1325), and (FIG. 9D) MG34-16 sgRNA 1 (SEQ ID NO: 1326).

FIG. 10A-FIG. 10B depicts cleavage characterization of SMART I nucleases as described in Example 1. (FIG. 10A) shows an Agilent TapeStation gel of the ligation products of a cleavage assay for MG34-1 with two sgRNA designs vs. the negative control. Lane L3: ladder. Lane A4: Apo, no sgRNA. Lanes B4 and C4: MG34-1 sgRNAs tested (sg1: SEQ ID No. 612, sg2: 613). Cleavage product bands are labeled with arrows. Lanes G3 and H3: greyed out, not relevant to this experiment. (FIG. 10B) shows a PCR gel of the ligation products show activity of MG34-1, 34-9 and 34-16. Lane 1: ladder. Lanes 2-7: sgRNA designs with six spacer lengths for MG34-1. Lanes 8 and 9: sgRNA design for 34-9 and 34-16, respectively. Arrows indicate cleavage confirmation bands.

FIG. 11A-FIG. 11C illustrates sequence cutting preference for MG34 nucleases. (FIG. 11A) shows a SeqLogo representation of a consensus PAM sequence (NGGN) for MG34-1 with sgRNA 1 (top, SEQ ID NO: 612) and sgRNA 2 (bottom, SEQ ID NO: 613). (FIG. 11B) shows a histogram showing the location of the cut site for MG34-1, demonstrating that MG34-1 prefers to cleave at about position 7 from the PAM. (FIG. 11C) shows a sanger sequencing chromatogram shows a preferred NGG PAM for MG34-9 (highlighted with a box). The arrow indicates the cut site at position 7 from the PAM. Figure discloses SEQ ID NOs: 1327-1328, respectively.

FIG. 12A-FIG. 12C illustrates the results of plasmid targeting experiments in E. coli for MG 34-1. (FIG. 12A) shows replica plating of E. coli strains demonstrating plasmid cutting; E. coli expressing MG34-1 and a sgRNA were transformed with a kanamycin resistance plasmid containing a target for the sgRNA (+sp). Plate quadrants that show growth impairment (+sp) vs. the negative control (without the target and PAM (−sp)) indicate successful targeting and cleavage by the enzyme. The experiment was replicated twice and performed in triplicate. (FIG. 12B) Shows graphs of colony forming unit (cfu) measurements from the replica plating experiments in A showing growth repression in the target condition (+sp) vs. the non-target control (−sp), demonstrating the plasmid was cut. (FIG. 12C) shows barplots of colony forming unit (cfu) measurements (in log-scale) showing E. coli growth repression in the target condition (white bars) vs. the non-target controls (green bars). Plasmid interference assays for each nuclease were done in triplicate along with the SpCas9 positive control.

(FIG. 13A) Shows the genomic context of the SMART II MG35-419 effector and CRISPR loci encoded in the vicinity. (FIG. 13B) Shows the genomic context of the SMART II effector MG35-3 showing a transcribed 5' UTR.

FIG. 16A depicts the genomic context of the SMART II MG35-419 effector. Figure discloses "RRXRR" motif as SEQ ID NO: 1361. FIG. 16B depicts the genomic context of the SMART II MG35-102 effector. Figure discloses "RRXRR" motif as SEQ ID NO: 1361.

FIG. 17A depicts the genomic context of the MG34-420 effector. The effector is represented by a dark arrow in the reverse orientation, predicted PFAM domains are represented by rectangles below arrows, and intergenic regions possibly encoding guide RNAs are annotated as "IG" on the black line. A CRISPR-like repetitive region is present in the contig. Figure discloses "RRXRR" motif as SEQ ID NO: 1361. FIG. 17B depicts the results of purified protein preps tested for cleavage activity in TXTL. Experiments incubated purified protein with a PAM library (dsDNA target), a CRISPR-like repetitive region predicted in the locus (cr1) in both forward and reverse orientations (fw and rv), and with intergenic regions potentially encoding relevant cofactors. Lanes 2-9 (no cr array): control experiments without a repetitive region. Apo: only protein prep with a target PAM library. Labels 1-2.5 represent seven different intergenic regions. -IG: no intergenic region included as control. PCR gel of the ligation products shows putative cleavage bands (arrows) suggesting dsDNA cleavage. Bands recovered on lanes labeled "4" represent cleavage bands from incubating the enzyme with the CRISPR-like region and the SMART II 5' UTR.

FIG. 18A depicts the genomic context of the MG34-420 effector showing RNASeq reads sequenced from an in vitro transcription reaction of the SMART II effector with its 5' UTR. The effector is represented by a dark arrow in the reverse orientation, predicted PFAM domains are represented by rectangles below arrows, and a predicted guide RNA is annotated on the black line. Figure discloses "RRXRR" motif as SEQ ID NO: 1361. FIG. 18B depicts secondary structure representation of the SMART II MG35-420 putative guide RNA.

FIG. 19A depicts full-length MSA of the region immediately upstream from the start codon of SMART II effectors. Percent identity histogram above the alignment indicates regions of conservation (annotated as 5' UTR guide RNA, grey arrow). FIG. 19B depicts a highly conserved region within the putative guide RNA encoded sequence. Percent identity histogram and Sequence Logo representation are shown above the alignment. Identical bases are highlighted by black boxes. Figure discloses SEQ ID NOs: 1329-1339, respectively.

FIG. 20A depicts the results of an in vitro cleavage assay. Effectors with (sg) and without (Apo) sgRNA were assayed in in-vitro transcription/translation reactions incubated with a PAM library (dsDNA target). Cleavage products were amplified via PCR (successful RNA guided cleavage by the nuclease produced bands at the expected size; arrows). FIG. 20B depicts target-adjacent motifs (TAMs).

FIGS. 21A-FIG. 21F depict data demonstrating that SMART enzymes are novel nucleases with diverse targeting ability. FIG. 21A depicts the predicted domain architecture of SMART nucleases vs. SpCas9. Figure discloses "RRXRR" motif as SEQ ID NO: 1361. FIG. 21B depicts the genomic context of the SMART MG102-2 system. The tracrRNA and CRISPR array orientations were confirmed by in vitro cleavage activity with the effector. FIG. 21C depicts the genomic context of the SMART MG34-1 system. Adaptation module genes (Cas1, Cas2, Cas4 and putative Csn2) were identified. Environmental RNASeq reads mapped in the forward orientation to the array and intergenic region encoding a tracrRNA. Other genes encoded in the locus are represented by yellow arrows. The tracrRNA and CRISPR array orientations were confirmed by in vitro cleavage activity with the effector. Figure discloses "RRXRR" motif as SEQ ID NO: 1361. FIG. 21D depicts the HEARO RNA secondary structure for two active SMART HEARO nucleases. SeqLogo representation of consensus target motif sequences are shown. Figure discloses SEQ ID NOs: 1340 and 685, respectively. FIG. 21E depicts a phylogenetic protein tree of SMART nucleases vs. Cas9 and IscB reference sequences. SMART effectors and archaeal Cas9 sequences (teal and violet branches) are distantly related to documented Cas9 reference sequences (Type II-A, II-B, and II-C, grey branches). The tree was inferred from a multiple sequence alignment of the shared RuvC-II/HNH/RuvC-III domains. The SMART MG33 family of nucleases (burgundy branches) clusters with CRISPR Type II-C variant systems, while other CRISPR-associated SMART nucleases (teal branches) cluster with sequences recently classified as Type II-D. SMART HEARO nucleases (lilac branches) cluster with HEARO ORF and IscB sequences. FIG. 21F depicts phylogenetic clades of SMART CRISPR Type II families. The clades are a zoom in representation of the phylogenetic tree depicted in FIG. 21E. Local support values for internal family split nodes are shown and range from 0 to 1. SeqLogo representation of consensus target motif sequences and sgRNA designs from biochemical cleavage activity assays for active SMART nucleases are shown.

FIG. 22A depicts a histogram of cut position preference showing that MG34-1 cleaves dsDNA preferentially at position 7 from the PAM. The inset shows that MG34-1 produces a staggered cut, where a cut at position 3 occurs on the target strand (TS), while a cut at positions 6-7 occurs on the non-target strand (NTS). Figure discloses SEQ ID NOs: 1341-1343, respectively. FIG. 22B depicts the distribution of percent DNA cleavage with varying spacer lengths, indicating a preference for 18 bp spacers for MG34-1. FIG. 22C depicts time series cleavage assays for MG34-1, suggesting slower kinetics vs. SpCas9. FIG. 22D depicts a plasmid targeting assay. Left: diagram of the methods show an engineered E. coli strain, which expresses the effector nuclease (MG34-1 or MG34-9) and the sgRNA cofactor. When transformed with a plasmid containing an antibiotic resistance gene with a target or non-target spacer (negative control), growth impairment occurs for the target plasmid. Middle and right: bar graphs indicating approximately 2-fold growth repression for the plasmid encoding the MG34-1 (middle) or MG34-9 (right) enzymes and sgRNA.

FIG. 23 depicts percent amino acid content over the full protein length for a group of SMART HNH endonuclease-associated RNA and ORF (HEARO) (35-1, 35-2, 35-3, 35-6, 35-102, and IscB) and SMART (34-1, 102-2, 102-14, 102-35, 102-45) nucleases. High percent arginine (R) and lysine (K) content is highlighted in green, while low methionine (M) content is highlighted in orange. Percent amino acid content of most proteins in the Uniref50 database (Carugo, vol. 17, 12 (2008): 2187-91) was used for comparison.

FIG. 24A depicts a scatterplot of the average amino acid content of proteins in the Uniref50 database (X axis) vs. the percentage of amino acid content in SMART proteins (Y axis). The arginine (R) and lysine (K) content deviates from the linear trend. FIG. 24B depicts a graph showing the ratio of Amino Acid percentages in SMART proteins to the percentages in the Uniref50 database. The mean of all ratios is 0.99, with SD 0.22. Green lines show two standard deviations from the average, assuming normalcy.

FIG. 25A depicts histograms of cut position preference for three SMART nucleases on the non-target strand (NTS) from next-generation sequencing (NGS). The insets show that SMART nucleases produce a staggered cut, where cleavage at position 3 occurs on the target strand (TS), while cleavage at positions 5-7 from the PAM occur on the NTS. TS cleavage site was determined via Sanger run-off sequencing. Figure discloses SEQ ID NOs: 1341-1343, 1341, 1344, 1343, and 1345-1347, respectively. FIG. 25B depicts a bar plot of colony forming unit (cfu) measurements (in log-scale) showing *E. coli* growth repression in the target condition vs. the non-target controls. Plasmid interference assays for each nuclease were done in triplicate along with the SpCas9 positive control. FIG. 25C depicts measurement of in vitro DNA cleavage efficiency with varying spacer lengths, indicating a preference for 18-20 bp spacers for SMART nucleases, while the SMART HEARO 35-1 prefers 24 bp spacers. (*) spacer lengths 14 bp (34-1) and 30 bp (35-1 and 102-2) were not evaluated. FIG. 25D depicts mismatch kill assays indicating high specificity for target spacers at positions −1 to −13 from the PAM. Left: Bar plot of colony forming unit (cfu) measurements (log-scale) showing *E. coli* growth repression in the target condition vs. a spacer containing mismatches, as well as the non-target controls. Top right: Diagram of the mismatch kill assay. *E. Coli* containing two plasmids for nuclease expression and guide expression are transformed with a library of target plasmids with mismatches in the protospacer. Bottom right: heatmap showing mismatch tolerance at each position of the target spacer. For the target spacer and spacers with tolerated mismatches, growth is expected to be repressed (purple). Positions with required base pairing will not cut efficiently and will be relatively enriched in the output library (yellow). Plasmid interference (kill) assays with the library for each nuclease were done in duplicate.

FIG. 30A depicts data for MG102-2 targeting the AAVS1 locus. FIGS. 30B, 30C, 30D, 30E, 30F, and 30G depict data for MG102-39, MG102-42, MG102-48, MG33-34, MG102-26, and MG102-45 targeting the TRAC locus, respectively.

FIGS. 32A-FIG. 32G depict the genomic context of SMART HEARO nucleases. While the vast majority of SMART HEARO nucleases are not CRISPR-associated (e.g. MG35-104, FIG. 32A), few SMART HEARO nucleases are associated with CRISPR arrays (e.g. MG35-463 and MG35-556 in FIGS. 32B and 32C). The SMART HEARO nuclease is represented by a dark grey arrow with RRXRR ("RRXRR" motif is SEQ ID NO: 1361) and HNH Pfam domains annotated underneath the gene. HEARO RNAs predicted from covariance models (CM) are shown upstream from the SMART HEARO effector genes (CM HEARO RNA). RAR: repeat-antirepeat. FIGS. 32D-32G depict HEARO RNA secondary structures for three active nucleases: MG35-104 sg1, MG35-463 sg2 (CRISPR-independent), MG35-463 sg3 (CRISPR-associated), and MG35-556 dual guide HEARO RNA (CRISPR-associated), respectively. FIGS. 32D-32G disclose SEQ ID NOs: 1353-1356, respectively.

FIGS. 35A-FIG. 35B depict in vitro cleavage efficiency for active SMART HEARO nucleases. For FIG. 35A, cleavage was measured by the supercoiled (uncut) to linear (cut) transition of reaction products and visualized on the Agilent Tapestation. Arrows indicate initial dsDNA product (supercoiled) and dsDNA product after successful targeted cleavage by the enzyme (linearized). PE: PUREXPRESS®; sgRNA, single guide RNA. FIG. 35B depicts a barplot representation of the quantification from FIG. 35A. DNA: DNA-only control without RNP reaction (negative control); Apo: RNP reaction without sgRNA added; Holo: RNP reaction with sgRNA.

FIG. 36A depicts an example guide RNA with poly-T regions and engineered guide sequences for MG35-518. Figure discloses SEQ ID NOs: 1357-1360, respectively. FIG. 36B depicts cleavage efficiency of engineered SMART HEARO guide RNAs vs. the native guide. Apo: no guide added (negative control); WT: native guide RNA.

FIG. 37A-FIG. 37D depicts phylogenetic analysis of SMART I nucleases. Phylogenetic trees were inferred with FastTree or RAXML from global (g-ins-i) or local (l-ins-i) multiple sequence alignments. To account for phylogenetic uncertainty, six reconstructed sequences were obtained from multiple trees (nodes highlighted with a closed circle: MG34-26, MG34-27, MG34-28, MG34-29, MG34-30 and MG34-31).

BRIEF DESCRIPTION OF THE SEQUENCE LISTING

Figure 2:
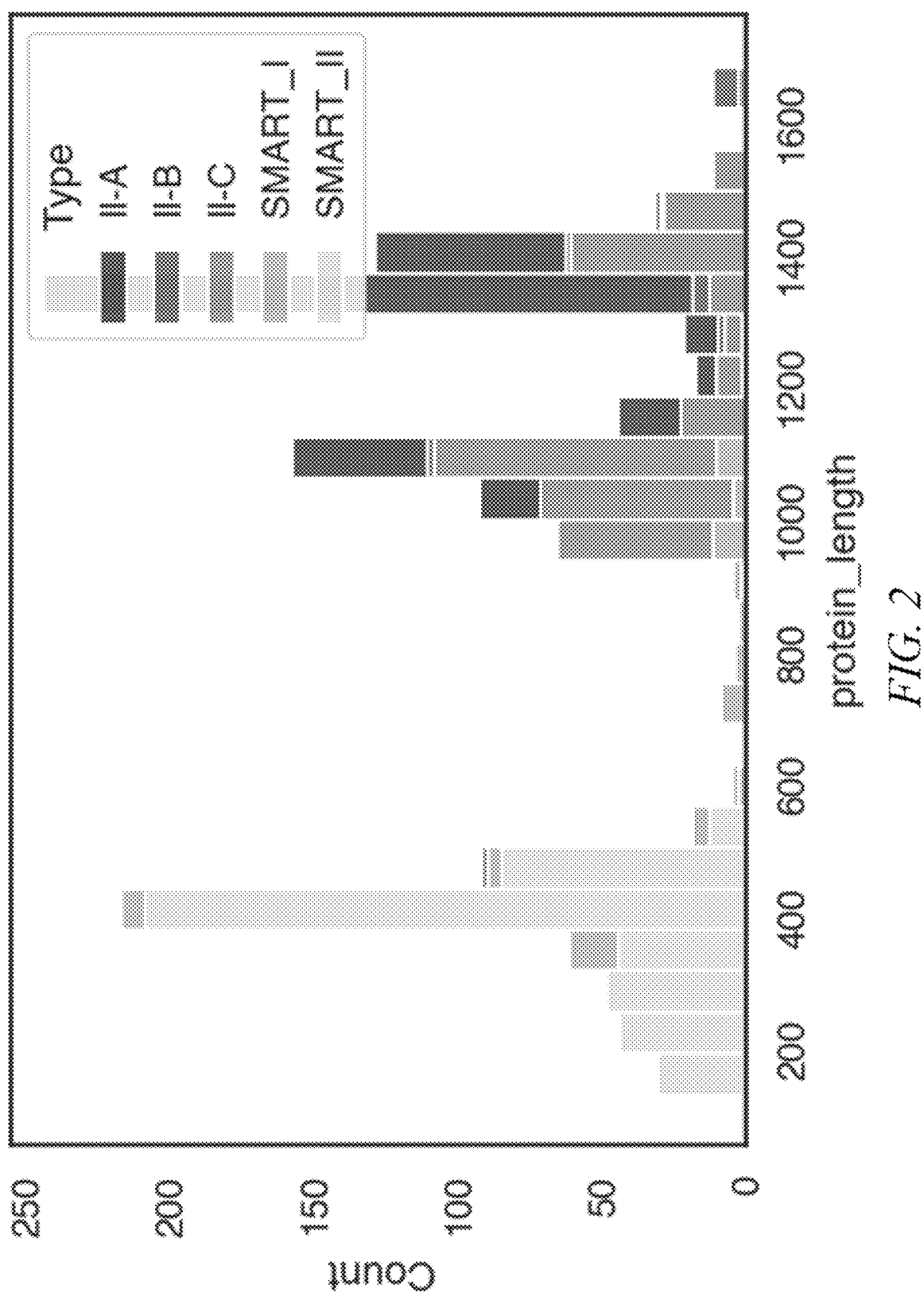
FIG. 2 shows length distribution for SMART effectors described herein, showing that SMART I and II enzymes are clustered at a lower molecular weight than Cas9-like enzymes. SMART nucleases show a bimodal distribution with one peak around 400 aa (SMART II) and a second peak around 750 aa (SMART I). Cas9 nucleases also show a bimodal distribution with peaks around 1,100 aa (e.g. SaCas9) and 1,300 aa (e.g. SpCas9).

The Sequence Listing filed herewith provides exemplary polynucleotide and polypeptide sequences for use in methods, compositions and systems according to the disclosure. Below are exemplary descriptions of sequences therein.

MG33 Nucleases

SEQ ID NOs: 1, 463-486, 981-988, and 1289-1312 show the full-length peptide sequences of MG33 nucleases.

SEQ ID NOs: 199 and 669-670 show the nucleotide sequence of a tracrRNA predicted to function with an MG33 nuclease.

SEQ ID NOs: 201 and 1003-1005 show the nucleotide sequences of predicted single-guide RNA (sgRNA) sequences predicted to function with an MG33 nuclease. "N"s denote variable residues and non-N-residues represent the scaffold sequence.

SEQ ID NOs: 1023-1028 show PAM sequences compatible with MG33 nucleases.

SEQ ID NOs: 1045-1054 show CRISPR repeats of MG33 nucleases described herein.

MG34 Nucleases

SEQ ID NOs: 2-24, 487-488, and 1313-1321 show the full-length peptide sequences of MG34 nucleases.

SEQ ID NO: 200 shows the nucleotide sequence of a tracrRNA predicted to function with an MG34 nuclease.

SEQ ID NOs: 202, 203, and 613-616 show the nucleotide sequences of predicted single-guide RNA (sgRNA) sequences predicted to function with an MG34 nuclease. "N"s denote variable residues and non-N-residues represent the scaffold sequence.

SEQ ID NOs: 1023-1028 show PAM sequences compatible with MG34 nucleases.

SEQ ID NOs: 1055-1057 show CRISPR repeats of MG34 nucleases described herein.

MG35 Nucleases

SEQ ID NOs: 25-198, 221-459, 489-580, 617-668, and 674-675 show the full-length peptide sequences of MG35 nucleases.

SEQ ID NOs: 460-461 show the nucleotide sequences of MG35 tracrRNAs derived from the same loci as MG35 nucleases.

SEQ ID NOs: 462, 676, and 1229-1230 show CRISPR repeats of MG35 nucleases described herein.

SEQ ID NOs: 677-686, 1006-1012, and 1231-1259 show the nucleotide sequences of MG35 single guide RNAs.

SEQ ID NOs: 687-974 show the nucleotide sequences of MG35 single guide RNA encoding sequences.

SEQ ID NOs: 1029-1034 show PAM sequences compatible with MG35 nucleases.

SEQ ID NOs: 1172-1228 show the nucleotide sequences of loci encoding MG35 nucleases described herein.

MG102 Nucleases

SEQ ID NOs: 581-612, 989-1002, and 1260-1273 show the full-length peptide sequences of MG102 nucleases.

SEQ ID NOs: 672-673 show the nucleotide sequences of MG102 tracrRNAs derived from the same loci as MG102 nucleases SEQ ID NOs: 205-220 show the sequences of example nuclear localization sequences (NLSs) that can be appended to nucleases according to the disclosure.

SEQ ID NOs: 1013-1022 show the nucleotide sequences of MG102 single guide RNAs.

SEQ ID NOs: 1035-1044 show PAM sequences compatible with MG102 nucleases.

SEQ ID NOs: 1058-1072 show CRISPR repeats of MG102 nucleases described herein.

SEQ ID NO: 1171 shows the nucleotide sequence of a locus encoding an MG102 nuclease described herein.

MG143 Nucleases

SEQ ID NO: 975 shows the full-length peptide sequence of an MG143 nuclease.

SEQ ID NOs: 1073 shows a CRISPR repeat of an MG143 nuclease described herein.

MG144 Nucleases

SEQ ID NOs: 976-979 and 1274-1288 show the full-length peptide sequences of MG144 nucleases.

SEQ ID NOs: 1074-1077 show CRISPR repeats of MG144 nucleases described herein.

MG145 Nucleases

SEQ ID NO: 980 shows the full-length peptide sequence of an MG145 nuclease.

SEQ ID NOs: 1078 shows a CRISPR repeat of an MG145 nuclease described herein.

MG102 TRAC Targeting

SEQ ID NOs: 1079-1082 and 1145-1166 show the DNA sequences of TRAC target sites.

SEQ ID NOs: 1083-1086 and 1123-1144 show the nucleotide sequences of sgRNAs engineered to function with an MG102 nuclease in order to target TRAC.

MG33 TRAC Targeting

SEQ ID NOs: 1167-1168 show the nucleotide sequences of sgRNAs engineered to function with an MG33 nuclease in order to target TRAC.

SEQ ID NOs: 1169-1170 show the DNA sequences of TRAC target sites.

AAVS1 Targeting

SEQ ID NOs: 1087-1104 show the nucleotide sequences of sgRNAs engineered to function with an MG102 nuclease in order to target AAVS1.

SEQ ID NOs: 1105-1122 show the DNA sequences of AAVS1 target sites.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The practice of some methods disclosed herein employ, unless otherwise indicated, techniques of immunology, biochemistry, chemistry, molecular biology, microbiology, cell biology, genomics and recombinant DNA. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)) (which is entirely incorporated by reference herein).

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within one or more than one standard deviation, per the practice in the art. Alternatively, "about" can mean a range of up to 20%, up to 15%, up to 10%, up to 5%, or up to 1% of a given value.

As used herein, a "cell" generally refers to a biological cell. A cell may be the basic structural, functional or biological unit of a living organism. A cell may originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, cannabis, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens C. Agardh*, and the like), seaweeds (e.g., kelp), a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell is not originating from a natural organism (e.g., a cell can be synthetically made, sometimes termed an artificial cell).

The term "nucleotide," as used herein, generally refers to a base-sugar-phosphate combination. A nucleotide may comprise a synthetic nucleotide. A nucleotide may comprise a synthetic nucleotide analog. Nucleotides may be monomeric units of a nucleic acid sequence (e.g., deoxyribonucleic acid (DNA) and ribonucleic acid (RNA)). The term nucleotide may include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives may include, for example, [αS]dATP, 7-deaza-dGTP and 7-deaza-dATP, and nucleotide derivatives that confer nuclease resistance on the nucleic acid molecule containing them. The term nucleotide as used herein may refer to dideoxyribonucleoside triphosphates (ddNTPs) and their derivatives. Illustrative examples of dideoxyribonucleoside triphosphates may include, but are not limited to, ddATP, ddCTP, ddGTP, ddITP, and ddTTP. A nucleotide may be unlabeled or detectably labeled, such as using moieties comprising optically detectable moieties (e.g., fluorophores). Labeling may also be carried out with quantum dots. Detectable labels may include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl) aminonaphthalene-1-sulfonic acid (EDANS). Specific examples of fluorescently labeled nucleotides can include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA]ddGTP, [ROX]ddTTP, [dR6G] ddATP, [dR110]ddCTP, [dTAMRA]ddGTP, and [dROX] ddTTP available from Perkin Elmer, Foster City, Calif; FluoroLink DeoxyNucleotides, FluoroLink Cy3-dCTP, FluoroLink Cy5-dCTP, FluoroLink Fluor X-dCTP, Fluoro- Link Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g., biotin-11-dUTP, biotin-16-dUTP, biotin-20-dUTP). A nucleotide may comprise a nucleotide analog. In some embodiments, nucleotide analogs may comprise structures of natural nucleotides that are modified at any position so as to alter certain chemical properties of the nucleotide yet retain the ability of the nucleotide analog to perform its intended function (e.g. hybridization to other nucleotides in RNA or DNA). Examples of positions of the nucleotide which may be derivatized include the 5 position, e.g., 5-(2-amino) propyl uridine, 5-bromo uridine, 5-propyne uridine, 5-propenyl uridine, etc.; the 6 position, e.g., 6-(2-amino) propyl uridine; the 8-position for adenosine or guanosines, e.g., 8-bromo guanosine, 8-chloro guanosine, 8-fluoroguanosine, etc. Nucleotide analogs also include deaza nucleotides, e.g., 7-deaza-adenosine: O- and N-modified (e.g., alkylated, e.g., N6-methyl adenosine) nucleotides; and other heterocyclically modified nucleotide analogs such as those described in Herdewijn, Antisense Nucleic Acid Drug Dev., 2000 Aug. 10 (4): 297-310. Nucleotide analogs may also comprise modifications to the sugar portion of the nucleotides. For example the 2' OH-group may be replaced by a group selected from H, OR, R, F, Cl, Br, I, SH, SR, NH2, NHR, NR2, COOR, or OR, wherein R is substituted or unsubstituted C1-C6 alkyl, alkenyl, alkynyl, aryl, etc. Other possible modifications include those described in U.S. Pat. Nos. 5,858,988, and 6,291,438. Examples of positions of the nucleotide which may be derivatized include the 5 position, e.g., 5-(2-amino) propyl uridine, 5-bromo uridine, 5-propyne uridine, 5-propenyl uridine, etc.; the 6 position, e.g., 6-(2-amino) propyl uridine; the 8-position for adenosine or guanosines, e.g., 8-bromo guanosine, 8-chloro guanosine, 8-fluoroguanosine, etc. Nucleotide analogs also include deaza nucleotides, e.g., 7-deaza-adenosine: O- and N-modified (e.g., alkylated, e.g., N6-methyl adenosine) nucleotides; and other heterocyclically modified nucleotide analogs such as those described in Herdewijn, Antisense Nucleic Acid Drug Dev., 2000 Aug. 10 (4): 297-310.

Nucleotide analogs may also comprise modifications to the sugar portion of the nucleotides. For example the 2' OH-group may be replaced by a group selected from H, OR, R, F, Cl, Br, I, SH, SR, NH2, NHR, NR2, COOR, or OR, wherein R is substituted or unsubstituted C1-C6 alkyl, alkenyl, alkynyl, aryl, etc. Other possible modifications include those described in U.S. Pat. Nos. 5,858,988, and 6,291,438.

The terms "polynucleotide," "oligonucleotide," and "nucleic acid" are used interchangeably to generally refer to a polymeric form of nucleotides of any length, either deoxyribonucleotides or ribonucleotides, or analogs thereof, either in single-, double-, or multi-stranded form. A polynucleotide may be exogenous or endogenous to a cell. A polynucleotide may exist in a cell-free environment. A polynucleotide may be a gene or fragment thereof. A polynucleotide may be DNA. A polynucleotide may be RNA. A polynucleotide may have any three-dimensional structure and may perform any function. A polynucleotide may comprise one or more analogs (e.g., altered backbone, sugar, or nucleobase). If present, modifications to the nucleotide structure may be imparted before or after assembly of the polymer. Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides may be interrupted by non-nucleotide components.

The terms "transfection" or "transfected" generally refer to introduction of a nucleic acid into a cell by non-viral or viral-based methods. The nucleic acid molecules may be gene sequences encoding complete proteins or functional portions thereof. See, e.g., Sambrook et al., 1989, Molecular Cloning: A Laboratory Manual, 18.1-18.88 (which is entirely incorporated by reference herein).

The terms "peptide," "polypeptide," and "protein" are used interchangeably herein to generally refer to a polymer of at least two amino acid residues joined by peptide bond(s). This term does not connote a specific length of polymer, nor is it intended to imply or distinguish whether the peptide is produced using recombinant techniques, chemical or enzymatic synthesis, or is naturally occurring. The terms apply to naturally occurring amino acid polymers as well as amino acid polymers comprising at least one modified amino acid. In some cases, the polymer may be interrupted by non-amino acids. The terms include amino acid chains of any length, including full length proteins, and proteins with or without secondary or tertiary structure (e.g., domains). The terms also encompass an amino acid polymer that has been modified, for example, by disulfide bond formation, glycosylation, lipidation, acetylation, phosphorylation, oxidation, and any other manipulation such as conjugation with a labeling component. The terms "amino acid" and "amino acids," as used herein, generally refer to natural and non-natural amino acids, including, but not limited to, modified amino acids and amino acid analogues. Modified amino acids may include natural amino acids and non-natural amino acids, which have been chemically modified to include a group or a chemical moiety not naturally present on the amino acid. Amino acid analogues may refer to amino acid derivatives. The term "amino acid" includes both D-amino acids and L-amino acids.

As used herein, the term "non-native" can generally refer to a nucleic acid or polypeptide sequence that is not found in a native nucleic acid or protein. Non-native may refer to affinity tags. Non-native may refer to fusions. Non-native may refer to a naturally occurring nucleic acid or polypeptide sequence that comprises mutations, insertions or deletions. A non-native sequence may exhibit or encode for an activity (e.g., enzymatic activity, methyltransferase activity, acetyltransferase activity, kinase activity, ubiquitinating activity, etc.) that may also be exhibited by the nucleic acid or polypeptide sequence to which the non-native sequence is fused. A non-native nucleic acid or polypeptide sequence may be linked to a naturally-occurring nucleic acid or polypeptide sequence (or a variant thereof) by genetic engineering to generate a chimeric nucleic acid or polypeptide sequence encoding a chimeric nucleic acid or polypeptide.

The term "promoter", as used herein, generally refers to the regulatory DNA region which controls transcription or expression of a gene and which may be located adjacent to or overlapping a nucleotide or region of nucleotides at which RNA transcription is initiated. A promoter may contain specific DNA sequences which bind protein factors, often referred to as transcription factors, which facilitate binding of RNA polymerase to the DNA leading to gene transcription. A 'basal promoter', also referred to as a 'core promoter', may generally refer to a promoter that contains all the basic elements to promote transcriptional expression of an operably linked polynucleotide. Eukaryotic basal promoters typically, though not necessarily, contain a TATA-box or a CAAT box.

The term "expression", as used herein, generally refers to the process by which a nucleic acid sequence or a polynucleotide is transcribed from a DNA template (such as into mRNA or other RNA transcript) or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, "operably linked", "operable linkage", "operatively linked", or grammatical equivalents thereof generally refer to juxtaposition of genetic elements, e.g., a promoter, an enhancer, a polyadenylation sequence, etc., wherein the elements are in a relationship permitting them to operate in the expected manner. For instance, a regulatory element, which may comprise promoter or enhancer sequences, is operatively linked to a coding region if the regulatory element helps initiate transcription of the coding sequence. There may be intervening residues between the regulatory element and coding region so long as this functional relationship is maintained.

A "vector" as used herein, generally refers to a macromolecule or association of macromolecules that comprises or associates with a polynucleotide and which may be used to mediate delivery of the polynucleotide to a cell. Examples of vectors include plasmids, viral vectors, liposomes, and other gene delivery vehicles. The vector generally comprises genetic elements, e.g., regulatory elements, operatively linked to a gene to facilitate expression of the gene in a target.

As used herein, "an expression cassette" and "a nucleic acid cassette" are used interchangeably generally to refer to a combination of nucleic acid sequences or elements that are expressed together or are operably linked for expression. In some cases, an expression cassette refers to the combination of regulatory elements and a gene or genes to which they are operably linked for expression.

A "functional fragment" of a DNA or protein sequence generally refers to a fragment that retains a biological activity (either functional or structural) that is substantially similar to a biological activity of the full-length DNA or protein sequence. A biological activity of a DNA sequence may be its ability to influence expression in a manner attributed to the full-length sequence.

As used herein, an "engineered" object generally indicates that the object has been modified by human intervention. According to non-limiting examples: a nucleic acid may be modified by changing its sequence to a sequence that does not occur in nature; a nucleic acid may be modified by ligating it to a nucleic acid that it does not associate with in nature such that the ligated product possesses a function not present in the original nucleic acid; an engineered nucleic acid may synthesized in vitro with a sequence that does not exist in nature; a protein may be modified by changing its amino acid sequence to a sequence that does not exist in nature; an engineered protein may acquire a new function or property. An "engineered" system comprises at least one engineered component.

As used herein, the term "optimally aligned" generally refers to an alignment of two amino acid sequences that give the highest percent identity score or maximizes the number of matched residues.

As used herein, "synthetic" and "artificial" are used interchangeably to refer to a protein or a domain thereof that has low sequence identity (e.g., less than 50% sequence identity, less than 25% sequence identity, less than 10% sequence identity, less than 5% sequence identity, less than 1% sequence identity) to a naturally occurring human protein. For example, VPR and VP64 domains are synthetic transactivation domains.

The term "tracrRNA" or "tracr sequence", as used herein, can generally refer to a nucleic acid with at least about 5%, 10%, 20%, 30%, 40%, 50%, 60%, 70%, 80%, 90%, 95%, or 100% sequence identity or sequence similarity to a wild type exemplary tracrRNA sequence (e.g., a tracrRNA from S. pyogenes S. aureus, etc.). tracrRNA can refer to a nucleic acid with at most about 5%, 10%, 20%, 30%, 40%, 50%, 60%, 70%, 80%, 90%, or 100% sequence identity or sequence similarity to a wild type exemplary tracrRNA sequence (e.g., a tracrRNA from S. pyogenes S. aureus, etc). tracrRNA may refer to a modified form of a tracrRNA that can comprise a nucleotide change such as a deletion, insertion, or substitution, variant, mutation, or chimera. A tracrRNA may refer to a nucleic acid that can be at least about 60% identical to a wild type exemplary tracrRNA (e.g., a tracrRNA from S. pyogenes S. aureus, etc.) sequence over a stretch of at least 6 contiguous nucleotides. For example, a tracrRNA sequence can be at least about 60% identical, at least about 65% identical, at least about 70% identical, at least about 75% identical, at least about 80% identical, at least about 85% identical, at least about 90% identical, at least about 95% identical, at least about 98% identical, at least about 99% identical, or 100% identical to a wild type exemplary tracrRNA (e.g., a tracrRNA from S. pyogenes S. aureus, etc.) sequence over a stretch of at least 6 contiguous nucleotides. Type II tracrRNA sequences can be predicted on a genome sequence by identifying regions with complementarity to part of the repeat sequence in an adjacent CRISPR array.

As used herein, a "guide nucleic acid" can generally refer to a nucleic acid that may hybridize to another nucleic acid. A guide nucleic acid may be RNA. A guide nucleic acid may be DNA. The guide nucleic acid may be programmed to bind to a sequence of nucleic acid site-specifically. The nucleic acid to be targeted, or the target nucleic acid, may comprise nucleotides. The guide nucleic acid may comprise nucleotides. A portion of the target nucleic acid may be complementary to a portion of the guide nucleic acid. The strand of a double-stranded target polynucleotide that is complementary to and hybridizes with the guide nucleic acid may be called the complementary strand. The strand of the double-stranded target polynucleotide that is complementary to the complementary strand, and therefore may not be complementary to the guide nucleic acid may be called noncomplementary strand. A guide nucleic acid may comprise a polynucleotide chain and can be called a "single guide nucleic acid." A guide nucleic acid may comprise two polynucleotide chains and may be called a "double guide nucleic acid." If not otherwise specified, the term "guide nucleic acid" may be inclusive, referring to both single guide nucleic acids and double guide nucleic acids. A guide nucleic acid may comprise a segment that can be referred to as a "nucleic acid-targeting segment" or a "nucleic acid-targeting sequence." A nucleic acid-targeting segment may comprise a sub-segment that may be referred to as a "protein binding segment" or "protein binding sequence" or "Cas protein binding segment".

The term "sequence identity" or "percent identity" in the context of two or more nucleic acids or polypeptide sequences, generally refers to two (e.g., in a pairwise alignment) or more (e.g., in a multiple sequence alignment) sequences that are the same or have a specified percentage of amino acid residues or nucleotides that are the same, when compared and aligned for maximum correspondence over a local or global comparison window, as measured using a sequence comparison algorithm. Suitable sequence comparison algorithms for polypeptide sequences include, e.g., BLASTP using parameters of a wordlength (W) of 3, an expectation (E) of 10, and the BLOSUM62 scoring matrix setting gap costs at existence of 11, extension of 1, and using a conditional compositional score matrix adjustment for polypeptide sequences longer than 30 residues; BLASTP using parameters of a wordlength (W) of 2, an expectation (E) of 1000000, and the PAM30 scoring matrix setting gap costs at 9 to open gaps and 1 to extend gaps for sequences of less than 30 residues (these are the default parameters for BLASTP in the BLAST suite available at blast.ncbi.nlm.nih.gov); or CLUSTALW with parameters of the Smith-Waterman homology search algorithm with parameters of a match of 2, a mismatch of −1, and a gap of −1; MUSCLE with default parameters; MAFFT with parameters retree of 2 and maxiterations of 1000; Novafold with default parameters; HMMER hmmalign with default parameters.

As used herein, the term "RuvC_III domain" generally refers to a third discontinuous segment of a RuvC endonuclease domain (the RuvC nuclease domain being comprised of three discontiguous segments, RuvC_I, RuvC_II, and RuvC_III). A RuvC domain or segments thereof (e.g. RuvC_I, RuvC_II, or RuvC_III) can generally be identified by alignment to documented domain sequences, structural alignment to proteins with annotated domains, or by comparison to Hidden Markov Models (HMMs) built based on documented domain sequences (e.g., Pfam HMM PF18541 for RuvC_III).

As used herein, the term "HNH domain" generally refers to an endonuclease domain having characteristic histidine and asparagine residues. An HNH domain can generally be identified by alignment to documented domain sequences, structural alignment to proteins with annotated domains, or by comparison to Hidden Markov Models (HMMs) built based on documented domain sequences (e.g., Pfam HMM PF01844 for domain HNH).

As used herein, the term "bridge helix domain" or "BH domain" generally refers to an arginine-rich helix domain present in Cas enzymes that plays an important role in initiating cleavage activity upon binding of target DNA.

As used herein, the term "recognition domain" or "REC domain" generally refers to a domain thought to interact with the repeat: anti-repeat duplex of the gRNA and to mediate the formation of a Cas endonuclease/gRNA complex.

As used herein, the term "wedge domain" or "WED domain" generally refers to a fold comprising a twisted five-stranded beta sheet flanked by four alpha helices, which is generally responsible for the recognition of the distorted repeat: anti-repeat duplex for Cas enzymes. WED domains can be responsible for the recognition of single-guide RNA scaffolds.

As used herein, the term "PAM interacting domain" or "PI domain" generally refers to a domain found in Cas enzymes positioned in the endonuclease-DNA-complex to recognize the PAM sequence on the non-complementary DNA strand of the guide RNA.

Overview

The discovery of new Cas enzymes with unique functionality and structure may offer the potential to further disrupt deoxyribonucleic acid (DNA) editing technologies, improving speed, specificity, functionality, and ease of use. Relative to the predicted prevalence of Clustered Regularly Interspaced Short Palindromic Repeats (CRISPR) systems in microbes and the sheer diversity of microbial species, relatively few functionally characterized CRISPR/Cas enzymes exist in the literature. This is partly because a huge number of microbial species may not be readily cultivated in laboratory conditions. Metagenomic sequencing from natural environmental niches that represent large numbers of microbial species may offer the potential to drastically increase the number of new CRISPR/Cas systems documented and speed the discovery of new oligonucleotide editing functionalities. A recent example of the fruitfulness of such an approach is demonstrated by the 2016 discovery of CasX/CasY CRISPR systems from metagenomic analysis of natural microbial communities.

CRISPR/Cas systems are RNA-directed nuclease complexes that have been described to function as an adaptive immune system in microbes. In their natural context, CRISPR/Cas systems occur in CRISPR (clustered regularly interspaced short palindromic repeats) operons or loci, which generally comprise two parts: (i) an array of short repetitive sequences (30-40 bp) separated by equally short spacer sequences, which encode the RNA-based targeting element; and (ii) ORFs encoding the Cas encoding the nuclease polypeptide directed by the RNA-based targeting element alongside accessory proteins/enzymes. Efficient nuclease targeting of a particular target nucleic acid sequence generally requires both (i) complementary hybridization between the first 6-8 nucleic acids of the target (the target seed) and the crRNA guide; and (ii) the presence of a protospacer-adjacent motif (PAM) sequence within a defined vicinity of the target seed (the PAM usually being a sequence not commonly represented within the host genome). Depending on the exact function and organization of the system, CRISPR-Cas systems are commonly organized into 2 classes, 5 types and 16 subtypes based on shared functional characteristics and evolutionary similarity.

Class I CRISPR-Cas systems have large, multisubunit effector complexes, and comprise Types I, III, and IV.

Type I CRISPR-Cas systems are considered of moderate complexity in terms of components. In Type I CRISPR-Cas systems, the array of RNA-targeting elements is transcribed as a long precursor crRNA (pre-crRNA) that is processed at repeat elements to liberate short, mature crRNAs that direct the nuclease complex to nucleic acid targets when they are followed by a suitable short consensus sequence called a protospacer-adjacent motif (PAM). This processing occurs via an endoribonuclease subunit (Cas6) of a large endonuclease complex called Cascade, which also comprises a nuclease (Cas3) protein component of the crRNA-directed nuclease complex. Cas I nucleases function primarily as DNA nucleases.

Type III CRISPR systems may be characterized by the presence of a central nuclease, known as Cas10, alongside a repeat-associated mysterious protein (RAMP) that comprises Csm or Cmr protein subunits. Like in Type I systems, the mature crRNA is processed from a pre-crRNA using a Cas6-like enzyme. Unlike type I and II systems, type III systems appear to target and cleave DNA-RNA duplexes (such as DNA strands being used as templates for an RNA polymerase).

Type IV CRISPR-Cas systems possess an effector complex that comprises a highly reduced large subunit nuclease (csf1), two genes for RAMP proteins of the Cas5 (csf3) and Cas7 (csf2) groups, and, in some cases, a gene for a predicted small subunit; such systems are commonly found on endogenous plasmids.

Class II CRISPR-Cas systems generally have single-polypeptide multidomain nuclease effectors, and comprise Types II, V and VI.

Type II CRISPR-Cas systems are considered the simplest in terms of components. In Type II CRISPR-Cas systems, the processing of the CRISPR array into mature crRNAs does not require the presence of a special endonuclease subunit, but rather a small trans-encoded crRNA (tracrRNA) with a region complementary to the array repeat sequence; the tracrRNA interacts with both its corresponding effector nuclease (e.g. Cas9) and the repeat sequence to form a precursor dsRNA structure, which is cleaved by endogenous RNAse III to generate a mature effector enzyme loaded with both tracrRNA and crRNA. Cas II nucleases are DNA nucleases. Type II effectors generally exhibit a structure comprising a RuvC-like endonuclease domain that adopts the RNase H fold with an unrelated HNH nuclease domain inserted within the folds of the RuvC-like nuclease domain. The RuvC-like domain is responsible for the cleavage of the target (e.g., crRNA complementary) DNA strand, while the HNH domain is responsible for cleavage of the displaced DNA strand.

Type V CRISPR-Cas systems are characterized by a nuclease effector (e.g. Cas12) structure similar to that of Type II effectors, comprising a RuvC-like domain. Similar to Type II, most (but not all) Type V CRISPR systems use a tracrRNA to process pre-crRNAs into mature crRNAs; however, unlike Type II systems which requires RNAse III to cleave the pre-crRNA into multiple crRNAs, type V systems are capable of using the effector nuclease itself to cleave pre-crRNAs. Like Type-II CRISPR-Cas systems, Type V CRISPR-Cas systems are DNA nucleases. Unlike Type II CRISPR-Cas systems, some Type V enzymes (e.g., Cas12a) appear to have a robust single-stranded nonspecific deoxyribonuclease activity that is activated by the first crRNA directed cleavage of a double-stranded target sequence.

Type VI CRISPR-Cas systems have RNA-guided RNA endonucleases. Instead of RuvC-like domains, the single polypeptide effector of Type VI systems (e.g. Cas13) comprises two HEPN ribonuclease domains. Differing from both Type II and V systems, Type VI systems also appear to not need a tracrRNA for processing of pre-crRNA into crRNA. Similar to type V systems, however, some Type VI systems (e.g., C2C2) appear to possess robust single-stranded non-specific nuclease (ribonuclease) activity activated by the first crRNA directed cleavage of a target RNA.

Because of their simpler architecture, Class II CRISPR-Cas have been most widely adopted for engineering and development as designer nuclease/genome editing applications.

One of the early adaptations of such a system for in vitro use can be found in Jinek et al. (Science. 2012 Aug. 17; 337 (6096): 816-21, which is entirely incorporated herein by reference). The Jinek study first described a system that involved (i) recombinantly-expressed, purified full-length Cas9 (e.g., a Class II, Type II Cas enzyme) isolated from S. pyogenes SF370, (ii) purified mature ~42 nt crRNA bearing a ~20 nt 5' sequence complementary to the target DNA sequence to be cleaved followed by a 3' tracr-binding sequence (the whole crRNA being in vitro transcribed from a synthetic DNA template carrying a T7 promoter sequence); (iii) purified tracrRNA in vitro transcribed from a synthetic DNA template carrying a T7 promoter sequence, and (iv) $Mg^{2+}$. Jinek later described an improved, engineered system wherein the crRNA of (ii) is joined to the 5' end of (iii) by a linker (e.g., GAAA) to form a single fused synthetic guide RNA (sgRNA) capable of directing Cas9 to a target by itself (compare top and bottom panel of FIG. 2).

Mali et al. (Science. 2013 Feb. 15; 339 (6121): 823-826.), which is entirely incorporated herein by reference, later adapted this system for use in mammalian cells by providing DNA vectors encoding (i) an ORF encoding codon-optimized Cas9 (e.g., a Class II, Type II Cas enzyme) under a suitable mammalian promoter with a C-terminal nuclear localization sequence (e.g., SV40 NLS) and a suitable polyadenylation signal (e.g., TK pA signal); and (ii) an ORF encoding an sgRNA (having a 5' sequence beginning with G followed by 20 nt of a complementary targeting nucleic acid sequence joined to a 3' tracr-binding sequence, a linker, and the tracrRNA sequence) under a suitable Polymerase III promoter (e.g., the U6 promoter).

MG Enzymes

In one aspect, the present disclosure provides for an engineered nuclease system. The engineered nuclease system may comprise (a) an endonuclease. In some cases, the endonuclease comprises a RuvC domain and an HNH domain. The endonuclease may be from an uncultivated microorganism. The endonuclease may be a Cas endonuclease. The endonuclease may be a class 2 endonuclease. The endonuclease may be a class 2, type II Cas endonuclease. The engineered nuclease system may comprise (b) an engineered guide ribonucleic acid structure. The engineered guide ribonucleic acid structure may be configured to form a complex with the endonuclease. In some cases, the engineered guide ribonucleic acid structure configured to form a complex with the endonuclease comprises a guide ribonucleic acid sequence. The guide ribonucleic acid sequence may be configured to hybridize to a target deoxyribonucleic acid sequence. In some cases, the engineered guide ribonucleic acid structure configured to form a complex with the endonuclease comprises a tracr ribonucleic acid sequence. The tracr ribonucleic acid sequence may be configured to bind to the endonuclease. In some cases, the endonuclease has a molecular weight of about 120 kDa or less, about 110 kDa or less, about 100 kDa or less, about 90 kDa or less, about 80 kDa or less, about 70 kDa or less, about 60 kDa or less, about 50 kDa or less, about 40 kDa or less, about 30 kDa or less, about 20 kDa or less, or about 10 kDa or less.

In some cases, the endonuclease comprises a sequence with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NOs: 1-198, 221-459, 463-612, 617-668, 674-675, 975-1002, 1260-1321, or a variant thereof.

In one aspect, the present disclosure provides an engineered nuclease system. The engineered nuclease system may comprise (a) an endonuclease. The endonuclease may comprise a RuvC-1 domain or a RuvC domain. The endonuclease may comprise an HNH domain. The endonuclease may comprise a RuvC-1 domain and an HNH domain. The endonuclease may be a Cas endonuclease. The endonuclease may be a class 2 endonuclease. The endonuclease may be a class 2, type II Cas endonuclease. The engineered nuclease system may comprise (b) an engineered guide ribonucleic acid. The engineered guide ribonucleic acid structure may be configured to form a complex with the endonuclease. The guide ribonucleic acid structure configured to form a complex with the endonuclease may comprise a guide ribonucleic acid sequence. The guide ribonucleic acid sequence may be configured to hybridize to a target deoxyribonucleic acid sequence. The engineered guide ribonucleic acid structure configured to form a complex with the endonuclease may comprise a tracr ribonucleic acid sequence. The tracr ribonucleic acid sequence may be configured to bind to the endonuclease. The endonuclease may comprise a sequence with at least 50%, at least 55%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any one of 1-198, 221-459, 463-612, 617-668, 674-675, 975-1002, 1260-1321. The endonuclease may be an archaeal endonuclease. The endonuclease may be a Class 2, Type II Cas endonuclease. The endonuclease may comprise an arginine rich region comprising an RRxRR motif (SEQ ID NO: 1361) or a domain with PF14239 homology. The arginine-rich region or domain with PF14239 homology can comprise a sequence with at least 50%, at least 55%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an arginine rich region or a domain with PF14239 homology of any one of SEQ ID NOs: 1-198, 221-459, 463-612, 617-668, 674-675, 975-1002, 1260-1321, or a variant thereof. The domain boundaries of the arginine rich domain or the domain with PF14239 homology can be identified by optimal alignment to MG34-1 or MG34-9. The endonuclease may comprise REC domain. The REC domain can comprise a sequence with at least 50%, at least 55%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a REC domain of any one of SEQ ID NOs: 1-198, 221-459, 463-612, 617-668, 674-675, 975-1002, 1260-1321, or a variant thereof. The domain boundaries of the REC domain can be identified by optimal alignment to MG34-1 or MG34-9. The endonuclease may comprise BH (Bridge Helix) domain. The BH domain can comprise a sequence with at least 50%, at least 55%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a BH domain of any one of SEQ ID NOs: 1-198, 221-459, 463-612, 617-668, 674-675, 975-1002, 1260-1321, or a variant thereof. The domain boundaries of the BH domain can be identified by optimal alignment to MG34-1 or MG34-9.

The endonuclease may comprise WED (wedge) domain. The WED domain can comprise a sequence with at least 50%, at least 55%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a WED domain of any one of SEQ ID NOs: 1-198, 221-459, 463-612, 617-668, 674-675, 975-1002, 1260-1321, or a variant thereof. The domain boundaries of the WED domain can be identified by optimal alignment to MG34-1 or MG34-9. The endonuclease may comprise PI (PAM interacting) domain. The PI domain can comprise a sequence with at least 50%, at least 55%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to a PI domain of any one of SEQ ID NOs: 1-198, 221-459, 463-612, 617-668, 674-675, 975-1002, 1260-1321, or a variant thereof. The domain boundaries of the PI domain can be identified by optimal alignment to MG34-1 or MG34-9.

In some cases, the endonuclease is derived from an uncultivated microorganism. In some cases, the tracr ribonucleic acid sequence comprises a sequence with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to at least 50, at least 60, at least 70, at least 80 consecutive nucleotides from any one of SEQ ID NOs: 199-200, 460-461, or 669-673 or a sequence with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to at least 50, at least 60, at least 70, at least 80 consecutive nucleotides of the nonvariable nucleotides of any one of SEQ ID NOs: 201-203,613-616, 677-686, 1003-1022, or 1231-1259.

In some cases, the guide nucleic acid structure comprises SEQ ID NO: 201. In some cases, the guide nucleic acid structure comprises SEQ ID NO: 202. In some cases, the guide nucleic acid structure comprises SEQ ID NO: 203. In some cases, the guide nucleic acid structure comprises SEQ ID NO: 201-203. In some cases, the guide nucleic acid structure comprises SEQ ID NO: 613. In some cases, the guide nucleic acid structure comprises SEQ ID NO: 614. In some cases, the guide nucleic acid structure comprises SEQ ID NO: 615. In some cases, the guide nucleic acid structure comprises SEQ ID NO: 616.

In one aspect, the present disclosure provides an engineered nuclease system. The engineered nuclease system may comprise (a) an engineered guide ribonucleic acid structure. The engineered guide ribonucleic acid structure may comprise a guide ribonucleic acid sequence. The guide ribonucleic acid sequence may be configured to hybridize to a target deoxyribonucleic acid sequence. The engineered guide ribonucleic acid structure may comprise a tracr ribonucleic acid sequence. The tracr ribonucleic acid sequence may be configured to bind to an endonuclease. In some cases, the tracr ribonucleic acid sequence comprises a sequence with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to at least 50, at least 60, at least 70, at least 80 consecutive nucleotides from any one of SEQ ID NOs: 199-200, 460-461, or 669-673 or a sequence with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to at least 15, at least 20, at least 25, at least 30, at least 35, at least 40, at least 45, at least 50, at least 60, at least 70, at least 80 consecutive nucleotides of the nonvariable nucleotides of any one of SEQ ID NOs: 201-203,613-616, 677-686, 1003-1022, or 1231-1259.

In some cases, the engineered nuclease system comprises an endonuclease. The endonuclease may be a class 2 endonuclease. The endonuclease may be a Cas endonuclease. The endonuclease may be a class 2, Type II Cas endonuclease.

In some cases, the endonuclease has a particular molecular weight range. In some embodiments the endonuclease has a molecular weight of about 120 kDa or less, about 110 kDa or less, about 105 kDa or less, about 100 kDa or less, about 95 kDa or less, about 90 kDa or less, about 95 kDa or less, about 80 kDa or less, about 75 kDa or less, about 70 kDa or less, about 65 kDa or less, about 60 kDa or less, about 55 kDa or less, about 50 kDa or less, about 45 kDa or less, about 40 kDa or less, about 35 kDa or less, about 30 kDa or less, about 25 kDa or less, about 20 kDa or less, about 15 kDa or less, or about 10 kDa or less. In some cases, the engineered guide ribonucleic acid structure comprises at least two ribonucleic acid polynucleotides. In some cases, the endonuclease comprises a particular number of residues. The endonuclease can comprise equal to or fewer than about 1,100 residues, equal to or fewer than about 1,000 residues, equal to or fewer than about 950 residues, equal to or fewer than about 900 residues, equal to or fewer than about 850 residues, equal to or fewer than about 800 residues, equal to or fewer than about 750 residues, equal to or fewer than about 700 residues, equal to or fewer than about 650 residues, equal to or fewer than about 600 residues, equal to or fewer than about 550 residues, equal to or fewer than about 500 residues, equal to or fewer than about 450 residues, equal to or fewer than about 400 residues, or equal to or fewer than about 350 residues. The endonuclease can comprise about 700 to about 1,100 residues. The endonuclease can comprise about 400 to about 600 residues. In some cases, the engineered guide ribonucleic acid structure comprises a single ribonucleic acid polynucleotide. The single ribonucleic acid polynucleotide may comprise the guide ribonucleic acid sequence and the tracr ribonucleic acid sequence.

In some cases, the guide ribonucleic acid sequence is complementary to a prokaryotic, bacterial, archaeal, eukaryotic, fungal, plant, mammalian, or human genomic sequence. In some cases, the guide ribonucleic acid sequence is complementary to a prokaryotic genomic sequence. In some cases, the guide ribonucleic acid sequence is complementary to a bacterial genomic sequence. In some cases, the guide ribonucleic acid sequence is complementary to an archaeal genomic sequence. In some cases, the guide ribonucleic acid sequence is complementary to a eukaryotic genomic sequence. In some cases, the guide ribonucleic acid sequence is complementary to a fungal genomic sequence. In some cases, the guide ribonucleic acid sequence is complementary to a plant genomic sequence. In some cases, the guide ribonucleic acid sequence is complementary to a mammalian genomic sequence. In some cases, the guide ribonucleic acid sequence is complementary to a human genomic sequence.

In some cases, the guide ribonucleic acid targeting sequence or spacer is 10-30 nucleotides in length, or 12-28 nucleotides in length, or 15-24 nucleotides in length. In some cases, the endonuclease comprises one or more nuclear localization sequences (NLSs) proximal to an N- or C-terminus of the endonuclease. In some cases, the NLS comprises a sequence selected from SEQ ID NOs: 205-220.

TABLE 1

Examples NLS Sequences that may be used with Cas effectors according to the present disclosure.

| Source | NLS amino acid sequence | SEQ ID NO: |
|---|---|---|
| SV40 NLS | PKKKRKV | 205 |
| nucleoplasmin bipartite | KRPAATKKAGQAKKKK | 206 |
| c-myc | PAAKRVKLD | 207 |
| c-myc | RQRRNELKRSP | 208 |
| hnRNPA1 M9 | NQSSNFGPMKGGNFGGRSSGPYGGGGQYFAKPRNQGGY | 209 |
| Importin- | RMRIZFKNKGKDTAELRRRRVEVSVELRKAKKDEQILKRRNV | 210 |

TABLE 1-continued

Examples NLS Sequences that may be used with Cas effectors according to the present disclosure.

| Source | NLS amino acid sequence | SEQ ID NO: |
|---|---|---|
| alpha IBB domain | | |
| Myoma T protein | VSRKRPRP | 211 |
| Myoma T protein | PPKKARED | 212 |
| p53 | PQPKKKPL | 213 |
| mouse c-abl IV | SALIKKKKMAP | 214 |
| influenza virus NS1 | DRLRR | 215 |
| influenza virus NS1 | PKQKKRK | 216 |
| Hepatitis virus delta antigen | RKLKKKIKKL | 217 |
| mouse Mx1 protein | REKKKFLKRR | 218 |
| human poly (ADP-ribose) polymerase | KRKGDEVDGVDEVAKKKSKK | 219 |
| steroid hormone receptors glucocorticoid | RKCLQAGMNLEARKTKK | 220 |

Included in the current disclosure are variants of any of the enzymes described herein with one or more conservative amino acid substitutions. Such conservative substitutions can be made in the amino acid sequence of a polypeptide without disrupting the three-dimensional structure or function of the polypeptide. Conservative substitutions can be accomplished by substituting amino acids with similar hydrophobicity, polarity, and R chain length for one another. Additionally, or alternatively, by comparing aligned sequences of homologous proteins from different species, conservative substitutions can be identified by locating amino acid residues that have been mutated between species (e.g., non-conserved residues) without altering the basic functions of the encoded proteins. Such conservatively substituted variants may include variants with at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% identity to any one of the endonuclease protein sequences described herein. In some embodiments, such conservatively substituted variants are functional variants. Such functional variants can encompass sequences with substitutions such that the activity of one or more critical active site residues or guide RNA binding residues of the endonuclease are not disrupted. In some embodiments, a functional variant of any of the proteins described herein lacks substitution of at least one of the conserved or functional residues called out in FIG. 4. In some embodiments, a functional variant of any of the proteins described herein lacks substitution of all of the conserved or functional residues called out in FIG. 4. Also provided for by the disclosure herein are altered activity variants of any of the nucleases described herein. Such altered activity variants may comprise an inactivating mutation in one or more catalytic residues identified herein (e.g. in FIG. 4) or generally described for RuvC domains. Such altered activity variants may comprise a change-switch mutation in a catalytic residue of a RuvCI, RuvCII, or RuvCIII domain.

Conservative substitution tables providing functionally similar amino acids are available from a variety of references (see, for e.g., Creighton, Proteins: Structures and Molecular Properties (W H Freeman & Co.; 2nd edition (December 1993)). The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine(S), Threonine (T); and
8) Cysteine (C), Methionine (M)

Included in the current disclosure are variants of any of the endonucleases described herein with sequence identity to particular domains. The domain can be an arginine rich domain (e.g. a domain with PF14239 homology), a REC (recognition) domain, a BH (bridge helix) domain, a WED (wedge) domain, a PI (PAM-interacting) domain, a PF14239 homology domain, or any other domain described herein. In some embodiments, residues encompassing one or more of these domains is identified in a protein by alignment to one of the proteins below (e.g. when one of the proteins below and the protein of interest are optimally aligned), wherein the residue boundaries for example domains are described.

TABLE 2

Example domain boundaries for endonucleases described herein

| | RuvC-I | BH | REC | Domain w/PF14239 homology | RuvC-II | HNH | RuvC-III | WED and PI |
|---|---|---|---|---|---|---|---|---|
| MG34-1 effector | 1-41 | 42-76 | 77-281 | 4-65; 123-339 | 282-323 | 324-459 | 460-551 | 552-747 |
| MG34-9 effector | 1-41 | 42-76 | 77-280 | 4-65; 123-338 | 281-322 | 323-490 | 491-582 | 583-778 |

In some cases, the engineered nuclease system further comprises a single-stranded DNA repair template. In some cases, the engineered nuclease system further comprises a double-stranded DNA repair template. In some cases, the single- or double-stranded DNA repair template comprises from 5' to 3' a first homology arm comprising a sequence of at least 20 nucleotides 5' to the target deoxyribonucleic acid sequence. In some cases, the single- or double-stranded DNA repair template comprises from 5' to 3' a synthetic DNA sequence of at least 10 nucleotides. In some cases, the single- or double-stranded DNA repair template comprises from 5' to 3' a second homology arm comprising a sequence of at least 20 nucleotides 3' to the target sequence. In some cases, the single- or double-stranded DNA repair template comprises from 5' to 3': a first homology arm comprising a sequence of at least 20 nucleotides 5' to the target deoxyribonucleic acid sequence, a synthetic DNA sequence of at least 10 nucleotides, or a second homology arm comprising a sequence of at least 20 nucleotides 3' to the target sequence.

In some cases, the first homology arm comprises a sequence of at least 10, at least 20, at least 30, at least 40, at least 50, at least 60, at least 70, at least 80, at least 90, at least 100, at least 110, at least 120, at least 130, at least 140, at least 150, at least 175, at least 200, at least 250, at least 300, at least 400, at least 500, at least 750, or at least 1000 nucleotides. In some cases, the engineered nuclease system further comprises a source of $Mg^{2+}$. In some cases, the endonuclease and the tracr ribonucleic acid sequence are derived from distinct bacterial species. In some cases, the endonuclease and the tract ribonucleic acid sequence are derived from distinct bacterial species within a same phylum.

In some cases, the endonuclease comprises a sequence with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NOs: 1-24 or 462-488. In some cases, the guide RNA structure comprises an RNA sequence predicted to comprise a hairpin. In some cases, the hair pin comprises a stem and a loop. In some cases, the stem comprises at least 12 pairs, at least 14 pairs, at least 16 pairs or at least 18 pairs or ribonucleotides.

In some cases, the guide RNA structure further comprises a second stem and a second loop. In some cases, the second stem comprises at least 5 pairs, at least 6 pairs, at least 7 pairs, at least 8 pairs, at least 9 pairs or at least 10 pairs of ribonucleotides. In some cases, the guide RNA structure further comprises an RNA structure and this RNA structure comprises at least two hairpins. In some cases, the endonuclease comprises a sequence with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO: 1 and the guide RNA structure comprises an RNA sequence predicted to comprise at least four hairpins. In some cases, each of these four hairpins comprises a stem and a loop.

In some cases, the engineered nuclease system comprises a sequence at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 1. In some cases, the engineered nuclease system comprises the guide RNA structure which comprises a sequence at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to at least one of SEQ ID NO: 199 or the nonvariable nucleotides of SEQ ID NO: 201.

In some cases, the engineered nuclease system comprises a sequence at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NOs: 1-24 or 462-488. In some cases, the engineered nuclease system comprises a sequence at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NOs: 199-200, 460-461, or 669-673 or the nonvariable nucleotides of any one of SEQ ID NOs: 201-203, 613-616, 677-686, 1003-1022, or 1231-1259.

In some cases, the sequence identity is determined by a BLASTP, CLUSTALW, MUSCLE, MAFFT, or CLUSTALW with the Smith-Waterman homology search algorithm parameters. In some cases, the sequence identity is determined by said BLASTP homology search algorithm using parameters of a wordlength (W) of 3, an expectation (E) of 10, and a BLOSUM62 scoring matrix setting gap costs at existence of 11, extension of 1, and using a conditional compositional score matrix adjustment.

In some cases, the endonuclease is not a Cas9 endonuclease, a Cas14 endonuclease, a Cas12a endonuclease, a Cas12b endonuclease, a Cas 12c endonuclease, a Cas12d endonuclease, a Cas 12e endonuclease, a Cas13a endonuclease, a Cas13b endonuclease, a Cas13c endonuclease, or a Cas 13d endonuclease. In some cases, the endonuclease has less than less than 80% identity, less than 75% identity, less than 70% identity, less than 65% identity, less than 60% identity, less than 55% identity, or less than 50% identity to a Cas9 endonuclease.

In one aspect, the present disclosure provides an engineered guide RNA comprising (a) a DNA-targeting segment. In some cases, the DNA-targeting segment comprises a nucleotide sequence that is complementary to a target sequence in a target DNA molecule. In some cases, the engineered single guide ribonucleic acid polynucleotide comprises a protein-binding segment. The protein-binding segment comprises two complementary stretches of nucleotides that hybridize to form a double-stranded RNA (dsRNA) duplex. In some cases, the two complementary stretches of nucleotides are covalently linked to one another with intervening nucleotides. In some cases, the engineered guide ribonucleic acid polynucleotide is configured to form a complex with an endonuclease comprising a variant having at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NOs: 1-198, 221-459, 463-612, 617-668, 674-675, 975-1002, 1260-1321, or a variant thereof.

In some cases, the DNA-targeting segment is positioned 5' of both of the two complementary stretches of nucleotides. In some cases, the protein binding segment comprises a sequence at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to any one of SEQ ID NOs: 199-200, 460-461, 669-673 or the nonvariable nucleotides of any one of SEQ ID NOs: 201-203, 613-616, 677-686, 1003-1022, or 1231-1259. In some cases, a deoxyribonucleic acid polynucleotide encodes the engineered guide ribonucleic acid polynucleotide described herein.

In one aspect, the present disclosure provides a nucleic acid comprising an engineered nucleic acid sequence. In some cases, the engineered nucleic acid sequence is optimized for expression in an organism. In some cases, the nucleic acid encodes an endonuclease. The endonuclease may be a Cas endonuclease. The endonuclease may be a class 2 endonuclease. The endonuclease may be a class 2, type II Cas endonuclease. In some cases, the endonuclease comprises a RuvC domain and an HNH domain. In some cases, the endonuclease is derived from an uncultivated microorganism. In some cases, the endonuclease has a particular molecular weight range. In some embodiments the endonuclease has a molecular weight of about 120 kDa or less, about 110 kDa or less, about 105 kDa or less, about 100 kDa or less, about 95 kDa or less, about 90 kDa or less, about 95 kDa or less, about 80 kDa or less, about 75 kDa or less, about 70 kDa or less, about 65 kDa or less, about 60 kDa or less, about 55 kDa or less, about 50 kDa or less, about 45 kDa or less, about 40 kDa or less, about 35 kDa or less, about 30 kDa or less, about 25 kDa or less, about 20 kDa or less, about 15 kDa or less, or about 10 kDa or less. In some cases, the engineered guide ribonucleic acid structure comprises at least two ribonucleic acid polynucleotides. In some cases, the endonuclease comprises a particular number of residues. The endonuclease can comprise equal to or fewer than about 1,100 residues, equal to or fewer than about 1,000 residues, equal to or fewer than about 950 residues, equal to or fewer than about 900 residues, equal to or fewer than about 850 residues, equal to or fewer than about 800 residues, equal to or fewer than about 750 residues, equal to or fewer than about 700 residues, equal to or fewer than about 650 residues, equal to or fewer than about 600 residues, equal to or fewer than about 550 residues, equal to or fewer than about 500 residues, equal to or fewer than about 450 residues, equal to or fewer than about 400 residues, or equal to or fewer than about 350 residues. The endonuclease can comprise about 700 to about 1,100 residues. The endonuclease can comprise about 400 to about 600 residues. In some cases, the endonuclease comprises SEQ ID NOs: 1-198, 221-459, 463-612, 617-668, 674-675, 975-1002, 1260-1321, or a variant thereof having at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity thereto. In some cases, the endonuclease further comprises a sequence encoding one or more nuclear localization sequences (NLSs) proximal to an N- or C-terminus of said endonuclease. In some cases, the NLS comprises a sequence selected from SEQ ID NOs: 205-220.

In some cases, the organism is prokaryotic, bacterial, eukaryotic, fungal, plant, mammalian, rodent, or human. In some cases, the organism is prokaryotic. In some cases, the organism is bacterial. In some cases, the organism is eukaryotic. In some cases, the organism is fungal. In some cases, the organism is plant. In some cases, the organism is mammalian. In some cases, the organism is rodent. In some cases, the organism is human. Where the organism is prokaryotic or bacterial, then the organism may be a different organism from an organism from which the endonuclease is derived. In some cases, the organisms is not the uncultivated microorganism.

In one aspect, the present disclosure provides a vector which comprises a nucleic acid sequence. In some cases, the nucleic acid sequence encodes an endonuclease. In some cases, the endonuclease is a Cas endonuclease. In some cases, the endonuclease is a class 2 endonuclease. In some cases, the endonuclease is a class 2, type II Case endonuclease. The endonuclease may comprise a RuvC-I domain and an HNH domain. In some cases, the endonuclease is derived from an uncultivated microorganism. In some cases, the endonuclease has a particular molecular weight range. In some embodiments the endonuclease has a molecular weight of about 120 kDa or less, about 110 kDa or less, about 105 kDa or less, about 100 kDa or less, about 95 kDa or less, about 90 kDa or less, about 95 kDa or less, about 80 kDa or less, about 75 kDa or less, about 70 kDa or less, about 65 kDa or less, about 60 kDa or less, about 55 kDa or less, about 50 kDa or less, about 45 kDa or less, about 40 kDa or less, about 35 kDa or less, about 30 kDa or less, about 25 kDa or less, about 20 kDa or less, about 15 kDa or less, or about 10 kDa or less. In some cases, the engineered guide ribonucleic acid structure comprises at least two ribonucleic acid polynucleotides. In some cases, the endonuclease comprises a particular number of residues. The endonuclease can comprise equal to or fewer than about 1,100 residues, equal to or fewer than about 1,000 residues, equal to or fewer than about 950 residues, equal to or fewer than about 900 residues, equal to or fewer than about 850 residues, equal to or fewer than about 800 residues, equal to or fewer than about 750 residues, equal to or fewer than about 700 residues, equal to or fewer than about 650 residues, equal to or fewer than about 600 residues, equal to or fewer than about 550 residues, equal to or fewer than about 500 residues, equal to or fewer than about 450 residues, equal to or fewer than about 400 residues, or equal to or fewer than about 350 residues. The endonuclease can comprise about 700 to about 1,100 residues. The endonuclease can comprise about 400 to about 600 residues.

In some aspects, the present disclosure provides for an endonuclease described herein configured to induce a double stranded break proximal to said target locus 5' to a protospacer adjacent motif (PAM). The endonuclease can induce a double-stranded break 6-8 nucleotides from the PAM or 7 nucleotides from the PAM. In some aspects, the present disclosure provides for an endonuclease described herein configured to induce a single-stranded break proximal to said target locus 5' to a protospacer adjacent motif (PAM). The endonuclease can induce a single-stranded break 6-8 nucleotides from the PAM or 7 nucleotides from the PAM. In some cases, an endonuclease configured to induce a single-stranded break comprises an inactivating mutation in one or more catalytic residues of an endonuclease described herein.

In some aspects, the present disclosure provides for an endonuclease system described herein configured to cause a chemical modification of a nucleotide base within or proximal to a target locus targeted by the endonuclease system. In this case, chemical modification of a nucleotide base generally refers to modification of the chemical moiety involved in base-pairing rather than modification of the sugar or phosphate portion of the nucleotide. The chemical modification can comprise deamination of an adenosine or a cytosine nucleotide. In some cases, endonuclease systems configured to cause a chemical modification comprises an endonuclease having a base editor coupled or fused in frame to said endonuclease. The endonuclease to which the base editor is fused or coupled can comprise a deactivating mutation in at least one catalytic residue of the endonuclease (e.g. in the RuvC domain). The base editor can be fused N- or C-terminally to said endonuclease, or linked via chemical conjugation. Base editors can include any adenosine or cytosine deaminases, including but not limited to Adenosine Deaminase RNA Specific 1 (ADAR1), Adenosine Deaminase RNA Specific 2 (ADAR2), Apolipoprotein B MRNA Editing Enzyme Catalytic Subunit 1 (APOBEC1), Apolipoprotein B MRNA Editing Enzyme Catalytic Subunit 2 (APOBEC2), Apolipoprotein B MRNA Editing Enzyme Catalytic Subunit 3A (APOBEC3A), Apolipoprotein B MRNA Editing Enzyme Catalytic Subunit 3B (APOBEC3B), Apolipoprotein B MRNA Editing Enzyme Catalytic Subunit 3C (APOBEC3C), Apolipoprotein B MRNA Editing Enzyme Catalytic Subunit 3D (APOBEC3D), Apolipoprotein B MRNA Editing Enzyme Catalytic Subunit 3F (APOBEC3F), Apolipoprotein B MRNA Editing Enzyme Catalytic Subunit 3G (APOBEC3G), Apolipoprotein B MRNA Editing Enzyme Catalytic Subunit 3H (APOBEC3H), or Apolipoprotein B MRNA Editing Enzyme Catalytic Subunit 4 (APOBEC4), or a functional fragment thereof. The base editor can comprise a yeast, eukaryotic, mammalian, or human base editor.

In some aspects, the present disclosure provides for an endonuclease system described herein configured to cause a chemical modification of histone within or proximal to a target locus targeted by the endonuclease system. In some cases, endonuclease systems configured to cause a chemical modification of a histone comprise an endonuclease having a histone editor coupled or fused in frame to said endonuclease. The histone editor can be coupled or fused N- or C-terminally to the endonuclease. In some embodiments, the chemical modification can comprise methylation, acetylation, demethylation, or deacetylation. The endonuclease to which the histone editor is fused or coupled can comprise a deactivating mutation in at least one catalytic residue of the endonuclease (e.g. in the RuvC domain). The histone editor can comprise a histone methyltransferase (e.g. ASH1L, DOT1L, EHMT1, EHMT2, EZH1, EZH2, MLL, MLL2, MLL3, MLL4, MLL5, NSD1, PRDM2, SET, SETBP1, SETD1A, SETD1B, SETD2, SETD3, SETD4, SETD5, SETD6, SETD7, SETD8, SETD9, SETDB1, SETDB2, SETMAR, SMYD1, SMYD2, SMYD3, SMYD4, SMYD5, SUV39H1, SUV39H2, SUV420H1, or SUV420H2), a histone demethylase (e.g. the KDM1, KDM2, KDM3, KDM4, KDM5, or KDM6 families), a histone acetyltransferase (e.g. GNATs or HAT family acetyltransferases), or a histone deacetylase (e.g. HDAC1, HDAC2, HDAC 3, HDAC4, HDAC5, HDAC6, HDAC7, HDAC8, HDAC9, HDAC10, HDAC11, SIRT1, SIRT2, SIRT3, SIRT4, SIRT5, SIRT6, or SIRT7). The histone editor can comprise a yeast, eukaryotic, mammalian, or human histone editor.

In one aspect, the present disclosure provides a vector comprising the nucleic acid described herein. In some cases, the vector further comprises a nucleic acid encoding an engineered guide ribonucleic acid structure. The engineered guide ribonucleic acid structure may be configured to form a complex with the endonuclease. In some cases, the engineered guide ribonucleic acid structure comprises a guide ribonucleic acid sequence. In some cases, the guide ribonucleic acid sequence is configured to hybridize to a target deoxyribonucleic acid sequence. In some cases, the engineered guide ribonucleic acid structure comprises a tracr ribonucleic acid sequence. In some cases, the tracr ribonucleic acid sequence is configured to bind to the endonuclease. In some cases, the vector is a plasmid, a minicircle, a CELiD, an adeno-associated virus (AAV) derived virion, or a lentivirus.

In one aspect, the present disclosure provides a cell comprising any of the vectors described herein.

In one aspect, the present disclosure provides a method of manufacturing an endonuclease. The method can comprise cultivating any of the cells described herein.

In one aspect, the present disclosure provides a method for binding, cleaving, marking, or modifying a double-stranded deoxyribonucleic acid polynucleotide. The method may comprise contacting the double-stranded deoxyribonucleic acid polynucleotide with an endonuclease. In some cases, the endonuclease is a Cas endonuclease. In some cases, the endonuclease is a class 2 endonuclease. In some cases, the endonuclease is a class 2, type II Cas endonuclease. The endonuclease may complex with an engineered guide ribonucleic acid structure. In some cases, the engineered guide ribonucleic acid structure is configured to bind to the endonuclease and the double-stranded deoxyribonucleic acid polynucleotide. In some cases, the double-stranded deoxyribonucleic acid polynucleotide comprises a protospacer adjacent motif (PAM). In some cases, the endonuclease has a molecular weight of about 120 kDa or less, about 110 kDa or less, about 100 kDa or less, about 90 kDa or less, about 80 kDa or less, about 70 kDa or less, about 60 kDa or less, about 50 kDa or less, about 40 kDa or less, about 30 kDa or less, about 20 kDa or less, or about 10 kDa or less. In some cases, the endonuclease comprises a variant with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NOs: 1-198, 221-459, 463-612, 617-668, 674-675, 975-1002, 1260-1321, or a variant thereof.

In one aspect, the present disclosure provides a method for binding, cleaving, marking, or modifying a double-stranded deoxyribonucleic acid polynucleotide. The method may comprise contacting the double-stranded deoxyribonucleic acid polynucleotide with an endonuclease. In some cases, the endonuclease is a Cas endonuclease. In some cases, the endonuclease is a class 2 endonuclease. In some cases, the endonuclease is a class 2, type II Cas endonuclease. The endonuclease may complex with an engineered guide ribonucleic acid structure. In some cases, the engineered guide ribonucleic acid structure may be configured to bind to the endonuclease and the double-stranded deoxyribonucleic acid polynucleotide. In some cases, the double-stranded deoxyribonucleic acid polynucleotide comprises a protospacer adjacent motif (PAM). In some cases, the PAM is NGG. In some cases, the endonuclease comprises a variant with at least 50%, at least 55%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to any one of SEQ ID NOs: 1-198, 221-459, 463-612, 617-668, 674-675, 975-1002, 1260-1321, or a variant thereof.

In some cases, the endonuclease is not a Cas9 endonuclease, a Cas14 endonuclease, a Cas12a endonuclease, a Cas12b endonuclease, a Cas 12c endonuclease, a Cas12d endonuclease, a Cas 12e endonuclease, a Cas13a endonuclease, a Cas13b endonuclease, a Cas13c endonuclease, or a Cas 13d endonuclease. In some cases, the endonuclease is derived from an uncultivated microorganism. In some cases, the double-stranded deoxyribonucleic acid polynucleotide is a prokaryotic, archaeal, bacterial, eukaryotic, plant, fungal, mammalian, rodent, or human double-stranded deoxyribonucleic acid polynucleotide. In some cases, the double-stranded deoxyribonucleic acid polynucleotide is a prokaryotic, archaeal, or bacterial double-stranded deoxyribonucleic acid polynucleotide from a species other than a species from which the endonuclease is derived.

In one aspect, the present disclosure provides a method of modifying a target nucleic acid locus. The method may comprise delivering to the target nucleic acid locus the engineered nuclease system described herein. In some cases, the endonuclease is configured to form a complex with the engineered guide ribonucleic acid structure. In some cases, the complex is configured such that upon binding of the complex to the target nucleic acid locus, the complex modifies the target nucleic locus. In some cases, modifying the target nucleic acid locus comprises binding, nicking, cleaving, or marking the target nucleic acid locus.

In some cases, the target nucleic acid locus comprises deoxyribonucleic acid (DNA) or ribonucleic acid (RNA). In some cases, the target nucleic acid comprises genomic eukaryotic DNA, viral DNA, or bacterial DNA. In some cases, the target nucleic acid comprises bacterial DNA. The bacterial DNA may be derived from a bacterial species different to a species from which the endonuclease was derived. In some cases, the target nucleic acid locus is in vitro. In some cases, the nucleic acid locus is within a cell. In some cases, the endonuclease and the engineered guide nucleic acid structure are provided encoded on separate nucleic acid molecules. In some cases, the cell is a prokaryotic cell, a bacterial cell, a eukaryotic cell, a fungal cell, a plant cell, an animal cell, a mammalian cell, a rodent cell, a primate cell, or a human cell. In some cases, the cell is derived from a species different to a species from which the endonuclease is derived.

In some cases, delivering the engineered nuclease system to the target nucleic acid locus comprises delivering the nucleic acid described herein or the vector described herein. In some cases, delivering the engineered nuclease system to the target nucleic acid locus comprises delivering a nucleic acid comprising an open reading frame encoding the endonuclease. In some cases, the nucleic acid comprises a promoter to which the open reading frame encoding the endonuclease is operably linked. In some cases, delivering the engineered nuclease system to the target nucleic acid locus comprises delivering a capped mRNA containing the open reading frame encoding said endonuclease. In some cases, delivering the engineered nuclease system to said target nucleic acid locus comprises delivering a translated polypeptide.

In some cases, delivering the engineered nuclease system to the target nucleic acid locus comprises delivering a deoxyribonucleic acid (DNA) encoding the engineered guide ribonucleic acid structure operably linked to a ribonucleic acid (RNA) pol III promoter. In some cases, the endonuclease induces a single-stranded break or a double-stranded break at or proximal to the target locus.

Systems of the present disclosure may be used for various applications, such as, for example, nucleic acid editing (e.g., gene editing), binding to a nucleic acid molecule (e.g., sequence-specific binding). Such systems may be used, for example, for addressing (e.g., removing or replacing) a genetically inherited mutation that may cause a disease in a subject, inactivating a gene in order to ascertain its function in a cell, as a diagnostic tool to detect disease-causing genetic elements (e.g. via cleavage of reverse-transcribed viral RNA or an amplified DNA sequence encoding a disease-causing mutation), as deactivated enzymes in combination with a probe to target and detect a specific nucleotide sequence (e.g. sequence encoding antibiotic resistance int bacteria), to render viruses inactive or incapable of infecting host cells by targeting viral genomes, to add genes or amend metabolic pathways to engineer organisms to produce valuable small molecules, macromolecules, or secondary metabolites, to establish a gene drive element for evolutionary selection, to detect cell perturbations by foreign small molecules and nucleotides as a biosensor.

EXAMPLES

Example 1—Discovery of New Cas Effectors by Metagenomics

Metagenomic Mining

Metagenomic samples were collected from sediment, soil and animal. Deoxyribonucleic acid (DNA) was extracted with a Zymobiomics DNA mini-prep kit and sequenced on an Illumina HiSeq® 2500. Samples were collected with consent of property owners. DNA was extracted from samples using either the Qiagen DNeasy PowerSoil Kit or the ZymoBIOMICS DNA Miniprep Kit. DNA was sent for sequencing library preparation (Illumina TruSeq) and sequencing on an Illumina HiSeq 4000 or Novaseq to the Vincent J. Coates Genomics Sequencing Laboratory at UC Berkeley (paired 150 base pair (bp) reads with a 400-800 bp target insert size). Additionally, publicly available high temperature, as well as soil and ocean metagenomic sequencing data were downloaded from the NCBI SRA. Sequencing reads were trimmed using BBMap (Bushnell B., sourceforge.net/projects/bbmap/) and assembled with Megahit (paperpile.com/c/QSZG6K/clMrh). Protein sequences were predicted with Prodigal (paperpile.com/c/QSZG6K/BJ60W). HMM profiles of documented Type II CRISPR nucleases were built and searched against all predicted proteins using HMMER3 (hmmer.org). CRISPR arrays were predicted on assembled contigs with Minced (github.com/ctSkennerton/minced or paperpile.com/c/QSZG6K/OPC44). Taxonomy was assigned to proteins with Kaiju paperpile.com/c/QSZG6K/nMi6k and contig taxonomy was determined by finding the consensus of all encoded proteins.

Predicted and reference (e.g. SpCas9, SaCas9, and AsCas9) Type II effector proteins were aligned with MAFFT (paperpile.com/c/QSZG6K/sVHNH) and phylogenetic trees were inferred using FastTree2 (paperpile.com/c/QSZG6K/osZNM). Novel families were identified from clades composed of sequences recovered from this study. From within families, candidates were selected if they contained all components for laboratory analysis (i.e. they were found on a well-assembled and annotated contig with a CRISPR array and predicted tracrRNA). Selected representative and reference sequences were aligned using MUSCLE (paperpile.com/c/QSZG6K/ITOla) to identify catalytic and PAM interacting residues.

This metagenomic workflow resulted in the delineation of the SMART (SMall ARchaeal-associaTed) endonuclease systems described herein.

Discovery of SMART Endonucleases Containing Active Residue Signatures

Figures 21A, 21B:
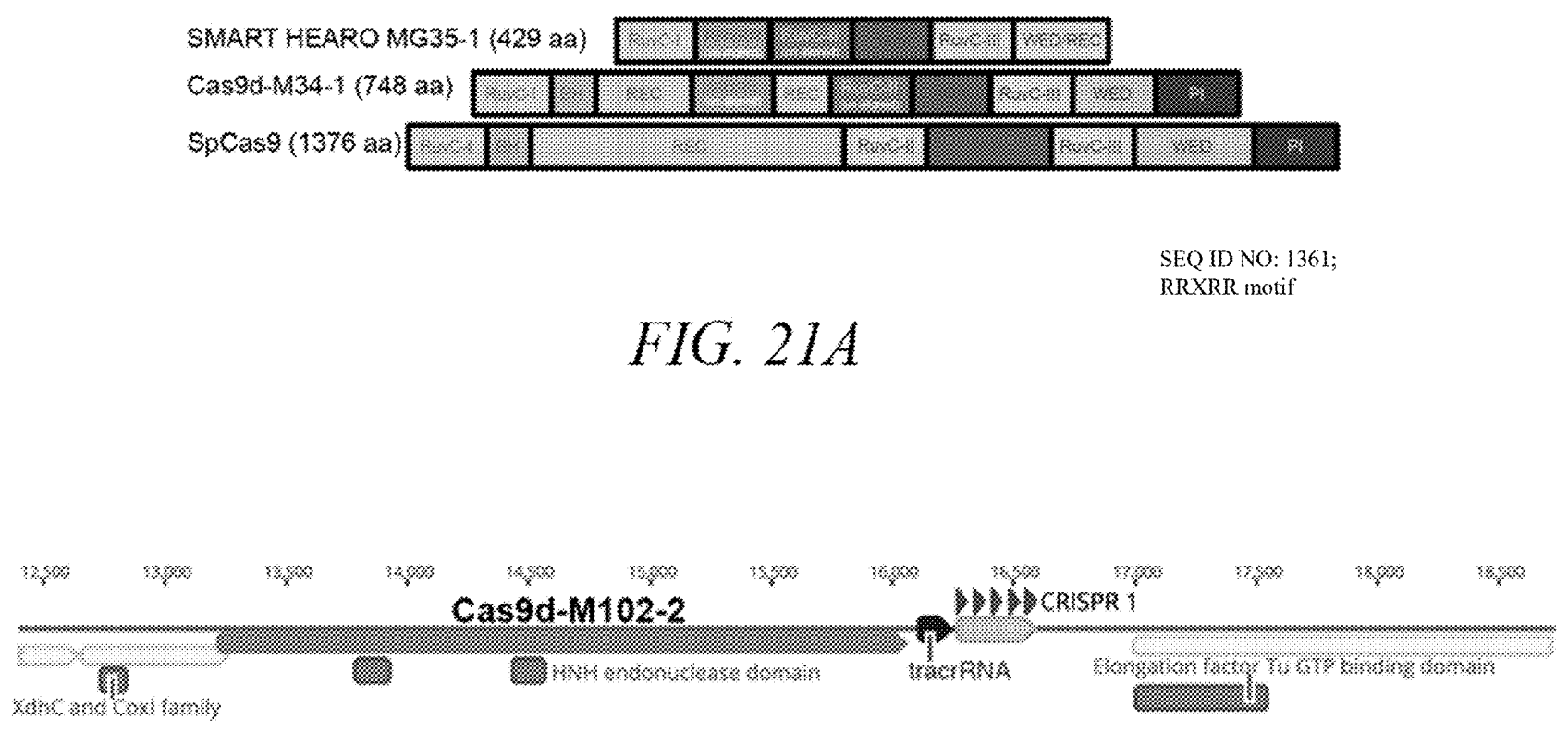

Mining of tens of thousands of high quality CRISPR Cas systems assembled from metagenomic data uncovered novel effectors containing both RuvC and HNH domains, but that were of unusually small size (<900 aa) (FIG. 21A). These effector nucleases showed low sequence similarity (<20% amino acid identity) to archaeal Cas9 endonucleases as a reference point. Phylogenetic analysis of effector protein sequences indicated that the SMART systems are a divergent group relative to well-studied Type II systems from subtype A, B, or C (FIGS. 1A and 21B).

Figure 3A:
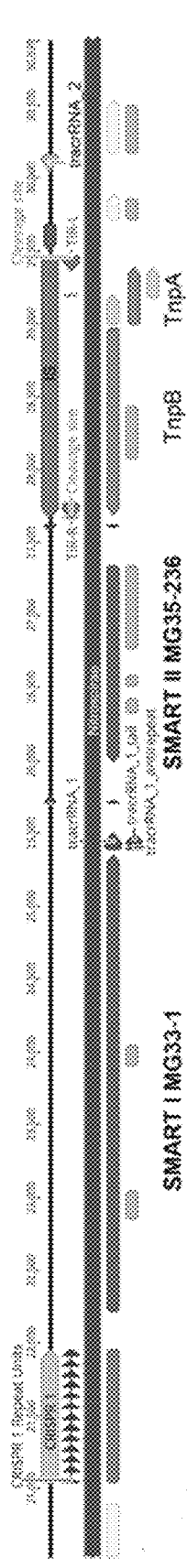
FIG. 3A-FIG. 3D depicts the genomic context of 'small' Type II nucleases MG33-1, MG35-236. SMART nucleases and CRISPR accessory proteins are shown as dark grey arrows, other genes are depicted as light grey arrows. Domains predicted for all genes in a genomic fragment are shown as grey boxes under the arrows. Shown are.
Figure 3B:
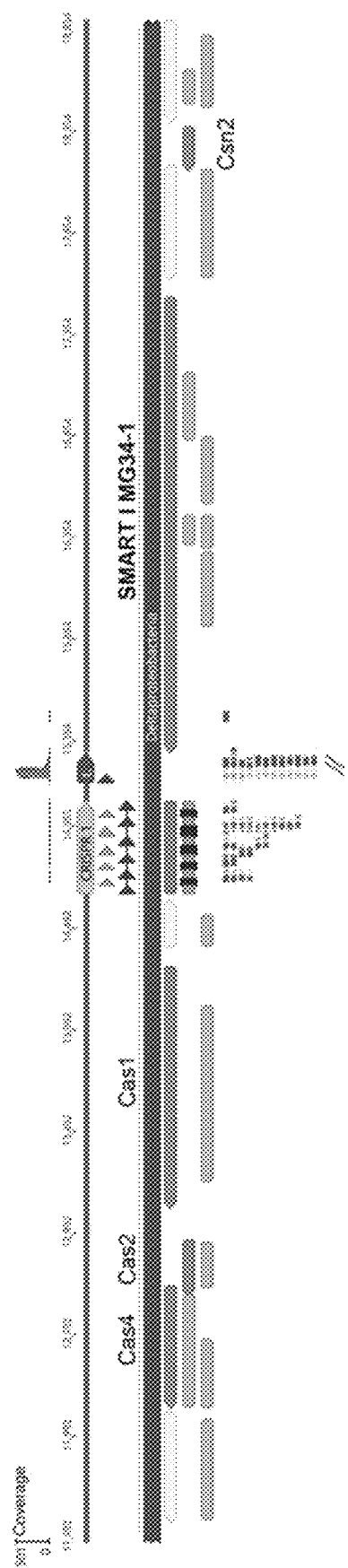
Figures 3C, 3D:
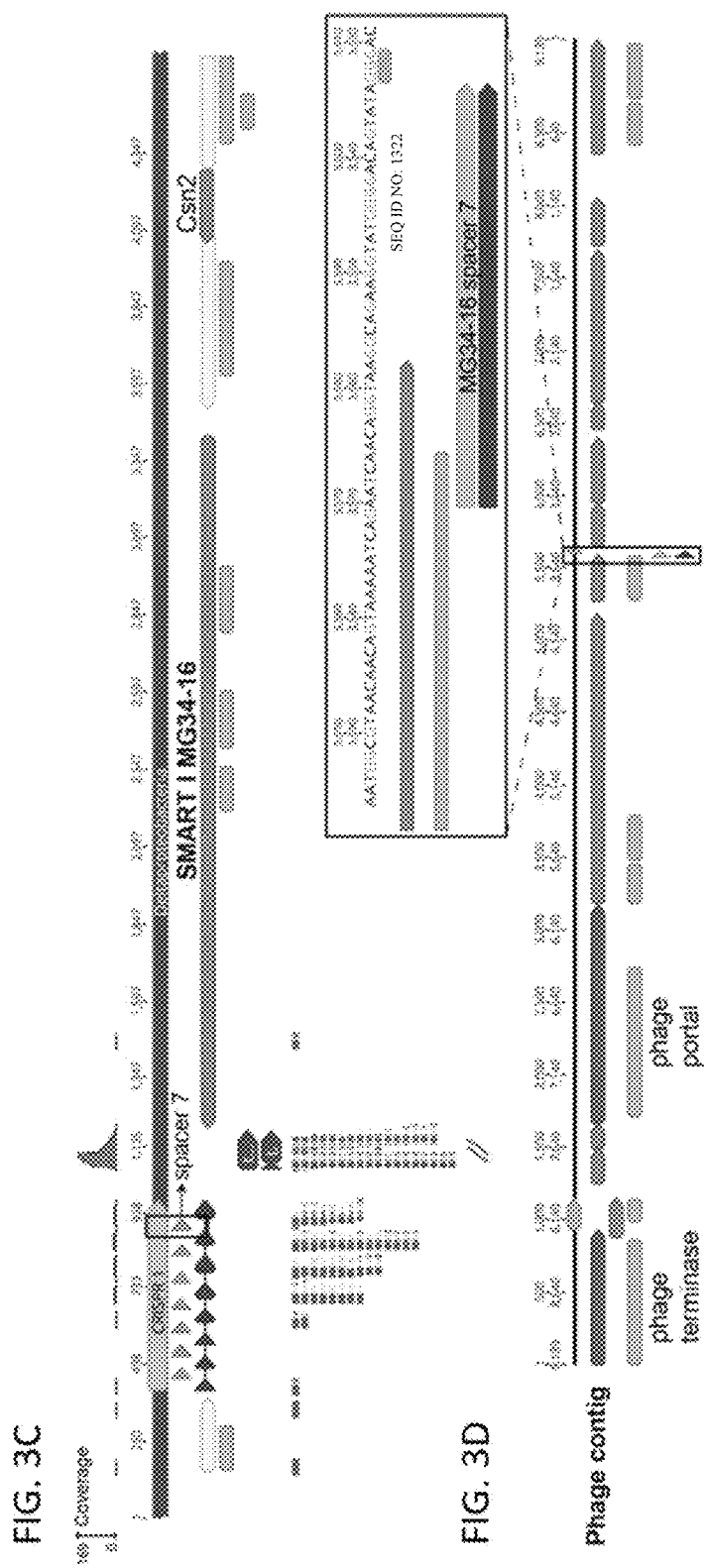
Figure 4B:
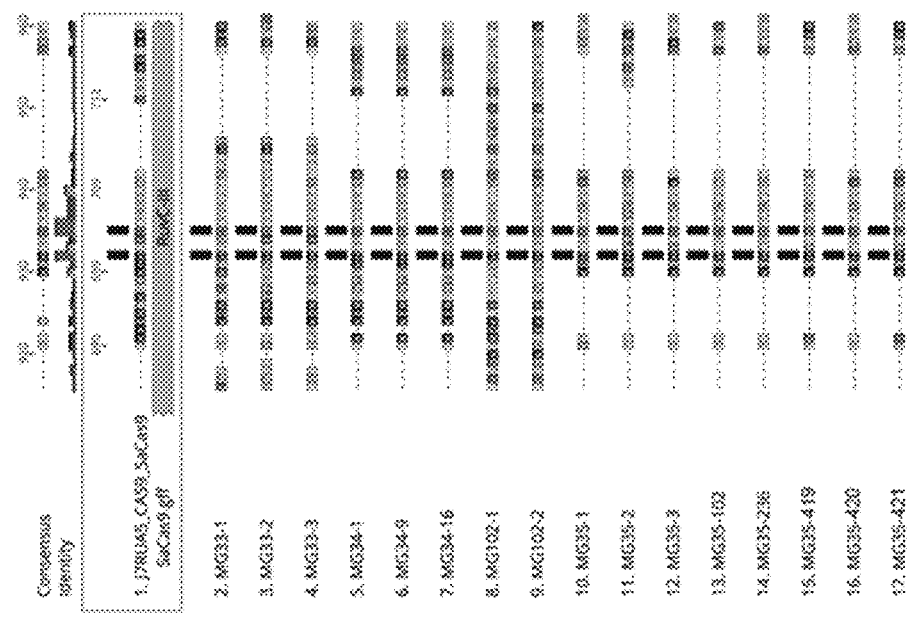
FIG. 4A-FIG. 4C shows a multiple sequence alignment of example SMART endonucleases (MG33-1 (SEQ ID NO: 1), MG33-2 (SEQ ID NO: 463), MG33-3 (SEQ ID NO: 464), MG34-1 (SEQ ID NO: 2), MG 34-9 (SEQ ID NO: 10), MG34-16 (SEQ ID NO: 17), MG 102-1 (SEQ ID NO: 581), MG102-2 (SEQ ID NO: 582), MG35-1 (SEQ ID NO: 25), MG 35-2 (SEQ ID NO: 26), MG 35-3 (SEQ ID NO: 27), MG 35-102 (SEQ ID NO: 126), MG35-236 (SEQ ID NO: 284), MG35-419 (SEQ ID NO: 222), MG35-420 (SEQ ID NO: 223), and MG 35-421 (SEQ ID NO: 224)), where the sequence of SaCas9 was used as reference domains are shown as a rectangles below the reference sequence, and catalytic residues are shown as squares above each sequence. Shown are.
Figure 4A:
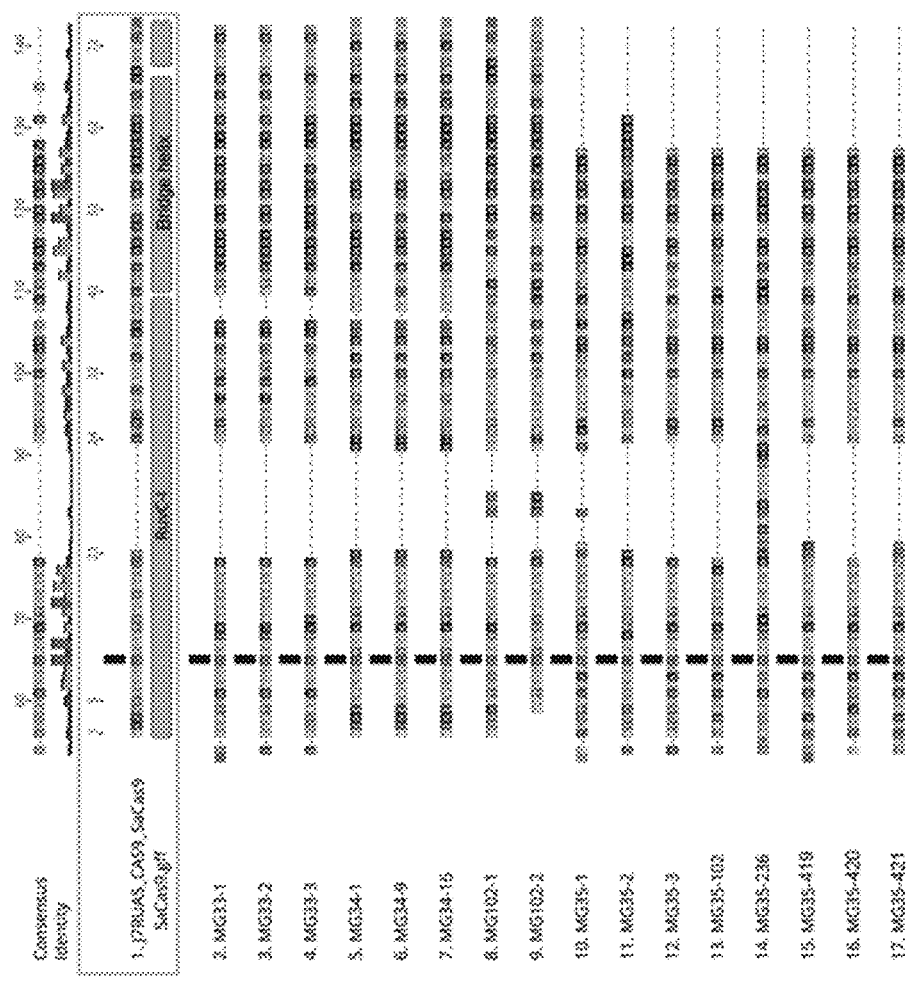
Figure 4C:
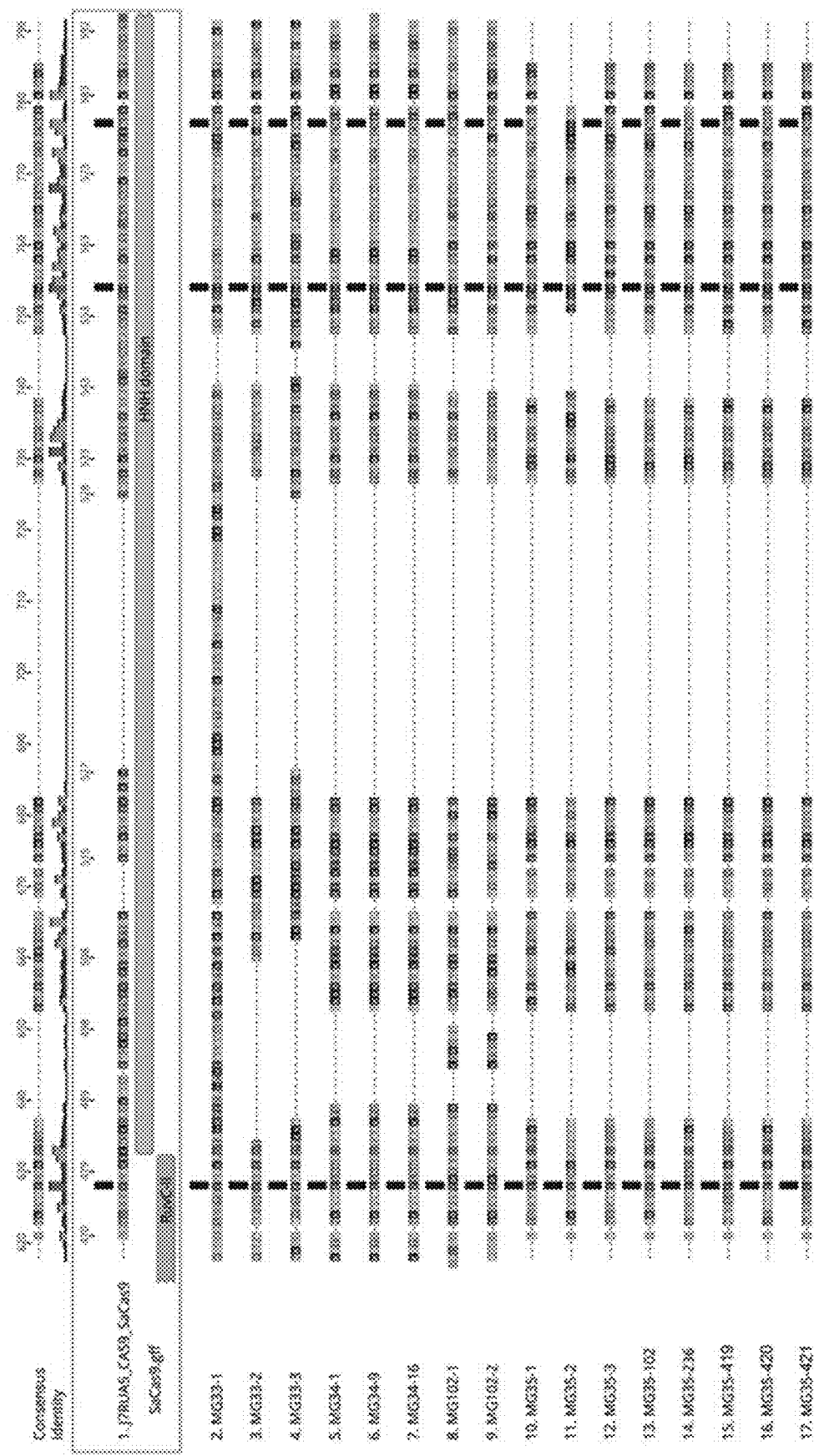

These compact "SMART" effectors (~400-1000 amino acids, FIG. 2) appeared in loci in the genome adjacent to CRISPR arrays. Some of these adjacent SMART loci also included sequences predicted to encode tracrRNAs and the CRISPR adaptation genes (e.g. genes involved in spacer acquisition) cas1, cas2, or cas4 within the same operon (FIGS. 3 and 21A). Despite their compact size, SMART effectors contain six putative HNH and RuvC catalytic residues when aligned with a reference SaCas9 sequence (FIG. 4). In addition, 3D structure predictions identified residues involved in guide and target binding, as well as in recognition of a PAM, suggesting that that the SMART effectors are active dsDNA endonucleases.

Multiple Groups of SMART Endonucleases

Figure 7B:
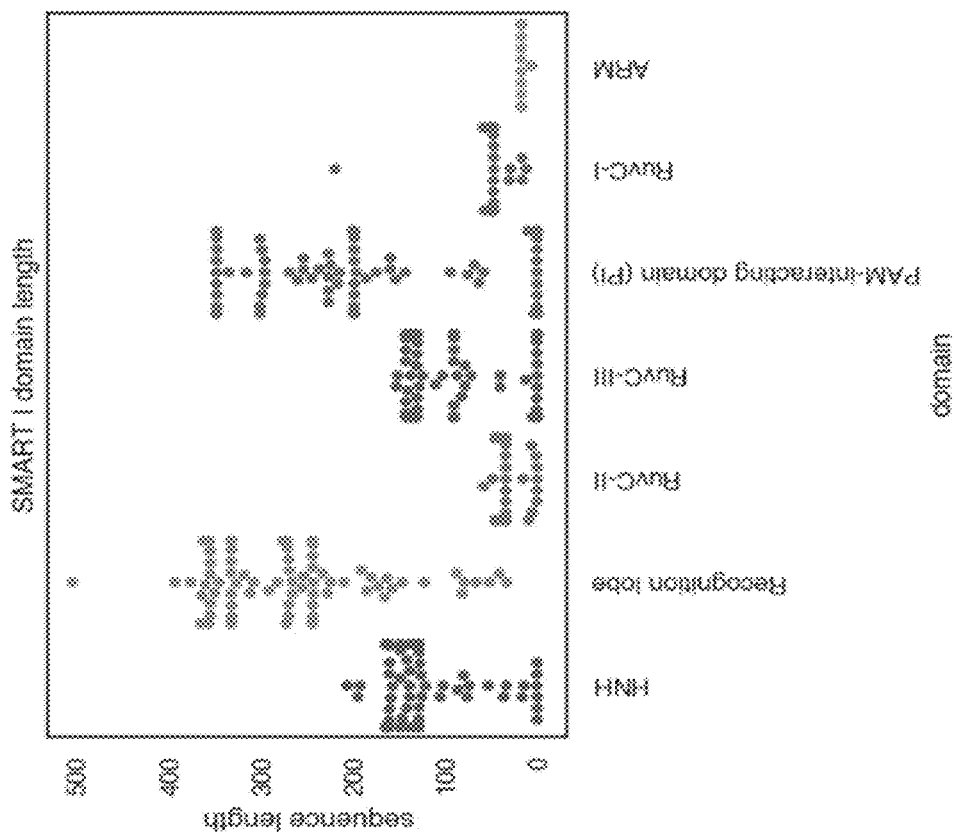
FIG. 7A-FIG. 7B illustrates various features of SMART enzymes. Shown are (FIG. 7A) a dot plot showing identity of SMART I domains of various enzymes depicted herein versus those of spCas9 showing that these have a maximum of about 35% sequence identity.
Figure 7A:
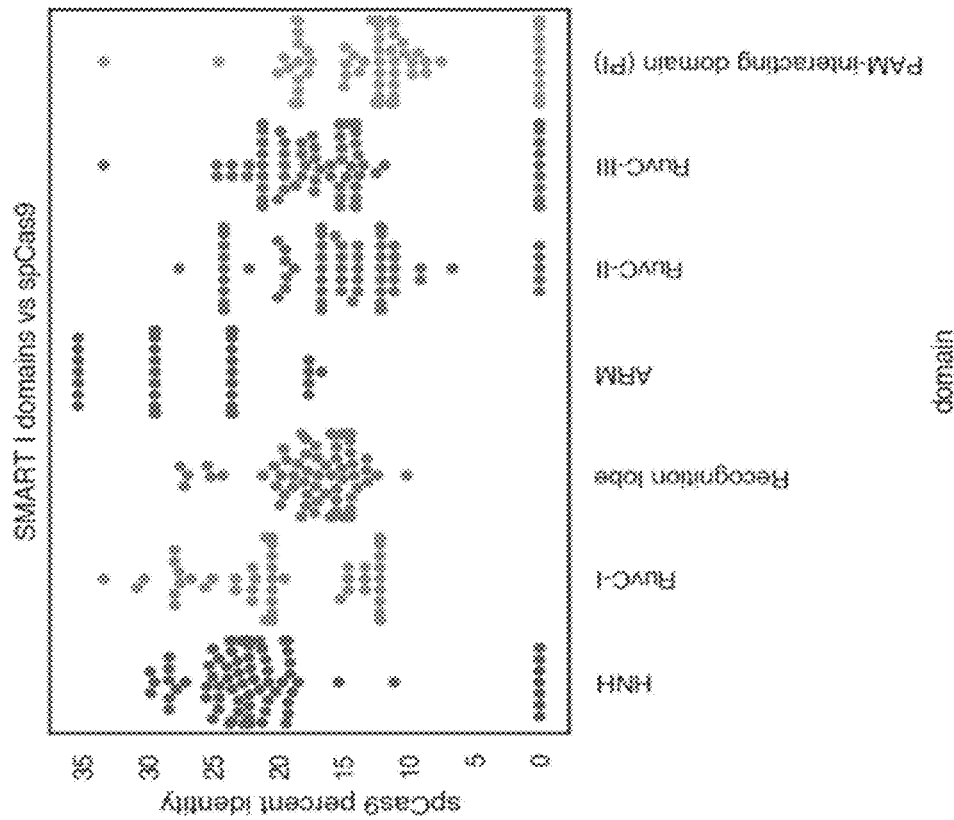

Based on the location of important catalytic and binding residues, SMART nucleases comprise three RuvC domains, an arginine rich region usually containing an RRxRR motif (SEQ ID NO: 1361) (e.g. a domain with PF14239 homology), an HNH endonuclease domain, and a putative recognition domain (FIG. 5 and FIG. 6). These domains share low sequence similarity with reference sequences (FIG. 7). In addition, SMART effectors, as well as reference archaeal sequences, contain RRxRR ("RRXRR" motif is SEQ ID NO: 1361) and zinc-binding ribbon motifs (CX[2-4]C or CX[2-4]H) significantly more frequently than Cas9 nucleases (FIG. 8). In addition, unlike Cas9 effector sequences, most SMART effectors contain significant hits to the Pfam domain PF14239, which is often associated with diverse endonucleases. Based upon differences in SMART effector size, phylogenetic relationship, and both operon and domain architecture, we classified these systems into two primary groups: SMART I and SMART II. The salient features of these groups are outlined in Table 3 below, which also illustrates differences compared to Class 2, Type II A/B/C Cas enzymes.

TABLE 3

Attributes of SMART I and II group enzymes described herein

| Attribute | SMART I | SMART II | Type II: A, B, C |
|---|---|---|---|
| Zn-binding residues | yes | yes | no |
| Bridge helix | yes | no | yes |
| PAM interacting and WED domain | yes | no | yes |
| RRxRR motif (SEQ ID NO: 1361) | yes | yes | no |
| REC domain | Novel domain w/homology to PF14239 | Novel domain at C-terminus | Cas9 REC domain |
| Domain w/ PF14239 homology | yes | yes | no |
| Monophyletic clade | yes | no | yes |
| Related to TnpB | yes | yes | yes |
| Operon contains IS605 Tns repeats | no | sometimes | no |
| <900 aa | sometimes | yes | no |
| CRISPR-associated | yes | sometimes | yes |
| Contains RuvC and HNH | yes | yes | yes |

Figure 21C:
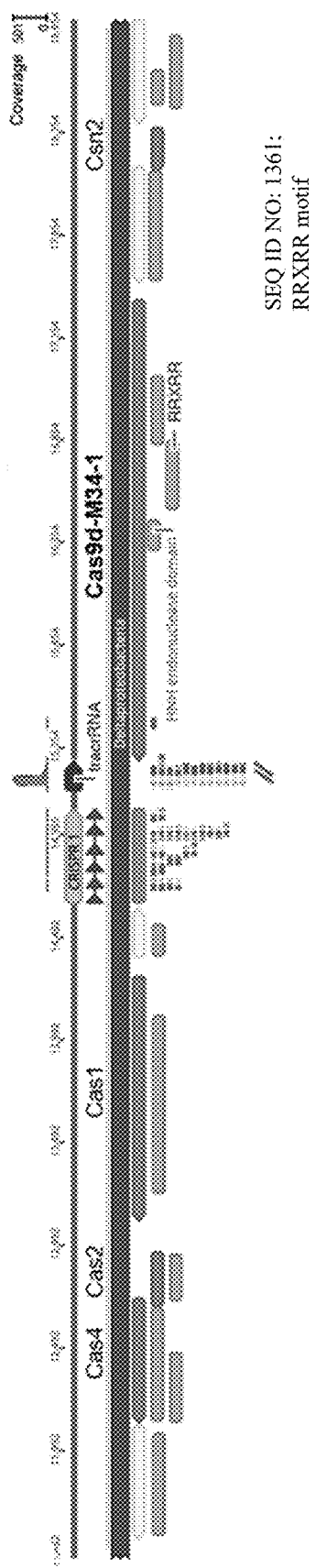
Figures 21E, 21F:
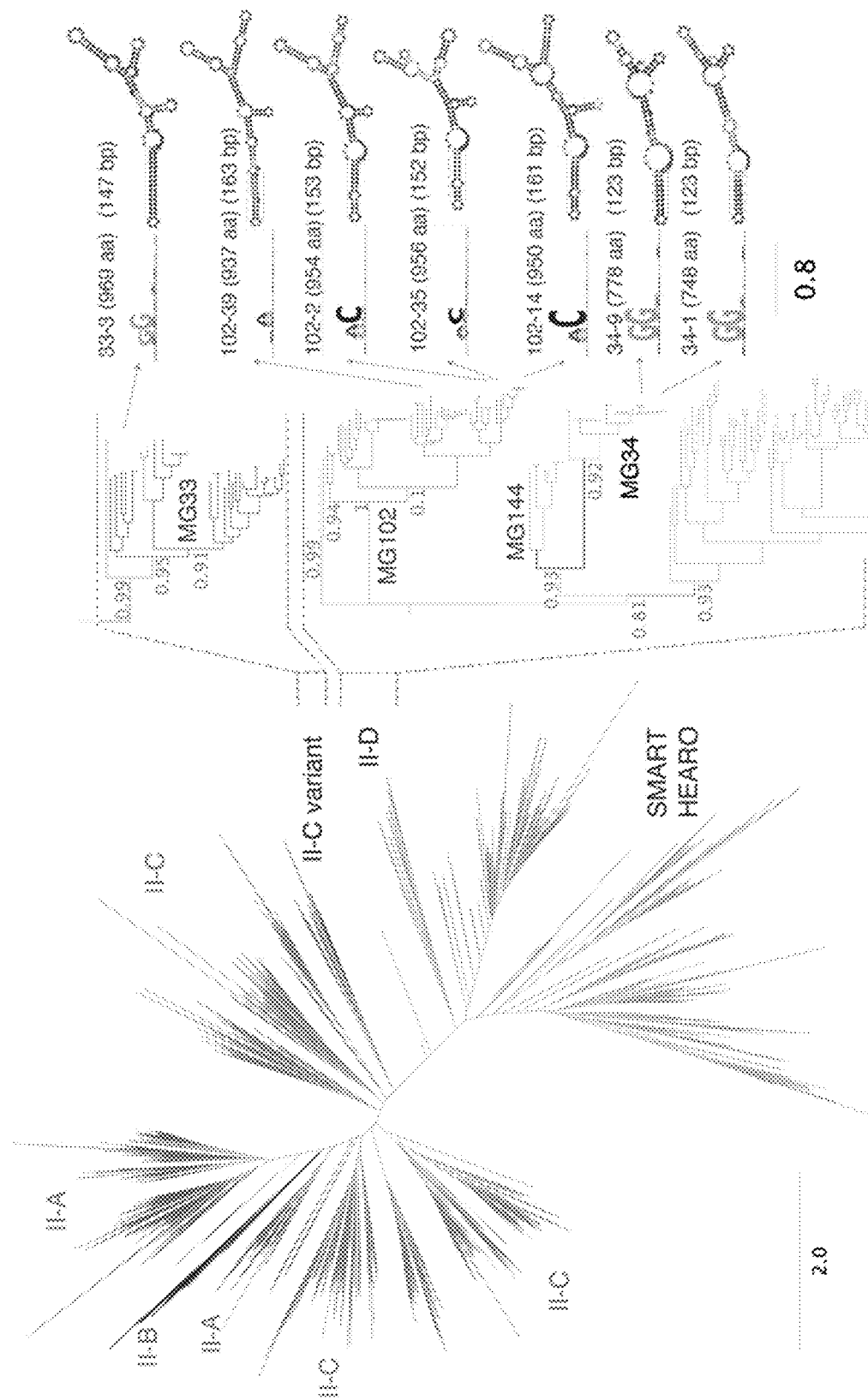

Although SMART nucleases contain RuvC and HNH domains as in Cas9, the RuvC-I, bridge helix, and recognition domains align poorly. In order to best understand the evolutionary relationships between SMART nucleases and reference sequences, a multiple sequence alignment of full-length SMART, reference Type II sequences documented and classified (see e.g. Burstein, D. et al. New CRISPR-Cas systems from uncultivated microbes. *Nature* 2017, 542, 237-241; and Gasiunas, G. et al. A catalogue of biochemically diverse CRISPR-Cas9 orthologs. *Nat Commun* 2020, 11, 5512, each of which is incorporated by reference in its entirety herein), as well as with >10,300 recently reported Cas9 homologs and IscB sequences (see e.g. Altae-Tran, H. et al. The widespread IS200/605 transposon family encodes diverse programmable RNA-guided endonucleases. *Science* 2021, 374, 57-65, which is incorporated by reference in its entirety herein) was generated. The trimmed, well-aligned region encompassing the RuvC-II/HNH/RuvC-III domains was retained. Phylogenetic analysis inferred from this final alignment indicated divergent clades of effectors clustering away from documented Cas9 effectors currently classified as II-A, II-B, and II-C (FIG. 21E). Two SMART clades, which were found phylogenetically closer to classified Type II effectors, were more likely to be encoded adjacent to CRISPR arrays (FIGS. 21B, 21C, and 21E). The MG33 family of SMART nucleases clusters with Type II-C2 effectors and greatly expands this clade (FIGS. 21E and 21F, mauve branches). This family contains representatives of 900-1050 aa, the largest of the SMART enzymes, and their length distribution overlaps with the smallest classified Type II-C enzymes. A more distant SMART clade (FIGS. 21E and 21F, teal, green, and yellow branches) contains "early Cas9" sequences, which were recently classified as Type II-D (FIGS. 21E and 21F, light grey branches). These CRISPR systems may generally be referred to collectively as SMARTs.

SMART I Endonucleases

SMART I effectors range between approximately 600 amino acids and 1,050 amino acids in size. Common features in their genomic context were adaptation module genes (e.g. genes involved in spacer acquisition) and predicted tracrRNAs near the CRISPR array, the organization of which resembled Type II and Type V CRISPR systems (FIGS. 3A, 3B and 3C). The RRXRR ("RRXRR" motif is SEQ ID NO: 1361) motif-containing region in SMART I effectors is unique but may play a similar functional role as the arginine-rich bridge helix in Cas9 nucleases. When modeled against the SaCas9 crystal structure, predicted 3D structures of SMART I effectors showed unaligned regions within the recognition lobe (which often contains the Pfam domain PF14239) and RuvC-II domains (FIG. 5). The results indicated that these domains have different origins relative to other Type II effectors. Taken together with their divergent placement in a Type II effector phylogenetic tree and their low sequence similarity to documented Type II effectors (FIGS. 1A and 21B), these results indicate that SMART I endonucleases belong to a new group of Type II CRISPR systems. Following the accepted classification of CRISPR systems, these SMART I systems were classified as Type II-D.

Figure 22C:
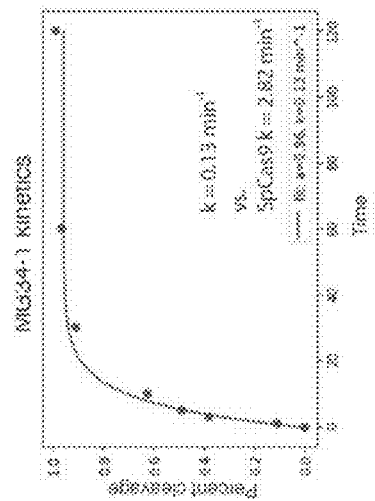
FIGS. 22A-FIG. 22D depict data demonstrating that SMART I's are dsDNA nucleases.
Figure 22B:
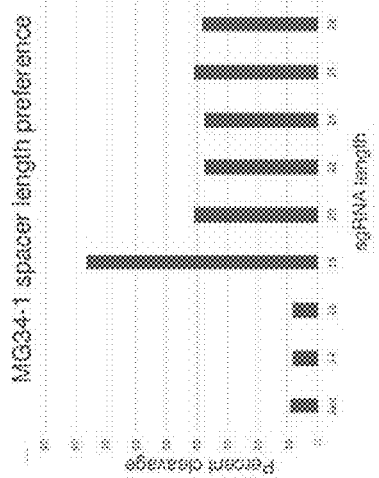
Figure 22A:
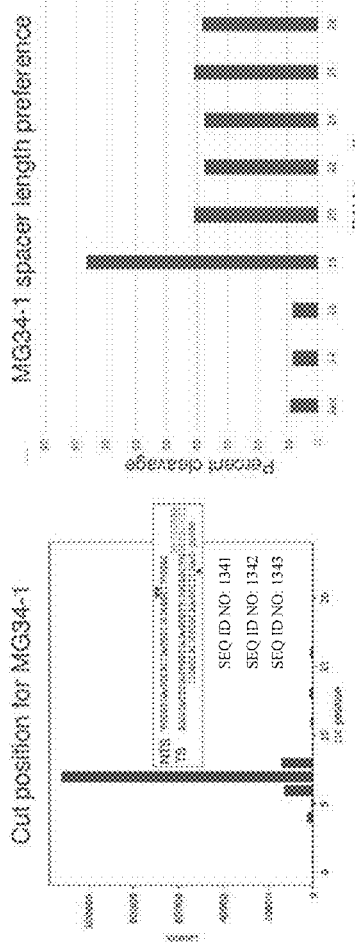

Putative single guide RNAs (sgRNAs) were engineered using environmental RNA expression data for the SMART I MG34-1 system. In addition, multiple sgRNAs designed from SMART I repeat and tracrRNA predictions were tested in vitro in PAM enrichment assays. In the case of SMART I enzymes, optimal identification of PAM sequences was performed using end repair and blunt-end ligation at this stage, suggesting that these enzymes can produce staggered double-stranded DNA breaks. Assays confirmed dsDNA cleavage for MG34-1 (SEQ ID NO: 2), MG34-9 (SEQ ID NO: 9), and MG34-16 (SEQ ID NO: 17) with multiple sgRNA designs (FIG. 7, depicting use of SEQ ID NOs: 612-615). MG34-1 demonstrated a preference for an NGGN PAM for target recognition and cleavage (FIG. 8A), while members of the MG102 family recognize a 3' NRC PAM for target recognition and cleavage (FIG. 21C). Analysis of the cut site indicated preferential cleavage at position 7 (FIGS. 8B and 22A). These results suggest a novel biochemical mechanism compared with cleavage mechanisms from other Type II enzymes, which preferentially cleave at positions 2-3 from the PAM, supporting a new classification for SMART I CRISPR systems.

Environmental expression data for some SMART I systems confirmed in situ transcription of the CRISPR array and intergenic region encoding the predicted tracrRNA (FIGS. 3B and 3C). Additionally, cases of active CRISPR targeting were evaluated by searching spacer sequences that match other genomic sequences assembled from the same, or related metagenomes. Along these lines, a phage genome being targeted by one of the spacers encoded in a SMART I CRISPR array (FIGS. 3C and 3D) was identified. Analysis of the region adjacent to the target sequence suggests a 3' PAM sequence containing a GG motif (FIG. 3D). These results indicate that SMART I CRISPR systems are active in their natural environments as RNA guided effectors involved in phage defense, likely functioning as nucleases that cut or degrade targeted DNA or RNA.

SMART I Effectors are Active, RNA Guided dsDNA CRISPR Endonucleases

Putative single guide RNA (sgRNA) were engineered using the environmental RNA expression data for SMART I MG34-1 and MG34-16 systems (FIGS. 3B and 3C, and FIG. 9). In addition, multiple sgRNAs designed from SMART I repeat and tracrRNA predictions were tested in vitro in PAM enrichment assays (FIG. 10). Assays confirmed programmable dsDNA cleavage for MG34-1, MG34-9, and MG34-16 with multiple sgRNA designs (FIG. 10). MG34-1 and MG34-9 require an NGGN PAM for target recognition and cleavage (FIGS. 11A and 11C). Analysis of the cut site indicates preferential cleavage at position 7 (FIGS. 11B and 11C). These results suggest a novel biochemical cleavage mechanism compared with Cas9 enzymes, which preferentially cleave at position 3 from the PAM, and provide further support for a new classification for SMART I CRISPR systems.

PAM enrichment assays without an end repair procedure did not show activity for SMART I nucleases. The requirement for end repair to create blunt-end fragments prior to ligation in the PAM enrichment protocol indicates that these enzymes create a staggered double strand DNA break. A staggered double strand break was confirmed by sequencing of cleavage products of the MG34-1 nuclease (FIG. 22A). These results suggest a novel biochemical cleavage mechanism compared with mechanisms from most documented Type II enzymes, which preferentially cleave at positions 2-3 from the PAM. In vitro cleavage assays with purified protein indicates that MG34-1 is more efficient at targeted DNA cleavage with target guides 18 bp long, and time series cleavage assays indicate that MG34-1 cuts at a slower rate compared with the reference SpCas9 when tested with identical guides (FIGS. 22B and 22C).

Figure 22D:
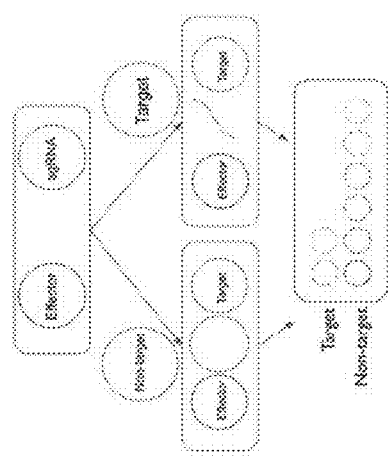

Experiments conducted in *E. coli* showed that the system has the required activity to function as a nuclease in cells. *E. coli* strains expressing MG34-1 and MG34-9 sgRNAs were transformed with a kanamycin resistance plasmid containing a target for the sgRNA. In the presence of the antibiotic, successful targeting and cutting of the antibiotic resistance plasmid will result in a growth defect. The assay showed an approximately 2-fold to 10-fold growth repression compared with control experiments conducted with a kanamycin resistance plasmid that did not contain a target for the sgRNA (FIGS. 12 and 22D).

SMART II Endonucleases

SMART II effectors have a size distribution that skews smaller (~400 amino acids-600 amino acids) vs. SMART I effectors. Their genomic context suggested unusual repetitive regions or CRISPR arrays. The non-CRISPR repetitive regions contain direct repeats that range in size from about 10 to over 30 bp. In some cases, these include multiple distinct repeating units. Sometimes, common CRISPR identification algorithms will flag these regions as CRISPR systems; however, closer inspection will reveal that the regions identified as spacer sequences are repeated in the array. The arrays are not immediately adjacent to the effectors, but they are in the same genomic region (FIG. 3A, MG35-236 and FIG. 13A, e.g., >20 kb from the effector gene). SMART II system operons were generally devoid of adaptation module genes (e.g. genes involved in spacer acquisition).

Figure 14:
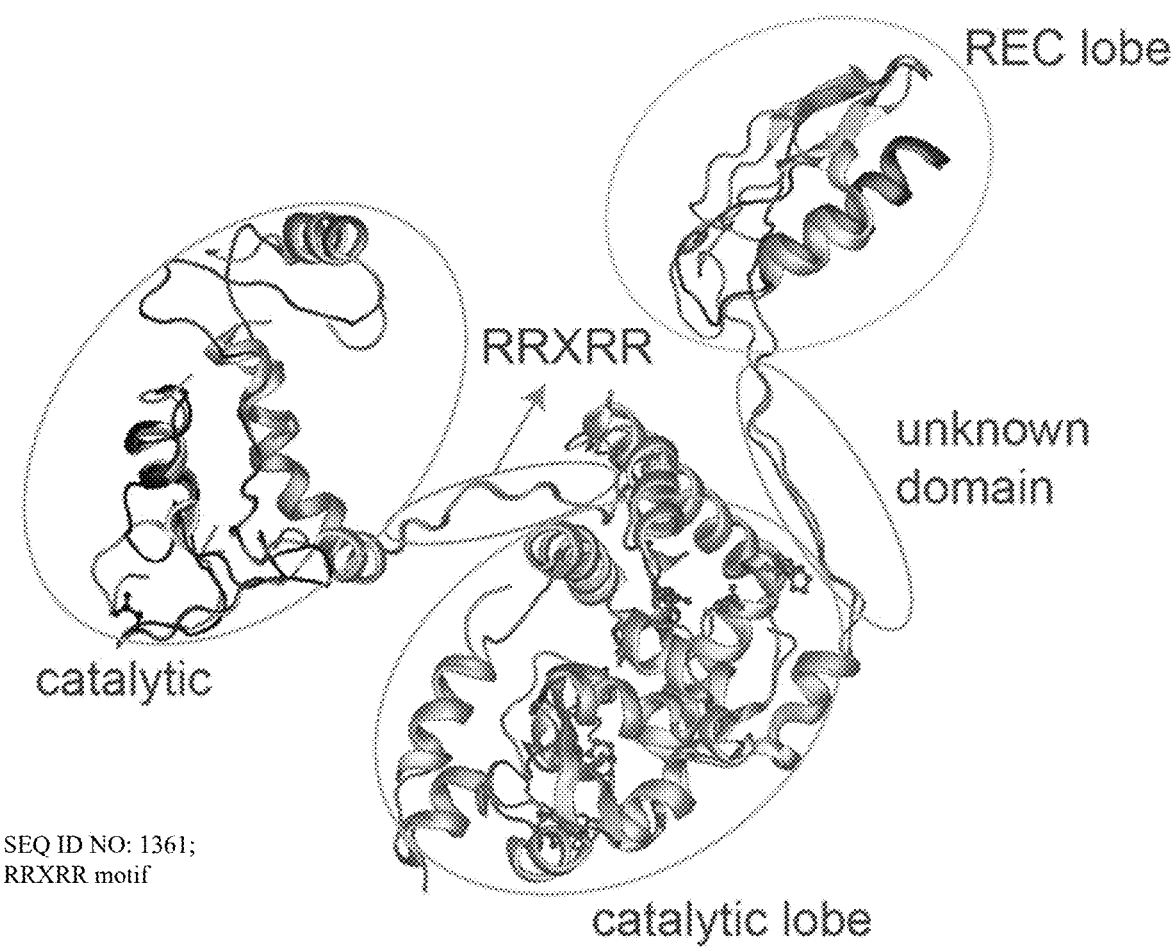
FIG. 14 shows a 3D structural prediction for SMART II MG35-419. This 3D model aligns well with regions of the SaCas9 crystal structure, despite being less than half its size. Regions that aligned with the SaCas9 template include the catalytic lobe (RuvC-I, HNH and RuvC-III domains) and a short region of the recognition (REC) lobe. SMART II-specific domains include a domain containing an RRXRR motif (SEQ ID NO: 1361) and homology to a Pfam PF14239, and a domain of unknown function.

Structural predictions identified characteristic residues of Cas enzymes involved in guide RNA binding, target cleavage, and recognition of and interaction with a PAM, in addition to all six RuvC and HNH nuclease catalytic residues (FIG. 6) often found in class 2, type II Cas effectors. In addition, SMART II effectors contained multiple RRXRR ("RRXRR" motif is SEQ ID NO: 1361) and zinc binding ribbon motifs (CX[2-4]C or CX[2-4]H), which are possibly involved in recognition and binding of a target nucleic acid motif. Based on the location of important residues, the predicted domain architecture of SMART II nucleases comprised three RuvC subdomains, an arginine-rich region containing an RRxRR motif (SEQ ID NO: 1361) (e.g. a domain with PF14239 homology), an HNH endonuclease domain, an unknown domain, and a recognition domain (REC) (FIG. 6). The domain architecture of SMART II effectors differed from the documented domain architecture for Type II Cas9 nucleases (FIG. 6 and FIG. 14).

Figures 13A, 13B:
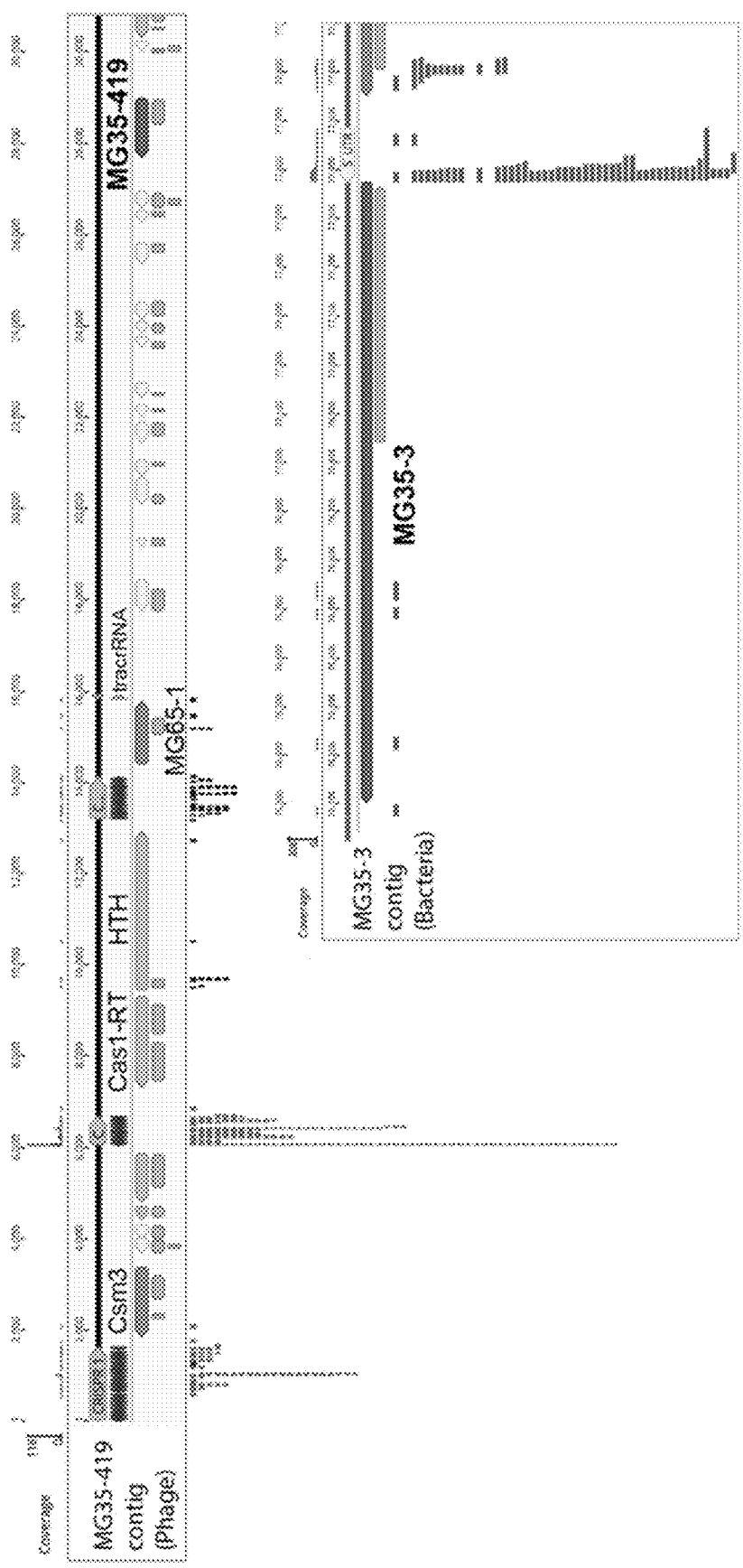
FIG. 13A-FIG. 13B shows an example genomic context of a SMART system for MG35-419. SMART nucleases are shown as dark grey arrows, other genes are depicted as lighter grey arrows. Domains predicted for all genes in a genomic fragment are shown as grey boxes under the arrows. Environmental expression sequencing reads are shown aligned under the CRISPR arrays in (FIG. 13A) and upstream from the effector in (FIG. 13B). Transcriptomic coverage for the regions showing expression is illustrated above the contig sequence.
Figure 16A:
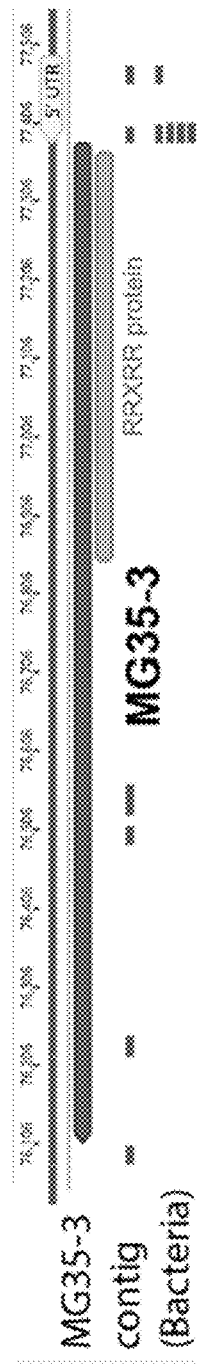
FIGS. 16A-FIG. 16B depict the genomic context of SMART systems. SMART nucleases are shown as dark grey arrows, other genes are depicted as lighter grey arrows. Domains predicted for all genes in a genomic fragment are shown as grey boxes under the arrows. Environmental expression sequencing reads are shown aligned upstream from the effector.
Figure 16B:
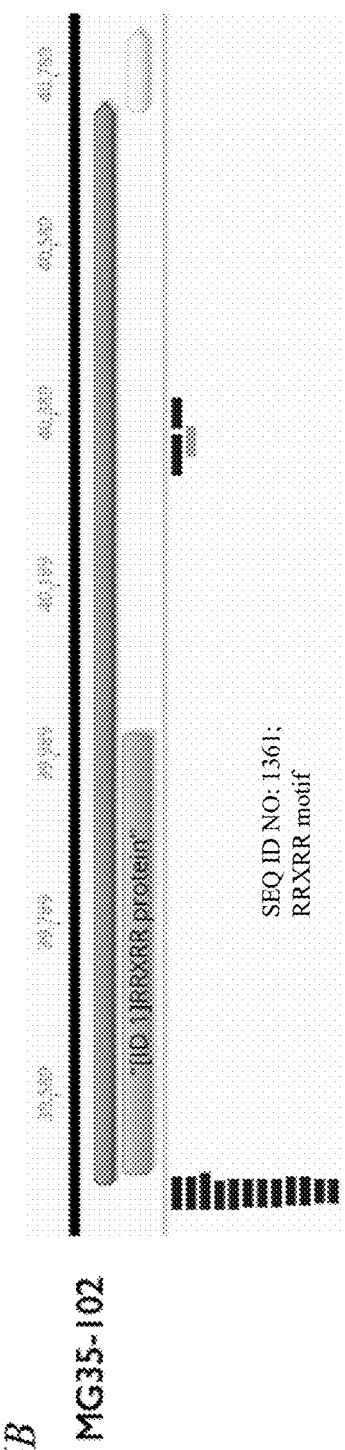

Environmental transcriptomic data for some SMART II systems confirmed in situ expression of CRISPR arrays and other repetitive regions in the natural environment (FIG. 13A). Transcription of the 5' untranslated region (UTR) of some SMART II effectors was also observed from environmental expression data (FIGS. 13B and 16), suggesting that this region may be important for either nuclease activity or regulation of the SMART system.

Figure 15:
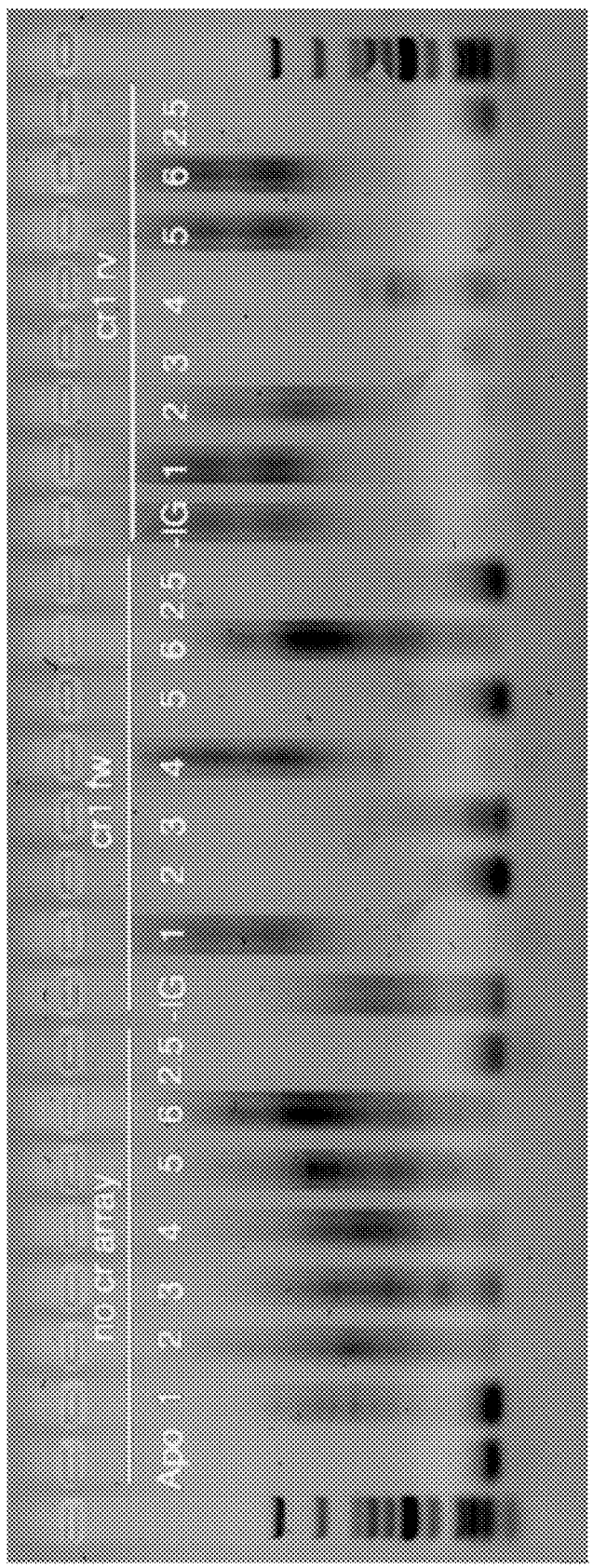
FIG. 15 depicts results of preliminary cleavage assays for SMART II effectors. MG35-420 (SEQ ID NO: 223) protein preps were tested for cleavage activity in TXTL extracts where the entire locus was expressed. Experiments incubated the protein prep with a PAM library (dsDNA target), a repetitive region predicted in the locus (cr1) in both forward and reverse orientations (fw and rv), and with intergenic regions potentially encoding relevant cofactors. Lanes 2-9 (no cr array): control experiments without a repetitive region. Apo: only protein prep with a target PAM library. Labels 1-2.5 represent seven different intergenic regions. -IG: no intergenic region included as control. PCR gel of the ligation products shows putative cleavage bands (arrows) suggesting dsDNA cleavage.
Figure 17A:
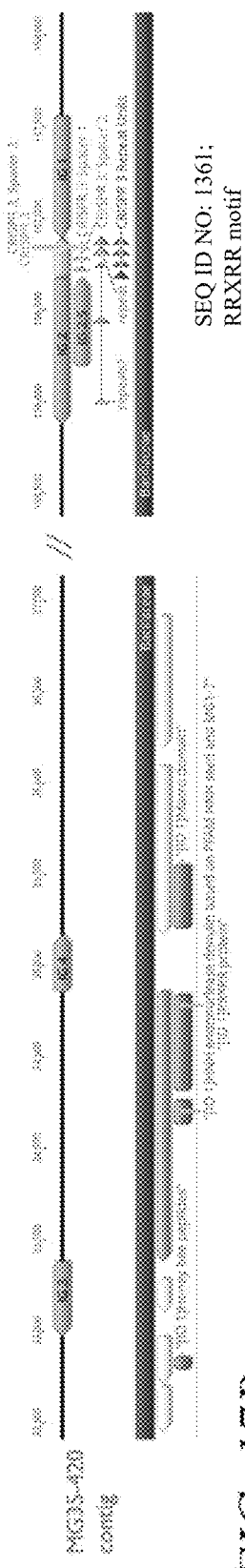
FIGS. 17A-FIG. 17B depict data demonstrating that MG35-420 is an active dsDNA nuclease.
Figure 17B:
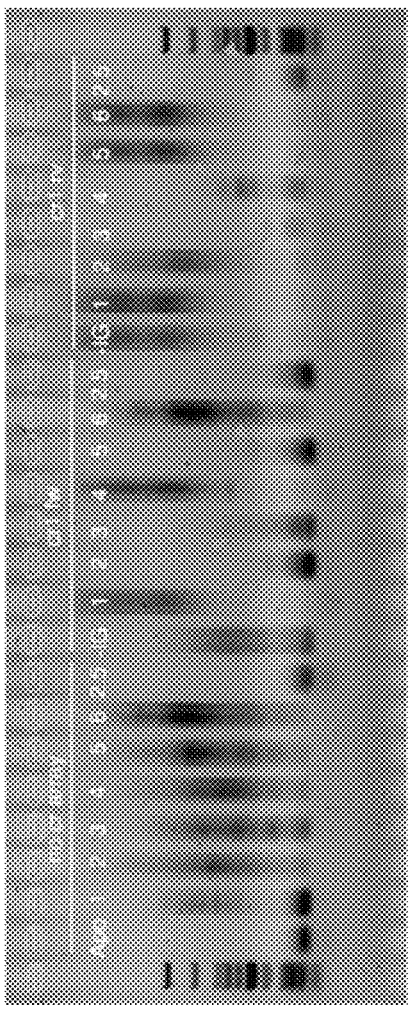
Figures 18A, 18B:
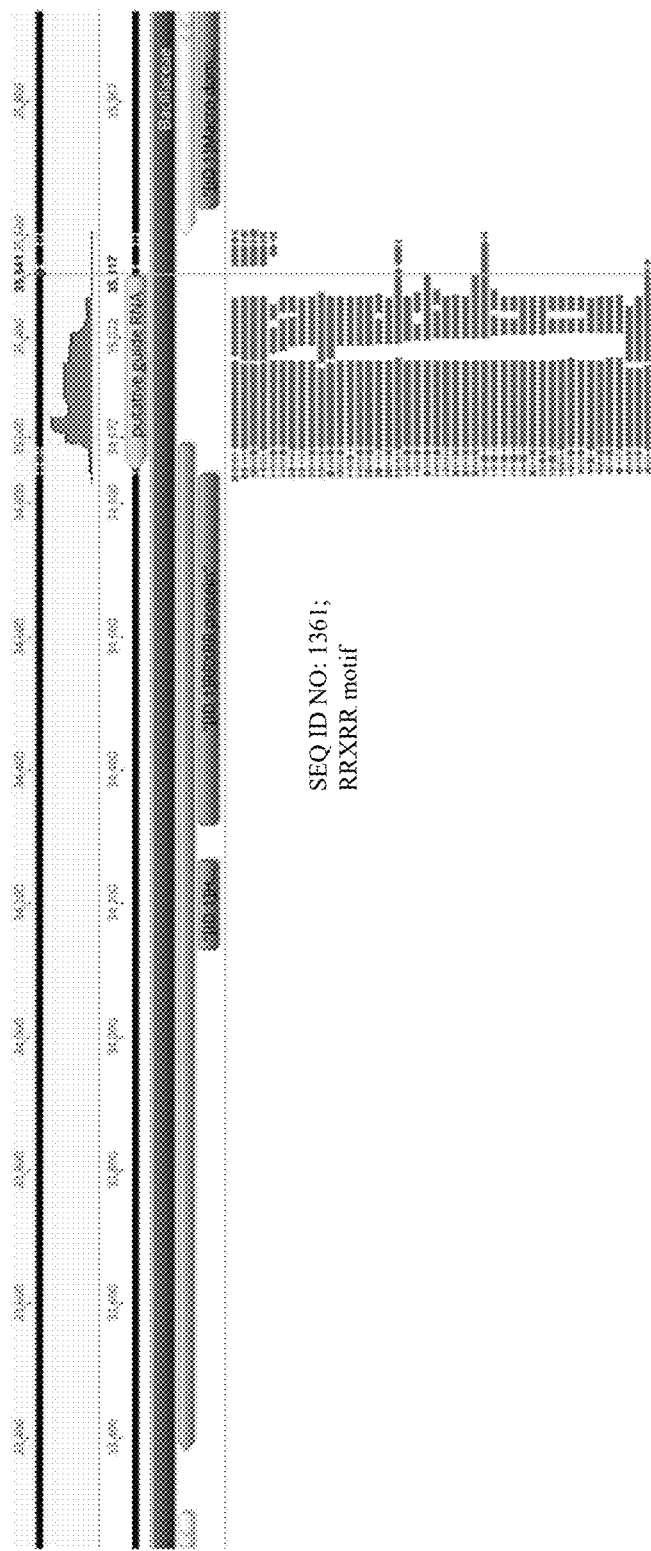
FIGS. 18A-FIG. 18B depict the predicted guide RNA for MG35-420.
Figure 19A:
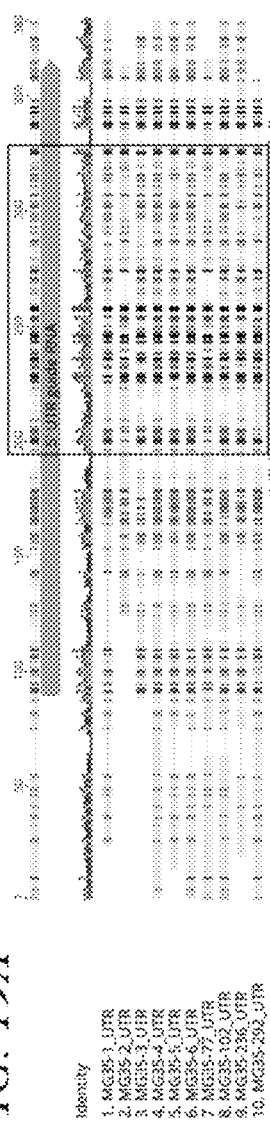
FIGS. 19A-FIG. 19B depict multiple sequence alignment (MSA) of conserved UTR regions associated with SMART II effectors.
Figure 19B:
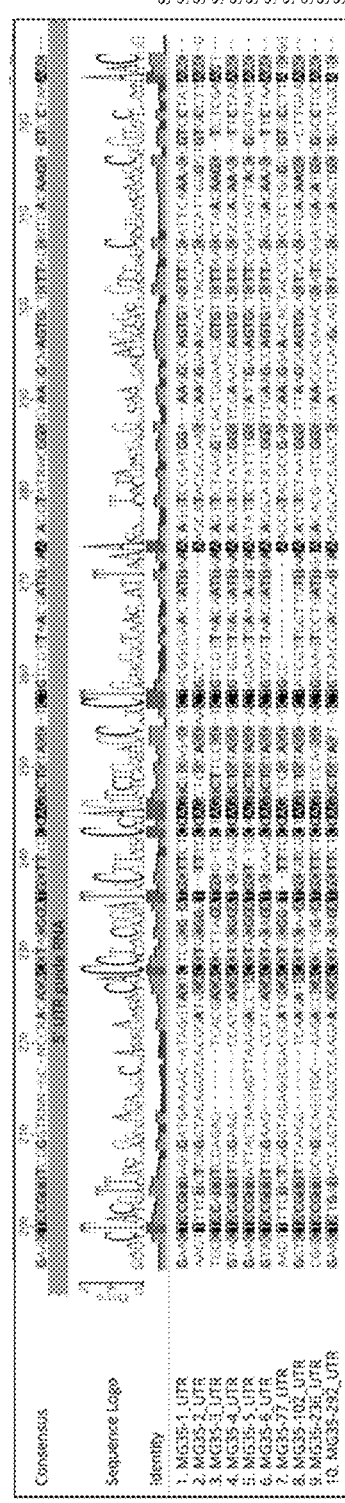

Preliminary in vitro experiments conducted with SMART II effector proteins, repetitive regions, and associated intergenic regions show that these enzymes have the ability to cleave dsDNA, possibly in a programmable manner (FIGS. 15 and 17). Results suggest that SMART II nuclease activity may be RNA or DNA guided, which may require using a repetitive region such as a CRISPR array, or via recognition of features encoded within the loci such as TIR or 5' UTR. The 5' UTR of SMART II effectors are actively transcribed in in vitro transcription assays and display high secondary structures (FIG. 18). A multiple sequence alignment of the region immediately upstream from the start codon of SMART II effectors demonstrates blocks of conservation (FIG. 19), suggesting that the 5' UTR associated with SMART II effectors encodes an RNA guide for the effector to target DNA for cleavage activity.

Figures 20A, 20B:
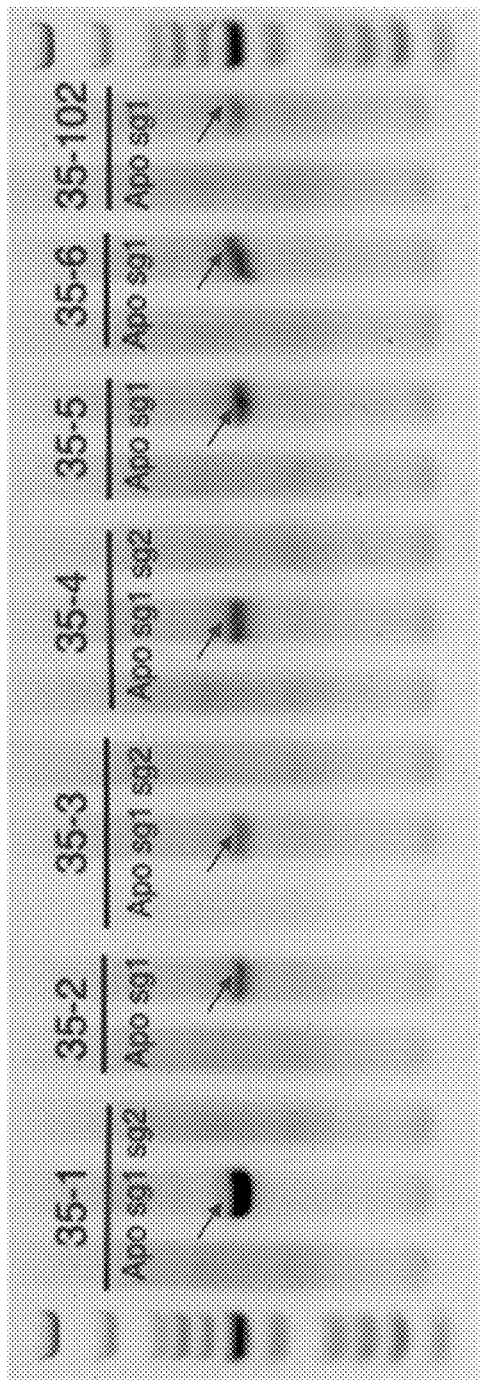
FIGS. 20A-FIG. 20B depict data demonstrating that MG35 effectors are active dsDNA nucleases using an sgRNA.

Recently, short Cas9 homologs were reported to be programmable dsDNA nucleases using a guide RNA encoded in the 5' UTR region of the effector (Altae-Tran, Kannan, et al. *Science* 2021). In these systems, a targeting "spacer" was identified upstream from the transcribed 5' UTR of the effectors, suggesting that SMART II enzymes can be reprogrammed to target and cleave a specific DNA site by adding a "target spacer" to the 5' end of predicted guide RNAs encoded in their 5' UTR. Appending a target spacer to the 5' end of the guide RNA encoded in the 5' UTR region of SMART II effectors activated the effectors for targeted dsDNA cleavage, with a variety of target-adjacent motifs (TAMs) (FIG. 20).

Some SMART II effectors were observed next to a putative insertion sequence (IS) encoding transposases TnpA and TnpB (FIG. 3A). The ends of the IS were identified as containing terminal inverted repeats (TIR) with predicted hairpin structures, and the target site duplication at which the IS most likely integrated into was also identified). In addition, some SMART II loci encoded putative TIRs flanking the SMART II effector (e.g. FIG. 3).

SMART HEARO Clades Contain Virus-Associated RNA-Guided dsDNA Nucleases

Phylogenetic analysis indicated that SMART nucleases of less than 600 aa in length (FIG. 21E, lilac branches) cluster together with documented IscB sequences ("insertion sequences Cas9-like" (see e.g. Kapitonov, V. V., Makarova, K. S. & Koonin, E. V. ISC, a Novel Group of Bacterial and Archaeal DNA Transposons That Encode Cas9 Homologs. *J Bacteriol* 2016, 198, 797-807, which is incorporated by reference in its entirety herein)) (FIG. 21E, dark gray branches) forming two main clades. Kapitonov and colleagues reported IscB homology with Cas9 based on the presence of RuvC and HNH domains, and subsequently described a PLMP domain in this same group of enzymes (see e.g. Altae-Tran, H. et al. The widespread IS200/605 transposon family encodes diverse programmable RNA-guided endonucleases. *Science* 2021, 374, 57-65, which is incorporated by reference in its entirety herein). 3D structure prediction was used to show that these proteins contain an arginine rich region usually containing an RRXRR motif (SEQ ID NO: 1361). The arginine rich region was suggested to be analogous to the bridge helix in Cas9; however, neither this region nor the RuvC-I domain were found to align well in 3D space with the bridge helix and RuvC-I domains of a reference 3D structure. Such IscB/SMART enzymes lack a PAM interacting domain. Instead, a C-terminal "WED/REC" domain containing Zn-binding ribbon motifs can be involved in target motif recognition. Although protein domains, catalytic residues, and 3D models suggest an evolutionary relationship with Cas9, most IscB/SMART effectors are not CRISPR-associated (e.g. not found proximal to a CRISPR repeat in their genomic context). The group comprising the IscB/SMART systems are generally compact in size (approximately 400 to 600 aa) and are widely distributed in bacterial and archaeal genomes. It was found that over 16% of genomic fragments encoding these effectors were classified as likely viral or prophage-derived, implicating viruses in the evolution of these systems.

Searches for non-coding RNAs (ncRNA) associated with SMART systems found that 65% of IscB/SMART 5' untranslated regions (UTRs) contain hits to HNH Endonuclease-Associated RNA and ORF (HEARO) RNAs from the RFam database (RF02033). These ncRNAs were first described as highly structured RNAs from a bioinformatics analysis (see e.g. Weinberg, Z., Perreault, J., Meyer, M. M. & Breaker, R. R. Exceptional structured noncoding RNAs revealed by bacterial metagenome analysis. *Nature* 2009, 462, 656-659, which is incorporated by reference in its entirety herein), but the function of their associated HEARO ORF was not reported (see e.g. Harris, K. A. & Breaker, R. R. Large Noncoding RNAs in Bacteria. *Microbiol Spectr* 2018, 6, which is incorporated by reference in its entirety herein). It was confirmed that putative HEARO HNH endonuclease ORFs also contain RuvC and HNH catalytic domains and cluster together with IscB/SMART effectors. Therefore, IscB, small SMARTs, and HEARO ORFs represent a large group of non-Cas endonucleases. Recently, it was reported that the 5' UTR of IscB encodes a single guide RNA required for dsDNA nuclease activity, which the authors refer to as an Omega RNA (see e.g. Altae-Tran, H. et al. The widespread IS200/605 transposon family encodes diverse programmable RNA-guided endonucleases. Science 2021, 374, 57-65, which is incorporated by reference in its entirety herein). In confirmation of the requirement of a guide RNA for function, we observed in situ natural expression of the 5' UTR of IscB/SMART/HEARO systems, which was recapitulated by in vitro transcription assays. Omega RNA structures share high structure similarity with HEARO RNAs. In recognition of the features that unite IscB/SMART/HEARO systems (broad taxonomic origin and enrichment of arginine residues), as well as of the chronological discovery of the guide RNAs associated to these enzymes, we advocate for a broad functional classification for IscB/SMART/HEARO systems as SMART HEARO (FIG. 21E). We evaluated SMART HEARO cleavage activity in vitro and identified required targeting motifs by reprogramming the 5' "spacer" region of their HEARO RNA (FIG. 21D), as described by Altae-Tran and Kannan et al (see e.g. Altae-Tran, H. et al. The widespread IS200/605 transposon family encodes diverse programmable RNA-guided endonucleases. Science 2021, 374, 57-65). Moreover, plasmid interference assays in E. coli show that SMART HEARO nucleases are highly active compared to SpCas9 (>570-fold repression for MG35-1 vs. ~98-fold repression shown by SpCas9, FIG. 25B) and specificity experiments indicate low tolerance for mismatches in the protospacer (FIG. 25D).

Example 2—PAM Sequence Identification/Confirmation for the Endonucleases Described Herein Putative SMART endonucleases were expressed in an E. coli lysate-based expression system (PUREXPRESS®, New England Biolabs). In this system, the endonuclease was codon optimized for E. coli and cloned into a vector with a T7 promoter and C-terminal His tag. The gene was PCR amplified with primer binding sites 150 bp upstream and downstream from the T7 promoter and terminator sequences, respectively. This PCR product was added to NEB PUREXPRESS® at 5 nM concentration and expressed for 2 hr at 37° to produce the endonucleases for the PAM assays.

The putative sgRNAs compatible with each SMART Cas enzyme described herein were identified from RNAseq reads assembled to the contig CRISPR locus assembled from sequencing data: secondary structure was determined for the tracr region from RNAseq data along with the repeat sequence from the CRISPR array in the Geneious software package (www.geneious.com), and the resulting helix was trimmed and concatenated with a GAAA tetra-loop. Multiple lengths of repeat-anti-repeat helix trimming were tested, as well as different spacer lengths and different tracr termination points (FIG. 12, which demonstrates SEQ ID NOs: 612-615). Each sgRNA was then assembled via assembly PCR, purified with SPRI beads, and in vitro transcribed (IVT) following manufacturer's recommended protocol for short RNA transcripts (HiScribe T7 kit, NEB). RNA transcription reactions were cleaned with the Monarch RNA kit and checked for purity via Tapestation (Agilent).

PAM sequences were determined by sequencing plasmids containing randomly-generated potential PAM sequences that can be cleaved by the putative nucleases. In this system, an E. coli codon optimized nucleotide sequence encoding the putative nuclease was transcribed and translated in vitro from a PCR fragment under control of a T7 promoter. A second PCR fragment with a minimal CRISPR array composed of a T7 promoter followed by a repeat-spacer-repeat sequence was transcribed in the same reaction. Successful expression of the endonuclease and repeat-spacer-repeat sequence in the TXTL system followed by CRISPR array processing provides active in vitro CRISPR nuclease complexes.

A library of target plasmids containing a spacer sequence matching that in the minimal array preceded by 8N mixed degenerate bases (potential PAM sequences) were incubated with the output of the TXTL reaction (10 mM Tris pH 7.5, 100 mM NaCl, and 10 mM $MgCl_2$ with a 5-fold dilution of translated Cas enzyme, 5 nM of an 8N PAM plasmid library, and 50 nM of sgRNA targeting the PAM library). After 1-3 hr, the reaction was stopped, and the DNA was recovered via a DNA clean-up kit. Adapter sequences were blunt-end ligated to DNA with active PAM sequences that had been cleaved by the endonuclease, whereas DNA that had not been cleaved was inaccessible for ligation. DNA segments comprising active PAM sequences were then amplified by PCR with primers specific to the library and the adapter sequence. The PCR amplification products were resolved on a gel to identify amplicons that correspond to cleavage events. The amplified segments of the cleavage reaction were also used as a template for preparation of an NGS library or as a substrate for Sanger sequencing. Sequencing this resulting library, which was a subset of the starting 8N library, revealed sequences with PAM activity compatible with the CRISPR complex. For PAM testing with a processed RNA construct, the same procedure was repeated except that an in vitro transcribed RNA was added along with the plasmid library and the minimal CRISPR array/tracr template was omitted. The following spacer sequence was used as a target in these assays (5'-CGUGAGCCAC-CACGUCGCAAGCCUCGAC-3' (SEQ ID NO: 204)).

Having obtained raw sequencing reads from the PAM assays, reads were filtered by Phred quality score >20. The 24 bp representing the documented DNA sequence from the backbone adjacent to the PAM was used as a reference to find the PAM-proximal region and the 8 bp adjacent were identified as the putative PAM. The distance between the PAM and the ligated adapter was also measured for each read. Reads that did not have an exact match to the reference sequence or adapter sequence were excluded. PAM sequences were filtered by cut site frequency such that PAMs with the most frequent cut site ±2 bp were selectively included in the analysis. The filtered list of PAMs was used to generate a sequence logo using Logomaker (Tareen A, Kinney JB. Logomaker: beautiful sequence logos in Python. Bioinformatics. 2020; 36 (7): 2272-2274, which is incorporated by reference herein).

Example 3—Protocol for Predicted RNA Folding

Predicted RNA folding of the active single RNA sequence is computed at 37° using the method of Andronescu 2007. The color of the bases corresponds to the probability of base pairing of that base, where red is high probability and blue is low probability.

Example 4—In Vitro Cleavage Efficiency

Endonucleases are expressed as His-tagged fusion proteins from an inducible T7 promoter in a protease deficient E. coli B strain. The endonuclease was fused to two nuclear localization signals (N-term NLS nucleoplasmin bipartite and C-term simian virus 40 T-antigen NLS PPKKKRK (SEQ ID NO: 1362)), a maltose binding protein (MBP) tag, a tobacco etch virus (TEV) protease cleavage site, and a 6XHis tag in the following order from N to C termini: 6XHis-MBP-TEV-NLS-gene-NLS-STOP. This protein was expressed under a pTac promoter in NEB Iq E. coli by autoinduction media (MagicMedia ThermoFisher), grown at 30° C., and induced at 16° C.

Cells expressing the His-tagged proteins were lysed by sonication and the His-tagged proteins purified by Ni-NTA affinity chromatography on a HisTrap FF column (GE Lifescience) on an AKTA Avant FPLC (GE Lifescience). The eluate was resolved by SDS-PAGE on acrylamide gels (Bio-Rad) and stained with InstantBlue Ultrafast Coomassie (Sigma-Aldrich). Purity was determined using densitometry of the protein band with ImageLab software (Bio-Rad). Purified endonucleases were dialyzed into a storage buffer composed of 50 mM Tris-HCl, 300 mM NaCl, 1 mM TCEP, 5% glycerol; pH 7.5 and stored at −80° C.

Target DNAs containing spacer sequences and PAM sequences (determined e.g., as in Example 2) were constructed by DNA synthesis. A single representative PAM is chosen for testing when the PAM has degenerate bases. The target DNAs are comprised of 2200 bp of linear DNA derived from a plasmid via PCR amplification with a PAM and spacer located 700 bp from one end. Successful cleavage results in fragments of 700 and 1500 bp. The target DNA, in vitro transcribed single RNA, and purified recombinant protein are combined in cleavage buffer (10 mM Tris, 100 mM NaCl, 10 mM $MgCl_2$) with an excess of protein and RNA and are incubated for 5 minutes to 3 hours, usually 1 hr. The reaction is stopped via addition of RNAse A and incubation at 60 minutes. The reaction is then resolved on a 1.2% TAE agarose gel and the fraction of cleaved target DNA is quantified in ImageLab software.

Example 5—Activity in *E. coli*

*E. coli* lacks the capacity to efficiently repair double-stranded DNA breaks. Thus, cleavage of genomic DNA can be a lethal event. Exploiting this phenomenon, endonuclease activity is tested in *E. coli* by recombinantly expressing an endonuclease and a guide RNA in a target strain with spacer/target and PAM sequences integrated into its genomic DNA.

For testing of nuclease activity in bacterial cells, BL21 (DE3) strains (NEB) were transformed with plasmids containing T7-driven effector and sgRNA (10 ng each plasmid), plated and grown overnight. The resulting colonies were cultured overnight in triplicate, then subcultured in SOB and grown to OD 0.4-0.6. 0.5 OD equivalent of cell culture was made chemocompetent according to standard kit protocol (Zymo Mix and Go kit) and transformed with 130 ng of a kanamycin plasmid either with or without a spacer and PAM in the backbone. After heat shock, transformations were recovered in SOC for 1 hr at 37° C., and nuclease efficiency was determined by a 5-fold dilution series grown on induction media (LB agar plates with antibiotics and 0.05 mM IPTG). Colonies were quantified from the dilution series to measure overall repression due to nuclease-driven plasmid cleavage.

The results for such an assay are shown in FIG. 12. In FIG. 12, panel (A) shows replica plating of *E. coli* strains demonstrating plasmid cutting; *E. coli* expressing MG34-1 and a sgRNA were transformed with a kanamycin resistance plasmid containing a target for the sgRNA (+sp). Plate quadrants that show growth impairment (+sp) vs. the negative control (without the target and PAM (−sp)) indicate successful targeting and cleavage by the enzyme. The experiment was replicated twice and performed in triplicate. In FIG. 12, panel B shows graphs of colony forming unit (cfu) measurements from the replica plating experiments in A showing growth repression in the target condition (+sp) vs. the non-target control (−sp), demonstrating the plasmid was cut. In FIG. 12, panel C shows barplots of colony forming unit (cfu) measurements (in log-scale) showing *E. coli* growth repression in the target condition (white bars) vs. the non-target controls (green bars) for various SMART nucleases. Plasmid interference assays for each nuclease was done in triplicate along with the SpCas9 positive control Engineered strains with PAM sequences (determined e.g. as in Example 2) integrated into their genomic DNA are transformed with DNA encoding the endonuclease. Transformants are then made chemocompetent and are transformed with 50 ng of guide RNAs (e.g., crRNAs) either specific to the target sequence ("on target"), or non-specific to the target ("non target"). After heat shock, transformations are recovered in SOC for 2 hrs at 37° C. Nuclease efficiency is then determined by a 5-fold dilution series grown on induction media. Colonies are quantified from the dilution series in triplicate.

Example 6—Testing Genome Cleavage Activity of MG CRISPR Complexes in Mammalian Cells To show targeting and cleavage activity in mammalian cells, the MG Cas effector protein sequences are tested in two mammalian expression vectors: (a) one with a C-terminal SV40 NLS and a 2A-GFP tag, and (b) one with no GFP tag and two SV40 NLS sequences, one on the N-terminus and one on the C-terminus. The NLS sequences comprise any of the NLS sequences described herein. In some instances, nucleotide sequences encoding the endonucleases are codon-optimized for expression in mammalian cells.

The corresponding crRNA sequence with targeting sequence attached is cloned into a second mammalian expression vector. The two plasmids are cotransfected into HEK293T cells. 72 hr after co-transfection of the expression plasmid and a gRNA targeting plasmid into HEK293T cells, the DNA is extracted and used for the preparation of an NGS-library. Percent NHEJ is measured via indels in the sequencing of the target site to demonstrate the targeting efficiency of the enzyme in mammalian cells. At least 10 different target sites are chosen to test each protein's activity.

Example 7—Predicted Activity of MG Families Described Herein

In situ expression and protein sequence analyses indicate that these enzymes are active nucleases. They contain predicted endonuclease-associated domains (matching RRXRR ("RRXRR" motif is SEQ ID NO: 1361) and HNH_endonuclease Pfam domains; FIGS. 2, 3A and 3B), and contain predicted HNH and RuvC catalytic residues (e.g. FIGS. 2, 3A and 3B, rectangles). Furthermore, the presence of an RRXRR motif (SEQ ID NO: 1361), found in Ribonuclease H-like protein families, indicates potential RNA targeting or nuclease activity (See FIG. 2).

Expression data confirms in situ natural activity for candidate MG34-1 nuclease, tracrRNA and CRISPR array (FIG. 4).

Example 8—Activity in Mammalian Cells with mRNA Delivery

For genome editing using cell transfection/transformation with mRNA, the coding sequence is mouse or human codon optimized using algorithms from Twist Bioscience or Thermo Fisher Scientific (GeneArt). A cassette is constructed with two nuclear localization signals appended to the coding endonuclease sequence: SV40 and nucleoplasmin at the N and C terminal respectively. Additionally, untranslated regions from human complement 3 (C3) are appended to both the 5' and 3' to the coding sequence within the cassette.

This cassette is then cloned into a mRNA production vector upstream of a long poly A stretch. The mRNA construct organization can be as follows: 5' UTR from C3-SV40 NLS-codon optimized SMART gene-nucleoplasmin NLS-3' UTR from C3-107 polyA tail. Run-of transcription of the mRNA is then driven by a T7 promoter using an engineered T7 RNA polymerase (Hi-T7: New England Biolabs). 5' capping of the mRNA occurs co-transcriptionally using CLEANCAP AG® (Trilink Biolabs). mRNA is then purified using MEGACLEAR™ Transcription Clean-Up kit (Thermo Fisher Scientific).

Mammalian cells are co-transfected with transcribed mRNA and a set of at least 10 guides targeting a genomic region of interest using LIPOFECTAMINE™ MESSENGER MAX™ (Thermo Fisher Scientific). Cells are incubated for a period of time (e.g. 48 hours) followed by genomic DNA isolation using a Purelink Genomic DNA extraction kit (Fisher Scientific). The region of interest is amplified using specific primers. Editing is then assessed by Sanger sequencing using Inference of CRISPR Edits and NGS for a thorough analysis of edit outcomes.

Example 9—SMART II Guide RNA Prediction

The region comprising 400 bp immediately upstream from the start codon of SMART II effector sequences was extracted as potentially encoding a guide RNA required for activity (UTR). UTR sequences were aligned with MAFFT (mafft-ginsi algorithm) and regions showing blocks of conservation were annotated as putative guide RNAs.

Example 10—Activity and PAM Determination Assays

The putative guide RNA predicted from RNASeq or from UTR alignment was folded in Geneious. A target spacer was appended to either the 5' or 3' end of the guide RNA to design a single guide RNA (sgRNA). The sgRNA was assembled via assembly PCR, purified with SPRI beads, and in vitro transcribed (IVT) following manufacturer's recommended protocol for short RNA transcripts (HiScribe T7 kit, NEB). RNA reactions were cleaned with the Monarch RNA kit and checked for purity via the Tapestation (Agilent).

Cleavage and PAM determination assays were performed with PUREXPRESS® (New England Biolabs). Briefly, the protein was codon optimized for *E. coli* and cloned into a vector with a T7 promoter and C-terminal His tag. The gene was PCR amplified with primer binding sites 150 bp upstream and downstream from the T7 promoter and terminator sequences, respectively. This PCR product was added to NEB PUREXPRESS® at 5 nM concentration and expressed for 2 hr at 37° C. After this point, a cleavage reaction was assembled in 10 mM Tris pH 7.5, 100 mM NaCl, and 10 mM $MgCl_2$ with a 5-fold dilution of PUREXPRESS®, 5 nM of an 8N PAM plasmid library, and 50 nM of sgRNA targeting the PAM library.

The cleavage products from the PUREXPRESS® reactions were recovered via clean up with AMPure SPRI beads (Beckman Coulter). The DNA was blunted via addition of Klenow fragments and dNTPs (New England Biolabs). Blunt-end products were ligated with a 100-fold excess of double stranded adapter sequences and used as template for the preparation of an NGS library, from which PAM requirements were determined from sequence analysis.

Raw NGS reads were filtered by Phred quality score >20. The 24 bp representing the documented DNA sequence from the backbone adjacent to the PAM was used as a reference to find the PAM-proximal region and the 8 bp adjacent were identified as the putative PAM. The distance between the PAM and the ligated adapter was also measured for each read. Reads that did not have an exact match to the reference sequence or adapter sequence were excluded. PAM sequences were filtered by cut site frequency such that PAMs with the most frequent cut site+2 bp were selectively included in the analysis. The filtered list of PAMs was used to generate a sequence logo using Logomaker.

Example 11—SMARTs Amino Acid Composition

To describe the amino acid composition of SMART protein sequences, the percent amino acid content for a group of SMART sequences was calculated as the number of times each residue was observed, divided by the total protein length, times 100. The amino acid composition was then compared to the percent content reported for a large set of protein sequences from the Uniprot50 database (Carugo, Protein Sci. 2008). Both groups of proteins, SMART HEARO and SMART (Type II-D), contain unusually high arginine and lysine amino acids content relative to the content observed in Uniref50 protein sequences (FIG. 23).

On average, the percent arginine and lysine composition of SMARTs deviates from the linear trend observed for other residues in SMART sequences, as well as from the residue composition of proteins in the Uniref50 database (FIG. 24A). In addition, the methionine content of SMARTs was observed to be statistically lower than the content observed in proteins from the Uniref50 database (FIG. 24B).

To describe the physicochemical properties of SMARTs, the isoelectric point, molecular weight, and charge were determined from the sequences with the "protr" and "Peptides" packages in R. The high arginine and lysine content observed in SMART sequences may contribute to the high isoelectric point and charge at neutral pH (Table 4).

TABLE 4

Theoretical properties of SMART family members

| Nuclease | length (a.a.) | MW (Da) | pI | Charge at pH 7.2 |
|---|---|---|---|---|
| MG35-1 | 428 | 48300.1 | 11.1 | 52.6 |
| MG35-2 | 524 | 59310.4 | 10.4 | 34.3 |
| MG35-3 | 423 | 47899.5 | 10.8 | 39.8 |
| MG35-6 | 428 | 48373.1 | 10.9 | 43.6 |
| MG35-102 | 424 | 47544.1 | 10.8 | 38.7 |
| IscB (Altae-Tran, 2021) | 439 | 49447.5 | 11.7 | 47.2 |
| MG34-1 | 747 | 86518.4 | 10.2 | 46.9 |
| MG102-2 | 946 | 107544.0 | 9.9 | 38.8 |
| MG102-14 | 949 | 108596.1 | 10.2 | 50.6 |
| MG102-35 | 954 | 108186.4 | 9.9 | 38.3 |
| MG102-45 | 952 | 107614.8 | 10.0 | 40.5 |

Properties were calculated using the R packages Peptides (The R Journal. 7(1), 4-14 (2015)) and protr (*Bioinformatics*, 2015 June 1;31(11):1857-9). pH 7.2 was selected because intracellular pH tends to range between 7.0 and 7.4 (*Biochemical Journal*, 1988, 250(1): 1-8.)

The high arginine and Zn-binding ribbon motif content of SMART nucleases suggest that these enzymes may contain intrinsically disordered regions, which may add flexibility for the protein to interact with large guide RNAs and target DNA. Intrinsically disordered regions are segments of proteins that lack a stable tertiary structure in their native, unbound state (see e.g. Bitard-Feildel, T., Lamiable, A., Mornon, J.-P. & Callebaut, I. Order in Disorder as Observed by the "Hydrophobic Cluster Analysis" of Protein Sequences. *Proteomics* 2018, 18, e1800054, which is incorporated by reference in its entirety herein), may be enriched in positively charged arginines that interact with polyanions (such as RNA) (see e.g. Murthy, A. C. et al. Molecular interactions underlying liquid-liquid phase separation of the FUS low complexity domain. *Nat Struct Mol Biol* 2019, 26, 637-648, which is incorporated by reference in its entirety herein), and may be found as linkers between Zn-binding ribbons to help with "search function" (see e.g. Dyson, H. J. Roles of intrinsic disorder in protein-nucleic acid interactions. *Mol Biosyst* 2011, 8, 97-104, which is incorporated by reference in its entirety herein), all of which are features observed in SMART nucleases.

Example 12—Mismatch Kill Assay

Figure 27:
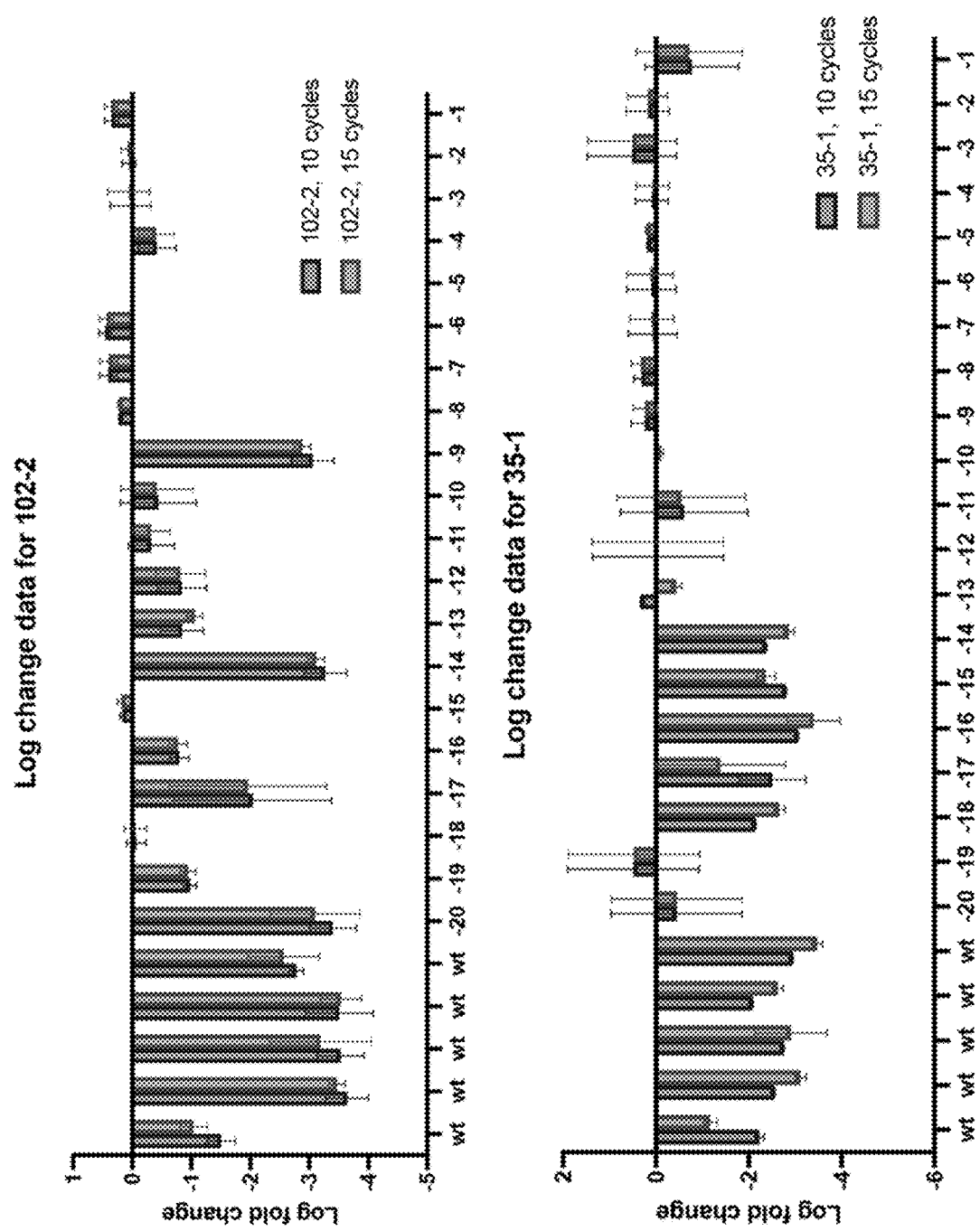
FIG. 27 depicts mismatch kill assays showing the log fold change cleavage activity for spacers with mismatches at each position of the tested spacer for MG102-2 and MG35-1.
Figure 28:
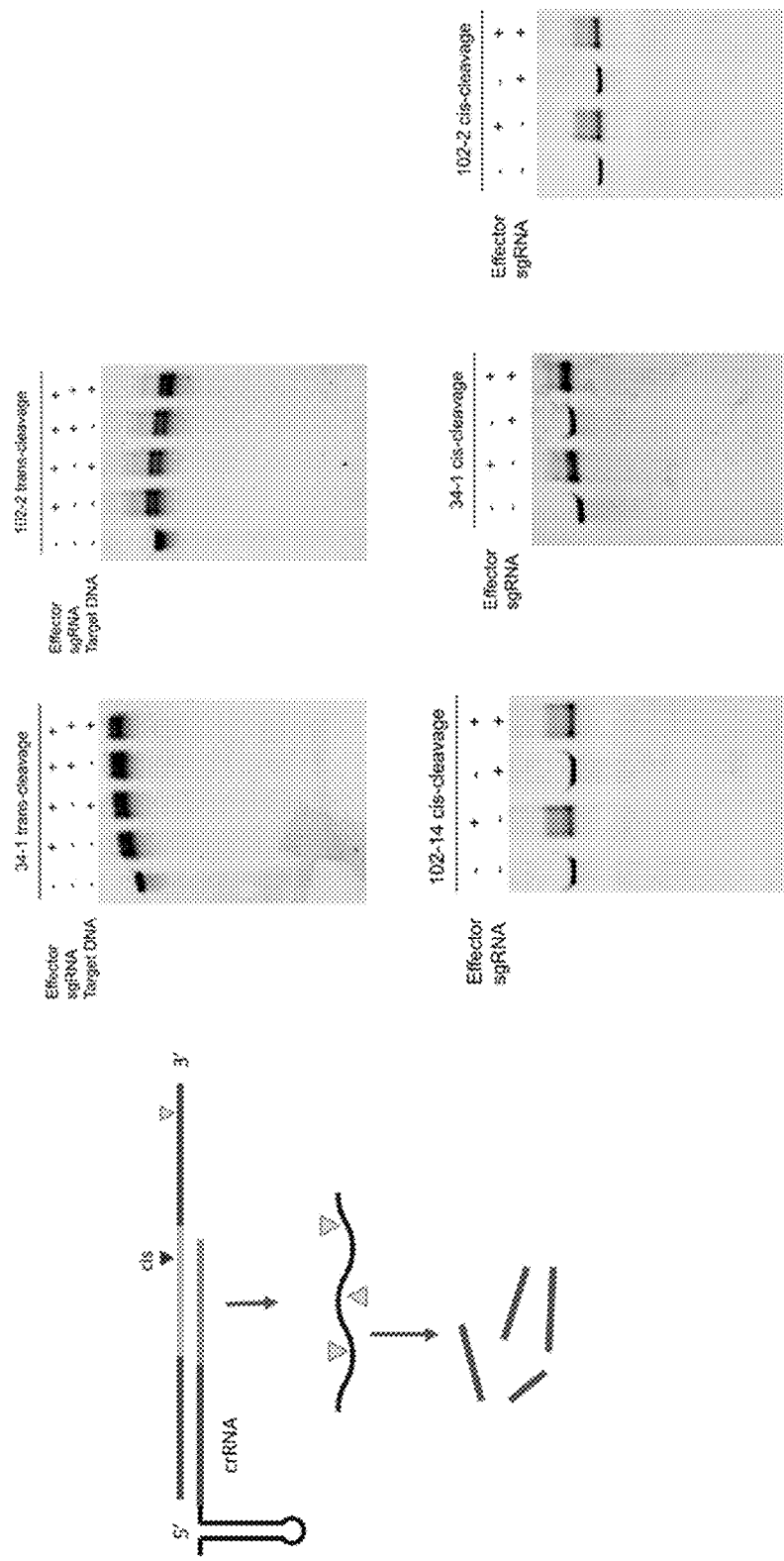
FIG. 28 depicts data demonstrating that SMART nucleases do not exhibit activity on ssDNA.

To determine the specificity of various SMART enzymes, a mismatch kill assay was developed in which *E. coli* BL21 (DE3) strains (NEB) were transformed with plasmids containing T7 driven effector (ampicillin resistance) and their T7-driven sgRNA (chloramphenicol resistance), plated, and grown overnight. The resulting colonies were made competent and transformed with 100 ng of a kanamycin plasmid in three conditions: a target spacer and PAM in the backbone, a library of 25 plasmids each containing a single mismatch along a 24nt spacer and constant PAM, or a control plasmid with no spacer or PAM (FIG. 25D). After heat shock, transformations were recovered in SOC medium for 2 h at 37° C. Cultures were plated and grown at 37° C. overnight on induction media (LB agar plates with antibiotics and 0.05 mM IPTG). Plasmids were extracted from the surviving mismatch colonies via miniprep kit (Qiagen). The target region was amplified via PCR and analyzed via NGS. Enriched spacers relative to the untreated library were unable to be recognized and cut by the nucleases, and thus are considered to be regions where the effectors do not tolerate a mismatch. If a mismatch is tolerated, the enzyme is expected to cleave the antibiotic resistance plasmid and growth impairment will be observed. The MG102-2 nuclease was observed to not tolerate mismatches along the first 13 positions of the target plasmid from the PAM, while variable mismatch tolerance was observed from position 14 (FIG. 25D and FIG. 27). These results suggest that the SMART nucleases can be highly specific and do not exhibit collateral ssDNA cleavage (FIG. 28).

Example 13—Human Cell Editing with the SMART Nuclease MG102-2

K562 cells from ATCC were cultured according to ATCC protocols. Two sgRNAs targeting the TRAC locus were designed based off the MG102-2 PAM and chemically synthesized by IDT. For gene editing experiments, 500 ng of in vitro synthesized MG102-2 mRNA and either 150, 300, or 450 pmol of the indicated sgRNA were co-nucleofected in $1.5 \times 10^5$ cells using the Lonza 4D NUCLEOFECTOR® (program FF-120). In parallel, cells were nucleofected with neither mRNA nor guide to assess background at sites targeted by TRAC guides. Cells were harvested 72 hours post-electroporation for genomic DNA extraction using QUICKEXTRACT™ (Lucigen #09050) and processed for next-generation sequencing on an Illumina Miseq. Resulting data were analyzed with an indel calculator script.

Figure 26:
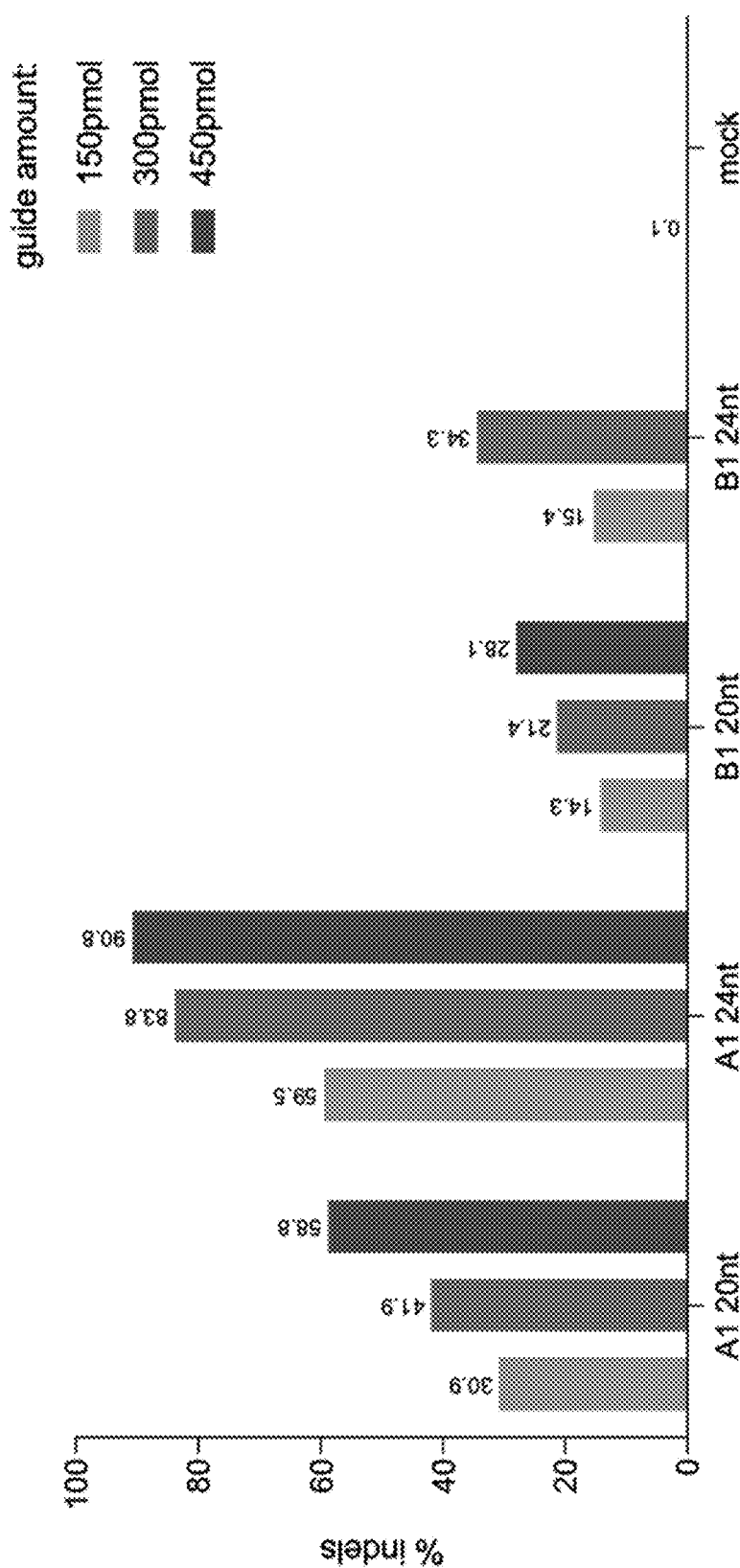
FIG. 26 depicts data demonstrating that MG102-2 is a highly active nuclease in human cells. Nuclease activity was tested by nucleofecting MG102-2 mRNA and two sgRNA targeting sites in the TRAC locus (guides A1 and B1) with increasing concentrations of sgRNA (150, 300 and 450 pmol/reaction). The mock control represents background editing levels at the target region in the absence of mRNA and guide.
Figure 29:
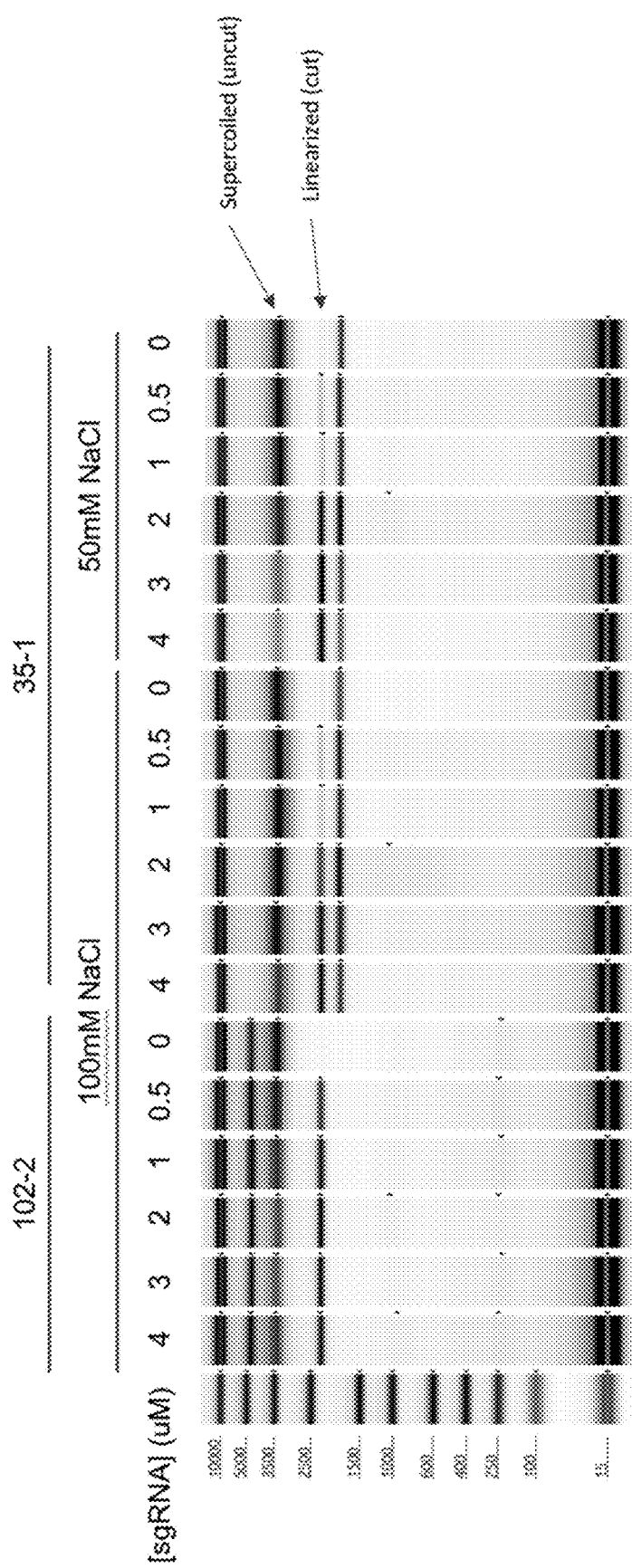
FIG. 29 depicts guide and salt concentration titration for SMART nucleases. In vitro cleavage assays for MG102-2 (lanes 1-6) and SMART HEARO 35-1 (lanes 7-18) show cleavage of target plasmid DNA (at ~3500 bp) into a linear DNA products (below 2500 bp).

Delivery of SMART nucleases via mRNA to human cells targeting the T cell receptor alpha constant locus (TRAC) resulted in over 90% editing activity at one of two TRAC target sites with the MG102-2 nuclease (FIG. 26). As observed in in vitro experiments (FIG. 29), increasing the amount of sgRNA improved editing efficiency at both target loci (FIG. 26). Although localization of the MG34-1 system to the nucleus of human cells (fused with nuclear localization signals, NLS) was confirmed, nuclease-induced InDel formation was not detected for this nuclease.

Example 14—Cleavage Preferences of SMART Nucleases

Figure 25A:
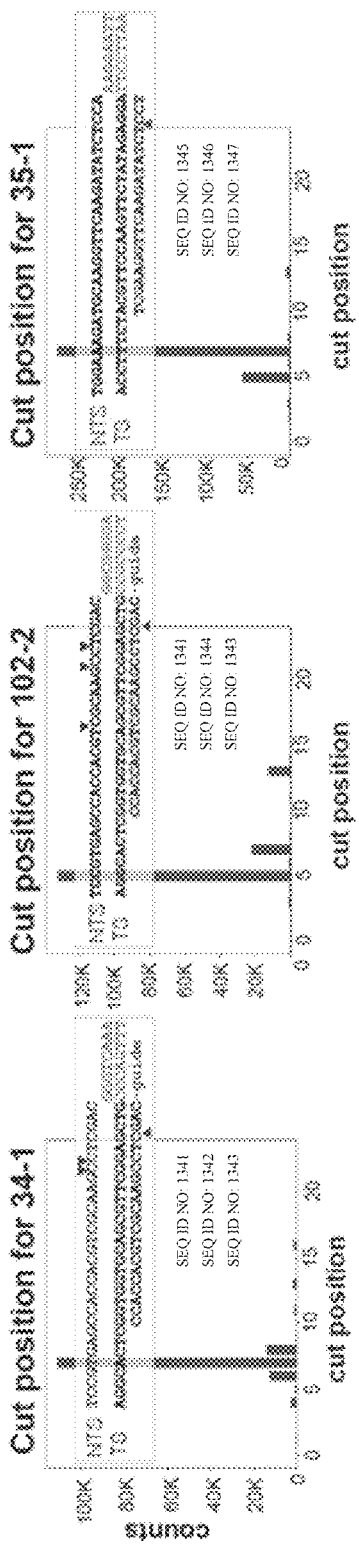
FIGS. 25A-FIG. 25D depict data demonstrating that SMART enzymes are dsDNA nucleases.
Figure 25B:
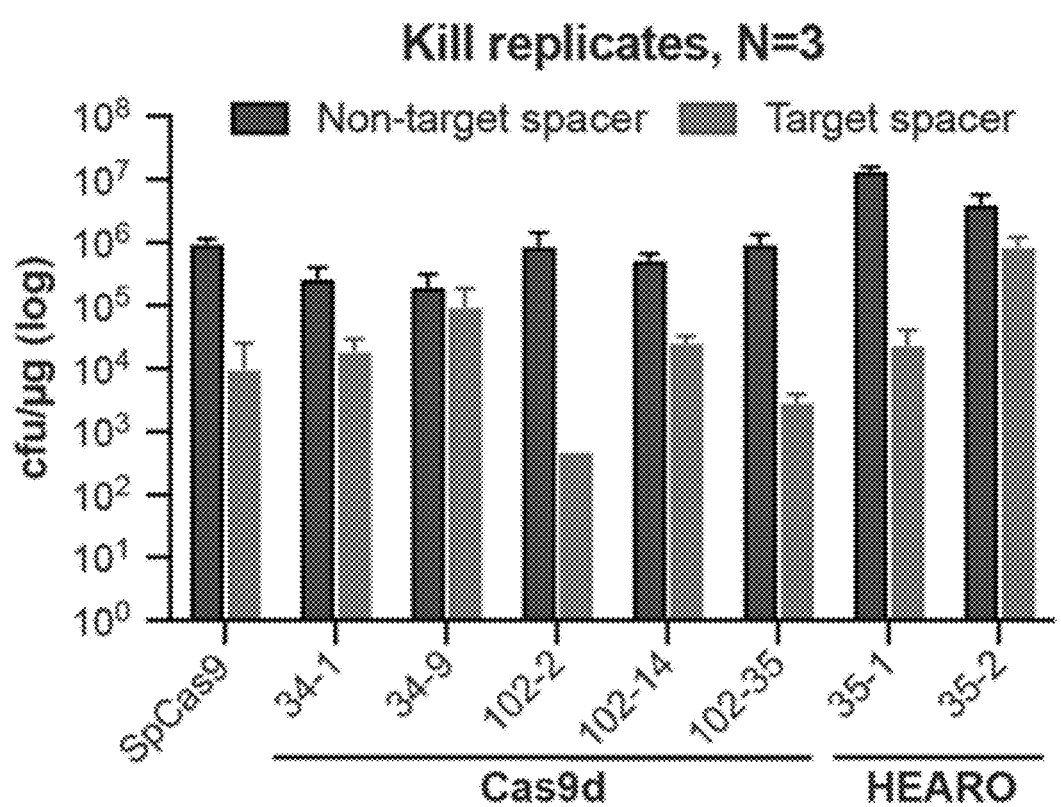
Figure 25C:
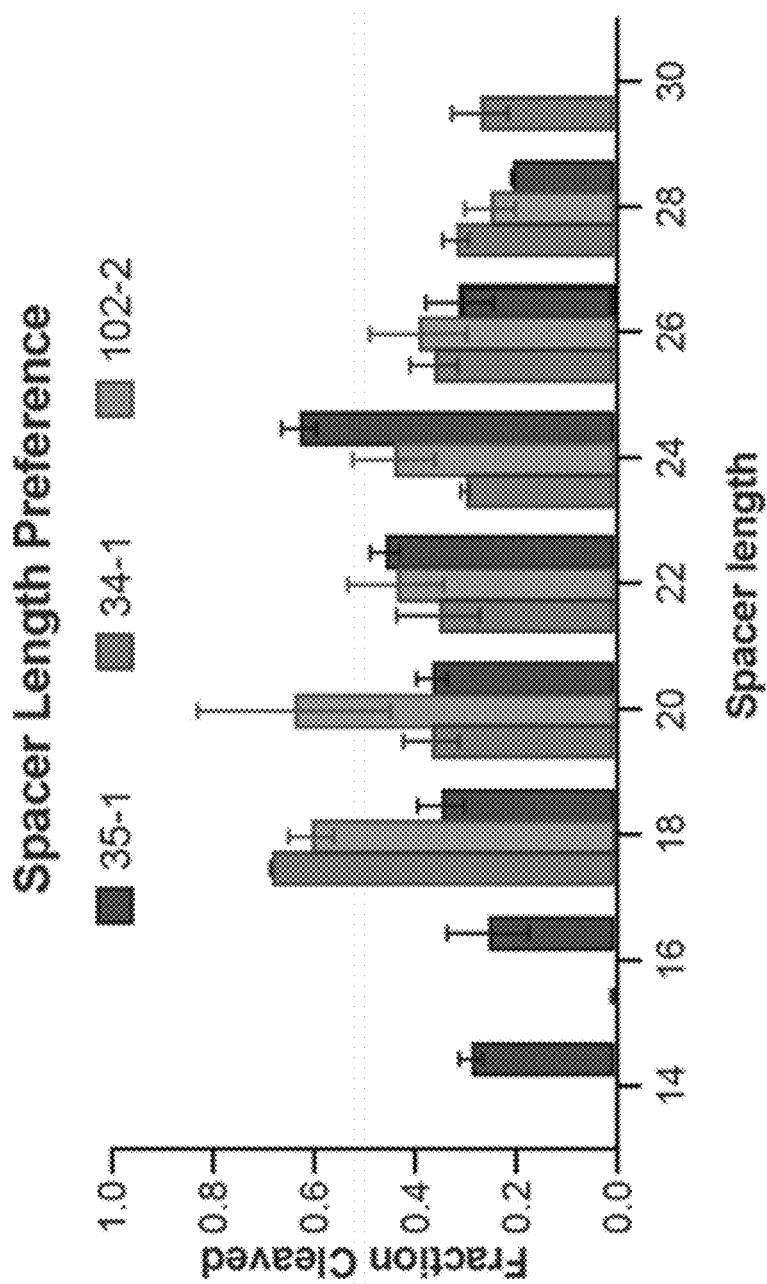
Figure 25D:
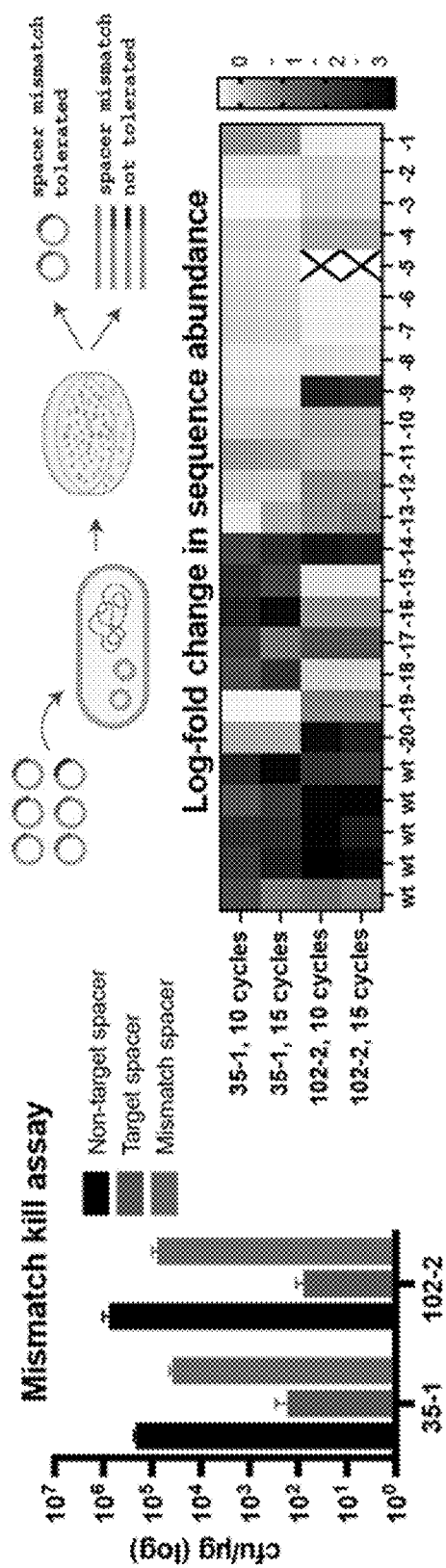

Sequencing the cleavage products of the MG34-1 and MG102-2 nucleases show that these enzymes create a staggered double strand DNA break (FIG. 25A). Analysis of the cut sites indicates selective cleavage at position five to seven from the PAM (FIG. 25A). These results suggest a rarely observed biochemical cleavage mechanism compared with most Cas9 enzymes, which create blunt end, as well as staggered cuts that are preferentially at positions 3 to 5 from the PAM. In vitro cleavage assays with in vitro transcription/translation reactions and with purified protein indicate that MG34-1 and MG102-2 are most efficient with 18 and 20 nucleotide spacers (FIG. 25C). Furthermore, activity was confirmed in vivo using *E. coli* plasmid interference assays, showing 2-fold (MG34-9) to >500-fold (MG102-2) growth repression for five SMART nucleases with the specified targeting spacer (FIG. 25B).

Example 15—SMART I Enzymes are Active Nucleases in Human Cells

K562 cells purchased from ATCC were cultured according to ATCC protocols. sgRNAs targeting the TRAC or AAVS1 loci were designed based on the PAMs recognized by MG102-2, MG102-36, MG102-39, MG102-42, MG102-45, and MG33-34 and chemically synthesized by IDT. For gene editing experiments, 500 ng of in vitro-synthesized nuclease mRNA and 450 pmol of the indicated sgRNA were co-nucleofected in $1.5 \times 10^5$ cells using the Lonza 4D NUCLEOFECTOR® (program FF-120). Cells were harvested 72 hours post-electroporation for genomic DNA extraction using QUICKEXTRACT™ (Lucigen #09050) and processed for amplicon next-generation sequencing on an Illumina Miseq. Resulting data were analyzed with an in-house indel calculator script.

Figure 30A:
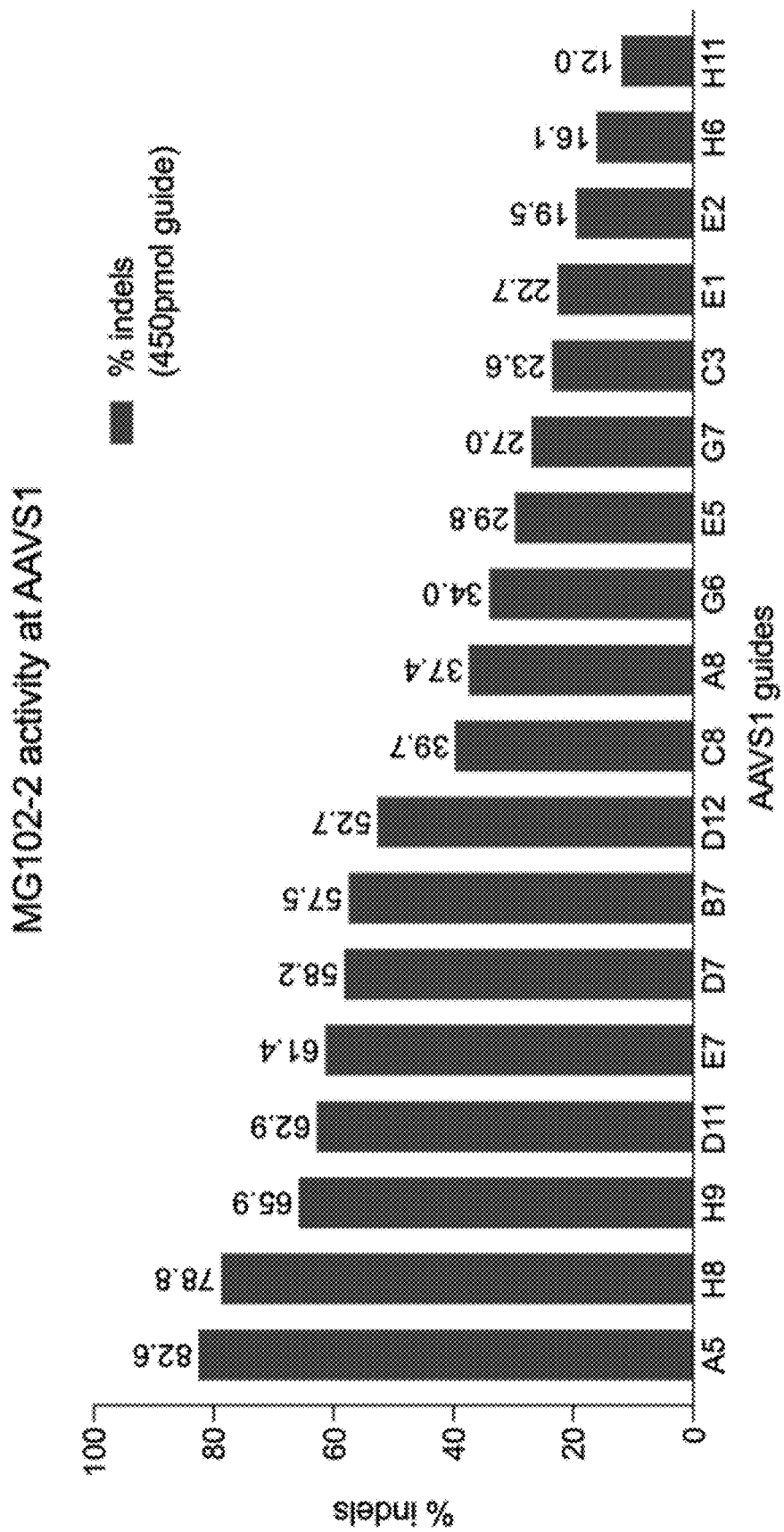
FIGS. 30A-FIG. 30G depict data demonstrating SMART I editing efficiency in human cells. Nuclease activity was tested by nucleofecting SMART I mRNA and sgRNAs (450 pmol/reaction) targeting multiple sites in the locus. Each bar represents editing efficiency at a site targeted by a specific spacer (guides).
Figures 30B, 30C, 30D:
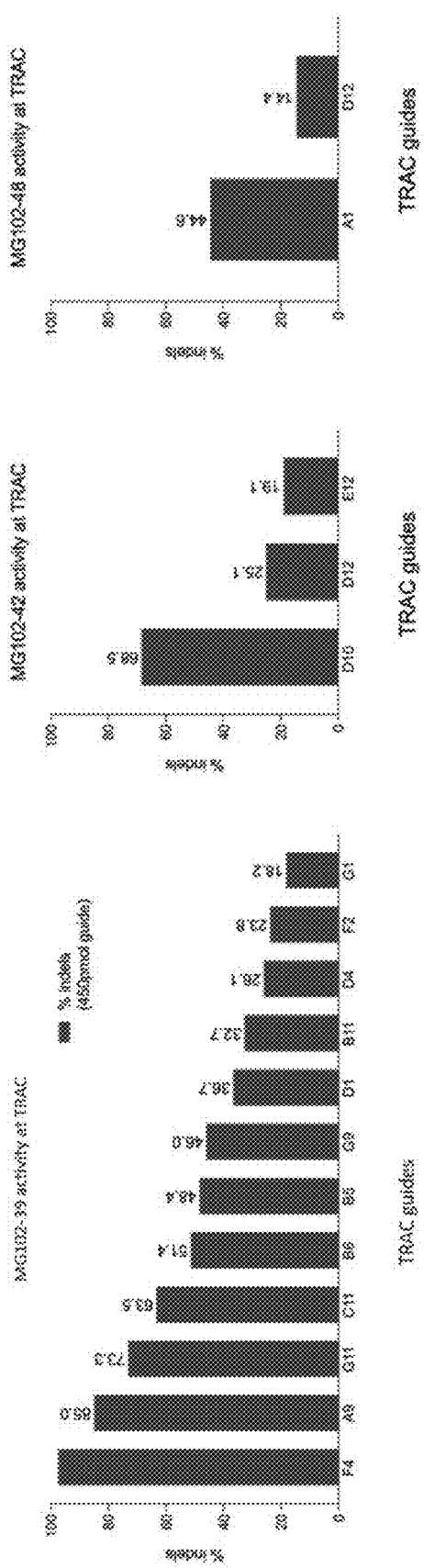
Figures 30E, 30F, 30G:
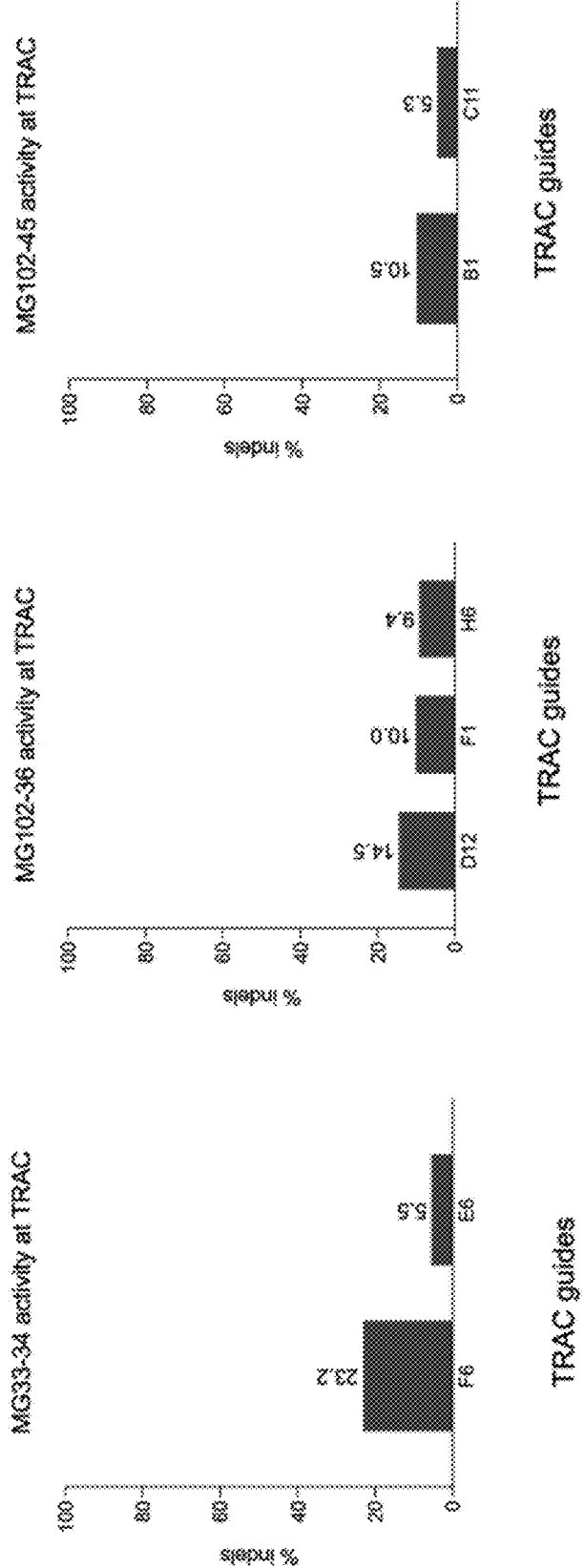

As described elsewhere herein, the SMART I nuclease MG102-2 is active at two target sites in the TRAC locus of the human genome when delivered via mRNA. It was further confirmed that MG102-2 (SEQ ID No: 582) is also active at the AAVS1 locus (a safe harbor locus) in the human genome, with the enzyme's cleavage efficiency as high as 82.6% and >50% editing efficiency at eight different target sites (FIG. 30A). In addition, MG102-39 (SEQ ID No: 993), MG102-42 (SEQ ID No: 996), and MG102-48 (SEQ ID No: 1002) showed cleavage activity >40% at the TRAC locus of the human genome when delivered by mRNA (FIGS. 30B-30D), while MG33-34 (SEQ ID No: 988), MG102-36 (SEQ ID No: 990), and MG102-45 (SEQ ID No: 999) showed cleavage efficiency above background (10%) at the TRAC locus (FIGS. 30E-30G).

TABLE 5

Guide RNA and Targeting Sequences Tested in Example 15

| SEQ ID NO | Name | Sequence |
| --- | --- | --- |
| 1087 | MG102-2 AAVS1 A5 | mU*mUmC*rUrGrGrArGrArGrGrUrArGrCrGrCrAr GrGrGrUrGrUrUrUrCrArArUrCrArArArCrUrGrArArArAr GrUrUrCrGrGrUrUrGrArArArArGrArGrCrArUrCrCrGr UrCrCrGrGrArGrGrGrUrGrCrArCrUrCrCrGrGrGrArUrGr GrGrGrCrArGrUrCrCrCrGrGrCrArCrUrUrGrCrGrUrUrUr UrCrCrCrGrGrCrUrUrArCrGrCrUrUrCrGrGrArArArAr ArGrCrCrCrUrCrGrGrCrArCrGrUrCrGrArArArArGrAr CrArGrGrArUrGrUrGrArGrCrCrCrArA*mU*mU*mU |
| 1088 | MG102-2 AAVS1 H8 | mG*mC*mC*rCrUrGrGrArArUrArUrArArGrUrGrGr UrCrCrGrUrUrUrCrArArUrCrArArArCrUrGrArArArAr GrUrUrCrGrGrUrUrGrArArArArGrArGrCrArUrCrCrGr UrCrCrGrGrArGrGrGrUrGrCrArCrUrCrCrGrGrGrArUrGr GrGrGrCrArGrUrCrCrCrGrGrCrArCrUrUrGrCrGrUrUrUr UrCrCrCrGrGrCrUrUrArCrGrCrUrCrUrCrGrGrArArArAr ArGrCrCrCrUrCrGrGrCrArCrGrUrCrGrArArArArGrAr CrArGrGrArUrGrUrGrArGrCrCrCrArA*mU*mU*mU |
| 1089 | MG102-2 AAVS1 H9 | mA*mU*mG*rCrUrGrUrCrCrUrGrArArGrUrGrGrArCrAr UrArGrGrUrUrUrCrArArUrCrArArArCrUrGrArArArAr GrUrUrCrGrGrUrUrGrArArArArGrArGrCrArUrCrCrGr UrCrCrGrGrArGrGrGrUrGrCrArCrUrCrCrGrGrGrArUrGr GrGrGrCrArGrUrCrCrCrGrGrCrArCrUrUrGrCrGrUrUrUr UrCrCrCrGrGrCrUrUrArCrGrCrUrUrCrGrGrArArArAr ArGrCrCrCrUrCrGrGrCrArCrGrUrCrGrArArArArGrAr CrArGrGrArUrGrUrGrArGrCrCrCrArA*mU*mU*mU |
| 1090 | MG102-2 AAVS1 D11 | mC*mU*mA*rGrArGrArGrGrUrArArGrGrGrGrGrUrAr GrGrGrGrGrUrUrCrArUrCrArArArCrUrGrArArArAr GrUrUrCrGrGrUrUrGrArArArArGrArGrCrArUrCrCrGr UrCrCrGrGrArGrGrGrUrGrCrArCrUrCrCrGrGrGrArUrGr GrGrGrCrArGrUrCrCrCrGrGrCrArCrUrUrGrCrGrUrUrUr UrCrCrCrGrGrCrUrUrArCrGrCrUrUrCrGrGrArArArAr ArGrCrCrCrUrCrGrGrCrArCrGrUrCrGrArArArArGrAr CrArGrGrArUrGrUrGrArGrCrCrCrArA*mU*mU*mU |
| 1091 | MG102-2 AAVS1 E7 | mA*mG*mG*rArArGrGrArGrArGrGrCrUrArArGrGr ArUrGrGrUrUrUrCrArArUrCrArArArCrUrGrArArArAr GrUrUrCrGrGrUrUrGrArArArArGrArGrCrArUrCrCrGr UrCrCrGrGrArGrGrGrUrGrCrArCrUrCrCrGrGrGrArUrGr GrGrGrCrArGrUrCrCrCrGrGrCrArCrUrUrGrCrGrUrUrUr UrCrCrCrGrGrCrUrUrArCrGrCrUrUrCrGrGrArArArAr ArGrCrCrCrUrCrGrGrCrArCrGrUrCrGrArArArArGrAr CrArGrGrArUrGrUrGrArGrCrCrCrArA*mU*mU*mU |
| 1092 | MG102-2 AAVS1 D7 | mA*mU*mA*rUrCrArGrGrArGrArCrUrArGrGrArArGrGr ArGrGrArGrUrUrUrCrArArUrCrArArArCrUrGrArArArAr GrUrUrCrGrGrUrUrGrArArArArGrArGrCrArUrCrCrGr UrCrCrGrGrArGrGrGrUrGrCrArCrUrCrCrGrGrGrArUrGr GrGrGrCrArGrUrCrCrCrGrGrCrArCrUrUrGrCrGrUrUrUr UrCrCrCrGrGrCrUrUrArCrGrCrUrUrCrGrGrArArArAr ArGrCrCrCrUrCrGrGrCrArCrGrUrCrGrArArArArGrAr CrArGrGrArUrGrUrGrArGrCrCrCrArA*mU*mU*mU |
| 1093 | MG102-2 AAVS1 B7 | mC*mU*mG*rCrCrUrArCrArGrGrArGrGrUrGrGrGrGr GrUrUrArGrUrUrUrCrArArUrCrArArArCrUrGrArArArAr GrUrUrCrGrGrUrUrGrArArArArGrArGrCrArUrCrCrGr UrCrCrGrGrArGrGrGrUrGrCrArCrUrCrCrGrGrGrArUrGr GrGrGrCrArGrUrCrCrCrGrGrCrArCrUrUrGrCrGrUrUrUr UrCrCrCrGrGrCrUrUrArCrGrCrUrCrUrCrGrGrArArArAr ArGrCrCrCrUrCrGrGrCrArCrGrUrCrGrArArArArGrAr CrArGrGrArUrGrUrGrArGrCrCrCrArA*mU*mU*mU |
| 1094 | MG102-2 AAVS1 D12 | mG*mC*mA*rArGrArGrGrArUrGrGrArGrArGrGrUrGrGr CrUrArGrUrUrUrCrArArUrCrArArArCrUrGrArArArAr GrUrUrCrGrGrUrUrGrArArArArGrArGrCrArUrCrCrGr UrCrCrGrGrArGrGrGrUrGrCrArCrUrCrCrGrGrGrArUrGr GrGrGrCrArGrUrCrCrCrGrGrCrArCrUrUrGrCrGrUrUrUr UrCrCrCrGrGrCrUrUrArCrGrCrUrUrCrGrGrArArArAr ArGrCrCrCrUrCrGrGrCrArCrGrUrCrGrArArArArGrAr CrArGrGrArUrGrUrGrArGrCrCrCrArA*mU*mU*mU |
| 1095 | MG102-2 AAVS1 C8 | mG*mA*mG*rGrGrGrArCrArGrArUrArArArArGrUrArCr CrCrArGrGrUrUrUrCrArArUrCrArArArCrUrGrArArArAr GrUrUrCrGrGrUrUrGrArArArArGrArGrCrArUrCrCrGr UrCrCrGrGrArGrGrGrUrGrCrArCrUrCrCrGrGrGrArUrGr |

TABLE 5-continued

Guide RNA and Targeting Sequences Tested in Example 15

| SEQ ID NO | Name | Sequence |
|---|---|---|
|  |  | GrGrGrCrArGrUrCrCrCrGrGrCrArCrUrUrGrCrGrGrUrUrUr<br>UrCrCrCrCrGrGrCrUrUrArCrGrCrUrUrCrGrGrArArArAr<br>ArGrCrCrCrUrUrCrGrGrCrArCrGrUrCrGrArArArGrAr<br>CrArGrGrArUrGrUrGrArGrCrCrCrArA*mU*mU*mU |
| 1096 | MG102-2 AAVS1 A8 | mG*mU*mG*rGrCrCrCrArCrUrGrUrGrGrGrUrGrGr<br>ArGrGrGrUrUrCrArArUrCrArArArCrUrGrArArArAr<br>GrUrUrCrCrGrGrUrUrGrArArArArGrArGrCrArUrCrCrGr<br>UrCrCrGrGrArGrGrGrUrGrCrArArCrUrCrCrGrGrArUrGr<br>GrGrGrCrArGrUrCrCrCrGrGrCrArCrUrUrGrCrGrUrUrUr<br>UrCrCrCrCrGrGrCrUrUrArCrGrCrUrUrCrGrGrArArArAr<br>ArGrGrCrCrCrUrUrCrGrGrCrArCrGrUrCrGrArArArGrAr<br>CrArGrGrArUrGrUrGrArGrCrCrCrArA*mU*mU*mU |
| 1097 | MG102-2 AAVS1 G6 | mU*mG*mG*rCrUrCrCrArGrGrArArArUrGrGrGrGrGrUr<br>GrUrGrUrGrUrUrUrCrArArUrCrArArArCrUrGrArArArAr<br>GrUrUrCrCrGrGrUrUrGrArArArArGrArGrCrArUrCrCrGr<br>UrCrCrGrGrArGrGrGrUrGrCrArArCrUrCrCrGrGrArUrGr<br>GrGrGrCrArGrUrCrCrCrGrGrCrArCrUrUrGrCrGrUrUrUr<br>UrCrCrCrCrGrGrCrUrUrArCrGrCrUrUrCrGrGrArArArAr<br>ArGrGrCrCrCrUrUrCrGrGrCrArCrGrUrCrGrArArArGrAr<br>CrArGrGrArUrGrUrGrArGrCrCrCrArA*mU*mU*mU |
| 1098 | MG102-2 AAVS1 E5 | mG*mUmG*rGrCrCrArCrUrGrArGrArArCrCrGrGrGrCr<br>ArGrGrUrGrUrUrUrCrArArUrCrArArArCrUrGrArArArAr<br>GrUrUrCrCrGrGrUrUrGrArArArArGrArGrCrArUrCrCrGr<br>UrCrCrGrGrArGrGrGrUrGrCrArArCrUrCrCrGrGrArUrGr<br>GrGrGrCrArGrUrCrCrCrGrGrCrArCrUrUrGrCrGrUrUrUr<br>UrCrCrCrCrGrGrCrUrUrArCrGrCrUrUrCrGrGrArArArAr<br>ArGrGrCrCrCrUrUrCrGrGrCrArCrGrUrCrGrArArArGrAr<br>CrArGrGrArUrGrUrGrArGrCrCrCrArA*mU*mU*mU |
| 1099 | MG102-2 AAVS1 G7 | mU*mC*mU*rGrUrCrArCrCrArArUrCrCrUrGrUrCrCrCrU<br>rArGrUrGrUrUrUrCrArArUrCrArArArCrUrGrArArArArG<br>rUrUrCrCrGrGrUrUrGrArArArArGrArGrCrArUrCrCrGrU<br>rCrCrGrGrArGrGrGrUrGrCrArArCrUrCrCrGrGrArUrGrG<br>rGrGrCrArGrUrCrCrCrGrGrCrArCrUrUrGrCrGrUrUrUrU<br>rCrCrCrCrGrGrCrUrUrArCrGrCrUrUrCrGrGrArArArArA<br>rGrGrCrCrCrUrUrCrGrGrCrArCrGrUrCrGrArArArGrArC<br>rArGrGrArUrGrUrGrArGrCrCrCrArA*mU*mU*mU |
| 1100 | MG102-2 AAVS1 C3 | mU*mU*mC*rUrCrCrUrCrUrUrGrGrGrArArGrUrGrUrArA<br>rGrGrArGrUrUrUrCrArArUrCrArArArCrUrGrArArArArG<br>rUrUrCrCrGrGrUrUrGrArArArArGrArGrCrArUrCrCrGrU<br>rCrCrGrGrArGrGrGrUrGrCrArArCrUrCrCrGrGrArUrGrG<br>rGrGrCrArGrUrCrCrCrGrGrCrArCrUrUrGrCrGrUrUrUrU<br>rCrCrCrCrGrGrCrUrUrArCrGrCrUrUrCrGrGrArArArArA<br>rGrGrCrCrCrUrUrCrGrGrCrArCrGrUrCrGrArArArGrArC<br>rArGrGrArUrGrUrGrArGrCrCrCrArA*mU*mU*mU |
| 1101 | MG102-2 AAVS1 E1 | mC*mC*mU*rGrCrCrArGrGrArCrGrGrGrGrCrUrGrCrCr<br>UrArCrGrUrUrUrCrArArUrCrArArArCrUrGrArArArAr<br>GrUrUrCrCrGrGrUrUrGrArArArArGrArGrCrArUrCrCrGr<br>UrCrCrGrGrArGrGrGrUrGrCrArArCrUrCrCrGrGrArUrGr<br>GrGrGrCrArGrUrCrCrCrGrGrCrArCrUrUrGrCrGrUrUrUr<br>UrCrCrCrCrGrGrCrUrUrArCrGrCrUrUrCrGrGrArArArAr<br>ArGrGrCrCrCrUrUrCrGrGrCrArCrGrUrCrGrArArArGrAr<br>CrArGrGrArUrGrUrGrArGrCrCrCrArA*mU*mU*mU |
| 1102 | MG102-2 AAVS1 E2 | mA*mA*mA*rUrUrGrGrGrArCrArGrArArArGrGrUr<br>GrArArGrUrUrUrCrArArUrCrArArArCrUrGrArArArAr<br>GrUrUrCrCrGrGrUrUrGrArArArArGrArGrCrArUrCrCrGr<br>UrCrCrGrGrArGrGrGrUrGrCrArArCrUrCrCrGrGrArUrGr<br>GrGrGrCrArGrUrCrCrCrGrGrCrArCrUrUrGrCrGrUrUrUr<br>UrCrCrCrCrGrGrCrUrUrArCrGrCrUrUrCrGrGrArArArAr<br>ArGrGrCrCrCrUrUrCrGrGrCrArCrGrUrCrGrArArArGrAr<br>CrArGrGrArUrGrUrGrArGrCrCrCrArA*mU*mU*mU |
| 1103 | MG102-2 AAVS1 H6 | mG*mG*mG*rUrGrUrGrUrCrArCrCrArGrArUrArArGrGr<br>ArArUrCrGrUrUrUrCrArArUrCrArArArCrUrGrArArArAr<br>GrUrUrCrCrGrGrUrUrGrArArArArGrArGrCrArUrCrCrGr<br>UrCrCrGrGrArGrGrGrUrGrCrArArCrUrCrCrGrGrArUrGr<br>GrGrGrCrArGrUrCrCrCrGrGrCrArCrUrUrGrCrGrUrUrUr<br>UrCrCrCrCrGrGrCrUrUrArCrGrCrUrUrCrGrGrArArArAr<br>ArGrGrCrCrCrUrUrCrGrGrCrArCrGrUrCrGrArArArGrAr<br>CrArGrGrArUrGrUrGrArGrCrCrCrArA*mU*mU*mU |

TABLE 5-continued

Guide RNA and Targeting Sequences Tested in Example 15

| SEQ ID NO | Name | Sequence |
|---|---|---|
| 1104 | MG102-2 AAVS1 H11 | mA*mG*mA*rGrGrUrGrArCrCrGrArArUrCrArArCrAr GrGrArGrGrUrUrUrCrArArUrCrArArArCrUrGrArArArAr GrUrUrCrCrGrGrUrUrGrArArArArGrArGrCrArUrCrCrGr UrCrCrUrGrGrUrUrGrArCrUrCrCrGrGrArUrGr GrGrGrCrArGrUrCrCrCrGrGrCrArCrUrGrCrGrUrUrUr UrCrCrCrGrGrCrUrUrArCrGrCrUrUrCrGrArArArAr ArGrGrCrCrCrUrCrGrGrCrArCrGrUrCrGrArArArGrAr CrArGrGrArUrGrUrGrArGrCrCrArA*mU*mU*mU |
| 1105 | MG102-2 AAVS1 A5 | TTCTGGGAGAGGGTAGCGCAGGGT |
| 1106 | MG102-2 AAVS1 H8 | GCCCTGGGAATATAAGGTGGTCCC |
| 1107 | MG102-2 AAVS1 H9 | ATGCTGTCCTGAAGTGGACATAGG |
| 1108 | MG102-2 AAVS1 D11 | CTAGAGAGGTAAGGGGGGTAGGGG |
| 1109 | MG102-2 AAVS1 E7 | AGGAAGGAGGAGGCCTAAGGATGG |
| 1110 | MG102-2 AAVS1 D7 | ATATCAGGAGACTAGGAAGGAGGA |
| 1111 | MG102-2 AAVS1 B7 | CTGCCTAACAGGAGGTGGGGGTTA |
| 1112 | MG102-2 AAVS1 D12 | GCAAGAGGATGGAGAGGTGGCTAA |
| 1113 | MG102-2 AAVS1 C8 | GAGGGGACAGATAAAAGTACCCAG |
| 1114 | MG102-2 AAVS1 A8 | GTGGCCCCACTGTGGGGTGGAGGG |
| 1115 | MG102-2 AAVS1 G6 | TGGCTCCAGGAAATGGGGTGTGT |
| 1116 | MG102-2 AAVS1 E5 | GTGGCCACTGAGAACCGGGCAGGT |
| 1117 | MG102-2 AAVS1 G7 | TCTGTCACCAATCCTGTCCCTAGT |
| 1118 | MG102-2 AAVS1 C3 | TTCTCCTCTTGGGAAGTGTAAGGA |
| 1119 | MG102-2 AAVS1 E1 | CCTGCCAGGACGGGGCTGGCTACT |
| 1120 | MG102-2 AAVS1 E2 | AAATTGGGGACTAGAAAGGTGAAG |
| 1121 | MG102-2 AAVS1 H6 | GGGTGTGTCACCAGATAAGGAATC |
| 1122 | MG102-2 AAVS1 H11 | AGAGGTGACCCGAATCCACAGGAG |
| 1123 | MG102-36 TRAC D12 | mG*mC*mC*rArCrUrUrUrCrArGrGrArGrGrArGrArUr UrCrGrGrGrUrUrUrCrArArUrCrArArArCrUrGrArArArAr GrUrUrCrCrGrGrUrUrGrArArArArGrArGrCrArUrCrCrGr UrCrUrGrGrUrUrCrArGrCrArCrUrCrCrGrGrArUrGrGr GrCrArGrUrCrCrCrGrGrCrUrCrUrUrGrCrGrGrUrUrArCr CrGrArUrGrCrGrGrCrArArArCrGrUrGrUrCrGrArUrGrAr GrCrCrArArCrUrGrCrCrArGrArCrArCrGrUrCrUrUrUrUr GrArCrArGrGrArUrGrUrGrArGrCrCrArU*mU*mUxmU*mU |
| 1124 | MG102-36 TRAC F1 | mG*mA*mC*rCrCrUrGrCrCrGrUrGrUrArCrArGrArGrCrUr GrGrArGrGrUrUrUrCrArArUrCrArArArCrUrGrArArArAr GrUrUrCrCrGrGrUrUrGrArArArArGrArGrCrArUrCrCrGr UrCrUrGrGrUrUrCrArGrCrArCrUrCrCrGrGrArUrGrGrGr GrCrArGrUrCrCrCrGrGrCrUrCrUrUrGrCrGrGrUrUrArCr CrGrArUrGrCrGrGrCrArArArCrGrUrGrUrCrGrArUrGrAr GrCrCrArArCrUrGrCrCrArGrArCrArCrGrUrCrUrUrUrUr GrArCrArGrGrArUrGrUrGrArGrCrCrArU*mU*mU*mU |
| 1125 | MG102-36 TRAC H6 | mU*mU*mG*rArArGrUrCrCrArUrArGrArCrCrUrCrArUrG rUrCrUrGrUrUrUrCrArArUrCrArArArCrUrGrArArArArGr UrUrCrCrGrGrUrUrGrArArArArGrArGrCrArUrCrCrGrUr CrUrGrUrCrArGrGrCrArCrUrCrCrGrGrArUrGrGrGrGr CrArGrUrCrCrCrGrGrCrUrCrUrUrGrCrGrGrUrUrArCrCr GrArUrGrCrGrGrCrArArArCrGrUrGrUrCrGrArUrGrArGr CrCrArArCrUrGrCrCrArGrArCrArCrGrUrCrUrUrUrUrGr ArCrArGrGrArUrGrUrGrArGrCrCrArU*mU*mU*mU |

TABLE 5-continued

Guide RNA and Targeting Sequences Tested in Example 15

| SEQ ID NO | Name | Sequence |
|---|---|---|
| 1126 | MG102-39 TRAC F4 | mG*mC*mU*rGrCrCrCrUrUrArCrCrUrGrGrGrCrUrGrGr GrGrArArGrUrUrUrCrArGrUrUrArCrCrUrGrArGrArAr ArUrCrArGrGrCrUrGrArArGrCrUrGrArArArArGrArGrCr ArUrCrCrGrUrCrCrGrGrArArGrGrUrCrCrArCrUrCrCrGr GrGrUrUrArGrGrGrCrArGrArArUrCrCrGrGrCrUrCrUrGr GrUrCrCrUrCrUrCrCrUrGrGrCrCrCrUrUrUrCrGrGrGr CrUrCrCrGrArGrArGrGrArArGrCrCrUrUrCrCrGrGrCrAr UrGrUrCrUrUrCrGrGrArCrArGrGrArUrGrUrGrArGrCrCr UrUrU*mU*mU*mU |
| 1127 | MG102-39 TRAC A9 | mU*mC*mU*rUrGrGrUrUrUrUrArCrArGrArUrArCrGrArA rCrUrCrUrGrUrUrCrArGrUrUrArCrCrCrUrGrArGrArArA rUrCrArGrGrCrUrGrArArGrCrUrGrArArArArGrArGrCrA rUrCrCrGrUrCrCrGrGrArArGrGrUrCrCrArCrUrCrCrGrG rGrUrUrArGrGrGrCrArGrArArUrCrCrGrGrCrUrCrUrGrG rUrCrCrUrCrUrCrCrUrGrGrCrCrCrUrUrUrCrGrGrGrC rUrCrCrGrArGrArGrGrArArGrCrCrUrUrCrCrGrGrCrArU rGrUrCrUrUrCrGrGrArCrArGrGrArUrGrUrGrArGrCrCrU rUrU*mU*mU*mU |
| 1128 | MG102-39 TRAC G11 | mG*mG*mC*rCrArCrUrUrCrArGrGrArGrGrArGrGrAr UrUrCrGrUrUrUrCrArGrUrUrArCrCrCrUrGrArGrArAr ArUrCrArGrGrCrUrGrArArGrCrUrGrArArArArGrArGrCr ArUrCrCrGrUrCrCrGrGrArArGrGrUrCrCrArCrUrCrCrGr GrGrUrUrArGrGrGrCrArGrArArUrCrCrGrGrCrUrCrUrGr GrUrCrCrUrCrUrCrCrUrGrGrCrCrCrUrUrUrCrGrGrGr CrUrCrCrGrArGrArGrGrArArGrCrCrUrUrCrCrGrGrCrAr UrGrUrCrUrUrCrGrGrArCrArGrGrArUrGrUrGrArGrCrCr UrUrU*mU*mU*mU |
| 1129 | MG102-39 TRAC C11 | mC*mA*mG*rCrCrGrCrArGrCrGrUrCrArUrGrArGrCrAr GrArUrGrUrUrUrCrArGrGrUrUrArCrCrCrUrGrArGrArAr ArUrCrArGrGrCrUrGrArArGrCrUrGrArArArArGrArGrCr ArUrCrCrGrUrCrCrGrGrArArGrGrUrCrCrArCrUrCrCrGr GrGrUrUrArGrGrGrCrArGrArArUrCrCrGrGrCrUrCrUrGr GrUrCrCrUrCrUrCrCrUrGrGrCrCrCrUrUrUrCrGrGrGr CrUrCrCrGrArGrArGrGrArArGrCrCrUrUrCrCrGrGrCrAr UrGrUrCrUrUrCrGrGrArCrArGrGrArUrGrUrGrArGrCrCr UrUrU*mU*mU*mU |
| 1130 | MG102-39 TRAC B6 | mC*mC*mA*rGrGrCrCrArCrArGrCrArCrUrGrUrUrGrCrU rCrUrUrGrUrUrUrCrArGrUrUrArCrCrCrUrGrArGrArArA rUrCrArGrGrCrUrGrArArGrCrUrGrArArArArGrArGrCrA rUrCrCrGrUrCrCrGrGrArArGrGrUrCrCrArCrUrCrCrGrG rGrUrUrArGrGrGrCrArGrArArUrCrCrGrGrCrUrCrUrGrG rUrCrCrUrCrUrCrCrUrGrGrCrCrCrUrUrUrCrGrGrGrC rUrCrCrGrArGrArGrGrArArGrCrCrUrUrCrCrGrGrCrArU rGrUrCrUrUrCrGrGrArCrArGrGrArUrGrUrGrArGrCrCrU rUrU*mU*mU*mU |
| 1131 | MG102-39 TRAC B5 | mG*mU*mC*rUrUrCrUrGrGrArArArArUrGrCrUrGrUrU rGrUrUrGrUrUrUrCrArGrUrUrArCrCrCrUrGrArGrArArA rUrCrArGrGrCrUrGrArArGrCrUrGrArArArArGrArGrCrA rUrCrCrGrUrCrCrGrGrArArGrGrUrCrCrArCrUrCrCrGrG rGrUrUrArGrGrGrCrArGrArArUrCrCrGrGrCrUrCrUrGrG rUrCrCrUrCrUrCrCrUrGrGrCrCrCrUrUrUrCrGrGrGrC rUrCrCrGrArGrArGrGrArArGrCrCrUrUrCrCrGrGrCrArU rGrUrCrUrUrCrGrGrArCrArGrGrArUrGrUrGrArGrCrCrU rUrU*mU*mU*mU |
| 1132 | MG102-39 TRAC G9 | mG*mA*mU*rUrGrGrUrUrCrCrGrArArUrCrCrUrCrCrU rCrCrUrGrUrUrCrArGrUrUrArCrCrCrUrGrArGrArArA rUrCrArGrGrCrUrGrArArGrCrUrGrArArArArGrArGrCrA rUrCrCrGrUrCrCrGrGrArArGrGrUrCrCrArCrUrCrCrGrG rGrUrUrArGrGrGrCrArGrArArUrCrCrGrGrCrUrCrUrGrG rUrCrCrUrCrUrCrCrUrGrGrCrCrCrUrUrUrCrGrGrGrC rUrCrCrGrArGrArGrGrArArGrCrCrUrUrCrCrGrGrCrArU rGrUrCrUrUrCrGrGrArCrArGrGrArUrGrUrGrArGrCrCrU rUrU*mU*mU*mU |
| 1133 | MG102-39 TRAC D1 | mA*mU*mU*rCrUrGrArUrGrUrGrUrArUrArUrCrArCrArG rArCrArGrUrUrCrArGrUrUrArCrCrCrUrGrArGrArArA rUrCrArGrGrCrUrGrArArGrCrUrGrArArArArGrArGrCrA rUrCrCrGrUrCrCrGrGrArArGrGrUrCrCrArCrUrCrCrGrG rGrUrUrArGrGrGrCrArGrArArUrCrCrGrGrCrUrCrUrGrG |

TABLE 5-continued

Guide RNA and Targeting Sequences Tested in Example 15

| SEQ ID NO | Name | Sequence |
|---|---|---|
| | | rUrCrCrUrCrUrCrCrUrGrGrCrCrUrUrUrCrGrGrC rUrCrCrGrArGrArGrArArGrCrCrUrUrCrCrGrGrCrArU rGrUrCrUrUrCrGrGrArCrArGrGrArUrGrUrGrArGrCrU rUrU*mU*mU*mU |
| 1134 | MG102-39 TRAC B11 | mA*mC*mA*rGrCrCrGrCrArGrCrGrUrCrArUrGrArGrCr ArGrArUrGrUrUrUrCrArGrUrUrArCrCrUrGrArGrArAr ArUrCrArGrGrCrUrGrArArGrCrUrGrArArArArGrArGrCr ArUrCrCrGrUrCrCrGrGrArArGrGrUrCrCrArCrUrCrCrGr GrGrUrArGrGrGrCrArGrArUrCrCrGrGrCrUrCrUrUrGr GrUrCrUrCrUrCrCrUrGrGrCrCrUrUrUrCrGrGrGr CrUrCrCrGrArGrArGrArArGrCrCrUrUrCrCrGrGrCrAr UrGrUrCrUrUrCrGrGrArCrArGrGrArUrGrUrGrArGrCrCr UrUrU*mU*mU*mU |
| 1135 | MG102-39 TRAC D4 | mA*mA*mA*rGrCrUrGrCrCrCrUrArCrCrUrGrGrGrCrU rGrGrGrGrUrUrUrCrArGrUrUrArCrCrUrGrArGrArArA rUrCrArGrGrCrUrGrArArGrCrUrGrArArArArGrArGrCrA rUrCrCrGrUrCrCrGrGrArArGrGrUrCrCrArCrUrCrCrGrG rGrUrUrArGrGrGrCrArGrArUrCrCrGrGrCrUrCrUrUrGrG rUrCrUrCrUrCrUrCrCrUrGrGrCrCrUrUrUrCrGrGrGrC rUrCrCrGrArGrArGrArArGrCrCrUrUrCrCrGrGrCrArU rGrUrCrUrUrCrGrGrArCrArGrGrArUrGrUrGrArGrCrCrU rUrU*mU*mU*mU |
| 1136 | MG102-39 TRAC F2 | mC*mA*mA*rCrArGrUrGrCrUrGrUrGrGrCrCrUrGrGrAr GrCrArArGrUrUrUrCrArGrUrUrArCrCrUrGrArGrArAr ArUrCrArGrGrCrUrGrArArGrCrUrGrArArArArGrArGrCr ArUrCrCrGrUrCrCrGrGrArArGrGrUrCrCrArCrUrCrCrGr GrGrUrUrArGrGrGrCrArGrArUrCrCrGrGrCrUrCrUrUrGr GrUrCrUrCrUrCrUrCrCrUrGrGrCrCrUrUrUrCrGrGrGr CrUrCrCrGrArGrArGrArArGrCrCrUrUrCrCrGrGrCrAr UrGrUrCrUrUrCrGrGrArCrArGrGrArUrGrUrGrArGrCrCr UrUrU*mU*mU*mU |
| 1137 | MG102-39 TRAC G1 | mG*mC*mU*rArGrArCrArUrGrArGrGrUrCrUrArUrGrGr ArCrUrGrUrUrUrCrArGrUrUrArCrCrUrGrArGrArArAr ArUrCrArGrGrCrUrGrArArGrCrUrGrArArArArGrArGrCrU ArUrCrCrGrUrCrCrGrGrArArGrGrUrCrUrCrArCrUrCrCrGr GrGrUrUrArGrGrGrCrArGrArUrCrCrGrGrCrUrCrUrUrGrG rUrCrUrCrUrCrUrCrCrUrGrGrCrCrUrUrUrCrGrGrGr CrUrCrCrGrArGrArGrArArGrCrCrUrUrCrCrGrGrCrAr UrGrUrCrUrUrCrGrGrArCrArGrGrArUrGrUrGrArGrCrCr UrUrU*mU*mU*mU |
| 1138 | MG102-42 TRAC D10 | mG*mU*mU*rCrCrGrArArUrCrCrUrCrCrUrCrCrUrGrArA rArGrUrGrGrUrUrUrCrArGrCrCrArArCrCrUrGrArArArArG rGrUrGrGrUrGrArCrUrGrArArArArGrArGrCrArCrArG rCrCrGrGrCrArGrCrCrArGrCrArCrCrCrGrGrGrArArUrG rGrArCrArGrUrUrCrCrGrGrCrCrCrUrGrGrCrArGrGrG rCrArGrCrArGrArGrArArGrCrGrUrGrCrCrGrArArA rUrGrGrCrGrCrCrGrGrCrUrUrArUrGrUrGrGrUrGrArGrU rCrCrArUrUrArUrU*mU*mU*mU |
| 1139 | MG102-42 TRAC D12 | mG*mC*mC*rArCrUrUrCrArGrGrArGrGrArGrGrArUr UrCrGrGrGrUrUrCrArGrGrCrArArCrCrUrGrArArArArAr GrUrGrGrUrGrArCrUrGrArArArArGrArGrArGrCrCrArCrAr GrCrCrGrGrCrArGrCrCrArGrCrArCrCrCrGrGrGrArArUr GrGrGrArCrArGrUrCrCrGrGrCrCrCrUrGrCrArGrGr GrCrArGrCrArGrArGrArArGrCrGrUrGrCrCrGrArAr ArUrGrGrCrGrCrCrGrCrUrUrArUrGrUrGrGrUrGrArGr UrCrCrArUrUrArUrUmUxmU*mU |
| 1140 | MG102-42 TRAC E12 | mC*mA*mG*rGrArGrGrArGrGrArUrUrCrGrGrArArCrCr CrArArUrGrUrUrUrCrArGrCrCrArArCrCrUrGrArArArAr GrUrGrGrUrGrArCrUrGrArArArArGrArGrCrArCrArAr GrCrCrGrGrCrArGrCrCrArGrCrArCrCrCrGrGrGrArArUr GrGrGrArCrArGrUrCrCrGrGrCrCrCrUrGrCrArGrGr GrCrArGrCrArGrArGrArArGrCrGrUrGrCrCrGrArAr ArUrGrGrCrGrCrCrGrCrUrUrArUrGrUrGrGrUrGrArGr UrCrCrArUrUrArUrU*mU*mU*mU |
| 1141 | MG102-45 TRAC B1 | mU*mG*mU*rCrCrCrArCrArGrArUrArUrCrCrArGrArArCr CrCrUrGrUrUrUrCrArArUrCrArArGrCrUrGrArArArArG rCrUrCrCrGrGrUrUrGrArArArArArGrArGrCrArUrCrCrGrU rCrUrGrArUrArGrCrCrArUrGrCrArCrUrCrCrGrGrArArU |

TABLE 5-continued

Guide RNA and Targeting Sequences Tested in Example 15

| SEQ ID NO | Name | Sequence |
|---|---|---|
| | | rGrGrGrGrCrArGrUrUrCrCrGrGrCrUrCrUrUrGrCrGrArC rUrCrArArUrGrGrGrUrGrUrArUrGrCrUrCrArUrUrGrArG rCrCrArArCrUrGrUrCrArGrArCrArCrGrUrCrUrCrUrCrUr GrArGrArCrArGrGrArUrGrUrGrArGrCrCrUrUrA*mU* mU*mU |
| 1142 | MG102-45 TRAC C11 | mC*mU*mU*rCrArArGrCrCrCrUrCrArCrCrUrCrArG rCrUrGrUrUrUrCrArArUrCrArArArGrCrUrGrArArArG rCrUrCrCrGrGrUrUrGrArArArArGrArGrCrArUrCrGrU rCrUrGrArUrArGrCrCrArUrGrCrArCrUrCrCrGrGrArArU rGrGrGrCrArGrUrCrCrGrGrCrUrCrUrUrGrCrGrArC rUrCrArArUrGrGrGrUrGrUrArUrGrCrUrCrArUrUrGrArG rCrCrArArCrUrGrUrCrArGrArCrArCrGrUrCrUrCrUrCrUr GrArGrArCrArGrGrArUrGrUrGrArGrCrCrUrUrA*mU* mU*mU |
| 1143 | MG102-48 TRAC A1 | mU*mC*mC*rUrCrUrUrGrUrCrCrArCrArGrArUrArUrC rCrArGrGrUrUrUrCrArArUrCrArArCrrCrGrGrArArArCrG rGrUrCrGrGrUrUrGrArArArArGrArGrCrArUrCrGrGrU rCrUrGrArArGrGrArUrGrCrArCrUrCrCrGrGrGrArUrArG rGrGrArGrArGrUrCrCrGrGrCrUrCrUrUrGrCrGrUrGrUrUrU rCrCrCrCrGrGrUrArArGrArCrCrUrCrGrGrArArArGrCrArA rGrUrCrUrUrCrArGrCrArArGrUrCrGrArArArArGrArCrA rCrGrArUrGrUrGrArGrCrCrUrArU*mU*mU*mU |
| 1144 | MG102-48 TRAC D12 | mG*mC*mC*rArCrUrUrUrCrArGrGrArGrGrArGrGrArUr UrCrGrGrUrUrUrCrArArUrCrArArCrrCrGrGrArArArCr GrGrUrCrCrGrGrUrUrGrArArArArGrArGrCrArUrCrGrGr UrCrUrGrArArGrGrArUrGrCrArCrUrCrCrGrGrGrArUrAr GrGrGrCrArGrUrCrCrGrGrCrUrCrUrUrGrCrUrGrUrUrUr UrCrCrCrGrGrUrArArGrArCrCrUrCrGrGrArArArGrCrAr ArGrUrCrUrUrCrArGrCrArArGrUrCrGrArArArArGrArCr ArCrGrArUrGrUrGrArGrCrCrUrArU*mU*mU*mU |
| 1145 | MG102-36 TRAC D12 | GCCACTTTCAGGAGGAGGATTCGG |
| 1146 | MG102-36 TRAC F1 | GACCCTGCCGTGTACCAGCTGAGA |
| 1147 | MG102-36 TRAC H6 | TTGAAGTCCATAGACCTCATGTCT |
| 1148 | MG102-39 TRAC F4 | GCTGCCCTTACCTGGGCTGGGGAA |
| 1149 | MG102-39 TRAC A9 | TCTTGGTTTTACAGATACGAACCT |
| 1150 | MG102-39 TRAC G11 | GGCCACTTTCAGGAGGAGGATTCG |
| 1151 | MG102-39 TRAC C11 | CAGCCGCAGCGTCATGAGCAGATT |
| 1152 | MG102-39 TRAC B6 | CCAGGCCACAGCACTGTTGCTCTT |
| 1153 | MG102-39 TRAC B5 | GTCTTCTGGAATAATGCTGTTGTT |
| 1154 | MG102-39 TRAC G9 | GATTGGGTTCCGAATCCTCCTCCT |
| 1155 | MG102-39 TRAC D1 | ATTCTGATGTGTATATCACAGACA |
| 1156 | MG102-39 TRAC B11 | ACAGCCGCAGCGTCATGAGCAGAT |
| 1157 | MG102-39 TRAC D4 | AAAGCTGCCCTTACCTGGGCTGGG |
| 1158 | MG102-39 TRAC F2 | CAACAGTGCTGTGGCCTGGAGCAA |
| 1159 | MG102-39 TRAC G1 | GCTAGACATGAGGTCTATGGACTT |
| 1160 | MG102-42 TRAC D10 | GTTCCGAATCCTCCTCCTGAAAGT |
| 1161 | MG102-42 TRAC D12 | GCCACTTTCAGGAGGAGGATTCGG |
| 1162 | MG102-42 TRAC E12 | CAGGAGGAGGATTCGGAACCCAAT |

TABLE 5-continued

Guide RNA and Targeting Sequences Tested in Example 15

| SEQ ID NO | Name | Sequence |
|---|---|---|
| 1163 | MG102-45 TRAC B1 | TGTCCCACAGATATCCAGAACCCT |
| 1164 | MG102-45 TRAC C11 | CTTCAAGGCCCCTCACCTCAGCTG |
| 1165 | MG102-48 TRAC A1 | TCCTCTTGTCCCACAGATATCCAG |
| 1166 | MG102-48 TRAC D12 | GCCACTTTCAGGAGGAGGATTCGG |
| 1167 | MG33-34 TRAC F6 | mA\*mC\*mC\*rCrGrGrCrCrArCrUrUrUrCrArGrGrArGrGrCrUrUrUrCrArCrUrCrUrArGrCrGrArArArGrCrUrArGrArGrUrGrArArArGrArArGrCrCrCrArGrGrCrGrCrUrGrCrUrCrCrArGrUrCrCrUrCrGrCrCrGrArUrGrUrArArCrCrCrArGrCrArUrCrGrGrCrArCrCrUrArGrGrUrGrUrArGrGrCrArGrCrCrCrGrCrGrCrArGrGrCrCrGrUrArCrUrCrGrGrArCrCrCrGrGrCrArArArGrGrGrCrArArGrGrGrUrU\*mG\*mG\*mU |
| 1168 | MG33-34 TRAC E6 | mU\*mA\*mA\*rArCrCrCrGrGrCrCrArCrUrUrUrCrArGrGrCrUrUrUrCrArCrUrCrUrArGrCrGrArArArGrCrUrArGrArGrUrGrArArArGrArArGrCrCrCrArGrGrCrGrCrUrGrCrUrCrCrArGrUrCrCrUrCrGrCrCrGrArUrGrUrArArCrCrCrArGrCrArUrCrGrGrCrArCrCrUrArGrGrUrGrUrArGrGrCrArGrCrCrCrGrCrGrCrArGrGrCrCrGrUrArCrUrCrCrGrGrCrArArGrGrCrCrGrUrArCrUrCrGrGrArCrCrCrGrGrCrArArArGrGrGrCrArArGrGrGrUrU\*mG\*mG\*mU |
| 1169 | MG33-34 TRAC F6 | ACCCGGCCACTTTCAGGAGG |
| 1170 | MG33-34 TRAC E6 | TAAACCCGGCCACTTTCAGG | r = native ribose base,
m = 2'-O methyl modified base,
F = 2' Fluro modified base,
\*= phosphorothioate bond

Example 16—SMART HEARO Enzymes are Active Nucleases

In Silico Prediction of SMART HEARO Guide RNAs

Figure 31:
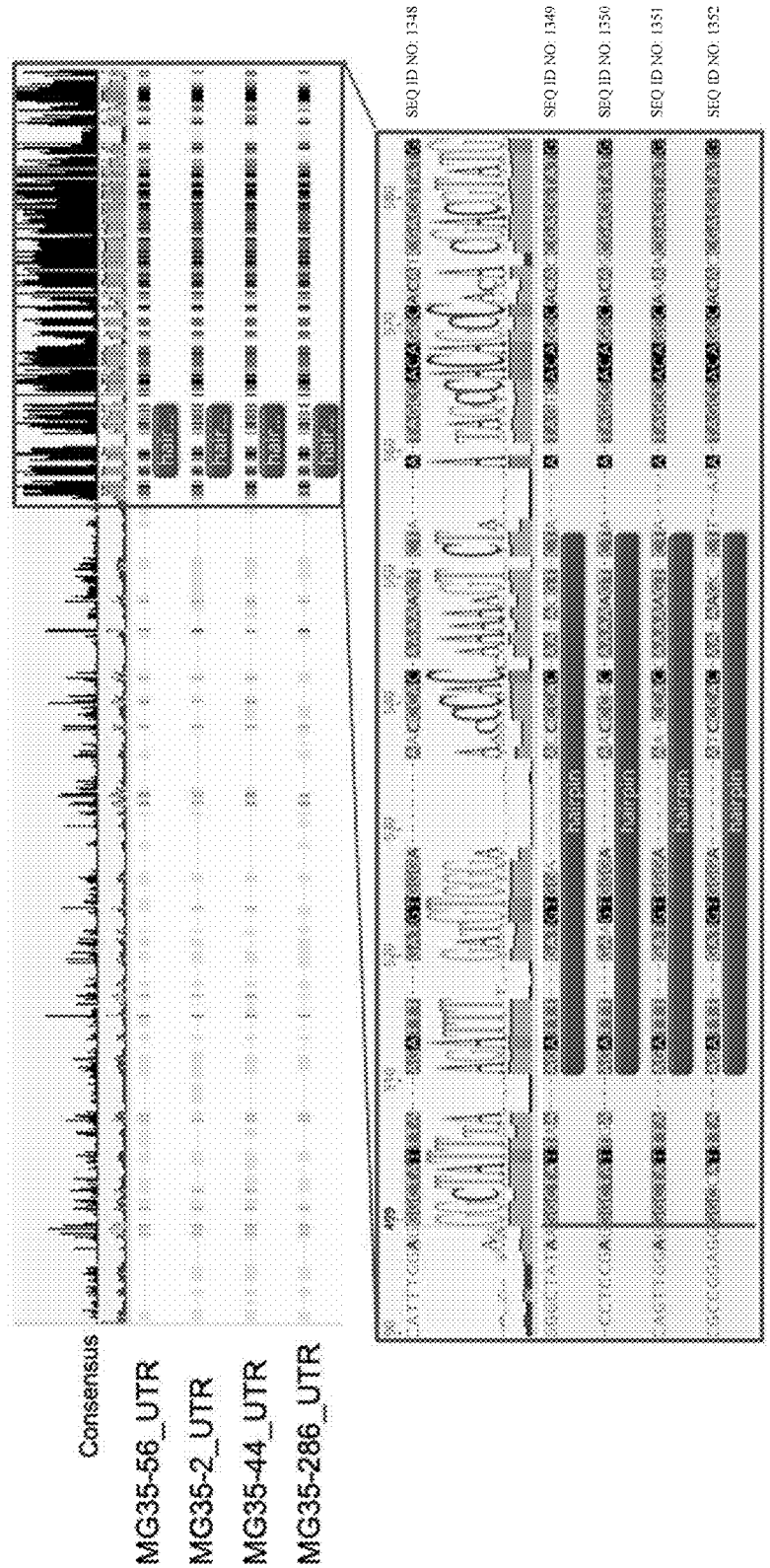
FIG. 31 depicts multiple sequence alignment of the 5' UTR nucleotide sequence of four SMART HEARO nucleases. The region preceding the start of the HEARO RNA (box) shows poor similarity, while strong conservation around the first structural hairpin is observed (inset). Figure discloses SEQ ID NOs: 1348-1352, respectively.

To identify guide (HEARO) RNAs associated with novel SMART HEARO nucleases, the nucleotide sequence corresponding to the 5' UTR regions of 305 putative effectors were extracted. These 5' UTR nucleotide sequences were aligned with MAFFT (Katoh K, Standley DM. MAFFT multiple sequence alignment software version 7: improvements in performance and usability. Mol Biol Evol. 2013, 30 (4), 772-780, which is incorporated by reference in its entirety herein) with parameter mafft-xinsi (mafft.cbrc.jp/alignment/software/), and regions of conservation were used to delineate the HEARO RNA boundaries (FIG. 31). In addition, the HEARO RNA sequences of active SMART HEARO nucleases were used to generate covariance models to predict additional HEARO RNAs in genomic fragments encoding novel SMART HEARO nucleases. Covariance models are built from a multiple sequence alignment (MSA) of the active HEARO RNA sequences with mafft-xinsi (mafft.cbrc.jp/alignment/software/). The secondary structure of the MSA was determined with RNAalifold (Vienna Package, www.tbi.univie.ac.at/RNA/) and the covariance models were built with Infernal packages (eddylab.org/infernal/). Contigs containing candidate SMART HEARO nucleases and the 305 5' UTR regions were searched using the covariance models with the Infernal command 'cmsearch'. HEARO RNAs predicted from 5' UTR alignments and from covariance models for novel candidates were tested in vitro.

In Vitro TAM Determination Assays

The sgRNA (HEARO RNAS) with a targeting spacer at the 5' end was constructed via assembly PCR and purified with SPRI beads or ordered as a gene fragments (IDT), and then in vitro transcribed (IVT, HiScribe T7 kit, New England Biolabs) following the manufacturer's recommended protocol for short RNA transcripts. RNA reactions were cleaned with the Monarch RNA kit and checked for purity via a Tapestation (Agilent). Cleavage and TAM determination assays were performed with PUREXPRESS® (New England Biolabs). Briefly, the protein was codon optimized for E. coli and cloned into a vector with a T7 promoter and C-terminal His tag. The gene was PCR amplified with primer binding sites 150 bp upstream and downstream from the T7 promoter and terminator sequences, respectively. This PCR product was added to PUREXPRESS® (New England Biolabs) at 5 nM final concentration and expressed for 2 hr at 37° C. A cleavage reaction was assembled in 10 mM Tris pH 7.5, 100 mM NaCl, and 10 mM MgCl$_2$ with a 5-fold dilution of PUREXPRESS®, 5 nM of an 8N PAM plasmid library, and 50 nM of sgRNA targeting the PAM library. The cleavage products from the PUREXPRESS® reactions were recovered via clean up with SPRI beads (AMPure Beckman Coulter or HighPrep Sigma-Aldritch). The DNA was blunted via addition of Klenow fragments and dNTPs (New England Biolabs). Blunt-end products were ligated with a 100-fold excess of double-stranded adapter sequences and used as template for the preparation of an NGS library, from which PAM requirements were determined from sequence analysis. Raw NGS reads were filtered by Phred quality score >20. The 14-24 bp representing the documented DNA sequence from the backbone adjacent to the PAM was used as a reference to find the PAM-proximal region, and the 8 bp adjacent were identified as the putative target adjacent motif (TAM). The distance between the TAM and the ligated adapter was also measured for each read. Reads that did not have an exact match to the reference sequence or adapter sequence were excluded. TAM sequences were filtered by cut site frequency such that only TAMs with the most frequent cut site ±2 bp were included in the analysis. The filtered list of TAM sequences was used to generate a sequence logo using Logomaker (Tareen, A. & Kinney, J. B. Logomaker: beautiful sequence logos in Python. *Bioinformatics* 2020, 36, 2272-2274).

Figure 32A:
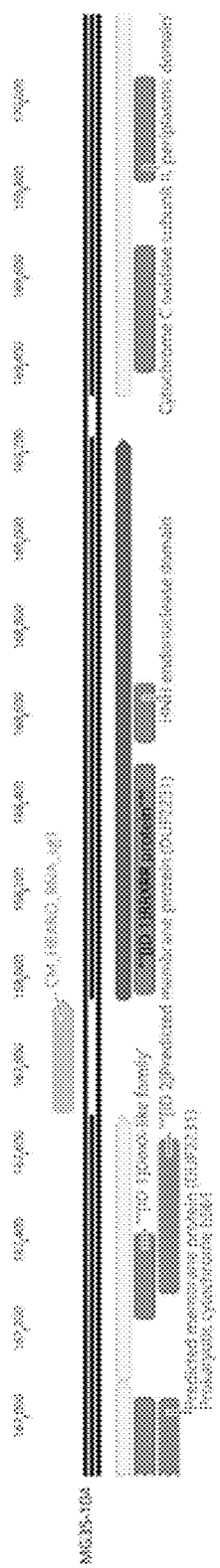
Figure 32B:
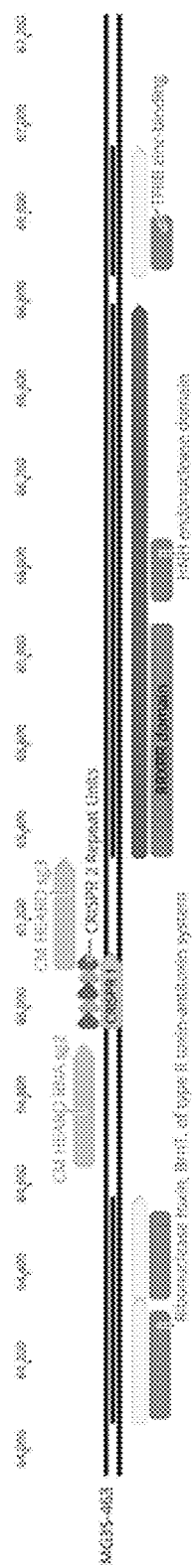
Figure 32C:
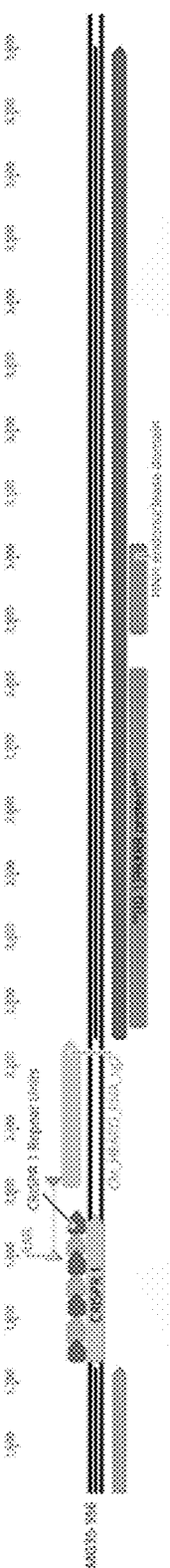

SMART II (HEARO) effectors are short (~ 400-600 aa long) nucleases that interact with a guide (HEARO) RNA encoded in their 5' UTR region for targeted dsDNA cleavage (FIGS. 32A and 32D). In most cases, SMART HEARO systems are not CRISPR-associated, but few SMART HEARO nucleases may be associated with CRISPRs. For example, the SMART HEARO MG35-463 (SEQ ID No. 530) is encoded downstream from a CRISPR array (FIG. 32B). The 5' end of a HEARO guide RNA predicted from covariance models overlaps with the last CRISPR repeat of the array (FIGS. 32B and 32F, g3) suggesting that a full targeting single guide RNA comprises the last spacer and the last repeat of the array, as well as the HEARO RNA (FIG. 32F, Furthermore, covariance models for this candidate predicted a second HEARO RNA upstream from, and unrelated to, the CRISPR array (FIGS. 32B and 32E, g2). Another example of a CRISPR-associated SMART HEARO system is MG35-556 (SEQ ID No. 659) (FIG. 32C), where the HEARO RNA is encoded in the 5' UTR region of the effector, which contains an antirepeat complementary to one of the CRISPR repeats (FIG. 32C). This represents an example of a dual guide RNA-guided HEARO system, where one CRISPR repeat (likely carrying a targeting spacer at its 5' end) anneals to the 5' end of the HEARO RNA folding into a structure that resembles other single guide HEARO RNAs (FIG. 32G).

Figure 33B:
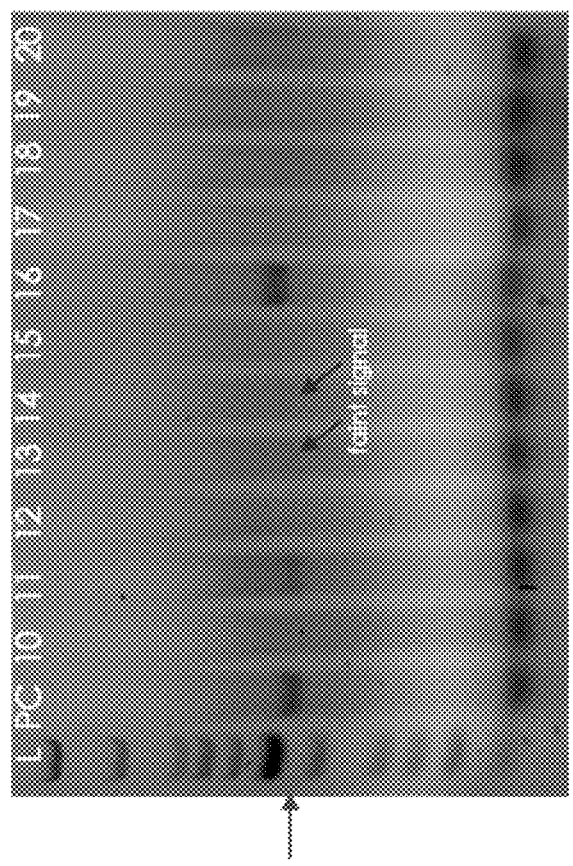
FIGS. 33A-FIG. 33C depict SMART HEARO cleavage activity in vitro. SMART II effectors were assayed in in vitro transcription/translation reactions incubated with their single guide RNA and a PAM library (dsDNA target). Cleavage products were amplified via ligation to the cut site and subsequent PCR (successful RNA-guided cleavage by the nuclease produced bands at the expected size: arrows). For FIG. 33A, lane labels are as follows: L: Ladder; PC: MG35-1 nuclease as positive control (PC); 1: MG35-94; 2: MG35-104; 3: MG35-346; 4: MG35-350; 5: MG35-423; 6: MG35-422; 7: MG35-461; 8: MG35-465; 9: MG35-515. For FIG. 33B, lane labels are as follows: L: Ladder; PC: MG35-1 nuclease as positive control (PC); 10: MG35-517; 11: MG35-518 with sgRNA design 1; 12: MG35-518 with sgRNA design 2; 13: MG35-519; 14: MG35-550 with sgRNA design 1; 15: MG35-550 with sgRNA design 2; 16: MG35-553; 17: MG35-554 with sgRNA design 1; 18: MG35-554 with sgRNA design 2; 19: MG35-555; and 20: MG35-556. For FIG. 33C, SMART II effectors were assayed for cleavage activity via a TAM/PAM enrichment protocol. The effectors were expressed in in vitro transcription/translation (IVTT) reactions in the presence of their single guide RNA and then added to a PAM library (dsDNA target). Cleavage products were amplified via ligation to the cut site and subsequent PCR (successful RNA-guided cleavage by the nuclease produced bands at the expected size: arrows). The reaction shown is prior to PCR clean-up, so primers and adapter-dimers bands are observed at sizes <100 bp.
Figure 33A:
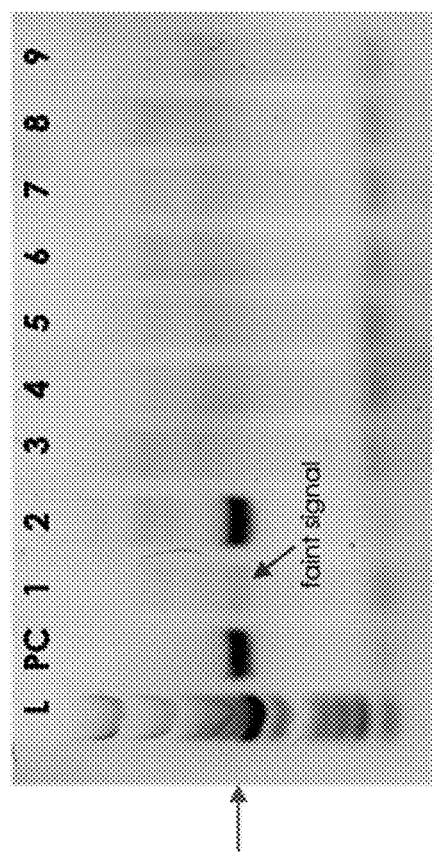
Figure 33C:
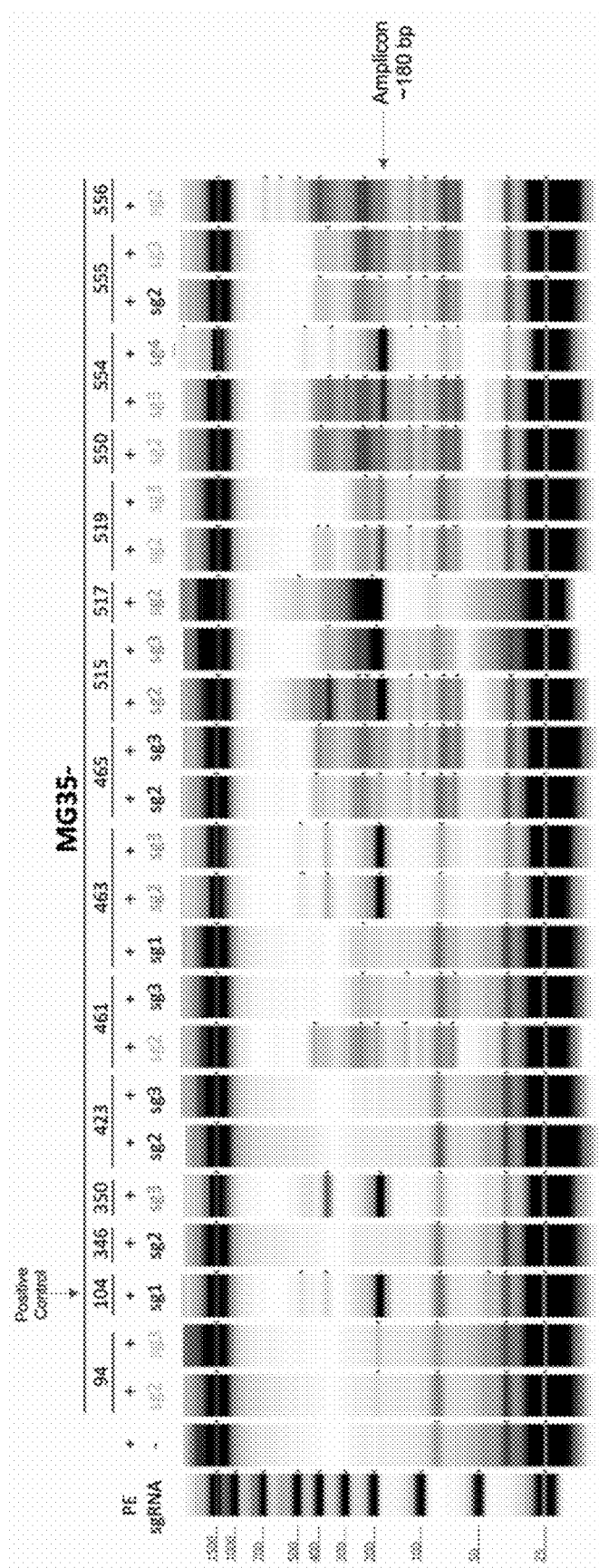
Figure 34:
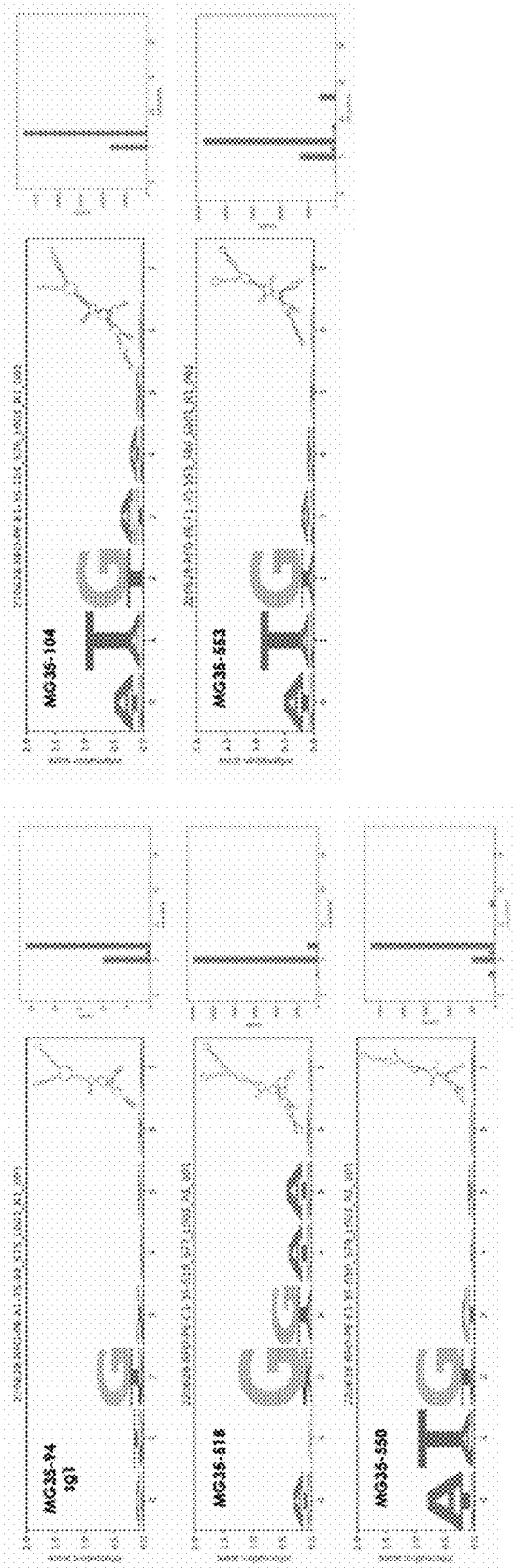
FIG. 34 depicts TAM recognition motifs for active SMART HEARO nucleases. NGS sequencing of the bands identified in FIG. 33A-33C were used to generate the TAMs and preferred cleavage position for each nuclease. The structure of the working guide as predicted by Geneious (Andronescu 2007) is shown inlaid. Cleavage usually occurs between position 5-10 on the non-target strand.
Figure 34:
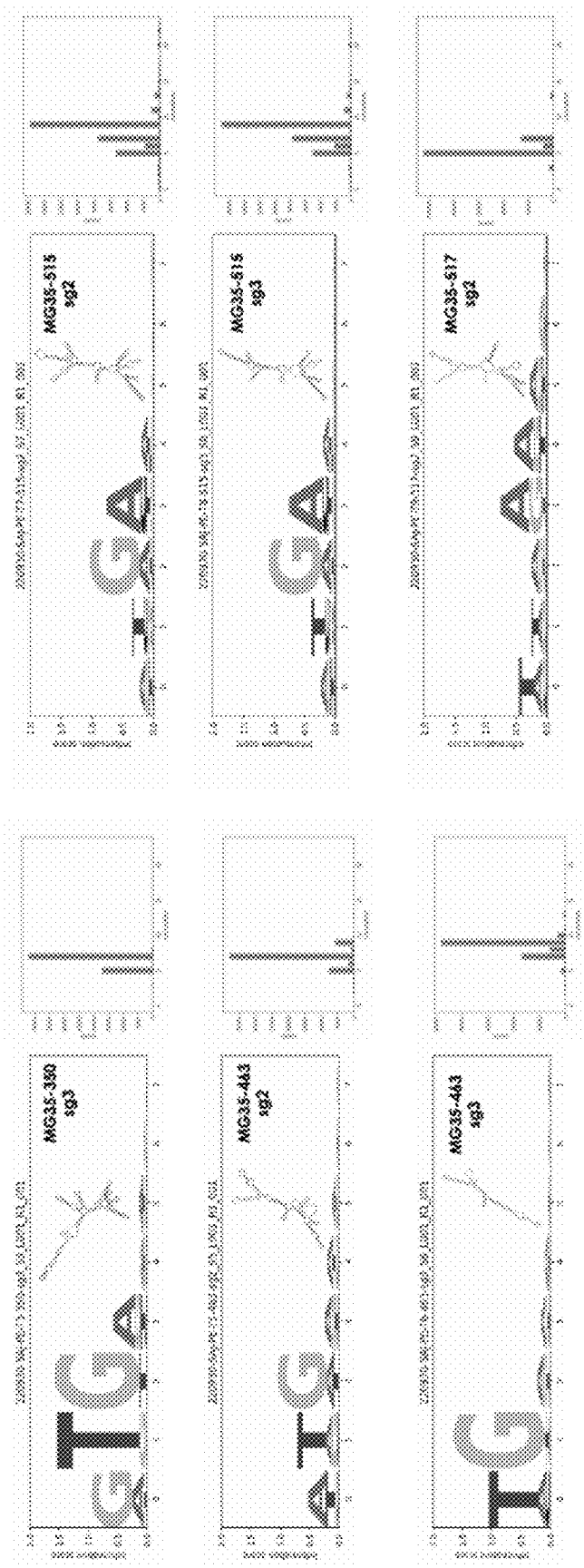
Figure 34:
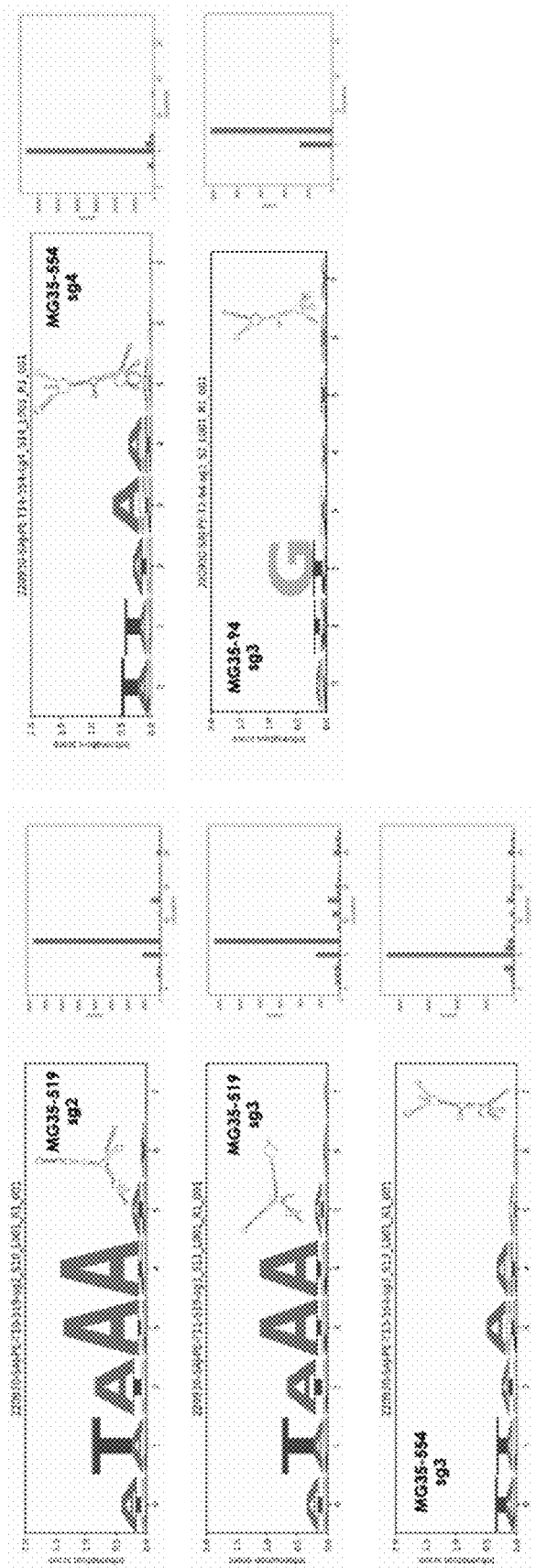

When tested for cleavage activity, many SMART HEARO nucleases were active in in vitro TAM determination assays, some of them with multiple sgRNA designs (FIGS. 33A-33C). MG35-104 (SEQ ID No. 128), HEARO MG35-463 (SEQ ID No. 530), and MG35-518 (SEQ ID No. 621) were among the most active nucleases, as shown by the strong band intensity readout (FIG. 33). Furthermore, the SMART HEARO MG35-463 (SEQ ID No. 530) is functional with both its CRISPR-associated (SEQ ID No. 1237) and CRISPR-independent (SEQ ID No. 1236) HEARO RNAs, despite the guide RNAs sharing only 65% pairwise nucleotide identity (FIGS. 32D, 32E, and 33C). Active MG35 candidates recognize diverse TAMs and display a cleavage selectivity for positions 5 or 7 from the TAM motif (FIG. 34).

Example 17—SMART HEARO Enzymes are Efficient Nucleases

In Vitro Cleavage Assays

MG35 nucleases were expressed using in vitro transcription/translation (IVTT) (New England Biolabs) at 37° C. for 2 hours. Transcription was driven by a T7 promoter on a linear DNA template coding for the nuclease. The guide RNA was in vitro transcribed separately and added into the IVTT mix at a chosen concentration, usually between 0.4 at 4 µM. In vitro cleavage reactions were performed by adding 3 µL of the RNP samples to 5 nM of supercoiled DNA in a 10 µL reaction volume in 1× Effector Buffer (10 mM Tris-HCl pH 7.5, 100 mM NaCl, 10 mM $MgCl_2$) or 1× New England Biolabs 2.1 buffer (10 mM Tris-HCl pH 7.9, 50 mM NaCl, 10 mM $MgCl_2$, 100 µg/ml BSA). The reactions were incubated at 37° C. for 1 hour and then quenched by adding 0.2 µg of RNAse A (New England Biolabs), followed by incubation at 37° C. for 20 minutes. Then, addition of 4 units of proteinase K (New England Biolabs) was followed by incubation at 55° C. for 30 minutes. Reactions were analyzed by capillary electrophoresis using a D5000 Tapestation kit (Agilent) following the instructions recommended by the manufacturer for analysis and visualization. Successful cleavage results in the supercoiled 2200 bp DNA being cut into linear dsDNA.

After identifying an active guide RNA and TAM recognition motif, SMART HEARO nucleases were tested for in vitro cleavage efficiency via in vitro transcription/translation co-expression of the nuclease with their guide RNA and subsequent incubation with a target plasmid containing the spacer targeted by the guide RNA and the TAM identified in the TAM/PAM enrichment screen. Cleavage is measured by the transition of non-cleaved product (supercoiled) to cleaved linear DNA (FIGS. 35A and 35B). Results indicate that MG35-104 (SEQ ID No. 128) is highly efficient at dsDNA cleavage compared to other active SMART HEARO nucleases (FIGS. 35A and 35B).

Example 18—SMART HEARO Guide Engineering

Figures 36A, 36B:
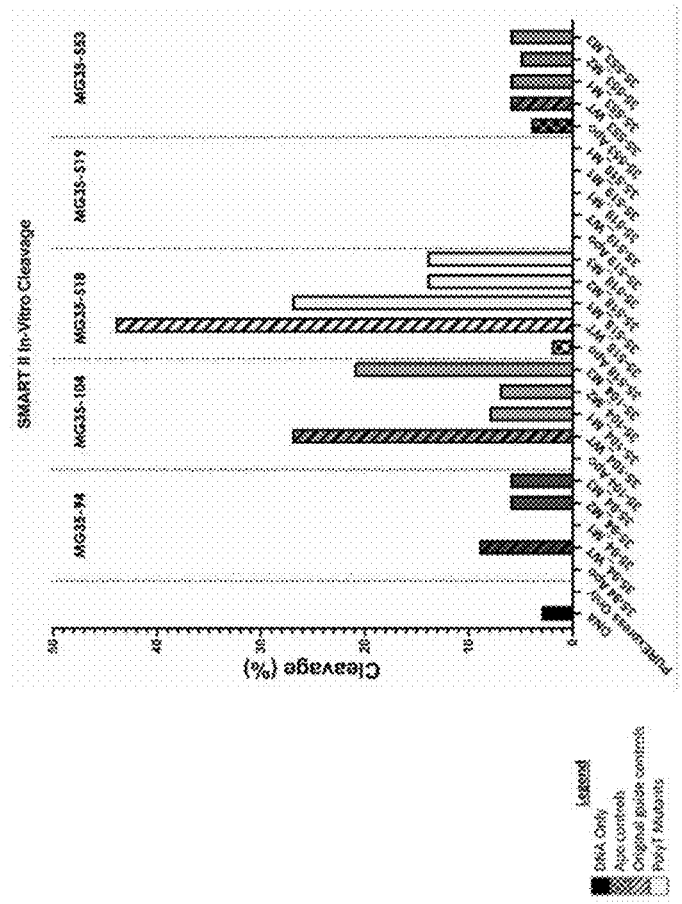
FIG. 36A-FIG. 36B depicts SMART HEARO guide engineering. Five active SMART HEARO sgRNAs had one or more PolyT tracts in their sequences. Three PolyT mutant sgRNAs were designed per candidate to compare the activity vs. the original guide. Guides were in vitro transcribed and normalized to the same concentration, then used in the in vitro cleavage efficiency reaction.

The guide RNA of some active SMART II nucleases contains one or more poly-T regions (four or more T bases sequentially) (FIG. 36A), which can limit transcription efficiency. Three PolyT mutant sgRNAs per candidate were designed and tested for cleavage activity in vitro, and their activity was compared to the candidate's activity with their native guide RNA (FIGS. 36A and 36B). Results indicate that MG35-94 is active with mutant guides M2 and M3, while MG35-104 is active with all three guide mutations M1-M3, where guide M3 retains the highest activity compared to other guides. MG35-518 is active with all three mutants tested but M1 shows the highest activity (FIG. 36B).

TABLE 6

Variant Guide RNAs tested in Example 18

| SEQ ID NO: | Description | Sequence |
|---|---|---|
| 1258 | MG35-94_M2 single guide RNA | (N20)GUAAUCGUCCAUAAAUAACUUAGGCAACUAAGU AGUUUAAGGUUACCCGCUUUGGUUCUUCGGAACUCC GUUAGGGGCGAAAAUAUAGGUACUCUUGGAUGCAUC UCCAGUCCGAGACUCUACGGGGAACGAUUAAACAGG UCUGAUGGAAAGGCCAGUGUCGUUUCCAUUUAAAAC |

TABLE 6-continued

Variant Guide RNAs tested in Example 18

| SEQ ID NO: | Description | Sequence |
|---|---|---|
| | | CGCUUUCUAACAUUAGCUAGGAAACCAUUACUCGCG CAAGCGAAGAUAUGUAACAAUUU |
| 1259 | MG35-94_M3 single guide RNA | (N20)GUAAUCGUCCAUAAAUAACUUAGGCAACUAAGU AGAUUAAGGUUACCCGCUUUGGUUCUUCGGAACUCC GUUAGGGGCGAAAAUAUAGGUACUCUUGGAUGCAUC UCCAGUCCGAGACUCUACGGGGAACGAUUAAACAGG UCUGAUGGAAAGGCCAGUGUCGUUUCCAUUUAAAAC CGCUUUCUAACAUUAGCUAGGAAACCAUUACUCGCG CAAGCGAAGAUAUGUAACAAUUU |
| 1249 | MG35-104_M1 single guide RNA | (N20)GUAAGGAACCCCGUAGCUAAAGCUAGGGGCUAU UCAUCCCCGUCCCUUCGGGCGGGCUUAGAUAGCCGA ACCUUACCAGCCUAAGACCUUCGAGGUCUACGUAUU CAAGGUCACGAUACCUAUCAAUGCGUCGCUAGUUGU UAGCUCUAUCGCUGGUUGUUAAACAUCUGUAAUGGG UUAAGGAAGUGCAAUCAGCCCAACAAGCCUUGAAUA CAUUGGCGAAGCGAACAUCACCCAGCAAUGGAGUCC UUCAAUCA |
| 1250 | MG35-104_M2 single guide RNA | (N20)GUAAGGAACCCCGUAGCUAAAGCUAGGGGCUUA UCAUCCCCGUCCCUUCGGGCGGGCUUAGUAAGCCGA ACCUUACCAGCCUAAGACCUUCGAGGUCUACGUAUU CAAGGUCACGAUACCUAUCAAUGCGUCGCUAGUUGU UAGCUCUAUCGCUGGUUGUUAAACAUCUGUAAUGGG UUAAGGAAGUGCAAUCAGCCCAACAAGCCUUGAAUA CAUUGGCGAAGCGAACAUCACCCAGCAAUGGAGUCC UUCAAUCA |
| 1251 | MG35-104_M3 single guide RNA | (N20)GUAAGGAACCCCGUAGCUAAAGCUAGGGGCUAU UCAUCCCCGUCCCUUCGGGCGGGCUUAGAUAGCCGA ACCUUACCAGCCUAAGACCUUCGAGGUCUACGUUCU CAAGGUCACGAUACCUAUCAAUGCGUCGCUAGUUGU UAGCUCUAUCGCUGGUUGUUAAACAUCUGUAAUGGG UUAAGGAAGUGCAAUCAGCCCAACAAGCCUUGAGAA CAUUGGCGAAGCGAACAUCACCCAGCAAUGGAGUCC UUCAAUCA |
| 1252 | MG35-518_M1 single guide RNA | (N20)AUCAAUAACCAACCCACUAAGUGGGCGGAUUGC UUGACUCUUAUACAAUGAGUUGAGAAACCGUGAUUG AUUAGCCUCAGUUAUAAACUACGUUAUUUGUAAAUAU AUAGGUACCGUCGGAUGUCCGCCUAGUCCUACGCGC UACGCUUUAUUAUUUAAACAGUUCUGAUUGGUAGGAA CAGUGUAAUAAAGAUAUAAAACUACAAGAUAACAUUG GCGAAGGCAAUAAAGGGUUUGUUUAUACCCGCUUAC CGCAUUAAAUAAACAU |
| 1253 | MG35-518_M2 single guide RNA | (N20)AUCAAUAACCAACCCACUAAGUGGGCGGAUUGC UUGACUCUAUUACAAUGAGUUGAGAAACCGUGAUUG AUUAGCCUCAGUUAUAAACUACGUUAUUUGUAAAUAU AUAGGUACCGUCGGAUGUCCGCCUAGUCCUACGCGC UACGCUUUAUUAUUUAAACAGUUCUGAUUGGUAGGAA CAGUGUAAUAAAGAUAUAAAACUACAAGAUAACAUUG GCGAAGGCAAUAAAGGGUUUGUUUAUACCCGCUUAC CGCAUUAAAUAAACAU |
| 1254 | MG35-518_M3 single guide RNA | (N20)AUCAAUAACCAACCCACUAAGUGGGCGGAUUGC UUGACUCUGUUACAAUGAGUUGAGAAACCGUGAUUG AUUAGCCUCAGUUAUAAACUACGUUAUUUGUAAAUAU AUAGGUACCGUCGGAUGUCCGCCUAGUCCUACGCGC UACGCUUUAUUAUUUAAACAGUUCUGAUUGGUAGGAA CAGUGUAAUAAAGAUAUAAAACUACAAGAUAACAUUG GCGAAGGCAAUAAAGGGUUUGUUUAUACCCGCUUAC CGCAUUAAAUAAACAU |
| 1255 | MG35-553_M1 single guide RNA | (N20)GUCAACUACCCACGACUAAAGUCGCGGGCUUGU AAUAAGGAUAGUGCUAUGUACUAGCCUUAUUCAGCC CGGUUGACUAGCCUAAGCACCAAUUGUGCUACGUUA UGCAGGAAAUAGGUACCUCGGGAUGUACAGCCUAGU CCCGGGCUCUACGGUAUGAGGUUAAACAGCUCUGAC GGGUAGGAGCAGUGCUUCAUGCGUUAAACCCUGCAA UAACAUUGGCGAAGGCUAACUAACGGAUGCUGCAUC CGGCUUACAGCAAUAAUGCAGCAGAAAA |

TABLE 6-continued

Variant Guide RNAs tested in Example 18

| SEQ ID NO: | Description | Sequence |
|---|---|---|
| 1256 | MG35-553_M2 single guide RNA | (N20)GUCAACUACCCACGACUAAAGUCGCGGGCUUGU AUUAAGGAUAGUGCUAUGUACUAGCCUUAAUCAGCC CGGUUGACUAGCCUAAGCACCAAUUGUGCUACGUUA UGCAGGAAAUAGGUACCUCGGGAUGUACAGCCUAGU CCCGGGCUCUACGGUAUGAGGUUAAACAGCUCUGAC GGGUAGGAGCAGUGCUUCAUGCGUUAAACCCUGCAA UAACAUUGGCGAAGGCUAACUAACGGAUGCUGCAUC CGGCUUACAGCAAUAAUGCAGCAGAAAA |
| 1257 | MG35-553_M3 single guide RNA | (N20)GUCAACUACCCACGACUAAAGUCGCGGGCUUGU AAUUAGGAUAGUGCUAUGUACUAGCCUAAUUCAGCC CGGUUGACUAGCCUAAGCACCAAUUGUGCUACGUUA UGCAGGAAAUAGGUACCUCGGGAUGUACAGCCUAGU CCCGGGCUCUACGGUAUGAGGUUAAACAGCUCUGAC GGGUAGGAGCAGUGCUUCAUGCGUUAAACCCUGCAA UAACAUUGGCGAAGGCUAACUAACGGAUGCUGCAUC CGGCUUACAGCAAUAAUGCAGCAGAAAA |

Example 19—Computational Reconstruction of Novel SMART I Nucleases

In Silico Reconstruction of Novel Sequences

In an effort to generate further diversity of SMART I nucleases, ancestral sequence reconstruction algorithms were used to reconstruct divergent nuclease sequences. Ancestral sequence reconstruction is a computational technique that uses existing protein sequences and the relationships inferred between them to reconstruct the sequences of ancient, now extinct, proteins (Harms, M. & Thornton J. W. Analyzing protein structure and function using ancestral gene reconstruction. *Current Opinion in Structural Biology* 2010, 20, 360-366). This technique was used to computationally reconstruct novel sequences of the SMART I MG34 family. For this analysis, 190 SMART I protein sequences were aligned using MAFFT with parameters L-INS-i or G-INS-i (Katoh K, Standley DM. MAFFT multiple sequence alignment software version 7: improvements in performance and usability. *Mol Biol Evol.* 2013, 30 (4), 772-780), and a phylogenetic tree was built using either Fasttree (Price, M. N., Dehal, P. S., and Arkin, A. P. FastTree 2—Approximately Maximum-Likelihood Trees for Large Alignments. *PLOS ONE* 2010, 5 (3), e9490) or RAxML (Stamatakis, A. RAXML version 8: a tool for phylogenetic analysis and post-analysis of large phylogenies. *Bioinformatics* 2014, 30 (9), 1312-1313) (FIG. 37). The trees were rooted using SpCas9 and SaCas9. Sequence reconstruction was done using the codeml package in PAML 4.8 (Yang, Z. PAML 4: a program package for phylogenetic analysis by maximum likelihood. *Molecular Biology and Evolution* 2007, 24, 1586-1591) and applied to all four combinations of alignment and tree building methods to account for uncertainties in the phylogenies. Insertions and deletions were identified manually for each reconstructed node.

In Vitro PAM Determination Assays

Candidate proteins were codon optimized for *E. coli* and cloned into a vector with a T7 promoter and C-terminal His tag. The gene was PCR amplified with primer binding sites 150 bp upstream and downstream from the T7 promoter and terminator sequences, respectively. This PCR product was added to PUREXPRESS® (New England Biolabs) at 5 nM final concentration and expressed for 2 hr at 37° C. A cleavage reaction was assembled in 10 mM Tris pH 7.5, 100 mM NaCl, and 10 mM MgCl$_2$ with a 5-fold dilution of PUREXPRESS®, 5 nM of an 8N PAM plasmid library, and 50 nM of sgRNA targeting the PAM library. The cleavage products from the PUREXPRESS® reactions were recovered via clean up with SPRI beads (AMPure Beckman Coulter or HighPrep Sigma-Aldrich). The DNA was blunted via addition of Klenow fragments and dNTPs (New England Biolabs). Blunt-end products were ligated with a 100-fold excess of double-stranded adapter sequences and used as template for the preparation of an NGS library, from which PAM requirements were determined from sequence analysis. Raw NGS reads were filtered by Phred quality score >20. The 14-24 bp representing the documented DNA sequence from the backbone adjacent to the PAM was used as a reference to find the PAM-proximal region, and the 8 bp adjacent were identified as the putative PAM. The distance between the PAM and the ligated adapter was also measured for each read. Reads that did not have an exact match to the reference sequence or adapter sequence were excluded. PAM sequences were filtered by cut site frequency such that only PAMs with the most frequent cut site ±2 bp were included in the analysis. The filtered list of PAM sequences was used to generate a sequence logo using Logomaker (Tareen, A. & Kinney, J. B. Logomaker: beautiful sequence logos in Python. *Bioinformatics* 2020, 36, 2272-2274).

Figure 38:
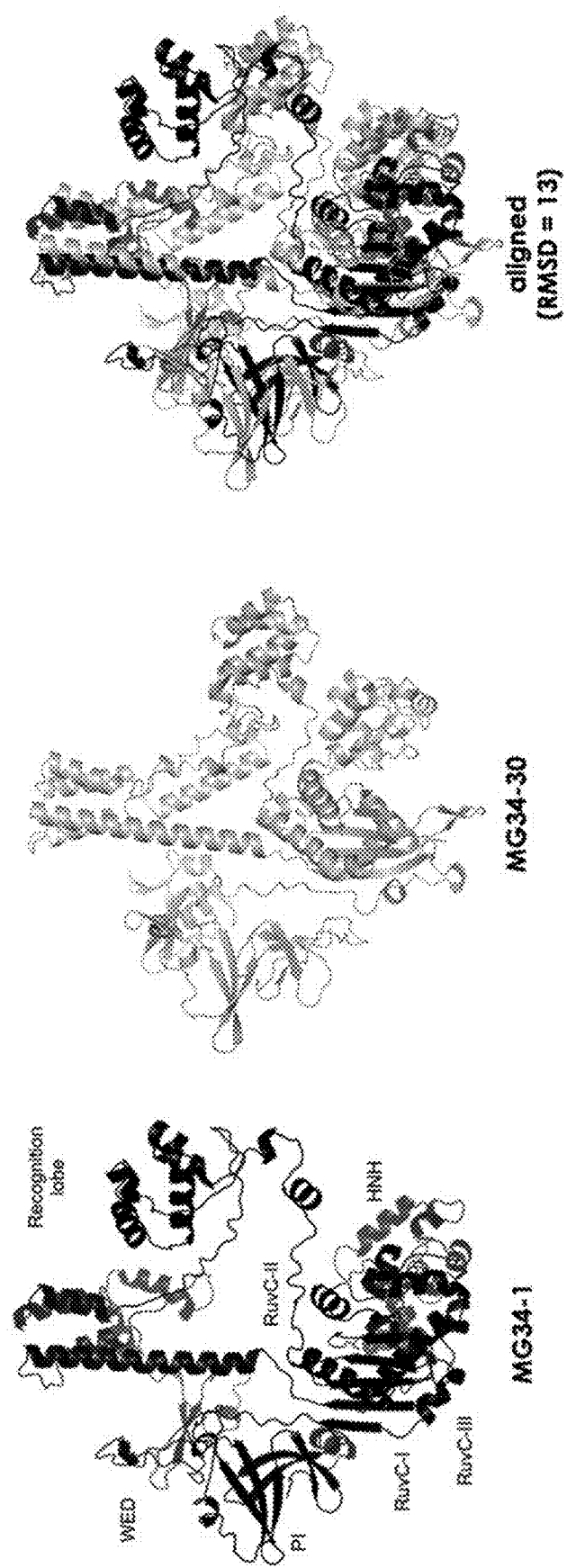
FIG. 38 depicts 3D structure prediction of reconstructed SMART I MG34-30 vs. the predicted structure of an active MG34-1 nuclease. Good structural alignment of proteins overall was observed by the overlap between the two structures, as well as by the low RMSD value.

Six sequences of the MG34 family were reconstructed with high confidence (Tables $ and FIG. 37) and catalytic and binding domains were confirmed from multiple sequence alignments and 3D structure prediction (FIG. 38).

TABLE 7

Comparison of computationally-derived MG34 candidates vs. the SMART I nuclease MG34-1

| Candidate | SEQ ID NO. | Mean Support | MG34-1 % Identity | Length (amino acids) |
|---|---|---|---|---|
| MG34-26 | 1313 | 0.73 | 66 | 768 |
| MG34-27 | 1314 | 0.93 | 78 | 745 |
| MG34-28 | 1315 | 0.75 | 70 | 765 |
| MG34-29 | 1316 | 0.92 | 79 | 748 |
| MG34-30 | 1317 | 0.74 | 79 | 766 |
| MG34-31 | 1318 | 0.74 | 72 | 768 |

Mean support values indicate the average probability for the reconstructed sequence, on a scale from 0 to 1. Support values >0.7 indicate high confidence in the reconstructed sequence.

Figure 39:
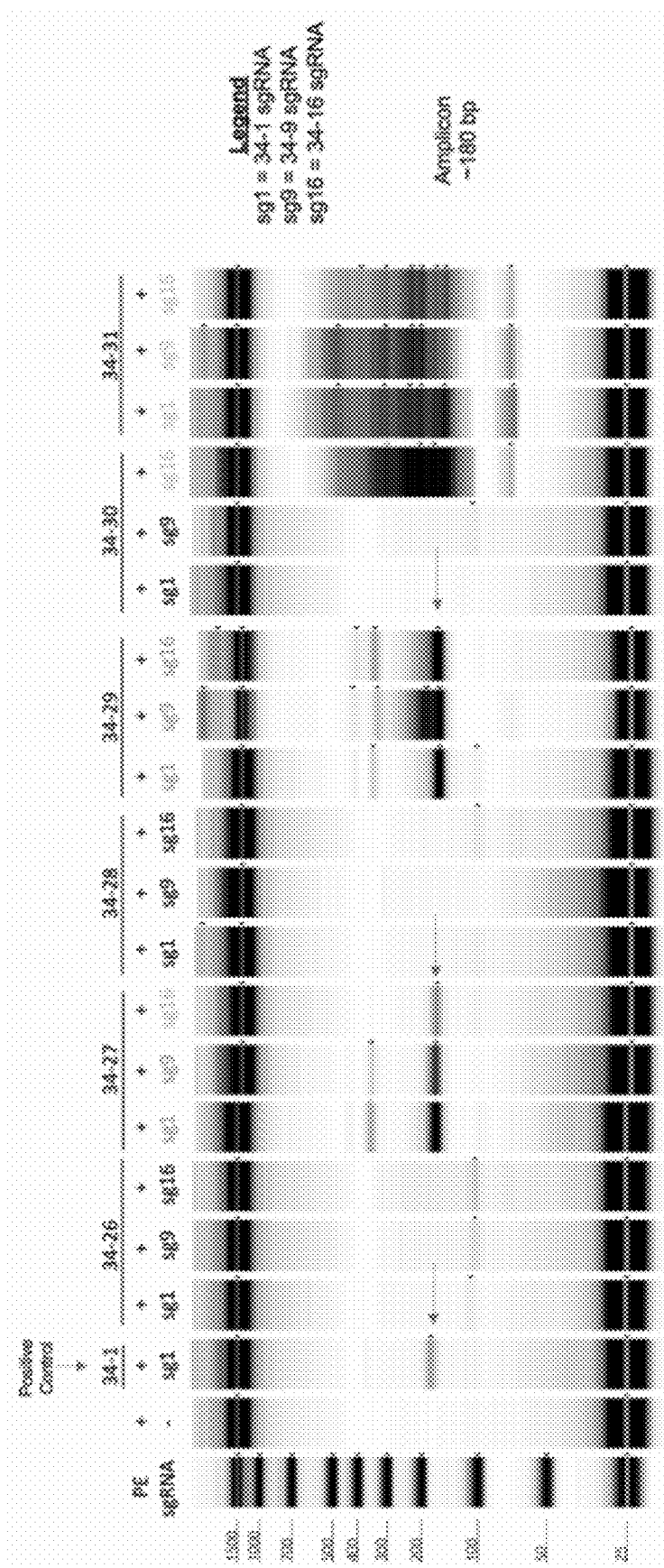
FIG. 39 depicts data demonstrating that reconstructed SMART I effectors are active nucleases. Novel SMART I effectors were assayed for cleavage activity via a PAM enrichment protocol. The effectors were expressed in in vitro transcription/translation (IVTT) reactions in the presence of the single guide RNA from other active MG34 nucleases, and added to a PAM library (dsDNA target). Cleavage products were amplified via ligation to the cut site and subsequent PCR amplification (successful RNA guided cleavage by the nuclease produced bands at the expected 180 bp size: arrows). MG34-27 and MG34-29 showed clear activity with the 3 tested guide RNAs.
Figure 40:
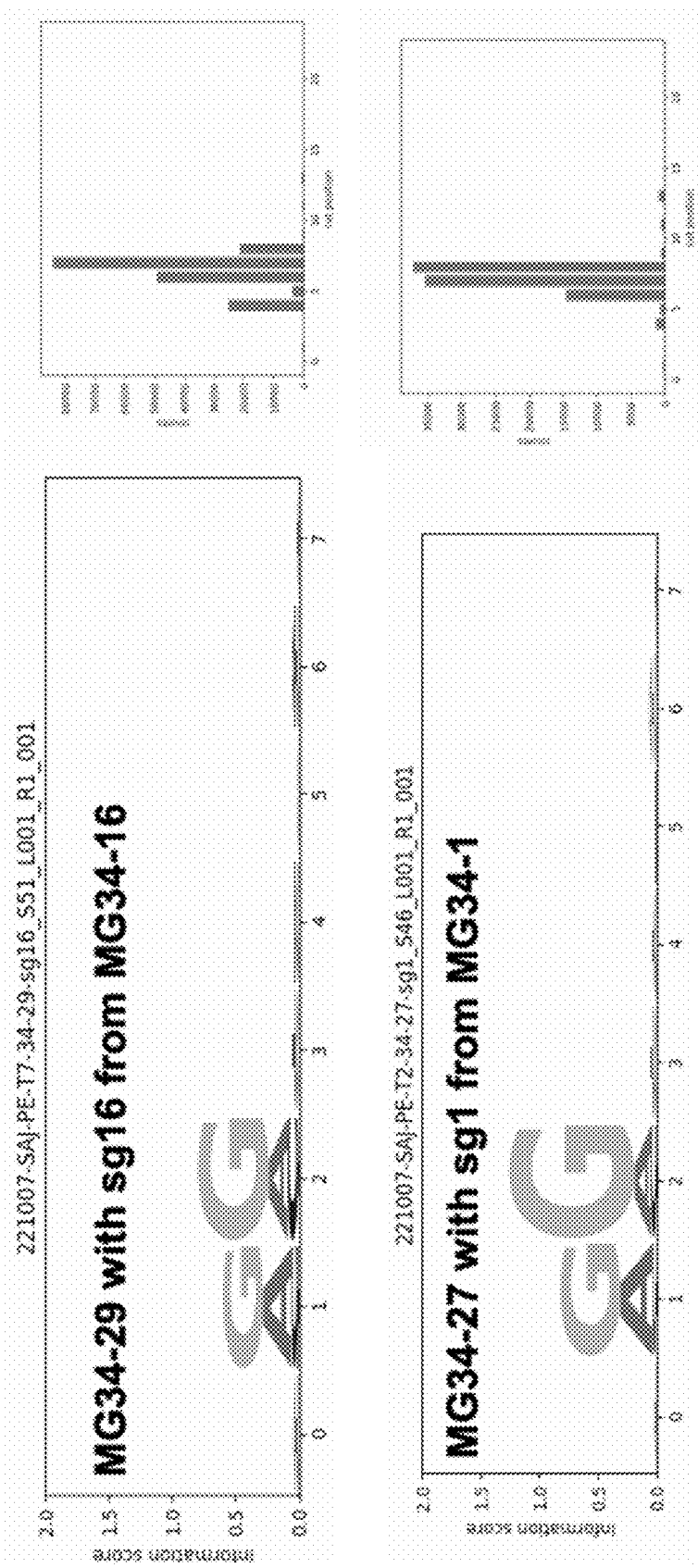
FIG. 40 depicts PAM recognition motifs for active SMART I nucleases from computational reconstruction. NGS sequencing of the bands identified in FIG. 39 were used to generate the PAMs and preferred cleavage position for each nuclease. Cleavage occurs between position 6 and 8 from the PAM on the non-target strand.

The primary differences between the structures are in the recognition lobe, which suggests that these reconstructed effectors may display similar nuclease activity to MG34-1. Given the strong support for newly reconstructed candidates, the six novel nucleases were tested for in vitro cleavage activity in PAM enrichment assays with the guide RNAs from three active MG34 nucleases: MG34-1 sgRNA 1 (SEQ ID No. 613), MG34-9 sgRNA 1 (SEQ ID No. 615), and MG34-16 sgRNA 1 (SEQ ID No. 616). Novel nucleases MG34-27 (SEQ ID No. 1314) and MG34-29 (SEQ ID No. 1316) were active with all three tested sgRNAs, as shown by the expected cleavage band at approximately 180 bp (FIG. 39). The PAM targeted by these novel nucleases is likely 3' nRR, with nGG being the most commonly recognized PAM (FIG. 40). Results indicate that the newly reconstructed nucleases have a more relaxed PAM recognition vs. other active MG34 nucleases (e.g. MG34-1 recognizes a 3' nGG PAM), with a flexible cleavage preference at position 6-9 from the PAM (FIG. 40).

TABLE 8

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG33 active effectors | 1 | MG33-1 effector | protein | unknown | uncultivated organism | |
| MG34 active effectors | 2 | MG34-1 effector | protein | unknown | uncultivated organism | |
| MG34 effectors | 3 | MG34-2 effector | protein | unknown | uncultivated organism | |
| MG34 effectors | 4 | MG34-3 effector | protein | unknown | uncultivated organism | |
| MG34 effectors | 5 | MG34-4 effector | protein | unknown | uncultivated organism | |
| MG34 effectors | 6 | MG34-5 effector | protein | unknown | uncultivated organism | |
| MG34 effectors | 7 | MG34-6 effector | protein | unknown | uncultivated organism | |
| MG34 effectors | 8 | MG34-7 effector | protein | unknown | uncultivated organism | |
| MG34 effectors | 9 | MG34-8 effector | protein | unknown | uncultivated organism | |
| MG34 effectors | 10 | MG34-9 effector | protein | unknown | uncultivated organism | |
| MG34 effectors | 11 | MG34-10 effector | protein | unknown | uncultivated organism | |
| MG34 effectors | 12 | MG34-11 effector | protein | unknown | uncultivated organism | |
| MG34 effectors | 13 | MG34-12 effector | protein | unknown | uncultivated organism | |
| MG34 effectors | 14 | MG34-13 effector | protein | unknown | uncultivated organism | |
| MG34 effectors | 15 | MG34-14 effector | protein | unknown | uncultivated organism | |
| MG34 effectors | 16 | MG34-15 effector | protein | unknown | uncultivated organism | |
| MG34 effectors | 17 | MG34-16 effector | protein | unknown | uncultivated organism | |
| MG34 effectors | 18 | MG34-17 effector | protein | unknown | uncultivated organism | |
| MG34 effectors | 19 | MG34-18 effector | protein | unknown | uncultivated organism | |
| MG34 effectors | 20 | MG34-19 effector | protein | unknown | uncultivated organism | |
| MG34 effectors | 21 | MG34-20 effector | protein | unknown | uncultivated organism | |
| MG34 effectors | 22 | MG34-21 effector | protein | unknown | uncultivated organism | |
| MG34 effectors | 23 | MG34-22 effector | protein | unknown | uncultivated organism | |
| MG34 effectors | 24 | MG34-23 effector | protein | unknown | uncultivated organism | |
| MG35 effectors | 25 | MG35-1 effector | protein | unknown | uncultivated organism | |
| MG35 effectors | 26 | MG35-2 effector | protein | unknown | uncultivated organism | |
| MG35 effectors | 27 | MG35-3 effector | protein | unknown | uncultivated organism | |
| MG35 effectors | 28 | MG35-4 effector | protein | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 effectors | 29 | MG35-5 effector | protein | unknown | uncultivated organism | |
| MG35 effectors | 30 | MG35-6 effector | protein | unknown | uncultivated organism | |
| MG35 effectors | 31 | MG35-7 effector | protein | unknown | uncultivated organism | |
| MG35 effectors | 32 | MG35-8 effector | protein | unknown | uncultivated organism | |
| MG35 effectors | 33 | MG35-9 effector | protein | unknown | uncultivated organism | |
| MG35 effectors | 34 | MG35-10 effector | protein | unknown | uncultivated organism | |
| MG35 effectors | 35 | MG35-11 effector | protein | unknown | uncultivated organism | |
| MG35 effectors | 36 | MG35-12 effector | protein | unknown | uncultivated organism | |
| MG35 effectors | 37 | MG35-13 effector | protein | unknown | uncultivated organism | |
| MG35 effectors | 38 | MG35-14 effector | protein | unknown | uncultivated organism | |
| MG35 effectors | 39 | MG35-15 effector | protein | unknown | uncultivated organism | |
| MG35 effectors | 40 | MG35-16 effector | protein | unknown | uncultivated organism | |
| MG35 effectors | 41 | MG35-17 effector | protein | unknown | uncultivated organism | |
| MG35 effectors | 42 | MG35-18 effector | protein | unknown | uncultivated organism | |
| MG35 effectors | 43 | MG35-19 effector | protein | unknown | uncultivated organism | |
| MG35 effectors | 44 | MG35-20 effector | protein | unknown | uncultivated organism | |
| MG35 effectors | 45 | MG35-21 effector | protein | unknown | uncultivated organism | |
| MG35 effectors | 46 | MG35-22 effector | protein | unknown | uncultivated organism | |
| MG35 effectors | 47 | MG35-23 effector | protein | unknown | uncultivated organism | |
| MG35 effectors | 48 | MG35-24 effector | protein | unknown | uncultivated organism | |
| MG35 effectors | 49 | MG35-25 effector | protein | unknown | uncultivated organism | |
| MG35 effectors | 50 | MG35-26 effector | protein | unknown | uncultivated organism | |
| MG35 effectors | 51 | MG35-27 effector | protein | unknown | uncultivated organism | |
| MG35 effectors | 52 | MG35-28 effector | protein | unknown | uncultivated organism | |
| MG35 effectors | 53 | MG35-29 effector | protein | unknown | uncultivated organism | |
| MG35 effectors | 54 | MG35-30 effector | protein | unknown | uncultivated organism | |
| MG35 effectors | 55 | MG35-31 effector | protein | unknown | uncultivated organism | |
| MG35 effectors | 56 | MG35-32 effector | protein | unknown | uncultivated organism | |
| MG35 effectors | 57 | MG35-33 effector | protein | unknown | uncultivated organism | |
| MG35 effectors | 58 | MG35-34 effector | protein | unknown | uncultivated organism | |
| MG35 effectors | 59 | MG35-35 effector | protein | unknown | uncultivated organism | |
| MG35 effectors | 50 | MG35-36 effector | protein | unknown | uncultivated organism | |
| MG35 effectors | 61 | MG35-37 effector | protein | unknown | uncultivated organism | |
| MG35 effectors | 62 | MG35-38 effector | protein | unknown | uncultivated organism | |
| MG35 effectors | 63 | MG35-39 effector | protein | unknown | uncultivated organism | |
| MG35 effectors | 64 | MG35-40 effector | protein | unknown | uncultivated organism | |
| MG35 effectors | 65 | MG35-41 effector | protein | unknown | uncultivated organism | |

TABLE 8-continued

Listing of additional protein and nucleic acid sequences referred to herein not included in the sequence listing
I.

| Category | SEQ ID: | Description | Type | Organism | Other Information | Comments or Sequence |
|---|---|---|---|---|---|---|
| MG35 effectors | 66 | MG35-42 effector | protein | unknown | uncultivated organism | |
| MG35 effectors | 67 | MG35-43 effector | protein | unknown | uncultivated organism | |
| MG35 effectors | 68 | MG35-44 effector | protein | unknown | uncultivated organism | |
| MG35 effectors | 69 | MG35-45 effector | protein | unknown | uncultivated organism | |
| MG35 effectors | 70 | MG35-46 effector | protein | unknown | uncultivated organism | |
| MG35 effectors | 71 | MG35-47 effector | protein | unknown | uncultivated organism | |
| MG35 effectors | 72 | MG35-48 effector | protein | unknown | uncultivated organism | |
| MG35 effectors | 73 | MG35-49 effector | protein | unknown | uncultivated organism | |
| MG35 effectors | 74 | MG35-50 effector | protein | unknown | uncultivated organism | |
| MG35 effectors | 75 | MG35-51 effector | protein | unknown | uncultivated organism | |
| MG35 effectors | 76 | MG35-52 effector | protein | unknown | uncultivated organism | |
| MG35 effectors | 77 | MG35-53 effector | protein | unknown | uncultivated organism | |
| MG35 effectors | 78 | MG35-54 effector | protein | unknown | uncultivated organism | |
| MG35 effectors | 79 | MG35-55 effector | protein | unknown | uncultivated organism | |
| MG35 effectors | 80 | MG35-56 effector | protein | unknown | uncultivated organism | |
| MG35 effectors | 81 | MG35-57 effector | protein | unknown | uncultivated organism | |
| MG35 effectors | 82 | MG35-58 effector | protein | unknown | uncultivated organism | |
| MG35 effectors | 83 | MG35-59 effector | protein | unknown | uncultivated organism | |
| MG35 effectors | 84 | MG35-60 effector | protein | unknown | uncultivated organism | |
| MG35 effectors | 85 | MG35-61 effector | protein | unknown | uncultivated organism | |
| MG35 effectors | 86 | MG35-62 effector | protein | unknown | uncultivated organism | |
| MG35 effectors | 87 | MG35-63 effector | protein | unknown | uncultivated organism | |
| MG35 effectors | 88 | MG35-64 effector | protein | unknown | uncultivated organism | |
| MG35 effectors | 89 | MG35-65 effector | protein | unknown | uncultivated organism | |
| MG35 effectors | 90 | MG35-66 effector | protein | unknown | uncultivated organism | |
| MG35 effectors | 91 | MG35-67 effector | protein | unknown | uncultivated organism | |
| MG35 effectors | 92 | MG35-68 effector | protein | unknown | uncultivated organism | |
| MG35 effectors | 93 | MG35-69 effector | protein | unknown | uncultivated organism | |
| MG35 effectors | 94 | MG35-70 effector | protein | unknown | uncultivated organism | |
| MG35 effectors | 95 | MG35-71 effector | protein | unknown | uncultivated organism | |
| MG35 effectors | 96 | MG35-72 effector | protein | unknown | uncultivated organism | |
| MG35 effectors | 97 | MG35-73 effector | protein | unknown | uncultivated organism | |
| MG35 effectors | 98 | MG35-74 effector | protein | unknown | uncultivated organism | |
| MG35 effectors | 99 | MG35-75 effector | protein | unknown | uncultivated organism | |
| MG35 effectors | 100 | MG35-76 effector | protein | unknown | uncultivated organism | |
| MG35 effectors | 101 | MG35-77 effector | protein | unknown | uncultivated organism | |
| MG35 effectors | 102 | MG35-78 effector | protein | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 effectors | 103 | MG35-79 effector | protein | unknown | uncultivated organism | |
| MG35 effectors | 104 | MG35-80 effector | protein | unknown | uncultivated organism | |
| MG35 effectors | 105 | MG35-81 effector | protein | unknown | uncultivated organism | |
| MG35 effectors | 106 | MG35-82 effector | protein | unknown | uncultivated organism | |
| MG35 effectors | 107 | MG35-83 effector | protein | unknown | uncultivated organism | |
| MG35 effectors | 108 | MG35-84 effector | protein | unknown | uncultivated organism | |
| MG35 effectors | 109 | MG35-85 effector | protein | unknown | uncultivated organism | |
| MG35 effectors | 110 | MG35-86 effector | protein | unknown | uncultivated organism | |
| MG35 effectors | 111 | MG35-87 effector | protein | unknown | uncultivated organism | |
| MG35 effectors | 112 | MG35-88 effector | protein | unknown | uncultivated organism | |
| MG35 effectors | 113 | MG35-89 effector | protein | unknown | uncultivated organism | |
| MG35 effectors | 114 | MG35-90 effector | protein | unknown | uncultivated organism | |
| MG35 effectors | 115 | MG35-91 effector | protein | unknown | uncultivated organism | |
| MG35 effectors | 116 | MG35-92 effector | protein | unknown | uncultivated organism | |
| MG35 effectors | 117 | MG35-93 effector | protein | unknown | uncultivated organism | |
| MG35 effectors | 118 | MG35-94 effector | protein | unknown | uncultivated organism | |
| MG35 effectors | 119 | MG35-95 effector | protein | unknown | uncultivated organism | |
| MG35 effectors | 120 | MG35-96 effector | protein | unknown | uncultivated organism | |
| MG35 effectors | 121 | MG35-97 effector | protein | unknown | uncultivated organism | |
| MG35 effectors | 122 | MG35-98 effector | protein | unknown | uncultivated organism | |
| MG35 effectors | 123 | MG35-99 effector | protein | unknown | uncultivated organism | |
| MG35 effectors | 124 | MG35-100 effector | protein | unknown | uncultivated organism | |
| MG35 effectors | 125 | MG35-101 effector | protein | unknown | uncultivated organism | |
| MG35 effectors | 126 | MG35-102 effector | protein | unknown | uncultivated organism | |
| MG35 effectors | 127 | MG35-103 effector | protein | unknown | uncultivated organism | |
| MG35 effectors | 128 | MG35-104 effector | protein | unknown | uncultivated organism | |
| MG35 effectors | 129 | MG35-105 effector | protein | unknown | uncultivated organism | |
| MG35 effectors | 130 | MG35-106 effector | protein | unknown | uncultivated organism | |
| MG35 effectors | 131 | MG35-107 effector | protein | unknown | uncultivated organism | |
| MG35 effectors | 132 | MG35-108 effector | protein | unknown | uncultivated organism | |
| MG35 effectors | 133 | MG35-109 effector | protein | unknown | uncultivated organism | |
| MG35 effectors | 134 | MG35-110 effector | protein | unknown | uncultivated organism | |
| MG35 effectors | 135 | MG35-111 effector | protein | unknown | uncultivated organism | |
| MG35 effectors | 136 | MG35-112 effector | protein | unknown | uncultivated organism | |
| MG35 effectors | 137 | MG35-113 effector | protein | unknown | uncultivated organism | |
| MG35 effectors | 138 | MG35-114 effector | protein | unknown | uncultivated organism | |
| MG35 effectors | 139 | MG35-115 effector | protein | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 effectors | 140 | MG35-116 effector | protein | unknown | uncultivated organism | |
| MG35 effectors | 141 | MG35-117 effector | protein | unknown | uncultivated organism | |
| MG35 effectors | 142 | MG35-118 effector | protein | unknown | uncultivated organism | |
| MG35 effectors | 143 | MG35-119 effector | protein | unknown | uncultivated organism | |
| MG35 effectors | 144 | MG35-120 effector | protein | unknown | uncultivated organism | |
| MG35 effectors | 145 | MG35-121 effector | protein | unknown | uncultivated organism | |
| MG35 effectors | 146 | MG35-122 effector | protein | unknown | uncultivated organism | |
| MG35 effectors | 147 | MG35-123 effector | protein | unknown | uncultivated organism | |
| MG35 effectors | 148 | MG35-124 effector | protein | unknown | uncultivated organism | |
| MG35 effectors | 149 | MG35-125 effector | protein | unknown | uncultivated organism | |
| MG35 effectors | 150 | MG35-126 effector | protein | unknown | uncultivated organism | |
| MG35 effectors | 151 | MG35-127 effector | protein | unknown | uncultivated organism | |
| MG35 effectors | 152 | MG35-128 effector | protein | unknown | uncultivated organism | |
| MG35 effectors | 153 | MG35-129 effector | protein | unknown | uncultivated organism | |
| MG35 effectors | 154 | MG35-130 effector | protein | unknown | uncultivated organism | |
| MG35 effectors | 155 | MG35-131 effector | protein | unknown | uncultivated organism | |
| MG35 effectors | 156 | MG35-132 effector | protein | unknown | uncultivated organism | |
| MG35 effectors | 157 | MG35-133 effector | protein | unknown | uncultivated organism | |
| MG35 effectors | 158 | MG35-134 effector | protein | unknown | uncultivated organism | |
| MG35 effectors | 159 | MG35-135 effector | protein | unknown | uncultivated organism | |
| MG35 effectors | 160 | MG35-136 effector | protein | unknown | uncultivated organism | |
| MG35 effectors | 161 | MG35-137 effector | protein | unknown | uncultivated organism | |
| MG35 effectors | 162 | MG35-138 effector | protein | unknown | uncultivated organism | |
| MG35 effectors | 163 | MG35-139 effector | protein | unknown | uncultivated organism | |
| MG35 effectors | 164 | MG35-140 effector | protein | unknown | uncultivated organism | |
| MG35 effectors | 165 | MG35-141 effector | protein | unknown | uncultivated organism | |
| MG35 effectors | 166 | MG35-142 effector | protein | unknown | uncultivated organism | |
| MG35 effectors | 167 | MG35-143 effector | protein | unknown | uncultivated organism | |
| MG35 effectors | 168 | MG35-144 effector | protein | unknown | uncultivated organism | |
| MG35 effectors | 169 | MG35-146 effector | protein | unknown | uncultivated organism | |
| MG35 effectors | 170 | MG35-147 effector | protein | unknown | uncultivated organism | |
| MG35 effectors | 171 | MG35-148 effector | protein | unknown | uncultivated organism | |
| MG35 effectors | 172 | MG35-149 effector | protein | unknown | uncultivated organism | |
| MG35 effectors | 173 | MG35-150 effector | protein | unknown | uncultivated organism | |
| MG35 effectors | 174 | MG35-151 effector | protein | unknown | uncultivated organism | |
| MG35 effectors | 175 | MG35-152 effector | protein | unknown | uncultivated organism | |
| MG35 effectors | 176 | MG35-153 effector | protein | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 effectors | 177 | MG35-154 effector | protein | unknown | uncultivated organism | |
| MG35 effectors | 178 | MG35-155 effector | protein | unknown | uncultivated organism | |
| MG35 effectors | 179 | MG35-156 effector | protein | unknown | uncultivated organism | |
| MG35 effectors | 180 | MG35-157 effector | protein | unknown | uncultivated organism | |
| MG35 effectors | 181 | MG35-158 effector | protein | unknown | uncultivated organism | |
| MG35 effectors | 182 | MG35-159 effector | protein | unknown | uncultivated organism | |
| MG35 effectors | 183 | MG35-160 effector | protein | unknown | uncultivated organism | |
| MG35 effectors | 184 | MG35-161 effector | protein | unknown | uncultivated organism | |
| MG35 effectors | 185 | MG35-162 effector | protein | unknown | uncultivated organism | |
| MG35 effectors | 186 | MG35-163 effector | protein | unknown | uncultivated organism | |
| MG35 effectors | 187 | MG35-164 effector | protein | unknown | uncultivated organism | |
| MG35 effectors | 188 | MG35-165 effector | protein | unknown | uncultivated organism | |
| MG35 effectors | 189 | MG35-166 effector | protein | unknown | uncultivated organism | |
| MG35 effectors | 190 | MG35-167 effector | protein | unknown | uncultivated organism | |
| MG35 effectors | 191 | MG35-168 effector | protein | unknown | uncultivated organism | |
| MG35 effectors | 192 | MG35-169 effector | protein | unknown | uncultivated organism | |
| MG35 effectors | 193 | MG35-170 effector | protein | unknown | uncultivated organism | |
| MG35 effectors | 194 | MG35-171 effector | protein | unknown | uncultivated organism | |
| MG35 effectors | 195 | MG35-172 effector | protein | unknown | uncultivated organism | |
| MG35 effectors | 196 | MG35-173 effector | protein | unknown | uncultivated organism | |
| MG35 effectors | 197 | MG35-174 effector | protein | unknown | uncultivated organism | |
| MG35 effectors | 198 | MG35-175 effector | protein | unknown | uncultivated organism | |
| MG33 active effectors tracrRNA sequence | 199 | MG33-1 tracrRNA sequence | nucleotide | artificial sequence | | |
| MG34 active effectors tracrRNA sequence | 200 | MG34-1 tracrRNA sequence | nucleotide | artificial sequence | | |
| putative sgRNA | 201 | putative MG33-1 sgRNA | nucleotide | artificial sequence | | |
| putative sgRNA | 202 | putative MG34-1 sgRNA | nucleotide | artificial sequence | | |
| putative sgRNA | 203 | putative MG34-1 sgRNA | nucleotide | artificial sequence | | |
| target | 204 | test target sequence | nucleotide | artificial sequence | | |
| NLS | 205 | SV40 NLS | protein | Simian vacuolating virus 40 T | | |
| NLS | 206 | nucleoplasmin bipartite NLS | protein | Human | | |
| NLS | 207 | c-myc NLS | protein | Human | | |
| NLS | 208 | c-myc NLS | protein | Human | | |
| NLS | 209 | hnRNPA1 M9 NLS | protein | Mouse | | |
| NLS | 210 | Importin-alpha IBB domain NLS | protein | Human | | |
| NLS | 211 | Myoma T protein NLS | protein | Murine polyomavirus | | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| NLS | 212 | Myoma T protein NLS | protein | Murine polyomavirus | | |
| NLS | 213 | p53 NLS | protein | Human | | |
| NLS | 214 | mouse c-abl IV NLS | protein | Mouse | | |
| NLS | 215 | influenza virus NS1 NLS | protein | Influenza virus NS1 | | |
| NLS | 216 | influenza virus NS1 NLS | protein | Influenza virus NS1 | | |
| NLS | 217 | Hepatitis virus delta antigen NLS | protein | Hepatitis virus delta | | |
| NLS | 218 | mouse Mx1 protein NLS | protein | Mouse | | |
| NLS | 219 | human poly(ADP-ribose) polymerase NLS | protein | Human | | |
| NLS | 220 | steroid hormone receptors glucocorticoid NLS | protein | Human | | |
| MG35 effectors | 221 | MG35-4 effector | protein | unknown | uncultivated organism | |
| MG35 effectors | 222 | MG35-419 effector | protein | unknown | uncultivated organism | |
| MG35 effectors | 223 | MG35-420 effector | protein | unknown | uncultivated organism | |
| MG35 effectors | 224 | MG35-421 effector | protein | unknown | uncultivated organism | |
| MG35 effectors | 225 | MG35-176 effector | protein | unknown | uncultivated organism | |
| MG35 effectors | 226 | MG35-177 effector | protein | unknown | uncultivated organism | |
| MG35 effectors | 227 | MG35-178 effector | protein | unknown | uncultivated organism | |
| MG35 effectors | 228 | MG35-179 effector | protein | unknown | uncultivated organism | |
| MG35 effectors | 229 | MG35-180 effector | protein | unknown | uncultivated organism | |
| MG35 effectors | 230 | MG35-181 effector | protein | unknown | uncultivated organism | |
| MG35 effectors | 231 | MG35-183 effector | protein | unknown | uncultivated organism | |
| MG35 effectors | 232 | MG35-184 effector | protein | unknown | uncultivated organism | |
| MG35 effectors | 233 | MG35-185 effector | protein | unknown | uncultivated organism | |
| MG35 effectors | 234 | MG35-186 effector | protein | unknown | uncultivated organism | |
| MG35 effectors | 235 | MG35-187 effector | protein | unknown | uncultivated organism | |
| MG35 effectors | 236 | MG35-188 effector | protein | unknown | uncultivated organism | |
| MG35 effectors | 237 | MG35-189 effector | protein | unknown | uncultivated organism | |
| MG35 effectors | 238 | MG35-190 effector | protein | unknown | uncultivated organism | |
| MG35 effectors | 239 | MG35-191 effector | protein | unknown | uncultivated organism | |
| MG35 effectors | 240 | MG35-192 effector | protein | unknown | uncultivated organism | |
| MG35 effectors | 241 | MG35-193 effector | protein | unknown | uncultivated organism | |
| MG35 effectors | 242 | MG35-194 effector | protein | unknown | uncultivated organism | |
| MG35 effectors | 243 | MG35-195 effector | protein | unknown | uncultivated organism | |
| MG35 effectors | 244 | MG35-196 effector | protein | unknown | uncultivated organism | |
| MG35 effectors | 245 | MG35-197 effector | protein | unknown | uncultivated organism | |
| MG35 effectors | 246 | MG35-198 effector | protein | unknown | uncultivated organism | |
| MG35 effectors | 247 | MG35-199 effector | protein | unknown | uncultivated organism | |
| MG35 effectors | 248 | MG35-200 effector | protein | unknown | uncultivated organism | |
| MG35 effectors | 249 | MG35-201 effector | protein | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 effectors | 250 | MG35-202 effector | protein | unknown | uncultivated organism | |
| MG35 effectors | 251 | MG35-203 effector | protein | unknown | uncultivated organism | |
| MG35 effectors | 252 | MG35-204 effector | protein | unknown | uncultivated organism | |
| MG35 effectors | 253 | MG35-205 effector | protein | unknown | uncultivated organism | |
| MG35 effectors | 254 | MG35-206 effector | protein | unknown | uncultivated organism | |
| MG35 effectors | 255 | MG35-207 effector | protein | unknown | uncultivated organism | |
| MG35 effectors | 256 | MG35-208 effector | protein | unknown | uncultivated organism | |
| MG35 effectors | 257 | MG35-209 effector | protein | unknown | uncultivated organism | |
| MG35 effectors | 258 | MG35-210 effector | protein | unknown | uncultivated organism | |
| MG35 effectors | 259 | MG35-211 effector | protein | unknown | uncultivated organism | |
| MG35 effectors | 260 | MG35-212 effector | protein | unknown | uncultivated organism | |
| MG35 effectors | 261 | MG35-213 effector | protein | unknown | uncultivated organism | |
| MG35 effectors | 262 | MG35-214 effector | protein | unknown | uncultivated organism | |
| MG35 effectors | 263 | MG35-215 effector | protein | unknown | uncultivated organism | |
| MG35 effectors | 264 | MG35-216 effector | protein | unknown | uncultivated organism | |
| MG35 effectors | 265 | MG35-217 effector | protein | unknown | uncultivated organism | |
| MG35 effectors | 266 | MG35-218 effector | protein | unknown | uncultivated organism | |
| MG35 effectors | 267 | MG35-219 effector | protein | unknown | uncultivated organism | |
| MG35 effectors | 268 | MG35-220 effector | protein | unknown | uncultivated organism | |
| MG35 effectors | 269 | MG35-221 effector | protein | unknown | uncultivated organism | |
| MG35 effectors | 270 | MG35-222 effector | protein | unknown | uncultivated organism | |
| MG35 effectors | 271 | MG35-223 effector | protein | unknown | uncultivated organism | |
| MG35 effectors | 272 | MG35-224 effector | protein | unknown | uncultivated organism | |
| MG35 effectors | 273 | MG35-225 effector | protein | unknown | uncultivated organism | |
| MG35 effectors | 274 | MG35-226 effector | protein | unknown | uncultivated organism | |
| MG35 effectors | 275 | MG35-227 effector | protein | unknown | uncultivated organism | |
| MG35 effectors | 276 | MG35-228 effector | protein | unknown | uncultivated organism | |
| MG35 effectors | 277 | MG35-229 effector | protein | unknown | uncultivated organism | |
| MG35 effectors | 278 | MG35-230 effector | protein | unknown | uncultivated organism | |
| MG35 effectors | 279 | MG35-231 effector | protein | unknown | uncultivated organism | |
| MG35 effectors | 280 | MG35-232 effector | protein | unknown | uncultivated organism | |
| MG35 effectors | 281 | MG35-233 effector | protein | unknown | uncultivated organism | |
| MG35 effectors | 282 | MG35-234 effector | protein | unknown | uncultivated organism | |
| MG35 effectors | 283 | MG35-235 effector | protein | unknown | uncultivated organism | |
| MG35 effectors | 284 | MG35-236 effector | protein | unknown | uncultivated organism | |
| MG35 effectors | 285 | MG35-237 effector | protein | unknown | uncultivated organism | |
| MG35 effectors | 286 | MG35-238 effector | protein | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 effectors | 287 | MG35-239 effector | protein | unknown | uncultivated organism | |
| MG35 effectors | 288 | MG35-240 effector | protein | unknown | uncultivated organism | |
| MG35 effectors | 289 | MG35-241 effector | protein | unknown | uncultivated organism | |
| MG35 effectors | 290 | MG35-242 effector | protein | unknown | uncultivated organism | |
| MG35 effectors | 291 | MG35-243 effector | protein | unknown | uncultivated organism | |
| MG35 effectors | 292 | MG35-244 effector | protein | unknown | uncultivated organism | |
| MG35 effectors | 293 | MG35-245 effector | protein | unknown | uncultivated organism | |
| MG35 effectors | 294 | MG35-246 effector | protein | unknown | uncultivated organism | |
| MG35 effectors | 295 | MG35-247 effector | protein | unknown | uncultivated organism | |
| MG35 effectors | 296 | MG35-248 effector | protein | unknown | uncultivated organism | |
| MG35 effectors | 297 | MG35-249 effector | protein | unknown | uncultivated organism | |
| MG35 effectors | 298 | MG35-250 effector | protein | unknown | uncultivated organism | |
| MG35 effectors | 299 | MG35-251 effector | protein | unknown | uncultivated organism | |
| MG35 effectors | 300 | MG35-252 effector | protein | unknown | uncultivated organism | |
| MG35 effectors | 301 | MG35-253 effector | protein | unknown | uncultivated organism | |
| MG35 effectors | 302 | MG35-254 effector | protein | unknown | uncultivated organism | |
| MG35 effectors | 303 | MG35-255 effector | protein | unknown | uncultivated organism | |
| MG35 effectors | 304 | MG35-256 effector | protein | unknown | uncultivated organism | |
| MG35 effectors | 305 | MG35-257 effector | protein | unknown | uncultivated organism | |
| MG35 effectors | 306 | MG35-258 effector | protein | unknown | uncultivated organism | |
| MG35 effectors | 307 | MG35-259 effector | protein | unknown | uncultivated organism | |
| MG35 effectors | 308 | MG35-260 effector | protein | unknown | uncultivated organism | |
| MG35 effectors | 309 | MG35-261 effector | protein | unknown | uncultivated organism | |
| MG35 effectors | 310 | MG35-262 effector | protein | unknown | uncultivated organism | |
| MG35 effectors | 311 | MG35-263 effector | protein | unknown | uncultivated organism | |
| MG35 effectors | 312 | MG35-264 effector | protein | unknown | uncultivated organism | |
| MG35 effectors | 313 | MG35-265 effector | protein | unknown | uncultivated organism | |
| MG35 effectors | 314 | MG35-266 effector | protein | unknown | uncultivated organism | |
| MG35 effectors | 315 | MG35-267 effector | protein | unknown | uncultivated organism | |
| MG35 effectors | 316 | MG35-268 effector | protein | unknown | uncultivated organism | |
| MG35 effectors | 317 | MG35-269 effector | protein | unknown | uncultivated organism | |
| MG35 effectors | 318 | MG35-270 effector | protein | unknown | uncultivated organism | |
| MG35 effectors | 319 | MG35-271 effector | protein | unknown | uncultivated organism | |
| MG35 effectors | 320 | MG35-272 effector | protein | unknown | uncultivated organism | |
| MG35 effectors | 321 | MG35-273 effector | protein | unknown | uncultivated organism | |
| MG35 effectors | 322 | MG35-274 effector | protein | unknown | uncultivated organism | |
| MG35 effectors | 323 | MG35-275 effector | protein | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 effectors | 324 | MG35-276 effector | protein | unknown | uncultivated organism | |
| MG35 effectors | 325 | MG35-277 effector | protein | unknown | uncultivated organism | |
| MG35 effectors | 326 | MG35-278 effector | protein | unknown | uncultivated organism | |
| MG35 effectors | 327 | MG35-279 effector | protein | unknown | uncultivated organism | |
| MG35 effectors | 328 | MG35-280 effector | protein | unknown | uncultivated organism | |
| MG35 effectors | 329 | MG35-281 effector | protein | unknown | uncultivated organism | |
| MG35 effectors | 330 | MG35-282 effector | protein | unknown | uncultivated organism | |
| MG35 effectors | 331 | MG35-283 effector | protein | unknown | uncultivated organism | |
| MG35 effectors | 332 | MG35-284 effector | protein | unknown | uncultivated organism | |
| MG35 effectors | 333 | MG35-285 effector | protein | unknown | uncultivated organism | |
| MG35 effectors | 334 | MG35-286 effector | protein | unknown | uncultivated organism | |
| MG35 effectors | 335 | MG35-287 effector | protein | unknown | uncultivated organism | |
| MG35 effectors | 336 | MG35-288 effector | protein | unknown | uncultivated organism | |
| MG35 effectors | 337 | MG35-289 effector | protein | unknown | uncultivated organism | |
| MG35 effectors | 338 | MG35-290 effector | protein | unknown | uncultivated organism | |
| MG35 effectors | 339 | MG35-291 effector | protein | unknown | uncultivated organism | |
| MG35 effectors | 340 | MG35-292 effector | protein | unknown | uncultivated organism | |
| MG35 effectors | 341 | MG35-293 effector | protein | unknown | uncultivated organism | |
| MG35 effectors | 342 | MG35-294 effector | protein | unknown | uncultivated organism | |
| MG35 effectors | 343 | MG35-295 effector | protein | unknown | uncultivated organism | |
| MG35 effectors | 344 | MG35-296 effector | protein | unknown | uncultivated organism | |
| MG35 effectors | 345 | MG35-297 effector | protein | unknown | uncultivated organism | |
| MG35 effectors | 346 | MG35-298 effector | protein | unknown | uncultivated organism | |
| MG35 effectors | 347 | MG35-299 effector | protein | unknown | uncultivated organism | |
| MG35 effectors | 348 | MG35-300 effector | protein | unknown | uncultivated organism | |
| MG35 effectors | 349 | MG35-301 effector | protein | unknown | uncultivated organism | |
| MG35 effectors | 350 | MG35-302 effector | protein | unknown | uncultivated organism | |
| MG35 effectors | 351 | MG35-303 effector | protein | unknown | uncultivated organism | |
| MG35 effectors | 352 | MG35-304 effector | protein | unknown | uncultivated organism | |
| MG35 effectors | 353 | MG35-305 effector | protein | unknown | uncultivated organism | |
| MG35 effectors | 354 | MG35-307 effector | protein | unknown | uncultivated organism | |
| MG35 effectors | 355 | MG35-308 effector | protein | unknown | uncultivated organism | |
| MG35 effectors | 356 | MG35-309 effector | protein | unknown | uncultivated organism | |
| MG35 effectors | 357 | MG35-310 effector | protein | unknown | uncultivated organism | |
| MG35 effectors | 358 | MG35-311 effector | protein | unknown | uncultivated organism | |
| MG35 effectors | 359 | MG35-312 effector | protein | unknown | uncultivated organism | |
| MG35 effectors | 360 | MG35-313 effector | protein | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 effectors | 361 | MG35-314 effector | protein | unknown | uncultivated organism | |
| MG35 effectors | 362 | MG35-315 effector | protein | unknown | uncultivated organism | |
| MG35 effectors | 363 | MG35-316 effector | protein | unknown | uncultivated organism | |
| MG35 effectors | 364 | MG35-317 effector | protein | unknown | uncultivated organism | |
| MG35 effectors | 365 | MG35-318 effector | protein | unknown | uncultivated organism | |
| MG35 effectors | 366 | MG35-319 effector | protein | unknown | uncultivated organism | |
| MG35 effectors | 367 | MG35-320 effector | protein | unknown | uncultivated organism | |
| MG35 effectors | 368 | MG35-321 effector | protein | unknown | uncultivated organism | |
| MG35 effectors | 369 | MG35-322 effector | protein | unknown | uncultivated organism | |
| MG35 effectors | 370 | MG35-323 effector | protein | unknown | uncultivated organism | |
| MG35 effectors | 371 | MG35-324 effector | protein | unknown | uncultivated organism | |
| MG35 effectors | 372 | MG35-325 effector | protein | unknown | uncultivated organism | |
| MG35 effectors | 373 | MG35-326 effector | protein | unknown | uncultivated organism | |
| MG35 effectors | 374 | MG35-327 effector | protein | unknown | uncultivated organism | |
| MG35 effectors | 375 | MG35-328 effector | protein | unknown | uncultivated organism | |
| MG35 effectors | 376 | MG35-329 effector | protein | unknown | uncultivated organism | |
| MG35 effectors | 377 | MG35-330 effector | protein | unknown | uncultivated organism | |
| MG35 effectors | 378 | MG35-331 effector | protein | unknown | uncultivated organism | |
| MG35 effectors | 379 | MG35-333 effector | protein | unknown | uncultivated organism | |
| MG35 effectors | 380 | MG35-334 effector | protein | unknown | uncultivated organism | |
| MG35 effectors | 381 | MG35-335 effector | protein | unknown | uncultivated organism | |
| MG35 effectors | 382 | MG35-336 effector | protein | unknown | uncultivated organism | |
| MG35 effectors | 383 | MG35-337 effector | protein | unknown | uncultivated organism | |
| MG35 effectors | 384 | MG35-338 effector | protein | unknown | uncultivated organism | |
| MG35 effectors | 385 | MG35-339 effector | protein | unknown | uncultivated organism | |
| MG35 effectors | 386 | MG35-340 effector | protein | unknown | uncultivated organism | |
| MG35 effectors | 387 | MG35-341 effector | protein | unknown | uncultivated organism | |
| MG35 effectors | 388 | MG35-342 effector | protein | unknown | uncultivated organism | |
| MG35 effectors | 389 | MG35-343 effector | protein | unknown | uncultivated organism | |
| MG35 effectors | 390 | MG35-344 effector | protein | unknown | uncultivated organism | |
| MG35 effectors | 391 | MG35-345 effector | protein | unknown | uncultivated organism | |
| MG35 effectors | 392 | MG35-346 effector | protein | unknown | uncultivated organism | |
| MG35 effectors | 393 | MG35-347 effector | protein | unknown | uncultivated organism | |
| MG35 effectors | 394 | MG35-348 effector | protein | unknown | uncultivated organism | |
| MG35 effectors | 395 | MG35-349 effector | protein | unknown | uncultivated organism | |
| MG35 effectors | 396 | MG35-350 effector | protein | unknown | uncultivated organism | |
| MG35 effectors | 397 | MG35-351 effector | protein | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 effectors | 398 | MG35-352 effector | protein | unknown | uncultivated organism | |
| MG35 effectors | 399 | MG35-353 effector | protein | unknown | uncultivated organism | |
| MG35 effectors | 400 | MG35-354 effector | protein | unknown | uncultivated organism | |
| MG35 effectors | 401 | MG35-355 effector | protein | unknown | uncultivated organism | |
| MG35 effectors | 402 | MG35-356 effector | protein | unknown | uncultivated organism | |
| MG35 effectors | 403 | MG35-357 effector | protein | unknown | uncultivated organism | |
| MG35 effectors | 404 | MG35-358 effector | protein | unknown | uncultivated organism | |
| MG35 effectors | 405 | MG35-359 effector | protein | unknown | uncultivated organism | |
| MG35 effectors | 406 | MG35-360 effector | protein | unknown | uncultivated organism | |
| MG35 effectors | 407 | MG35-361 effector | protein | unknown | uncultivated organism | |
| MG35 effectors | 408 | MG35-362 effector | protein | unknown | uncultivated organism | |
| MG35 effectors | 409 | MG35-363 effector | protein | unknown | uncultivated organism | |
| MG35 effectors | 410 | MG35-364 effector | protein | unknown | uncultivated organism | |
| MG35 effectors | 411 | MG35-365 effector | protein | unknown | uncultivated organism | |
| MG35 effectors | 412 | MG35-366 effector | protein | unknown | uncultivated organism | |
| MG35 effectors | 413 | MG35-367 effector | protein | unknown | uncultivated organism | |
| MG35 effectors | 414 | MG35-368 effector | protein | unknown | uncultivated organism | |
| MG35 effectors | 415 | MG35-369 effector | protein | unknown | uncultivated organism | |
| MG35 effectors | 416 | MG35-370 effector | protein | unknown | uncultivated organism | |
| MG35 effectors | 417 | MG35-371 effector | protein | unknown | uncultivated organism | |
| MG35 effectors | 418 | MG35-372 effector | protein | unknown | uncultivated organism | |
| MG35 effectors | 419 | MG35-373 effector | protein | unknown | uncultivated organism | |
| MG35 effectors | 420 | MG35-374 effector | protein | unknown | uncultivated organism | |
| MG35 effectors | 421 | MG35-375 effector | protein | unknown | uncultivated organism | |
| MG35 effectors | 422 | MG35-376 effector | protein | unknown | uncultivated organism | |
| MG35 effectors | 423 | MG35-377 effector | protein | unknown | uncultivated organism | |
| MG35 effectors | 424 | MG35-378 effector | protein | unknown | uncultivated organism | |
| MG35 effectors | 425 | MG35-379 effector | protein | unknown | uncultivated organism | |
| MG35 effectors | 426 | MG35-384 effector | protein | unknown | uncultivated organism | |
| MG35 effectors | 427 | MG35-385 effector | protein | unknown | uncultivated organism | |
| MG35 effectors | 428 | MG35-386 effector | protein | unknown | uncultivated organism | |
| MG35 effectors | 429 | MG35-387 effector | protein | unknown | uncultivated organism | |
| MG35 effectors | 430 | MG35-388 effector | protein | unknown | uncultivated organism | |
| MG35 effectors | 431 | MG35-389 effector | protein | unknown | uncultivated organism | |
| MG35 effectors | 432 | MG35-390 effector | protein | unknown | uncultivated organism | |
| MG35 effectors | 433 | MG35-391 effector | protein | unknown | uncultivated organism | |
| MG35 effectors | 434 | MG35-392 effector | protein | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 effectors | 435 | MG35-393 effector | protein | unknown | uncultivated organism | |
| MG35 effectors | 436 | MG35-394 effector | protein | unknown | uncultivated organism | |
| MG35 effectors | 437 | MG35-395 effector | protein | unknown | uncultivated organism | |
| MG35 effectors | 438 | MG35-396 effector | protein | unknown | uncultivated organism | |
| MG35 effectors | 439 | MG35-397 effector | protein | unknown | uncultivated organism | |
| MG35 effectors | 440 | MG35-398 effector | protein | unknown | uncultivated organism | |
| MG35 effectors | 441 | MG35-399 effector | protein | unknown | uncultivated organism | |
| MG35 effectors | 442 | MG35-400 effector | protein | unknown | uncultivated organism | |
| MG35 effectors | 443 | MG35-401 effector | protein | unknown | uncultivated organism | |
| MG35 effectors | 444 | MG35-402 effector | protein | unknown | uncultivated organism | |
| MG35 effectors | 445 | MG35-403 effector | protein | unknown | uncultivated organism | |
| MG35 effectors | 446 | MG35-404 effector | protein | unknown | uncultivated organism | |
| MG35 effectors | 447 | MG35-405 effector | protein | unknown | uncultivated organism | |
| MG35 effectors | 448 | MG35-406 effector | protein | unknown | uncultivated organism | |
| MG35 effectors | 449 | MG35-408 effector | protein | unknown | uncultivated organism | |
| MG35 effectors | 450 | MG35-409 effector | protein | unknown | uncultivated organism | |
| MG35 effectors | 451 | MG35-410 effector | protein | unknown | uncultivated organism | |
| MG35 effectors | 452 | MG35-411 effector | protein | unknown | uncultivated organism | |
| MG35 effectors | 453 | MG35-412 effector | protein | unknown | uncultivated organism | |
| MG35 effectors | 454 | MG35-413 effector | protein | unknown | uncultivated organism | |
| MG35 effectors | 455 | MG35-414 effector | protein | unknown | uncultivated organism | |
| MG35 effectors | 456 | MG35-415 effector | protein | unknown | uncultivated organism | |
| MG35 effectors | 457 | MG35-416 effector | protein | unknown | uncultivated organism | |
| MG35 effectors | 458 | MG35-417 effector | protein | unknown | uncultivated organism | |
| MG35 effectors | 459 | MG35-418 effector | protein | unknown | uncultivated organism | |
| MG35 effectors tracrRNA sequence | 460 | MG35-4 tracrRNA sequence | nucleotide | artificial sequence | | |
| putative tracrRNA | 461 | putative MG35-3 tracrRNA | nucleotide | artificial sequence | | |
| repeat | 462 | MG35-3 repeat | nucleotide | artificial sequence | | |
| MG33 effectors | 463 | MG33-2 effector | protein | unknown | uncultivated organism | |
| MG33 effectors | 464 | MG33-3 effector | protein | unknown | uncultivated organism | |
| MG33 effectors | 465 | MG33-4 effector | protein | unknown | uncultivated organism | |
| MG33 effectors | 466 | MG33-5 effector | protein | unknown | uncultivated organism | |
| MG33 effectors | 467 | MG33-6 effector | protein | unknown | uncultivated organism | |
| MG33 effectors | 468 | MG33-7 effector | protein | unknown | uncultivated organism | |
| MG33 effectors | 469 | MG33-8 effector | protein | unknown | uncultivated organism | |
| MG33 effectors | 470 | MG33-9 effector | protein | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG33 effectors | 471 | MG33-10 effector | protein | unknown | uncultivated organism | |
| MG33 effectors | 472 | MG33-11 effector | protein | unknown | uncultivated organism | |
| MG33 effectors | 473 | MG33-12 effector | protein | unknown | uncultivated organism | |
| MG33 effectors | 474 | MG33-13 effector | protein | unknown | uncultivated organism | |
| MG33 effectors | 475 | MG33-14 effector | protein | unknown | uncultivated organism | |
| MG33 effectors | 476 | MG33-15 effector | protein | unknown | uncultivated organism | |
| MG33 effectors | 477 | MG33-16 effector | protein | unknown | uncultivated organism | |
| MG33 effectors | 478 | MG33-17 effector | protein | unknown | uncultivated organism | |
| MG33 effectors | 479 | MG33-18 effector | protein | unknown | uncultivated organism | |
| MG33 effectors | 480 | MG33-19 effector | protein | unknown | uncultivated organism | |
| MG33 effectors | 481 | MG33-20 effector | protein | unknown | uncultivated organism | |
| MG33 effectors | 482 | MG33-21 effector | protein | unknown | uncultivated organism | |
| MG33 effectors | 483 | MG33-22 effector | protein | unknown | uncultivated organism | |
| MG33 effectors | 484 | MG33-23 effector | protein | unknown | uncultivated organism | |
| MG33 effectors | 485 | MG33-24 effector | protein | unknown | uncultivated organism | |
| MG33 effectors | 486 | MG33-26 effector | protein | unknown | uncultivated organism | |
| MG34 effectors | 487 | MG34-23 effector | protein | unknown | uncultivated organism | |
| MG34 effectors | 488 | MG34-24 effector | protein | unknown | uncultivated organism | |
| MG35 effectors | 489 | MG35-422 effector | protein | unknown | uncultivated organism | |
| MG35 effectors | 490 | MG35-423 effector | protein | unknown | uncultivated organism | |
| MG35 effectors | 491 | MG35-424 effector | protein | unknown | uncultivated organism | |
| MG35 effectors | 492 | MG35-425 effector | protein | unknown | uncultivated organism | |
| MG35 effectors | 493 | MG35-426 effector | protein | unknown | uncultivated organism | |
| MG35 effectors | 494 | MG35-427 effector | protein | unknown | uncultivated organism | |
| MG35 effectors | 495 | MG35-428 effector | protein | unknown | uncultivated organism | |
| MG35 effectors | 496 | MG35-429 effector | protein | unknown | uncultivated organism | |
| MG35 effectors | 497 | MG35-430 effector | protein | unknown | uncultivated organism | |
| MG35 effectors | 498 | MG35-431 effector | protein | unknown | uncultivated organism | |
| MG35 effectors | 499 | MG35-432 effector | protein | unknown | uncultivated organism | |
| MG35 effectors | 500 | MG35-433 effector | protein | unknown | uncultivated organism | |
| MG35 effectors | 501 | MG35-434 effector | protein | unknown | uncultivated organism | |
| MG35 effectors | 502 | MG35-435 effector | protein | unknown | uncultivated organism | |
| MG35 effectors | 503 | MG35-436 effector | protein | unknown | uncultivated organism | |
| MG35 effectors | 504 | MG35-437 effector | protein | unknown | uncultivated organism | |
| MG35 effectors | 505 | MG35-438 effector | protein | unknown | uncultivated organism | |
| MG35 effectors | 506 | MG35-439 effector | protein | unknown | uncultivated organism | |
| MG35 effectors | 507 | MG35-440 effector | protein | unknown | uncultivated organism | |

TABLE 8-continued

Listing of additional protein and nucleic acid sequences referred to herein not included in the sequence listing
I.

| Category | SEQ ID: | Description | Type | Organism | Other Information | Comments or Sequence |
|---|---|---|---|---|---|---|
| MG35 effectors | 508 | MG35-441 effector | protein | unknown | uncultivated organism | |
| MG35 effectors | 509 | MG35-442 effector | protein | unknown | uncultivated organism | |
| MG35 effectors | 510 | MG35-443 effector | protein | unknown | uncultivated organism | |
| MG35 effectors | 511 | MG35-444 effector | protein | unknown | uncultivated organism | |
| MG35 effectors | 512 | MG35-445 effector | protein | unknown | uncultivated organism | |
| MG35 effectors | 513 | MG35-446 effector | protein | unknown | uncultivated organism | |
| MG35 effectors | 514 | MG35-447 effector | protein | unknown | uncultivated organism | |
| MG35 effectors | 515 | MG35-448 effector | protein | unknown | uncultivated organism | |
| MG35 effectors | 516 | MG35-449 effector | protein | unknown | uncultivated organism | |
| MG35 effectors | 517 | MG35-450 effector | protein | unknown | uncultivated organism | |
| MG35 effectors | 518 | MG35-451 effector | protein | unknown | uncultivated organism | |
| MG35 effectors | 519 | MG35-452 effector | protein | unknown | uncultivated organism | |
| MG35 effectors | 520 | MG35-453 effector | protein | unknown | uncultivated organism | |
| MG35 effectors | 521 | MG35-454 effector | protein | unknown | uncultivated organism | |
| MG35 effectors | 522 | MG35-455 effector | protein | unknown | uncultivated organism | |
| MG35 effectors | 523 | MG35-456 effector | protein | unknown | uncultivated organism | |
| MG35 effectors | 524 | MG35-457 effector | protein | unknown | uncultivated organism | |
| MG35 effectors | 525 | MG35-458 effector | protein | unknown | uncultivated organism | |
| MG35 effectors | 526 | MG35-459 effector | protein | unknown | uncultivated organism | |
| MG35 effectors | 527 | MG35-460 effector | protein | unknown | uncultivated organism | |
| MG35 effectors | 528 | MG35-461 effector | protein | unknown | uncultivated organism | |
| MG35 effectors | 529 | MG35-462 effector | protein | unknown | uncultivated organism | |
| MG35 effectors | 530 | MG35-463 effector | protein | unknown | uncultivated organism | |
| MG35 effectors | 531 | MG35-464 effector | protein | unknown | uncultivated organism | |
| MG35 effectors | 532 | MG35-465 effector | protein | unknown | uncultivated organism | |
| MG35 effectors | 533 | MG35-466 effector | protein | unknown | uncultivated organism | |
| MG35 effectors | 534 | MG35-467 effector | protein | unknown | uncultivated organism | |
| MG35 effectors | 535 | MG35-468 effector | protein | unknown | uncultivated organism | |
| MG35 effectors | 536 | MG35-469 effector | protein | unknown | uncultivated organism | |
| MG35 effectors | 537 | MG35-470 effector | protein | unknown | uncultivated organism | |
| MG35 effectors | 538 | MG35-471 effector | protein | unknown | uncultivated organism | |
| MG35 effectors | 539 | MG35-472 effector | protein | unknown | uncultivated organism | |
| MG35 effectors | 540 | MG35-473 effector | protein | unknown | uncultivated organism | |
| MG35 effectors | 541 | MG35-474 effector | protein | unknown | uncultivated organism | |
| MG35 effectors | 542 | MG35-475 effector | protein | unknown | uncultivated organism | |
| MG35 effectors | 543 | MG35-476 effector | protein | unknown | uncultivated organism | |
| MG35 effectors | 544 | MG35-477 effector | protein | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 effectors | 545 | MG35-478 effector | protein | unknown | uncultivated organism | |
| MG35 effectors | 546 | MG35-479 effector | protein | unknown | uncultivated organism | |
| MG35 effectors | 547 | MG35-480 effector | protein | unknown | uncultivated organism | |
| MG35 effectors | 548 | MG35-481 effector | protein | unknown | uncultivated organism | |
| MG35 effectors | 549 | MG35-482 effector | protein | unknown | uncultivated organism | |
| MG35 effectors | 550 | MG35-483 effector | protein | unknown | uncultivated organism | |
| MG35 effectors | 551 | MG35-484 effector | protein | unknown | uncultivated organism | |
| MG35 effectors | 552 | MG35-485 effector | protein | unknown | uncultivated organism | |
| MG35 effectors | 553 | MG35-486 effector | protein | unknown | uncultivated organism | |
| MG35 effectors | 554 | MG35-487 effector | protein | unknown | uncultivated organism | |
| MG35 effectors | 555 | MG35-488 effector | protein | unknown | uncultivated organism | |
| MG35 effectors | 556 | MG35-489 effector | protein | unknown | uncultivated organism | |
| MG35 effectors | 557 | MG35-490 effector | protein | unknown | uncultivated organism | |
| MG35 effectors | 558 | MG35-491 effector | protein | unknown | uncultivated organism | |
| MG35 effectors | 559 | MG35-492 effector | protein | unknown | uncultivated organism | |
| MG35 effectors | 560 | MG35-493 effector | protein | unknown | uncultivated organism | |
| MG35 effectors | 561 | MG35-494 effector | protein | unknown | uncultivated organism | |
| MG35 effectors | 562 | MG35-495 effector | protein | unknown | uncultivated organism | |
| MG35 effectors | 563 | MG35-496 effector | protein | unknown | uncultivated organism | |
| MG35 effectors | 564 | MG35-497 effector | protein | unknown | uncultivated organism | |
| MG35 effectors | 565 | MG35-498 effector | protein | unknown | uncultivated organism | |
| MG35 effectors | 566 | MG35-499 effector | protein | unknown | uncultivated organism | |
| MG35 effectors | 567 | MG35-500 effector | protein | unknown | uncultivated organism | |
| MG35 effectors | 568 | MG35-501 effector | protein | unknown | uncultivated organism | |
| MG35 effectors | 569 | MG35-502 effector | protein | unknown | uncultivated organism | |
| MG35 effectors | 570 | MG35-503 effector | protein | unknown | uncultivated organism | |
| MG35 effectors | 571 | MG35-504 effector | protein | unknown | uncultivated organism | |
| MG35 effectors | 572 | MG35-505 effector | protein | unknown | uncultivated organism | |
| MG35 effectors | 573 | MG35-506 effector | protein | unknown | uncultivated organism | |
| MG35 effectors | 574 | MG35-507 effector | protein | unknown | uncultivated organism | |
| MG35 effectors | 575 | MG35-508 effector | protein | unknown | uncultivated organism | |
| MG35 effectors | 576 | MG35-509 effector | protein | unknown | uncultivated organism | |
| MG35 effectors | 577 | MG35-510 effector | protein | unknown | uncultivated organism | |
| MG35 effectors | 578 | MG35-511 effector | protein | unknown | uncultivated organism | |
| MG35 effectors | 579 | MG35-512 effector | protein | unknown | uncultivated organism | |
| MG35 effectors | 580 | MG35-513 effector | protein | unknown | uncultivated organism | |
| MG102 effectors | 581 | MG102-1 effector | protein | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG102 effectors | 582 | MG102-2 effector | protein | unknown | uncultivated organism | |
| MG102 effectors | 583 | MG102-3 effector | protein | unknown | uncultivated organism | |
| MG102 effectors | 584 | MG102-4 effector | protein | unknown | uncultivated organism | |
| MG102 effectors | 585 | MG102-5 effector | protein | unknown | uncultivated organism | |
| MG102 effectors | 586 | MG102-6 effector | protein | unknown | uncultivated organism | |
| MG102 effectors | 587 | MG102-7 effector | protein | unknown | uncultivated organism | |
| MG102 effectors | 588 | MG102-8 effector | protein | unknown | uncultivated organism | |
| MG102 effectors | 589 | MG102-9 effector | protein | unknown | uncultivated organism | |
| MG102 effectors | 590 | MG102-10 effector | protein | unknown | uncultivated organism | |
| MG102 effectors | 591 | MG102-11 effector | protein | unknown | uncultivated organism | |
| MG102 effectors | 592 | MG102-12 effector | protein | unknown | uncultivated organism | |
| MG102 effectors | 593 | MG102-13 effector | protein | unknown | uncultivated organism | |
| MG102 effectors | 594 | MG102-14 effector | protein | unknown | uncultivated organism | |
| MG102 effectors | 595 | MG102-15 effector | protein | unknown | uncultivated organism | |
| MG102 effectors | 596 | MG102-16 effector | protein | unknown | uncultivated organism | |
| MG102 effectors | 597 | MG102-17 effector | protein | unknown | uncultivated organism | |
| MG102 effectors | 598 | MG102-18 effector | protein | unknown | uncultivated organism | |
| MG102 effectors | 599 | MG102-19 effector | protein | unknown | uncultivated organism | |
| MG102 effectors | 600 | MG102-20 effector | protein | unknown | uncultivated organism | |
| MG102 effectors | 601 | MG102-21 effector | protein | unknown | uncultivated organism | |
| MG102 effectors | 602 | MG102-22 effector | protein | unknown | uncultivated organism | |
| MG102 effectors | 603 | MG102-23 effector | protein | unknown | uncultivated organism | |
| MG102 effectors | 604 | MG102-24 effector | protein | unknown | uncultivated organism | |
| MG102 effectors | 605 | MG102-25 effector | protein | unknown | uncultivated organism | |
| MG102 effectors | 606 | MG102-27 effector | protein | unknown | uncultivated organism | |
| MG102 effectors | 607 | MG102-28 effector | protein | unknown | uncultivated organism | |
| MG102 effectors | 608 | MG102-29 effector | protein | unknown | uncultivated organism | |
| MG102 effectors | 609 | MG102-30 effector | protein | unknown | uncultivated organism | |
| MG102 effectors | 610 | MG102-31 effector | protein | unknown | uncultivated organism | |
| MG102 effectors | 611 | MG102-32 effector | protein | unknown | uncultivated organism | |
| MG102 effectors | 612 | MG102-33 effector | protein | unknown | uncultivated organism | |
| MG34 sgRNA | 613 | MG34-1 active effectors sgRNA 1 | nucleotide | unknown | uncultivated organism | |
| MG34 sgRNA | 614 | MG34-1 active effectors sgRNA 2 | nucleotide | unknown | uncultivated organism | |
| MG34 sgRNA | 615 | MG34-9 active effectors sgRNA 1 | nucleotide | unknown | uncultivated organism | |
| MG34 sgRNA | 616 | MG34-16 active effectors sgRNA 1 | nucleotide | unknown | uncultivated organism | |
| MG35 effectors | 617 | MG35-514 effector | protein | unknown | uncultivated organism | |
| MG35 effectors | 618 | MG35-515 effector | protein | unknown | uncultivated organism | |

TABLE 8-continued

Listing of additional protein and nucleic acid sequences referred to herein not included in the sequence listing

| Category | SEQ ID: | Description | Type | Organism | Other Information | Comments or Sequence |
|---|---|---|---|---|---|---|
| MG35 effectors | 619 | MG35-516 effector | protein | unknown | uncultivated organism | |
| MG35 effectors | 620 | MG35-517 effector | protein | unknown | uncultivated organism | |
| MG35 effectors | 621 | MG35-518 effector | protein | unknown | uncultivated organism | |
| MG35 effectors | 622 | MG35-519 effector | protein | unknown | uncultivated organism | |
| MG35 effectors | 623 | MG35-520 effector | protein | unknown | uncultivated organism | |
| MG35 effectors | 624 | MG35-521 effector | protein | unknown | uncultivated organism | |
| MG35 effectors | 625 | MG35-522 effector | protein | unknown | uncultivated organism | |
| MG35 effectors | 626 | MG35-523 effector | protein | unknown | uncultivated organism | |
| MG35 effectors | 627 | MG35-524 effector | protein | unknown | uncultivated organism | |
| MG35 effectors | 628 | MG35-525 effector | protein | unknown | uncultivated organism | |
| MG35 effectors | 629 | MG35-526 effector | protein | unknown | uncultivated organism | |
| MG35 effectors | 630 | MG35-527 effector | protein | unknown | uncultivated organism | |
| MG35 effectors | 631 | MG35-528 effector | protein | unknown | uncultivated organism | |
| MG35 effectors | 632 | MG35-529 effector | protein | unknown | uncultivated organism | |
| MG35 effectors | 633 | MG35-530 effector | protein | unknown | uncultivated organism | |
| MG35 effectors | 634 | MG35-531 effector | protein | unknown | uncultivated organism | |
| MG35 effectors | 635 | MG35-532 effector | protein | unknown | uncultivated organism | |
| MG35 effectors | 636 | MG35-533 effector | protein | unknown | uncultivated organism | |
| MG35 effectors | 637 | MG35-534 effector | protein | unknown | uncultivated organism | |
| MG35 effectors | 638 | MG35-535 effector | protein | unknown | uncultivated organism | |
| MG35 effectors | 639 | MG35-536 effector | protein | unknown | uncultivated organism | |
| MG35 effectors | 640 | MG35-537 effector | protein | unknown | uncultivated organism | |
| MG35 effectors | 641 | MG35-538 effector | protein | unknown | uncultivated organism | |
| MG35 effectors | 642 | MG35-539 effector | protein | unknown | uncultivated organism | |
| MG35 effectors | 643 | MG35-540 effector | protein | unknown | uncultivated organism | |
| MG35 effectors | 644 | MG35-541 effector | protein | unknown | uncultivated organism | |
| MG35 effectors | 645 | MG35-542 effector | protein | unknown | uncultivated organism | |
| MG35 effectors | 646 | MG35-543 effector | protein | unknown | uncultivated organism | |
| MG35 effectors | 647 | MG35-544 effector | protein | unknown | uncultivated organism | |
| MG35 effectors | 648 | MG35-545 effector | protein | unknown | uncultivated organism | |
| MG35 effectors | 649 | MG35-546 effector | protein | unknown | uncultivated organism | |
| MG35 effectors | 650 | MG35-547 effector | protein | unknown | uncultivated organism | |
| MG35 effectors | 651 | MG35-548 effector | protein | unknown | uncultivated organism | |
| MG35 effectors | 652 | MG35-549 effector | protein | unknown | uncultivated organism | |
| MG35 effectors | 653 | MG35-550 effector | protein | unknown | uncultivated organism | |
| MG35 effectors | 654 | MG35-551 effector | protein | unknown | uncultivated organism | |
| MG35 effectors | 655 | MG35-552 effector | protein | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 effectors | 656 | MG35-553 effector | protein | unknown | uncultivated organism | |
| MG35 effectors | 657 | MG35-554 effector | protein | unknown | uncultivated organism | |
| MG35 effectors | 658 | MG35-555 effector | protein | unknown | uncultivated organism | |
| MG35 effectors | 659 | MG35-556 effector | protein | unknown | uncultivated organism | |
| MG35 effectors | 660 | MG35-557 effector | protein | unknown | uncultivated organism | |
| MG35 effectors | 661 | MG35-558 effector | protein | unknown | uncultivated organism | |
| MG35 effectors | 662 | MG35-559 effector | protein | unknown | uncultivated organism | |
| MG35 effectors | 663 | MG35-560 effector | protein | unknown | uncultivated organism | |
| MG35 effectors | 664 | MG35-561 effector | protein | unknown | uncultivated organism | |
| MG35 effectors | 665 | MG35-562 effector | protein | unknown | uncultivated organism | |
| MG35 effectors | 666 | MG35-563 effector | protein | unknown | uncultivated organism | |
| MG35 effectors | 667 | MG35-564 effector | protein | unknown | uncultivated organism | |
| MG35 effectors | 668 | MG35-565 effector | protein | unknown | uncultivated organism | |
| MG33 tracrRNA | 669 | MG33-2 tracrRNA 1 | nucleotide | artificial sequence | MG33 tracrRNA | |
| MG33 tracrRNA | 670 | MG33-2 tracrRNA 2 | nucleotide | artificial sequence | MG33 tracrRNA | |
| MG33 tracrRNA | 671 | MG33-3 tracrRNA 1 | nucleotide | artificial sequence | MG33 tracrRNA | |
| MG102 tracrRNA | 672 | MG102-1 tracrRNA 1 | nucleotide | artificial sequence | MG102 tracrRNA | |
| MG102 tracrRNA | 673 | MG102-2 tracrRNA 1 | nucleotide | artificial sequence | MG102 tracrRNA | |
| MG35 effectors | 674 | MG35-566 effector | protein | unknown | uncultivated organism | |
| MG35 effectors | 675 | MG35-567 effector | protein | unknown | uncultivated organism | |
| MG35 predicted CRISPR repeat | 676 | MG35-420 predicted CRISPR repeat | nucleotide | unknown | uncultivated organism | |
| MG35 putative single guide RNAs | 677 | MG35-1 effector putative single guide RNA 1 | nucleotide | unknown | uncultivated organism | |
| MG35 putative single guide RNAs | 678 | MG35-1 effector putative single guide RNA 2 | nucleotide | unknown | uncultivated organism | |
| MG35 putative single guide RNAs | 679 | MG35-2 effector putative single guide RNA 1 | nucleotide | unknown | uncultivated organism | |
| MG35 putative single guide RNAs | 680 | MG35-3 effector putative single guide RNA 1 | nucleotide | unknown | uncultivated organism | |
| MG35 putative single guide RNAs | 681 | MG35-3 effector putative single guide RNA 2 | nucleotide | unknown | uncultivated organism | |
| MG35 putative single guide RNAs | 682 | MG35-419 effector putative single guide RNA 1 | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNAs | 683 | MG35-419 effector putative single guide RNA 2 | nucleotide | unknown | uncultivated organism | |
| MG35 putative single guide RNAs | 684 | MG35-420 effector putative single guide RNA 1 | nucleotide | unknown | uncultivated organism | |
| MG35 putative single guide RNAs | 685 | MG35-421 effector putative single guide RNA 1 | nucleotide | unknown | uncultivated organism | |
| MG35 putative single guide RNAs | 686 | MG35-102 effector putative single guide RNA 1 | nucleotide | unknown | uncultivated organism | |
| MG35 putative single guide RNA encoding sequences | 687 | MG35-1, MG35-90 effectors putative single guide RNA encoding sequence | nucleotide | unknown | uncultivated organism | |
| MG35 putative single guide RNA encoding sequences | 688 | MG35-2, MG35-50, MG35-51 effectors putative single guide RNA encoding sequence | nucleotide | unknown | uncultivated organism | |
| MG35 putative single guide RNA encoding sequences | 689 | MG35-3, MG35-85 effectors putative single guide RNA encoding sequence | nucleotide | unknown | uncultivated organism | |
| MG35 putative single guide RNA encoding sequences | 690 | MG35-32 effector putative single guide RNA encoding sequence | nucleotide | unknown | uncultivated organism | |
| MG35 putative single guide RNA encoding sequences | 691 | MG35-36, MG35-152, MG35-153, MG35-154, MG35-155 effectors putative single guide RNA encoding sequence | nucleotide | unknown | uncultivated organism | |
| MG35 putative single guide RNA encoding sequences | 692 | MG35-37 effector putative single guide RNA encoding sequence | nucleotide | unknown | uncultivated organism | |
| MG35 putative single guide RNA encoding sequences | 693 | MG35-38 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 694 | MG35-40, MG35-42, MG35-43 effectors putative single guide RNA encoding sequence | nucleotide | unknown | uncultivated organism | |
| MG35 putative single guide RNA encoding sequences | 695 | MG35-41 effector putative single guide RNA encoding sequence | nucleotide | unknown | uncultivated organism | |
| MG35 putative single guide RNA encoding sequences | 696 | MG35-44 effector putative single guide RNA encoding sequence | nucleotide | unknown | uncultivated organism | |
| MG35 putative single guide RNA encoding sequences | 697 | MG35-45, MG35-39, MG35-116, MG35-219 effectors putative single guide RNA encoding sequence | nucleotide | unknown | uncultivated organism | |
| MG35 putative single guide RNA encoding sequences | 698 | MG35-46 effector putative single guide RNA encoding sequence | nucleotide | unknown | uncultivated organism | |
| MG35 putative single guide RNA encoding sequences | 699 | MG35-48 effector putative single guide RNA encoding sequence | nucleotide | unknown | uncultivated organism | |
| MG35 putative single guide RNA encoding sequences | 700 | MG35-49 effector putative single guide RNA encoding sequence | nucleotide | unknown | uncultivated organism | |
| MG35 putative single guide RNA encoding sequences | 701 | MG35-52 effector putative single guide RNA encoding sequence | nucleotide | unknown | uncultivated organism | |
| MG35 putative single guide RNA encoding sequences | 702 | MG35-53, MG35-54 effectors putative single guide RNA encoding sequence | nucleotide | unknown | uncultivated organism | |
| MG35 putative single guide RNA encoding sequences | 703 | MG35-55 effector putative single guide RNA encoding sequence | nucleotide | unknown | uncultivated organism | |
| MG35 putative single guide | 704 | MG35-56, MG35-287 effectors putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| RNA encoding sequences MG35 putative single guide RNA encoding sequences | 705 | MG35-57 effector putative single guide RNA encoding sequence | nucleotide | unknown | uncultivated organism | |
| MG35 putative single guide RNA encoding sequences | 706 | MG35-58, MG35-59 effectors putative single guide RNA encoding sequence | nucleotide | unknown | uncultivated organism | |
| MG35 putative single guide RNA encoding sequences | 707 | MG35-60 effector putative single guide RNA encoding sequence | nucleotide | unknown | uncultivated organism | |
| MG35 putative single guide RNA encoding sequences | 708 | MG35-62 effector putative single guide RNA encoding sequence | nucleotide | unknown | uncultivated organism | |
| MG35 putative single guide RNA encoding sequences | 709 | MG35-63 effector putative single guide RNA encoding sequence | nucleotide | unknown | uncultivated organism | |
| MG35 putative single guide RNA encoding sequences | 710 | MG35-65 effector putative single guide RNA encoding sequence | nucleotide | unknown | uncultivated organism | |
| MG35 putative single guide RNA encoding sequences | 711 | MG35-66 effector putative single guide RNA encoding sequence | nucleotide | unknown | uncultivated organism | |
| MG35 putative single guide RNA encoding sequences | 712 | MG35-67, MG35-71 effectors putative single guide RNA encoding sequence | nucleotide | unknown | uncultivated organism | |
| MG35 putative single guide RNA encoding sequences | 713 | MG35-68, MG35-64, MG35-69, MG35-70, MG35-75 effectors putative single guide RNA encoding sequence | nucleotide | unknown | uncultivated organism | |
| MG35 putative single guide RNA encoding sequences | 714 | MG35-72 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 715 | MG35-73 effector putative single guide RNA encoding sequence | nucleotide | unknown | uncultivated organism | |
| MG35 putative single guide RNA encoding sequences | 716 | MG35-74 effector putative single guide RNA encoding sequence | nucleotide | unknown | uncultivated organism | |
| MG35 putative single guide RNA encoding sequences | 717 | MG35-77 effector putative single guide RNA encoding sequence | nucleotide | unknown | uncultivated organism | |
| MG35 putative single guide RNA encoding sequences | 718 | MG35-78 effector putative single guide RNA encoding sequence | nucleotide | unknown | uncultivated organism | |
| MG35 putative single guide RNA encoding sequences | 719 | MG35-79, MG35-97, MG35-98 effectors putative single guide RNA encoding sequence | nucleotide | unknown | uncultivated organism | |
| MG35 putative single guide RNA encoding sequences | 720 | MG35-80, MG35-81 effectors putative single guide RNA encoding sequence | nucleotide | unknown | uncultivated organism | |
| MG35 putative single guide RNA encoding sequences | 721 | MG35-82, MG35-95, MG35-96 effectors putative single guide RNA encoding sequence | nucleotide | unknown | uncultivated organism | |
| MG35 putative single guide RNA encoding sequences | 722 | MG35-86 effector putative single guide RNA encoding sequence | nucleotide | unknown | uncultivated organism | |
| MG35 putative single guide RNA encoding sequences | 723 | MG35-87, MG35-88, MG35-89 effectors putative single guide RNA encoding sequence | nucleotide | unknown | uncultivated organism | |
| MG35 putative single guide RNA encoding sequences | 724 | MG35-91, MG35-92 effectors putative single guide RNA encoding sequence | nucleotide | unknown | uncultivated organism | |
| MG35 putative single guide | 725 | MG35-93, MG35-94 effectors putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 726 | MG35-99 effector putative single guide RNA encoding sequence | nucleotide | unknown | uncultivated organism | |
| MG35 putative single guide RNA encoding sequences | 727 | MG35-101 effector putative single guide RNA encoding sequence | nucleotide | unknown | uncultivated organism | |
| MG35 putative single guide RNA encoding sequences | 728 | MG35-102 effector putative single guide RNA encoding sequence | nucleotide | unknown | uncultivated organism | |
| MG35 putative single guide RNA encoding sequences | 729 | MG35-103, MG35-104 effectors putative single guide RNA encoding sequence | nucleotide | unknown | uncultivated organism | |
| MG35 putative single guide RNA encoding sequences | 730 | MG35-105 effector putative single guide RNA encoding sequence | nucleotide | unknown | uncultivated organism | |
| MG35 putative single guide RNA encoding sequences | 731 | MG35-106 effector putative single guide RNA encoding sequence | nucleotide | unknown | uncultivated organism | |
| MG35 putative single guide RNA encoding sequences | 732 | MG35-107 effector putative single guide RNA encoding sequence | nucleotide | unknown | uncultivated organism | |
| MG35 putative single guide RNA encoding sequences | 733 | MG35-108 effector putative single guide RNA encoding sequence | nucleotide | unknown | uncultivated organism | |
| MG35 putative single guide RNA encoding sequences | 734 | MG35-109 effector putative single guide RNA encoding sequence | nucleotide | unknown | uncultivated organism | |
| MG35 putative single guide RNA encoding sequences | 735 | MG35-110, MG35-112 effectors putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 736 | MG35-111 effector putative single guide RNA encoding sequence | nucleotide | unknown | uncultivated organism | |
| MG35 putative single guide RNA encoding sequences | 737 | MG35-113 effector putative single guide RNA encoding sequence | nucleotide | unknown | uncultivated organism | |
| MG35 putative single guide RNA encoding sequences | 738 | MG35-114 effector putative single guide RNA encoding sequence | nucleotide | unknown | uncultivated organism | |
| MG35 putative single guide RNA encoding sequences | 739 | MG35-115 effector putative single guide RNA encoding sequence | nucleotide | unknown | uncultivated organism | |
| MG35 putative single guide RNA encoding sequences | 740 | MG35-116 effector putative single guide RNA encoding sequence | nucleotide | unknown | uncultivated organism | |
| MG35 putative single guide RNA encoding sequences | 741 | MG35-117, MG35-118, MG35-119 effectors putative single guide RNA encoding sequence | nucleotide | unknown | uncultivated organism | |
| MG35 putative single guide RNA encoding sequences | 742 | MG35-120 effector putative single guide RNA encoding sequence | nucleotide | unknown | uncultivated organism | |
| MG35 putative single guide RNA encoding sequences | 743 | MG35-121 effector putative single guide RNA encoding sequence | nucleotide | unknown | uncultivated organism | |
| MG35 putative single guide RNA encoding sequences | 744 | MG35-122 effector putative single guide RNA encoding sequence | nucleotide | unknown | uncultivated organism | |
| MG35 putative single guide RNA encoding sequences | 745 | MG35-123, MG35-124 effectors putative single guide RNA encoding sequence | nucleotide | unknown | uncultivated organism | |
| MG35 putative single guide | 746 | MG35-125 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| RNA encoding sequences MG35 putative single guide RNA encoding sequences | 747 | MG35-126, MG35-377 effectors putative single guide RNA encoding sequence | nucleotide | unknown | uncultivated organism | |
| MG35 putative single guide RNA encoding sequences | 748 | MG35-127 effector putative single guide RNA encoding sequence | nucleotide | unknown | uncultivated organism | |
| MG35 putative single guide RNA encoding sequences | 749 | MG35-128 effector putative single guide RNA encoding sequence | nucleotide | unknown | uncultivated organism | |
| MG35 putative single guide RNA encoding sequences | 750 | MG35-129 effector putative single guide RNA encoding sequence | nucleotide | unknown | uncultivated organism | |
| MG35 putative single guide RNA encoding sequences | 751 | MG35-130 effector putative single guide RNA encoding sequence | nucleotide | unknown | uncultivated organism | |
| MG35 putative single guide RNA encoding sequences | 752 | MG35-131 effector putative single guide RNA encoding sequence | nucleotide | unknown | uncultivated organism | |
| MG35 putative single guide RNA encoding sequences | 753 | MG35-147 effector putative single guide RNA encoding sequence | nucleotide | unknown | uncultivated organism | |
| MG35 putative single guide RNA encoding sequences | 754 | MG35-148 effector putative single guide RNA encoding sequence | nucleotide | unknown | uncultivated organism | |
| MG35 putative single guide RNA encoding sequences | 755 | MG35-149 effector putative single guide RNA encoding sequence | nucleotide | unknown | uncultivated organism | |
| MG35 putative single guide RNA encoding sequences | 756 | MG35-150 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 757 | MG35-151 effector putative single guide RNA encoding sequence | nucleotide | unknown | uncultivated organism | |
| MG35 putative single guide RNA encoding sequences | 758 | MG35-152 effector putative single guide RNA encoding sequence | nucleotide | unknown | uncultivated organism | |
| MG35 putative single guide RNA encoding sequences | 759 | MG35-153 effector putative single guide RNA encoding sequence | nucleotide | unknown | uncultivated organism | |
| MG35 putative single guide RNA encoding sequences | 760 | MG35-156, MG35-161 effectors putative single guide RNA encoding sequence | nucleotide | unknown | uncultivated organism | |
| MG35 putative single guide RNA encoding sequences | 761 | MG35-157 effector putative single guide RNA encoding sequence | nucleotide | unknown | uncultivated organism | |
| MG35 putative single guide RNA encoding sequences | 762 | MG35-159, MG35-158 effectors putative single guide RNA encoding sequence | nucleotide | unknown | uncultivated organism | |
| MG35 putative single guide RNA encoding sequences | 763 | MG35-160 effector putative single guide RNA encoding sequence | nucleotide | unknown | uncultivated organism | |
| MG35 putative single guide RNA encoding sequences | 764 | MG35-165, MG35-166 effectors putative single guide RNA encoding sequence | nucleotide | unknown | uncultivated organism | |
| MG35 putative single guide RNA encoding sequences | 765 | MG35-171 effector putative single guide RNA encoding sequence | nucleotide | unknown | uncultivated organism | |
| MG35 putative single guide RNA encoding sequences | 766 | MG35-214 effector putative single guide RNA encoding sequence | nucleotide | unknown | uncultivated organism | |
| MG35 putative single guide | 767 | MG35-217 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 768 | MG35-218 effector putative single guide RNA encoding sequence | nucleotide | unknown | uncultivated organism | |
| MG35 putative single guide RNA encoding sequences | 769 | MG35-220 effector putative single guide RNA encoding sequence | nucleotide | unknown | uncultivated organism | |
| MG35 putative single guide RNA encoding sequences | 770 | MG35-221, MG35-222, MG35-351, MG35-352, MG35-353 effectors putative single guide RNA encoding sequence | nucleotide | unknown | uncultivated organism | |
| MG35 putative single guide RNA encoding sequences | 771 | MG35-223 effector putative single guide RNA encoding sequence | nucleotide | unknown | uncultivated organism | |
| MG35 putative single guide RNA encoding sequences | 772 | MG35-224 effector putative single guide RNA encoding sequence | nucleotide | unknown | uncultivated organism | |
| MG35 putative single guide RNA encoding sequences | 773 | MG35-225 effector putative single guide RNA encoding sequence | nucleotide | unknown | uncultivated organism | |
| MG35 putative single guide RNA encoding sequences | 774 | MG35-226 effector putative single guide RNA encoding sequence | nucleotide | unknown | uncultivated organism | |
| MG35 putative single guide RNA encoding sequences | 775 | MG35-227 effector putative single guide RNA encoding sequence | nucleotide | unknown | uncultivated organism | |
| MG35 putative single guide RNA encoding sequences | 776 | MG35-228 effector putative single guide RNA encoding sequence | nucleotide | unknown | uncultivated organism | |
| MG35 putative single guide RNA encoding sequences | 777 | MG35-229 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 778 | MG35-230 effector putative single guide RNA encoding sequence | nucleotide | unknown | uncultivated organism | |
| MG35 putative single guide RNA encoding sequences | 779 | MG35-231 effector putative single guide RNA encoding sequence | nucleotide | unknown | uncultivated organism | |
| MG35 putative single guide RNA encoding sequences | 780 | MG35-232 effector putative single guide RNA encoding sequence | nucleotide | unknown | uncultivated organism | |
| MG35 putative single guide RNA encoding sequences | 781 | MG35-233 effector putative single guide RNA encoding sequence | nucleotide | unknown | uncultivated organism | |
| MG35 putative single guide RNA encoding sequences | 782 | MG35-235 effector putative single guide RNA encoding sequence | nucleotide | unknown | uncultivated organism | |
| MG35 putative single guide RNA encoding sequences | 783 | MG35-236 effector putative single guide RNA encoding sequence | nucleotide | unknown | uncultivated organism | |
| MG35 putative single guide RNA encoding sequences | 784 | MG35-238, MG35-237 effectors putative single guide RNA encoding sequence | nucleotide | unknown | uncultivated organism | |
| MG35 putative single guide RNA encoding sequences | 785 | MG35-239, MG35-240, MG35-241 effectors putative single guide RNA encoding sequence | nucleotide | unknown | uncultivated organism | |
| MG35 putative single guide RNA encoding sequences | 786 | MG35-242 effector putative single guide RNA encoding sequence | nucleotide | unknown | uncultivated organism | |
| MG35 putative single guide RNA encoding sequences | 787 | MG35-243 effector putative single guide RNA encoding sequence | nucleotide | unknown | uncultivated organism | |
| MG35 putative single guide | 788 | MG35-244 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| RNA encoding sequences MG35 putative single guide RNA encoding sequences | 789 | MG35-245 effector putative single guide RNA encoding sequence | nucleotide | unknown | uncultivated organism | |
| MG35 putative single guide RNA encoding sequences | 790 | MG35-246 effector putative single guide RNA encoding sequence | nucleotide | unknown | uncultivated organism | |
| MG35 putative single guide RNA encoding sequences | 791 | MG35-247 effector putative single guide RNA encoding sequence | nucleotide | unknown | uncultivated organism | |
| MG35 putative single guide RNA encoding sequences | 792 | MG35-248 effector putative single guide RNA encoding sequence | nucleotide | unknown | uncultivated organism | |
| MG35 putative single guide RNA encoding sequences | 793 | MG35-249 effector putative single guide RNA encoding sequence | nucleotide | unknown | uncultivated organism | |
| MG35 putative single guide RNA encoding sequences | 794 | MG35-250, MG35-251 effectors putative single guide RNA encoding sequence | nucleotide | unknown | uncultivated organism | |
| MG35 putative single guide RNA encoding sequences | 795 | MG35-252 effector putative single guide RNA encoding sequence | nucleotide | unknown | uncultivated organism | |
| MG35 putative single guide RNA encoding sequences | 796 | MG35-253 effector putative single guide RNA encoding sequence | nucleotide | unknown | uncultivated organism | |
| MG35 putative single guide RNA encoding sequences | 797 | MG35-255 effector putative single guide RNA encoding sequence | nucleotide | unknown | uncultivated organism | |
| MG35 putative single guide RNA encoding sequences | 798 | MG35-256 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 799 | MG35-257 effector putative single guide RNA encoding sequence | nucleotide | unknown | uncultivated organism | |
| MG35 putative single guide RNA encoding sequences | 800 | MG35-258 effector putative single guide RNA encoding sequence | nucleotide | unknown | uncultivated organism | |
| MG35 putative single guide RNA encoding sequences | 801 | MG35-259 effector putative single guide RNA encoding sequence | nucleotide | unknown | uncultivated organism | |
| MG35 putative single guide RNA encoding sequences | 802 | MG35-260 effector putative single guide RNA encoding sequence | nucleotide | unknown | uncultivated organism | |
| MG35 putative single guide RNA encoding sequences | 803 | MG35-262, MG35-263 effectors putative single guide RNA encoding sequence | nucleotide | unknown | uncultivated organism | |
| MG35 putative single guide RNA encoding sequences | 804 | MG35-266, MG35-270 effectors putative single guide RNA encoding sequence | nucleotide | unknown | uncultivated organism | |
| MG35 putative single guide RNA encoding sequences | 805 | MG35-267 effector putative single guide RNA encoding sequence | nucleotide | unknown | uncultivated organism | |
| MG35 putative single guide RNA encoding sequences | 806 | MG35-268 effector putative single guide RNA encoding sequence | nucleotide | unknown | uncultivated organism | |
| MG35 putative single guide RNA encoding sequences | 807 | MG35-269, MG35-264, MG35-265 effectors putative single guide RNA encoding sequence | nucleotide | unknown | uncultivated organism | |
| MG35 putative single guide RNA encoding sequences | 808 | MG35-271 effector putative single guide RNA encoding sequence | nucleotide | unknown | uncultivated organism | |
| MG35 putative single guide | 809 | MG35-272 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 810 | MG35-273 effector putative single guide RNA encoding sequence | nucleotide | unknown | uncultivated organism | |
| MG35 putative single guide RNA encoding sequences | 811 | MG35-274 effector putative single guide RNA encoding sequence | nucleotide | unknown | uncultivated organism | |
| MG35 putative single guide RNA encoding sequences | 812 | MG35-275 effector putative single guide RNA encoding sequence | nucleotide | unknown | uncultivated organism | |
| MG35 putative single guide RNA encoding sequences | 813 | MG35-276 effector putative single guide RNA encoding sequence | nucleotide | unknown | uncultivated organism | |
| MG35 putative single guide RNA encoding sequences | 814 | MG35-277 effector putative single guide RNA encoding sequence | nucleotide | unknown | uncultivated organism | |
| MG35 putative single guide RNA encoding sequences | 815 | MG35-278 effector putative single guide RNA encoding sequence | nucleotide | unknown | uncultivated organism | |
| MG35 putative single guide RNA encoding sequences | 816 | MG35-279 effector putative single guide RNA encoding sequence | nucleotide | unknown | uncultivated organism | |
| MG35 putative single guide RNA encoding sequences | 817 | MG35-280 effector putative single guide RNA encoding sequence | nucleotide | unknown | uncultivated organism | |
| MG35 putative single guide RNA encoding sequences | 818 | MG35-281 effector putative single guide RNA encoding sequence | nucleotide | unknown | uncultivated organism | |
| MG35 putative single guide RNA encoding sequences | 819 | MG35-282, MG35-283 effectors putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 820 | MG35-284 effector putative single guide RNA encoding sequence | nucleotide | unknown | uncultivated organism | |
| MG35 putative single guide RNA encoding sequences | 821 | MG35-285 effector putative single guide RNA encoding sequence | nucleotide | unknown | uncultivated organism | |
| MG35 putative single guide RNA encoding sequences | 822 | MG35-286 effector putative single guide RNA encoding sequence | nucleotide | unknown | uncultivated organism | |
| MG35 putative single guide RNA encoding sequences | 823 | MG35-292, MG35-293 effectors putative single guide RNA encoding sequence | nucleotide | unknown | uncultivated organism | |
| MG35 putative single guide RNA encoding sequences | 824 | MG35-296 effector putative single guide RNA encoding sequence | nucleotide | unknown | uncultivated organism | |
| MG35 putative single guide RNA encoding sequences | 825 | MG35-298, MG35-299 effectors putative single guide RNA encoding sequence | nucleotide | unknown | uncultivated organism | |
| MG35 putative single guide RNA encoding sequences | 826 | MG35-300 effector putative single guide RNA encoding sequence | nucleotide | unknown | uncultivated organism | |
| MG35 putative single guide RNA encoding sequences | 827 | MG35-302 effector putative single guide RNA encoding sequence | nucleotide | unknown | uncultivated organism | |
| MG35 putative single guide RNA encoding sequences | 828 | MG35-303 effector putative single guide RNA encoding sequence | nucleotide | unknown | uncultivated organism | |
| MG35 putative single guide RNA encoding sequences | 829 | MG35-305 effector putative single guide RNA encoding sequence | nucleotide | unknown | uncultivated organism | |
| MG35 putative single guide | 830 | MG35-307 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| RNA encoding sequences MG35 putative single guide RNA encoding sequences | 831 | MG35-308 effector putative single guide RNA encoding sequence | nucleotide | unknown | uncultivated organism | |
| MG35 putative single guide RNA encoding sequences | 832 | MG35-309 effector putative single guide RNA encoding sequence | nucleotide | unknown | uncultivated organism | |
| MG35 putative single guide RNA encoding sequences | 833 | MG35-310 effector putative single guide RNA encoding sequence | nucleotide | unknown | uncultivated organism | |
| MG35 putative single guide RNA encoding sequences | 834 | MG35-311 effector putative single guide RNA encoding sequence | nucleotide | unknown | uncultivated organism | |
| MG35 putative single guide RNA encoding sequences | 835 | MG35-312 effector putative single guide RNA encoding sequence | nucleotide | unknown | uncultivated organism | |
| MG35 putative single guide RNA encoding sequences | 836 | MG35-313 effector putative single guide RNA encoding sequence | nucleotide | unknown | uncultivated organism | |
| MG35 putative single guide RNA encoding sequences | 837 | MG35-314, MG35-261 effectors putative single guide RNA encoding sequence | nucleotide | unknown | uncultivated organism | |
| MG35 putative single guide RNA encoding sequences | 838 | MG35-315 effector putative single guide RNA encoding sequence | nucleotide | unknown | uncultivated organism | |
| MG35 putative single guide RNA encoding sequences | 839 | MG35-316 effector putative single guide RNA encoding sequence | nucleotide | unknown | uncultivated organism | |
| MG35 putative single guide RNA encoding sequences | 840 | MG35-317 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 841 | MG35-318 effector putative single guide RNA encoding sequence | nucleotide | unknown | uncultivated organism | |
| MG35 putative single guide RNA encoding sequences | 842 | MG35-319 effector putative single guide RNA encoding sequence | nucleotide | unknown | uncultivated organism | |
| MG35 putative single guide RNA encoding sequences | 843 | MG35-321 effector putative single guide RNA encoding sequence | nucleotide | unknown | uncultivated organism | |
| MG35 putative single guide RNA encoding sequences | 844 | MG35-322 effector putative single guide RNA encoding sequence | nucleotide | unknown | uncultivated organism | |
| MG35 putative single guide RNA encoding sequences | 845 | MG35-325 effector putative single guide RNA encoding sequence | nucleotide | unknown | uncultivated organism | |
| MG35 putative single guide RNA encoding sequences | 846 | MG35-326 effector putative single guide RNA encoding sequence | nucleotide | unknown | uncultivated organism | |
| MG35 putative single guide RNA encoding sequences | 847 | MG35-327 effector putative single guide RNA encoding sequence | nucleotide | unknown | uncultivated organism | |
| MG35 putative single guide RNA encoding sequences | 848 | MG35-328 effector putative single guide RNA encoding sequence | nucleotide | unknown | uncultivated organism | |
| MG35 putative single guide RNA encoding sequences | 849 | MG35-329 effector putative single guide RNA encoding sequence | nucleotide | unknown | uncultivated organism | |
| MG35 putative single guide RNA encoding sequences | 850 | MG35-330 effector putative single guide RNA encoding sequence | nucleotide | unknown | uncultivated organism | |
| MG35 putative single guide | 851 | MG35-331 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| RNA encoding sequences MG35 putative single guide RNA encoding sequences | 852 | MG35-332, MG35-333, MG35-335 effectors putative single guide RNA encoding sequence | nucleotide | unknown | uncultivated organism | |
| MG35 putative single guide RNA encoding sequences | 853 | MG35-334 effector putative single guide RNA encoding sequence | nucleotide | unknown | uncultivated organism | |
| MG35 putative single guide RNA encoding sequences | 854 | MG35-336 effector putative single guide RNA encoding sequence | nucleotide | unknown | uncultivated organism | |
| MG35 putative single guide RNA encoding sequences | 855 | MG35-340 effector putative single guide RNA encoding sequence | nucleotide | unknown | uncultivated organism | |
| MG35 putative single guide RNA encoding sequences | 856 | MG35-341 effector putative single guide RNA encoding sequence | nucleotide | unknown | uncultivated organism | |
| MG35 putative single guide RNA encoding sequences | 857 | MG35-342 effector putative single guide RNA encoding sequence | nucleotide | unknown | uncultivated organism | |
| MG35 putative single guide RNA encoding sequences | 858 | MG35-343 effector putative single guide RNA encoding sequence | nucleotide | unknown | uncultivated organism | |
| MG35 putative single guide RNA encoding sequences | 859 | MG35-344, MG35-345 effectors putative single guide RNA encoding sequence | nucleotide | unknown | uncultivated organism | |
| MG35 putative single guide RNA encoding sequences | 860 | MG35-346, MG35-347 effectors putative single guide RNA encoding sequence | nucleotide | unknown | uncultivated organism | |
| MG35 putative single guide RNA encoding sequences | 861 | MG35-348 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 862 | MG35-349 effector putative single guide RNA encoding sequence | nucleotide | unknown | uncultivated organism | |
| MG35 putative single guide RNA encoding sequences | 863 | MG35-350 effector putative single guide RNA encoding sequence | nucleotide | unknown | uncultivated organism | |
| MG35 putative single guide RNA encoding sequences | 864 | MG35-354 effector putative single guide RNA encoding sequence | nucleotide | unknown | uncultivated organism | |
| MG35 putative single guide RNA encoding sequences | 865 | MG35-355, MG35-356 effectors putative single guide RNA encoding sequence | nucleotide | unknown | uncultivated organism | |
| MG35 putative single guide RNA encoding sequences | 866 | MG35-357 effector putative single guide RNA encoding sequence | nucleotide | unknown | uncultivated organism | |
| MG35 putative single guide RNA encoding sequences | 867 | MG35-358 effector putative single guide RNA encoding sequence | nucleotide | unknown | uncultivated organism | |
| MG35 putative single guide RNA encoding sequences | 868 | MG35-359 effector putative single guide RNA encoding sequence | nucleotide | unknown | uncultivated organism | |
| MG35 putative single guide RNA encoding sequences | 869 | MG35-360, MG35-361 effectors putative single guide RNA encoding sequence | nucleotide | unknown | uncultivated organism | |
| MG35 putative single guide RNA encoding sequences | 870 | MG35-362 effector putative single guide RNA encoding sequence | nucleotide | unknown | uncultivated organism | |
| MG35 putative single guide RNA encoding sequences | 871 | MG35-363 effector putative single guide RNA encoding sequence | nucleotide | unknown | uncultivated organism | |
| MG35 putative single guide | 872 | MG35-364 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| RNA encoding sequences MG35 putative single guide RNA encoding sequences | 873 | MG35-365 effector putative single guide RNA encoding sequence | nucleotide | unknown | uncultivated organism | |
| MG35 putative single guide RNA encoding sequences | 874 | MG35-366 effector putative single guide RNA encoding sequence | nucleotide | unknown | uncultivated organism | |
| MG35 putative single guide RNA encoding sequences | 875 | MG35-367 effector putative single guide RNA encoding sequence | nucleotide | unknown | uncultivated organism | |
| MG35 putative single guide RNA encoding sequences | 876 | MG35-368, MG35-369 effectors putative single guide RNA encoding sequence | nucleotide | unknown | uncultivated organism | |
| MG35 putative single guide RNA encoding sequences | 877 | MG35-370 effector putative single guide RNA encoding sequence | nucleotide | unknown | uncultivated organism | |
| MG35 putative single guide RNA encoding sequences | 878 | MG35-371 effector putative single guide RNA encoding sequence | nucleotide | unknown | uncultivated organism | |
| MG35 putative single guide RNA encoding sequences | 879 | MG35-372, MG35-373 effectors putative single guide RNA encoding sequence | nucleotide | unknown | uncultivated organism | |
| MG35 putative single guide RNA encoding sequences | 880 | MG35-374 effector putative single guide RNA encoding sequence | nucleotide | unknown | uncultivated organism | |
| MG35 putative single guide RNA encoding sequences | 881 | MG35-375 effector putative single guide RNA encoding sequence | nucleotide | unknown | uncultivated organism | |
| MG35 putative single guide RNA encoding sequences | 882 | MG35-376 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 883 | MG35-378 effector putative single guide RNA encoding sequence | nucleotide | unknown | uncultivated organism | |
| MG35 putative single guide RNA encoding sequences | 884 | MG35-379 effector putative single guide RNA encoding sequence | nucleotide | unknown | uncultivated organism | |
| MG35 putative single guide RNA encoding sequences | 885 | MG35-384 effector putative single guide RNA encoding sequence | nucleotide | unknown | uncultivated organism | |
| MG35 putative single guide RNA encoding sequences | 886 | MG35-386 effector putative single guide RNA encoding sequence | nucleotide | unknown | uncultivated organism | |
| MG35 putative single guide RNA encoding sequences | 887 | MG35-388 effector putative single guide RNA encoding sequence | nucleotide | unknown | uncultivated organism | |
| MG35 putative single guide RNA encoding sequences | 888 | MG35-419, MG35-339 effectors putative single guide RNA encoding sequence | nucleotide | unknown | uncultivated organism | |
| MG35 putative single guide RNA encoding sequences | 889 | MG35-420, MG35-337 effectors putative single guide RNA encoding sequence | nucleotide | unknown | uncultivated organism | |
| MG35 putative single guide RNA encoding sequences | 890 | MG35-421, MG35-338 effectors putative single guide RNA encoding sequence | nucleotide | unknown | uncultivated organism | |
| MG35 putative single guide RNA encoding sequences | 891 | MG35-422 effector putative single guide RNA encoding sequence | nucleotide | unknown | uncultivated organism | |
| MG35 putative single guide RNA encoding sequences | 892 | MG35-423 effector putative single guide RNA encoding sequence | nucleotide | unknown | uncultivated organism | |
| MG35 putative single guide RNA encoding sequences | 893 | MG35-424 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 894 | MG35-426 effector putative single guide RNA encoding sequence | nucleotide | unknown | uncultivated organism | |
| MG35 putative single guide RNA encoding sequences | 895 | MG35-427 effector putative single guide RNA encoding sequence | nucleotide | unknown | uncultivated organism | |
| MG35 putative single guide RNA encoding sequences | 896 | MG35-428, MG35-436, MG35-437, MG35-457 effectors putative single guide RNA encoding sequence | nucleotide | unknown | uncultivated organism | |
| MG35 putative single guide RNA encoding sequences | 897 | MG35-429, MG35-449 effectors putative single guide RNA encoding sequence | nucleotide | unknown | uncultivated organism | |
| MG35 putative single guide RNA encoding sequences | 898 | MG35-430 effector putative single guide RNA encoding sequence | nucleotide | unknown | uncultivated organism | |
| MG35 putative single guide RNA encoding sequences | 899 | MG35-431, MG35-442 effectors putative single guide RNA encoding sequence | nucleotide | unknown | uncultivated organism | |
| MG35 putative single guide RNA encoding sequences | 900 | MG35-432 effector putative single guide RNA encoding sequence | nucleotide | unknown | uncultivated organism | |
| MG35 putative single guide RNA encoding sequences | 901 | MG35-433, MG35-425 effectors putative single guide RNA encoding sequence | nucleotide | unknown | uncultivated organism | |
| MG35 putative single guide RNA encoding sequences | 902 | MG35-434, MG35-455 effectors putative single guide RNA encoding sequence | nucleotide | unknown | uncultivated organism | |
| MG35 putative single guide RNA encoding sequences | 903 | MG35-435 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 904 | MG35-438 effector putative single guide RNA encoding sequence | nucleotide | unknown | uncultivated organism | |
| MG35 putative single guide RNA encoding sequences | 905 | MG35-439 effector putative single guide RNA encoding sequence | nucleotide | unknown | uncultivated organism | |
| MG35 putative single guide RNA encoding sequences | 906 | MG35-440 effector putative single guide RNA encoding sequence | nucleotide | unknown | uncultivated organism | |
| MG35 putative single guide RNA encoding sequences | 907 | MG35-441, MG35-443 effectors putative single guide RNA encoding sequence | nucleotide | unknown | uncultivated organism | |
| MG35 putative single guide RNA encoding sequences | 908 | MG35-444 effector putative single guide RNA encoding sequence | nucleotide | unknown | uncultivated organism | |
| MG35 putative single guide RNA encoding sequences | 909 | MG35-445 effector putative single guide RNA encoding sequence | nucleotide | unknown | uncultivated organism | |
| MG35 putative single guide RNA encoding sequences | 910 | MG35-446, MG35-448, MG35-456 effectors putative single guide RNA encoding sequence | nucleotide | unknown | uncultivated organism | |
| MG35 putative single guide RNA encoding sequences | 911 | MG35-447 effector putative single guide RNA encoding sequence | nucleotide | unknown | uncultivated organism | |
| MG35 putative single guide RNA encoding sequences | 912 | MG35-450 effector putative single guide RNA encoding sequence | nucleotide | unknown | uncultivated organism | |
| MG35 putative single guide RNA encoding sequences | 913 | MG35-451 effector putative single guide RNA encoding sequence | nucleotide | unknown | uncultivated organism | |
| MG35 putative single guide | 914 | MG35-452 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| RNA encoding sequences MG35 putative single guide RNA encoding sequences | 915 | MG35-453 effector putative single guide RNA encoding sequence | nucleotide | unknown | uncultivated organism | |
| MG35 putative single guide RNA encoding sequences | 916 | MG35-454 effector putative single guide RNA encoding sequence | nucleotide | unknown | uncultivated organism | |
| MG35 putative single guide RNA encoding sequences | 917 | MG35-458, MG35-523 effectors putative single guide RNA encoding sequence | nucleotide | unknown | uncultivated organism | |
| MG35 putative single guide RNA encoding sequences | 918 | MG35-459 effector putative single guide RNA encoding sequence | nucleotide | unknown | uncultivated organism | |
| MG35 putative single guide RNA encoding sequences | 919 | MG35-460 effector putative single guide RNA encoding sequence | nucleotide | unknown | uncultivated organism | |
| MG35 putative single guide RNA encoding sequences | 920 | MG35-461 effector putative single guide RNA encoding sequence | nucleotide | unknown | uncultivated organism | |
| MG35 putative single guide RNA encoding sequences | 921 | MG35-462 effector putative single guide RNA encoding sequence | nucleotide | unknown | uncultivated organism | |
| MG35 putative single guide RNA encoding sequences | 922 | MG35-463 effector putative single guide RNA encoding sequence | nucleotide | unknown | uncultivated organism | |
| MG35 putative single guide RNA encoding sequences | 923 | MG35-464 effector putative single guide RNA encoding sequence | nucleotide | unknown | uncultivated organism | |
| MG35 putative single guide RNA encoding sequences | 924 | MG35-465 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 925 | MG35-466 effector putative single guide RNA encoding sequence | nucleotide | unknown | uncultivated organism | |
| MG35 putative single guide RNA encoding sequences | 926 | MG35-510 effector putative single guide RNA encoding sequence | nucleotide | unknown | uncultivated organism | |
| MG35 putative single guide RNA encoding sequences | 927 | MG35-511, MG35-512 effectors putative single guide RNA encoding sequence | nucleotide | unknown | uncultivated organism | |
| MG35 putative single guide RNA encoding sequences | 928 | MG35-513 effector putative single guide RNA encoding sequence | nucleotide | unknown | uncultivated organism | |
| MG35 putative single guide RNA encoding sequences | 929 | MG35-514 effector putative single guide RNA encoding sequence | nucleotide | unknown | uncultivated organism | |
| MG35 putative single guide RNA encoding sequences | 930 | MG35-515 effector putative single guide RNA encoding sequence | nucleotide | unknown | uncultivated organism | |
| MG35 putative single guide RNA encoding sequences | 931 | MG35-516 effector putative single guide RNA encoding sequence | nucleotide | unknown | uncultivated organism | |
| MG35 putative single guide RNA encoding sequences | 932 | MG35-517 effector putative single guide RNA encoding sequence | nucleotide | unknown | uncultivated organism | |
| MG35 putative single guide RNA encoding sequences | 933 | MG35-518 effector putative single guide RNA encoding sequence | nucleotide | unknown | uncultivated organism | |
| MG35 putative single guide RNA encoding sequences | 934 | MG35-519 effector putative single guide RNA encoding sequence | nucleotide | unknown | uncultivated organism | |
| MG35 putative single guide | 935 | MG35-520 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 936 | MG35-521 effector putative single guide RNA encoding sequence | nucleotide | unknown | uncultivated organism | |
| MG35 putative single guide RNA encoding sequences | 937 | MG35-522, MG35-526, MG35-546, MG35-548 effectors putative single guide RNA encoding sequence | nucleotide | unknown | uncultivated organism | |
| MG35 putative single guide RNA encoding sequences | 938 | MG35-524 effector putative single guide RNA encoding sequence | nucleotide | unknown | uncultivated organism | |
| MG35 putative single guide RNA encoding sequences | 939 | MG35-525, MG35-537 effectors putative single guide RNA encoding sequence | nucleotide | unknown | uncultivated organism | |
| MG35 putative single guide RNA encoding sequences | 940 | MG35-527 effector putative single guide RNA encoding sequence | nucleotide | unknown | uncultivated organism | |
| MG35 putative single guide RNA encoding sequences | 941 | MG35-528 effector putative single guide RNA encoding sequence | nucleotide | unknown | uncultivated organism | |
| MG35 putative single guide RNA encoding sequences | 942 | MG35-529 effector putative single guide RNA encoding sequence | nucleotide | unknown | uncultivated organism | |
| MG35 putative single guide RNA encoding sequences | 943 | MG35-530 effector putative single guide RNA encoding sequence | nucleotide | unknown | uncultivated organism | |
| MG35 putative single guide RNA encoding sequences | 944 | MG35-531 effector putative single guide RNA encoding sequence | nucleotide | unknown | uncultivated organism | |
| MG35 putative single guide RNA encoding sequences | 945 | MG35-532 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 946 | MG35-533 effector putative single guide RNA encoding sequence | nucleotide | unknown | uncultivated organism | |
| MG35 putative single guide RNA encoding sequences | 947 | MG35-534 effector putative single guide RNA encoding sequence | nucleotide | unknown | uncultivated organism | |
| MG35 putative single guide RNA encoding sequences | 948 | MG35-535 effector putative single guide RNA encoding sequence | nucleotide | unknown | uncultivated organism | |
| MG35 putative single guide RNA encoding sequences | 949 | MG35-536 effector putative single guide RNA encoding sequence | nucleotide | unknown | uncultivated organism | |
| MG35 putative single guide RNA encoding sequences | 950 | MG35-538 effector putative single guide RNA encoding sequence | nucleotide | unknown | uncultivated organism | |
| MG35 putative single guide RNA encoding sequences | 951 | MG35-539 effector putative single guide RNA encoding sequence | nucleotide | unknown | uncultivated organism | |
| MG35 putative single guide RNA encoding sequences | 952 | MG35-540 effector putative single guide RNA encoding sequence | nucleotide | unknown | uncultivated organism | |
| MG35 putative single guide RNA encoding sequences | 953 | MG35-541 effector putative single guide RNA encoding sequence | nucleotide | unknown | uncultivated organism | |
| MG35 putative single guide RNA encoding sequences | 954 | MG35-542 effector putative single guide RNA encoding sequence | nucleotide | unknown | uncultivated organism | |
| MG35 putative single guide RNA encoding sequences | 955 | MG35-543 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 956 | MG35-544 effector putative single guide RNA encoding sequence | nucleotide | unknown | uncultivated organism | |
| MG35 putative single guide RNA encoding sequences | 957 | MG35-545 effector putative single guide RNA encoding sequence | nucleotide | unknown | uncultivated organism | |
| MG35 putative single guide RNA encoding sequences | 958 | MG35-547 effector putative single guide RNA encoding sequence | nucleotide | unknown | uncultivated organism | |
| MG35 putative single guide RNA encoding sequences | 959 | MG35-549 effector putative single guide RNA encoding sequence | nucleotide | unknown | uncultivated organism | |
| MG35 putative single guide RNA encoding sequences | 960 | MG35-550 effector putative single guide RNA encoding sequence | nucleotide | unknown | uncultivated organism | |
| MG35 putative single guide RNA encoding sequences | 961 | MG35-552 effector putative single guide RNA encoding sequence | nucleotide | unknown | uncultivated organism | |
| MG35 putative single guide RNA encoding sequences | 962 | MG35-553 effector putative single guide RNA encoding sequence | nucleotide | unknown | uncultivated organism | |
| MG35 putative single guide RNA encoding sequences | 963 | MG35-554 effector putative single guide RNA encoding sequence | nucleotide | unknown | uncultivated organism | |
| MG35 putative single guide RNA encoding sequences | 964 | MG35-555 effector putative single guide RNA encoding sequence | nucleotide | unknown | uncultivated organism | |
| MG35 putative single guide RNA encoding sequences | 965 | MG35-556 effector putative single guide RNA encoding sequence | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 putative single guide RNA encoding sequences | 966 | MG35-557 effector putative single guide RNA encoding sequence | nucleotide | unknown | uncultivated organism | |
| MG35 putative single guide RNA encoding sequences | 967 | MG35-558 effector putative single guide RNA encoding sequence | nucleotide | unknown | uncultivated organism | |
| MG35 putative single guide RNA encoding sequences | 968 | MG35-559 effector putative single guide RNA encoding sequence | nucleotide | unknown | uncultivated organism | |
| MG35 putative single guide RNA encoding sequences | 969 | MG35-560 effector putative single guide RNA encoding sequence | nucleotide | unknown | uncultivated organism | |
| MG35 putative single guide RNA encoding sequences | 970 | MG35-561 effector putative single guide RNA encoding sequence | nucleotide | unknown | uncultivated organism | |
| MG35 putative single guide RNA encoding sequences | 971 | MG35-562 effector putative single guide RNA encoding sequence | nucleotide | unknown | uncultivated organism | |
| MG35 putative single guide RNA encoding sequences | 972 | MG35-563 effector putative single guide RNA encoding sequence | nucleotide | unknown | uncultivated organism | |
| MG35 putative single guide RNA encoding sequences | 973 | MG35-564 effector putative single guide RNA encoding sequence | nucleotide | unknown | uncultivated organism | |
| MG35 putative single guide RNA encoding sequences | 974 | MG35-565 effector putative single guide RNA encoding sequence | nucleotide | unknown | uncultivated organism | |
| MG143 effectors | 975 | MG143-1 effector | protein | unknown | uncultivated organism | |
| MG144 effectors | 976 | MG144-1 effector | protein | unknown | uncultivated organism | |
| MG144 effectors | 977 | MG144-2 effector | protein | unknown | uncultivated organism | |
| MG144 effectors | 978 | MG144-3 effector | protein | unknown | uncultivated organism | |
| MG144 effectors | 979 | MG144-4 effector | protein | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG145 effectors | 980 | MG145-1 effector | protein | unknown | uncultivated organism | |
| MG33 effectors | 981 | MG33-27 effector | protein | unknown | uncultivated organism | |
| MG33 effectors | 982 | MG33-28 effector | protein | unknown | uncultivated organism | |
| MG33 effectors | 983 | MG33-29 effector | protein | unknown | uncultivated organism | |
| MG33 effectors | 984 | MG33-30 effector | protein | unknown | uncultivated organism | |
| MG33 effectors | 985 | MG33-31 effector | protein | unknown | uncultivated organism | |
| MG33 effectors | 986 | MG33-32 effector | protein | unknown | uncultivated organism | |
| MG33 effectors | 987 | MG33-33 effector | protein | unknown | uncultivated organism | |
| MG33 effectors | 988 | MG33-34 effector | protein | unknown | uncultivated organism | |
| MG102 effectors | 989 | MG102-35 effector | protein | unknown | uncultivated organism | |
| MG102 effectors | 990 | MG102-36 effector | protein | unknown | uncultivated organism | |
| MG102 effectors | 991 | MG102-37 effector | protein | unknown | uncultivated organism | |
| MG102 effectors | 992 | MG102-38 effector | protein | unknown | uncultivated organism | |
| MG102 effectors | 993 | MG102-39 effector | protein | unknown | uncultivated organism | |
| MG102 effectors | 994 | MG102-40 effector | protein | unknown | uncultivated organism | |
| MG102 effectors | 995 | MG102-41 effector | protein | unknown | uncultivated organism | |
| MG102 effectors | 996 | MG102-42 effector | protein | unknown | uncultivated organism | |
| MG102 effectors | 997 | MG102-43 effector | protein | unknown | uncultivated organism | |
| MG102 effectors | 998 | MG102-44 effector | protein | unknown | uncultivated organism | |
| MG102 effectors | 999 | MG102-45 effector | protein | unknown | uncultivated organism | |
| MG102 effectors | 1000 | MG102-46 effector | protein | unknown | uncultivated organism | |
| MG102 effectors | 1001 | MG102-47 effector | protein | unknown | uncultivated organism | |
| MG102 effectors | 1002 | MG102-48 effector | protein | unknown | uncultivated organism | |
| MG33 active effectors sgRNA | 1003 | MG33-3 active effectors sgRNA | nucleotide | artificial sequence | N/A | |
| MG33 active effectors sgRNA | 1004 | MG33-31 active effectors sgRNA | nucleotide | artificial sequence | N/A | |
| MG33 active effectors sgRNA | 1005 | MG33-34 active effectors sgRNA | nucleotide | artificial sequence | N/A | |
| MG35 active effectors sgRNA | 1006 | MG35-1 active effectors sgRNA | nucleotide | artificial sequence | N/A | |
| MG35 active effectors sgRNA | 1007 | MG35-2 active effectors sgRNA | nucleotide | artificial sequence | N/A | |
| MG35 active effectors sgRNA | 1008 | MG35-3 active effectors sgRNA | nucleotide | artificial sequence | N/A | |
| MG35 active effectors sgRNA | 1009 | MG35-4 active effectors sgRNA | nucleotide | artificial sequence | N/A | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 active effectors sgRNA | 1010 | MG35-5 active effectors sgRNA | nucleotide | artificial sequence | N/A | |
| MG35 active effectors sgRNA | 1011 | MG35-6 active effectors sgRNA | nucleotide | artificial sequence | N/A | |
| MG35 active effectors sgRNA | 1012 | MG35-102 active effectors sgRNA | nucleotide | artificial sequence | N/A | |
| MG102 active effectors sgRNA | 1013 | MG102-2 active effectors sgRNA | nucleotide | artificial sequence | N/A | |
| MG102 active effectors sgRNA | 1014 | MG102-14 active effectors sgRNA | nucleotide | artificial sequence | N/A | |
| MG102 active effectors sgRNA | 1015 | MG102-35 active effectors sgRNA | nucleotide | artificial sequence | N/A | |
| MG102 active effectors sgRNA | 1016 | MG102-36 active effectors sgRNA | nucleotide | artificial sequence | N/A | |
| MG102 active effectors sgRNA | 1017 | MG102-39 active effectors sgRNA | nucleotide | artificial sequence | N/A | |
| MG102 active effectors sgRNA | 1018 | MG102-42 active effectors sgRNA | nucleotide | artificial sequence | N/A | |
| MG102 active effectors sgRNA | 1019 | MG102-43 active effectors sgRNA | nucleotide | artificial sequence | N/A | |
| MG102 active effectors sgRNA | 1020 | MG102-45 active effectors sgRNA | nucleotide | artificial sequence | N/A | |
| MG102 active effectors sgRNA | 1021 | MG102-47 active effectors sgRNA | nucleotide | artificial sequence | N/A | |
| MG102 active effectors sgRNA | 1022 | MG102-48 active effectors sgRNA | nucleotide | artificial sequence | N/A | |
| MG33 active effectors PAM | 1023 | MG34-1, MG34-9, MG34-16, MG33-3, MG33-31, MG33-34 active effectors PAM | nucleotide | artificial sequence | N/A | nGG |
| MG33 active effectors PAM | 1024 | MG33-31, MG33-34 active effectors PAM | nucleotide | artificial sequence | N/A | nGGnnnnn |
| MG33 active effectors PAM | 1025 | MG33-31, MG33-34 active effectors PAM | nucleotide | artificial sequence | N/A | nGGnnnnn |
| MG34 active effectors PAM | 1026 | MG34-1, MG34-9, MG34-16, MG33-3 active effectors PAM | nucleotide | artificial sequence | N/A | nGG |
| MG34 active effectors PAM | 1027 | MG34-1, MG34-9, MG34-16, MG33-3 active effectors PAM | nucleotide | artificial sequence | N/A | nGG |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG34 active effectors PAM | 1028 | MG34-1, MG34-9, MG34-16, MG33-3 active effectors PAM | nucleotide | artificial sequence | N/A | nGG |
| MG35 active effectors PAM | 1029 | MG35-1 active effectors PAM | nucleotide | artificial sequence | N/A | AnGg |
| MG35 active effectors PAM | 1030 | MG35-2 active effectors PAM | nucleotide | artificial sequence | N/A | nARAA |
| MG35 active effectors PAM | 1031 | MG35-3 active effectors PAM | nucleotide | artificial sequence | N/A | ATGaaa |
| MG35 active effectors PAM | 1032 | MG35-4 active effectors PAM | nucleotide | artificial sequence | N/A | ATGA |
| MG35 active effectors PAM | 1033 | MG35-5 active effectors PAM | nucleotide | artificial sequence | N/A | WTGG |
| MG35 active effectors PAM | 1034 | MG35-102 active effectors PAM | nucleotide | artificial sequence | N/A | RTGA |
| MG102 active effectors PAM | 1035 | MG102-2 active effectors PAM | nucleotide | artificial sequence | N/A | nRC |
| MG102 active effectors PAM | 1036 | MG102-14, MG102-35, MG102-36, MG102-42, MG102-43, MG102-45, MG102-47, MG102-48 active effectors PAM | nucleotide | artificial sequence | N/A | nRCnnnnn |
| MG102 active effectors PAM | 1037 | MG102-14, MG102-35, MG102-36, MG102-42, MG102-43, MG102-45, MG102-47, MG102-48 active effectors PAM | nucleotide | artificial sequence | N/A | nRCnnnnn |
| MG102 active effectors PAM | 1038 | MG102-14, MG102-35, MG102-36, MG102-42, MG102-43, MG102-45, MG102-47, MG102-48 active effectors PAM | nucleotide | artificial sequence | N/A | nRCnnnnn |
| MG102 active effectors PAM | 1039 | MG102-39 active effectors PAM | nucleotide | artificial sequence | N/A | naRnnnnn |
| MG102 active effectors PAM | 1040 | MG102-14, MG102-35, MG102-36, MG102-42, MG102-43, MG102-45, MG102-47, MG102-48 active effectors PAM | nucleotide | artificial sequence | N/A | nRCnnnnn |
| MG102 active effectors PAM | 1041 | MG102-14, MG102-35, MG102-36, MG102-42, MG102-43, MG102-45, MG102-47, MG102-48 active effectors PAM | nucleotide | artificial sequence | N/A | nRCnnnnn |
| MG102 active effectors PAM | 1042 | MG102-14, MG102-35, MG102-36, MG102-42, MG102-43, MG102-45, MG102-47, MG102-48 active effectors PAM | nucleotide | artificial sequence | N/A | nRCnnnnn |
| MG102 active effectors PAM | 1043 | MG102-14, MG102-35, MG102-36, MG102-42, MG102-43, MG102-45, MG102-47, MG102-48 active effectors PAM | nucleotide | artificial sequence | N/A | nRCnnnnn |
| MG102 active effectors PAM | 1044 | MG102-14, MG102-35, MG102-36, MG102-42, MG102-43, MG102-45, MG102-47, MG102-48 active effectors PAM | nucleotide | artificial sequence | N/A | nRCnnnnn |
| MG33 CRISPR repeats | 1045 | MG33-1 CRISPR repeat | nucleotide | unknown | uncultivated organism | |
| MG33 CRISPR repeats | 1046 | MG33-2 CRISPR repeat | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG33 CRISPR repeats | 1047 | MG33-3 CRISPR repeat | nucleotide | unknown | uncultivated organism | |
| MG33 CRISPR repeats | 1048 | MG33-27 CRISPR repeat | nucleotide | unknown | uncultivated organism | |
| MG33 CRISPR repeats | 1049 | MG33-28 CRISPR repeat | nucleotide | unknown | uncultivated organism | |
| MG33 CRISPR repeats | 1050 | MG33-29 CRISPR repeat | nucleotide | unknown | uncultivated organism | |
| MG33 CRISPR repeats | 1051 | MG33-30 CRISPR repeat | nucleotide | unknown | uncultivated organism | |
| MG33 CRISPR repeats | 1052 | MG33-31 CRISPR repeat | nucleotide | unknown | uncultivated organism | |
| MG33 CRISPR repeats | 1053 | MG33-33 CRISPR repeat | nucleotide | unknown | uncultivated organism | |
| MG33 CRISPR repeats | 1054 | MG33-34 CRISPR repeat | nucleotide | unknown | uncultivated organism | |
| MG34 CRISPR repeats | 1055 | MG34-1, MG34-9 CRISPR repeat | nucleotide | unknown | uncultivated organism | |
| MG34 CRISPR repeats | 1056 | MG34-1, MG34-9 CRISPR repeat | nucleotide | unknown | uncultivated organism | |
| MG34 CRISPR repeats | 1057 | MG34-25 CRISPR repeat | nucleotide | unknown | uncultivated organism | |
| MG102 CRISPR repeats | 1058 | MG102-1 CRISPR repeat | nucleotide | unknown | uncultivated organism | |
| MG102 CRISPR repeats | 1059 | MG102-2 CRISPR repeat | nucleotide | unknown | uncultivated organism | |
| MG102 CRISPR repeats | 1060 | MG102-3 CRISPR repeat | nucleotide | unknown | uncultivated organism | |
| MG102 CRISPR repeats | 1061 | MG102-10 CRISPR repeat | nucleotide | unknown | uncultivated organism | |
| MG102 CRISPR repeats | 1062 | MG102-14 CRISPR repeat | nucleotide | unknown | uncultivated organism | |
| MG102 CRISPR repeats | 1063 | MG102-35 CRISPR repeat | nucleotide | unknown | uncultivated organism | |
| MG102 CRISPR repeats | 1064 | MG102-36 CRISPR repeat | nucleotide | unknown | uncultivated organism | |
| MG102 CRISPR repeats | 1065 | MG102-38 CRISPR repeat | nucleotide | unknown | uncultivated organism | |
| MG102 CRISPR repeats | 1066 | MG102-39 CRISPR repeat | nucleotide | unknown | uncultivated organism | |
| MG102 CRISPR repeats | 1067 | MG102-42 CRISPR repeat | nucleotide | unknown | uncultivated organism | |
| MG102 CRISPR repeats | 1068 | MG102-43 CRISPR repeat | nucleotide | unknown | uncultivated organism | |
| MG102 CRISPR repeats | 1069 | MG102-44 CRISPR repeat | nucleotide | unknown | uncultivated organism | |
| MG102 CRISPR repeats | 1070 | MG102-45 CRISPR repeat | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG102 CRISPR repeats | 1071 | MG102-47 CRISPR repeat | nucleotide | unknown | uncultivated organism | |
| MG102 CRISPR repeats | 1072 | MG102-48 CRISPR repeat | nucleotide | unknown | uncultivated organism | |
| MG143 CRISPR repeats | 1073 | MG143-1 CRISPR repeat | nucleotide | unknown | uncultivated organism | |
| MG144 CRISPR repeats | 1074 | MG144-1 CRISPR repeat | nucleotide | unknown | uncultivated organism | |
| MG144 CRISPR repeats | 1075 | MG144-2 CRISPR repeat | nucleotide | unknown | uncultivated organism | |
| MG144 CRISPR repeats | 1076 | MG144-3, MG144-4 CRISPR repeat | nucleotide | unknown | uncultivated organism | |
| MG144 CRISPR repeats | 1077 | MG144-3, MG144-4 CRISPR repeat | nucleotide | unknown | uncultivated organism | |
| MG145 CRISPR repeats | 1078 | MG145-1 CRISPR repeat | nucleotide | unknown | uncultivated organism | |
| MG102-2 human TRAC target site | 1079 | MG102-2 TRAC A1 24nt | nucleotide | artificial sequence | N/A | |
| MG102-2 human TRAC target site | 1080 | MG102-2 TRAC B1 24nt | nucleotide | artificial sequence | N/A | |
| MG102-2 human TRAC target site | 1081 | MG102-2 TRAC A1 20nt | nucleotide | artificial sequence | N/A | |
| MG102-2 human TRAC target site | 1082 | MG102-2 TRAC B1 20nt | nucleotide | artificial sequence | N/A | |
| MG102-2 human TRAC sgRNA | 1083 | MG102-2 TRAC A1 24nt sgRNA | nucleotide | artificial sequence | N/A | |
| MG102-2 human TRAC sgRNA | 1084 | MG102-2 TRAC B1 24nt sgRNA | nucleotide | artificial sequence | N/A | |
| MG102-2 human TRAC sgRNA | 1085 | MG102-2 TRAC A1 20nt sgRNA | nucleotide | artificial sequence | N/A | |
| MG102-2 human TRAC sgRNA | 1086 | MG102-2 TRAC B1 20nt sgRNA | nucleotide | artificial sequence | N/A | |
| MG102-2 guide targeting AAVS1 | 1087 | MG102-2 AAVS1 A5 | nucleotide | artificial sequence | | |
| MG102-2 guide targeting AAVS1 | 1088 | MG102-2 AAVS1 H8 | nucleotide | artificial sequence | | |
| MG102-2 guide targeting AAVS1 | 1089 | MG102-2 AAVS1 H9 | nucleotide | artificial sequence | | |
| MG102-2 guide targeting AAVS1 | 1090 | MG102-2 AAVS1 D11 | nucleotide | artificial sequence | | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG102-2 guide targeting AAVS1 | 1091 | MG102-2 AAVS1 E7 | nucleotide | artificial sequence | | |
| MG102-2 guide targeting AAVS1 | 1092 | MG102-2 AAVS1 D7 | nucleotide | artificial sequence | | |
| MG102-2 guide targeting AAVS1 | 1093 | MG102-2 AAVS1 B7 | nucleotide | artificial sequence | | |
| MG102-2 guide targeting AAVS1 | 1094 | MG102-2 AAVS1 D12 | nucleotide | artificial sequence | | |
| MG102-2 guide targeting AAVS1 | 1095 | MG102-2 AAVS1 C8 | nucleotide | artificial sequence | | |
| MG102-2 guide targeting AAVS1 | 1096 | MG102-2 AAVS1 A8 | nucleotide | artificial sequence | | |
| MG102-2 guide targeting AAVS1 | 1097 | MG102-2 AAVS1 G6 | nucleotide | artificial sequence | | |
| MG102-2 guide targeting AAVS1 | 1098 | MG102-2 AAVS1 E5 | nucleotide | artificial sequence | | |
| MG102-2 guide targeting AAVS1 | 1099 | MG102-2 AAVS1 G7 | nucleotide | artificial sequence | | |
| MG102-2 guide targeting AAVS1 | 1100 | MG102-2 AAVS1 C3 | nucleotide | artificial sequence | | |
| MG102-2 guide targeting AAVS1 | 1101 | MG102-2 AAVS1 E1 | nucleotide | artificial sequence | | |
| MG102-2 guide targeting AAVS1 | 1102 | MG102-2 AAVS1 E2 | nucleotide | artificial sequence | | |
| MG102-2 guide targeting AAVS1 | 1103 | MG102-2 AAVS1 H6 | nucleotide | artificial sequence | | |
| MG102-2 guide targeting AAVS1 | 1104 | MG102-2 AAVS1 H11 | nucleotide | artificial sequence | | |
| DNA Sequence of AAVS1 Target Site | 1105 | MG102-2 AAVS1 A5 | nucleotide | artificial sequence | | |
| DNA Sequence of AAVS1 Target Site | 1106 | MG102-2 AAVS1 H8 | nucleotide | artificial sequence | | |
| DNA Sequence of AAVS1 Target Site | 1107 | MG102-2 AAVS1 H9 | nucleotide | artificial sequence | | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| DNA Sequence of AAVS1 Target Site | 1108 | MG102-2 AAVS1 D11 | nucleotide | artificial sequence | | |
| DNA Sequence of AAVS1 Target Site | 1109 | MG102-2 AAVS1 E7 | nucleotide | artificial sequence | | |
| DNA Sequence of AAVS1 Target Site | 1110 | MG102-2 AAVS1 D7 | nucleotide | artificial sequence | | |
| DNA Sequence of AAVS1 Target Site | 1111 | MG102-2 AAVS1 B7 | nucleotide | artificial sequence | | |
| DNA Sequence of AAVS1 Target Site | 1112 | MG102-2 AAVS1 D12 | nucleotide | artificial sequence | | |
| DNA Sequence of AAVS1 Target Site | 1113 | MG102-2 AAVS1 C8 | nucleotide | artificial sequence | | |
| DNA Sequence of AAVS1 Target Site | 1114 | MG102-2 AAVS1 A8 | nucleotide | artificial sequence | | |
| DNA Sequence of AAVS1 Target Site | 1115 | MG102-2 AAVS1 G6 | nucleotide | artificial sequence | | |
| DNA Sequence of AAVS1 Target Site | 1116 | MG102-2 AAVS1 E5 | nucleotide | artificial sequence | | |
| DNA Sequence of AAVS1 Target Site | 1117 | MG102-2 AAVS1 G7 | nucleotide | artificial sequence | | |
| DNA Sequence of AAVS1 Target Site | 1118 | MG102-2 AAVS1 C3 | nucleotide | artificial sequence | | |
| DNA Sequence of AAVS1 Target Site | 1119 | MG102-2 AAVS1 E1 | nucleotide | artificial sequence | | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| DNA Sequence of AAVS1 Target Site | 1120 | MG102-2 AAVS1 E2 | nucleotide | artificial sequence | | |
| DNA Sequence of AAVS1 Target Site | 1121 | MG102-2 AAVS1 H6 | nucleotide | artificial sequence | | |
| DNA Sequence of AAVS1 Target Site | 1122 | MG102-2 AAVS1 H11 | nucleotide | artificial sequence | | |
| MG102-36 guide targeting TRAC | 1123 | MG102-36 TRAC D12 | nucleotide | artificial sequence | | |
| MG102-36 guide targeting TRAC | 1124 | MG102-36 TRAC F1 | nucleotide | artificial sequence | | |
| MG102-36 guide targeting TRAC | 1125 | MG102-36 TRAC H6 | nucleotide | artificial sequence | | |
| MG102-39 guide targeting TRAC | 1126 | MG102-39 TRAC F4 | nucleotide | artificial sequence | | |
| MG102-39 guide targeting TRAC | 1127 | MG102-39 TRAC A9 | nucleotide | artificial sequence | | |
| MG102-39 guide targeting TRAC | 1128 | MG102-39 TRAC G11 | nucleotide | artificial sequence | | |
| MG102-39 guide targeting TRAC | 1129 | MG102-39 TRAC C11 | nucleotide | artificial sequence | | |
| MG102-39 guide targeting TRAC | 1130 | MG102-39 TRAC B6 | nucleotide | artificial sequence | | |
| MG102-39 guide targeting TRAC | 1131 | MG102-39 TRAC B5 | nucleotide | artificial sequence | | |
| MG102-39 guide targeting TRAC | 1132 | MG102-39 TRAC G9 | nucleotide | artificial sequence | | |
| MG102-39 guide targeting TRAC | 1133 | MG102-39 TRAC D1 | nucleotide | artificial sequence | | |
| MG102-39 guide targeting TRAC | 1134 | MG102-39 TRAC B11 | nucleotide | artificial sequence | | |
| MG102-39 guide targeting TRAC | 1135 | MG102-39 TRAC D4 | nucleotide | artificial sequence | | |
| MG102-39 guide targeting TRAC | 1136 | MG102-39 TRAC F2 | nucleotide | artificial sequence | | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG102-39 guide targeting TRAC | 1137 | MG102-39 TRAC G1 | nucleotide | artificial sequence | | |
| MG102-42 guide targeting TRAC | 1138 | MG102-42 TRAC D10 | nucleotide | artificial sequence | | |
| MG102-42 guide targeting TRAC | 1139 | MG102-42 TRAC D12 | nucleotide | artificial sequence | | |
| MG102-42 guide targeting TRAC | 1140 | MG102-42 TRAC E12 | nucleotide | artificial sequence | | |
| MG102-45 guide targeting TRAC | 1141 | MG102-45 TRAC B1 | nucleotide | artificial sequence | | |
| MG102-45 guide targeting TRAC | 1142 | MG102-45 TRAC C11 | nucleotide | artificial sequence | | |
| MG102-48 guide targeting TRAC | 1143 | MG102-48 TRAC A1 | nucleotide | artificial sequence | | |
| MG102-48 guide targeting TRAC | 1144 | MG102-48 TRAC D12 | nucleotide | artificial sequence | | |
| DNA Sequence of TRAC Target Site | 1145 | MG102-36 TRAC D12 | nucleotide | artificial sequence | | |
| DNA Sequence of TRAC Target Site | 1146 | MG102-36 TRAC F1 | nucleotide | artificial sequence | | |
| DNA Sequence of TRAC Target Site | 1147 | MG102-36 TRAC H6 | nucleotide | artificial sequence | | |
| DNA Sequence of TRAC Target Site | 1148 | MG102-39 TRAC F4 | nucleotide | artificial sequence | | |
| DNA Sequence of TRAC Target Site | 1149 | MG102-39 TRAC A9 | nucleotide | artificial sequence | | |
| DNA Sequence of TRAC Target Site | 1150 | MG102-39 TRAC G11 | nucleotide | artificial sequence | | |
| DNA Sequence of TRAC Target Site | 1151 | MG102-39 TRAC C11 | nucleotide | artificial sequence | | |
| DNA Sequence of TRAC Target Site | 1152 | MG102-39 TRAC B6 | nucleotide | artificial sequence | | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| DNA Sequence of TRAC Target Site | 1153 | MG102-39 TRAC B5 | nucleotide | artificial sequence | | |
| DNA Sequence of TRAC Target Site | 1154 | MG102-39 TRAC G9 | nucleotide | artificial sequence | | |
| DNA Sequence of TRAC Target Site | 1155 | MG102-39 TRAC D1 | nucleotide | artificial sequence | | |
| DNA Sequence of TRAC Target Site | 1156 | MG102-39 TRAC B11 | nucleotide | artificial sequence | | |
| DNA Sequence of TRAC Target Site | 1157 | MG102-39 TRAC D4 | nucleotide | artificial sequence | | |
| DNA Sequence of TRAC Target Site | 1158 | MG102-39 TRAC F2 | nucleotide | artificial sequence | | |
| DNA Sequence of TRAC Target Site | 1159 | MG102-39 TRAC G1 | nucleotide | artificial sequence | | |
| DNA Sequence of TRAC Target Site | 1160 | MG102-42 TRAC D10 | nucleotide | artificial sequence | | |
| DNA Sequence of TRAC Target Site | 1161 | MG102-42 TRAC D12 | nucleotide | artificial sequence | | |
| DNA Sequence of TRAC Target Site | 1162 | MG102-42 TRAC E12 | nucleotide | artificial sequence | | |
| DNA Sequence of TRAC Target Site | 1163 | MG102-45 TRAC B1 | nucleotide | artificial sequence | | |
| DNA Sequence of TRAC Target Site | 1164 | MG102-45 TRAC C11 | nucleotide | artificial sequence | | |
| DNA Sequence of TRAC Target Site | 1165 | MG102-48 TRAC A1 | nucleotide | artificial sequence | | |
| DNA Sequence of TRAC Target Site | 1166 | MG102-48 TRAC D12 | nucleotide | artificial sequence | | |
| MG33-34 guide targeting TRAC | 1167 | MG33-34 TRAC F6 | nucleotide | artificial sequence | | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG33-34 guide targeting TRAC | 1168 | MG33-34 TRAC E6 | nucleotide | artificial sequence | | |
| DNA Sequence of TRAC Target Site | 1169 | MG33-34 TRAC F6 | nucleotide | artificial sequence | | |
| DNA Sequence of TRAC Target Site | 1170 | MG33-34 TRAC E6 | nucleotide | artificial sequence | | |
| MG102 locus encoding effectors | 1171 | MG102-33 locus encoding effector | nucleotide | unknown | uncultivated organism | |
| MG35 locus encoding effectors | 1172 | MG35-3 locus encoding effector | nucleotide | unknown | uncultivated organism | |
| MG35 locus encoding effectors | 1173 | MG35-7 locus encoding effector | nucleotide | unknown | uncultivated organism | |
| MG35 locus encoding effectors | 1174 | MG35-15 locus encoding effector | nucleotide | unknown | uncultivated organism | |
| MG35 locus encoding effectors | 1175 | MG35-20 locus encoding effector | nucleotide | unknown | uncultivated organism | |
| MG35 locus encoding effectors | 1176 | MG35-46 locus encoding effector | nucleotide | unknown | uncultivated organism | |
| MG35 locus encoding effectors | 1177 | MG35-58 locus encoding effector | nucleotide | unknown | uncultivated organism | |
| MG35 locus encoding effectors | 1178 | MG35-59 locus encoding effector | nucleotide | unknown | uncultivated organism | |
| MG35 locus encoding effectors | 1179 | MG35-76 locus encoding effector | nucleotide | unknown | uncultivated organism | |
| MG35 locus encoding effectors | 1180 | MG35-99 locus encoding effector | nucleotide | unknown | uncultivated organism | |
| MG35 locus encoding effectors | 1181 | MG35-100 locus encoding effector | nucleotide | unknown | uncultivated organism | |
| MG35 locus encoding effectors | 1182 | MG35-102 locus encoding effector | nucleotide | unknown | uncultivated organism | |
| MG35 locus encoding effectors | 1183 | MG35-103 locus encoding effector | nucleotide | unknown | uncultivated organism | |
| MG35 locus encoding effectors | 1184 | MG35-104 locus encoding effector | nucleotide | unknown | uncultivated organism | |
| MG35 locus encoding effectors | 1185 | MG35-114 locus encoding effector | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 locus encoding effectors | 1186 | MG35-132 locus encoding effector | nucleotide | unknown | uncultivated organism | |
| MG35 locus encoding effectors | 1187 | MG35-168 locus encoding effector | nucleotide | unknown | uncultivated organism | |
| MG35 locus encoding effectors | 1188 | MG35-176 locus encoding effector | nucleotide | unknown | uncultivated organism | |
| MG35 locus encoding effectors | 1189 | MG35-177 locus encoding effector | nucleotide | unknown | uncultivated organism | |
| MG35 locus encoding effectors | 1190 | MG35-179 locus encoding effector | nucleotide | unknown | uncultivated organism | |
| MG35 locus encoding effectors | 1191 | MG35-201 locus encoding effector | nucleotide | unknown | uncultivated organism | |
| MG35 locus encoding effectors | 1192 | MG35-231 locus encoding effector | nucleotide | unknown | uncultivated organism | |
| MG35 locus encoding effectors | 1193 | MG35-232 locus encoding effector | nucleotide | unknown | uncultivated organism | |
| MG35 locus encoding effectors | 1194 | MG35-233 locus encoding effector | nucleotide | unknown | uncultivated organism | |
| MG35 locus encoding effectors | 1195 | MG35-237 locus encoding effector | nucleotide | unknown | uncultivated organism | |
| MG35 locus encoding effectors | 1196 | MG35-238 locus encoding effector | nucleotide | unknown | uncultivated organism | |
| MG35 locus encoding effectors | 1197 | MG35-240 locus encoding effector | nucleotide | unknown | uncultivated organism | |
| MG35 locus encoding effectors | 1198 | MG35-291 locus encoding effector | nucleotide | unknown | uncultivated organism | |
| MG35 locus encoding effectors | 1199 | MG35-296 locus encoding effector | nucleotide | unknown | uncultivated organism | |
| MG35 locus encoding effectors | 1200 | MG35-298 locus encoding effector | nucleotide | unknown | uncultivated organism | |
| MG35 locus encoding effectors | 1201 | MG35-299 locus encoding effector | nucleotide | unknown | uncultivated organism | |
| MG35 locus encoding effectors | 1202 | MG35-302 locus encoding effector | nucleotide | unknown | uncultivated organism | |
| MG35 locus encoding effectors | 1203 | MG35-309 locus encoding effector | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 locus encoding effectors | 1204 | MG35-323 locus encoding effector | nucleotide | unknown | uncultivated organism | |
| MG35 locus encoding effectors | 1205 | MG35-326 locus encoding effector | nucleotide | unknown | uncultivated organism | |
| MG35 locus encoding effectors | 1206 | MG35-337 locus encoding effector | nucleotide | unknown | uncultivated organism | |
| MG35 locus encoding effectors | 1207 | MG35-339 locus encoding effector | nucleotide | unknown | uncultivated organism | |
| MG35 locus encoding effectors | 1208 | MG35-344 locus encoding effector | nucleotide | unknown | uncultivated organism | |
| MG35 locus encoding effectors | 1209 | MG35-345 locus encoding effector | nucleotide | unknown | uncultivated organism | |
| MG35 locus encoding effectors | 1210 | MG35-346 locus encoding effector | nucleotide | unknown | uncultivated organism | |
| MG35 locus encoding effectors | 1211 | MG35-347 locus encoding effector | nucleotide | unknown | uncultivated organism | |
| MG35 locus encoding effectors | 1212 | MG35-348 locus encoding effector | nucleotide | unknown | uncultivated organism | |
| MG35 locus encoding effectors | 1213 | MG35-349 locus encoding effector | nucleotide | unknown | uncultivated organism | |
| MG35 locus encoding effectors | 1214 | MG35-350 locus encoding effector | nucleotide | unknown | uncultivated organism | |
| MG35 locus encoding effectors | 1215 | MG35-354 locus encoding effector | nucleotide | unknown | uncultivated organism | |
| MG35 locus encoding effectors | 1216 | MG35-357 locus encoding effector | nucleotide | unknown | uncultivated organism | |
| MG35 locus encoding effectors | 1217 | MG35-358 locus encoding effector | nucleotide | unknown | uncultivated organism | |
| MG35 locus encoding effectors | 1218 | MG35-359 locus encoding effector | nucleotide | unknown | uncultivated organism | |
| MG35 locus encoding effectors | 1219 | MG35-364 locus encoding effector | nucleotide | unknown | uncultivated organism | |
| MG35 locus encoding effectors | 1220 | MG35-366 locus encoding effector | nucleotide | unknown | uncultivated organism | |
| MG35 locus encoding effectors | 1221 | MG35-393 locus encoding effector | nucleotide | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 locus encoding effectors | 1222 | MG35-404 locus encoding effector | nucleotide | unknown | uncultivated organism | |
| MG35 locus encoding effectors | 1223 | MG35-411 locus encoding effector | nucleotide | unknown | uncultivated organism | |
| MG35 locus encoding effectors | 1224 | MG35-418 locus encoding effector | nucleotide | unknown | uncultivated organism | |
| MG35 locus encoding effectors | 1225 | MG35-419 locus encoding effector | nucleotide | unknown | uncultivated organism | |
| MG35 locus encoding effectors | 1226 | MG35-420 locus encoding effector | nucleotide | unknown | uncultivated organism | |
| MG35 locus encoding effectors | 1227 | MG35-421 locus encoding effector | nucleotide | unknown | uncultivated organism | |
| MG35 locus encoding effectors | 1228 | MG35-423 locus encoding effector | nucleotide | unknown | uncultivated organism | |
| MG35 predicted CRISPR repeat | 1229 | MG35-463 CRISPR repeat | nucleotide | artificial sequence | | |
| MG35 predicted CRISPR repeat | 1230 | MG35-556 CRISPR repeat | nucleotide | artificial sequence | | |
| MG35 active effectors sgRNA | 1231 | MG35-94 sg1 single guide RNA | nucleotide | artificial sequence | | |
| MG35 active effectors sgRNA | 1232 | MG35-94 sg2 single guide RNA | nucleotide | artificial sequence | | |
| MG35 active effectors sgRNA | 1233 | MG35-94 sg3 single guide RNA | nucleotide | artificial sequence | | |
| MG35 active effectors sgRNA | 1234 | MG35-104 sg1 single guide RNA | nucleotide | artificial sequence | | |
| MG35 active effectors sgRNA | 1235 | MG35-350 sg3 single guide RNA | nucleotide | artificial sequence | | |
| MG35 active effectors sgRNA | 1236 | MG35-463 sg2 single guide RNA | nucleotide | artificial sequence | | |
| MG35 active effectors sgRNA | 1237 | MG35-463 sg3 single guide RNA | nucleotide | artificial sequence | | |
| MG35 active effectors sgRNA | 1238 | MG35-515 sg2 single guide RNA | nucleotide | artificial sequence | | |
| MG35 active effectors sgRNA | 1239 | MG35-515 sg3 single guide RNA | nucleotide | artificial sequence | | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 active effectors sgRNA | 1240 | MG35-517 sg2 single guide RNA | nucleotide | artificial sequence | | |
| MG35 active effectors sgRNA | 1241 | MG35-518 sg1 single guide RNA | nucleotide | artificial sequence | | |
| MG35 active effectors sgRNA | 1242 | MG35-519 sg1 single guide RNA | nucleotide | artificial sequence | | |
| MG35 active effectors sgRNA | 1243 | MG35-519 sg2 single guide RNA | nucleotide | artificial sequence | | |
| MG35 active effectors sgRNA | 1244 | MG35-519 sg3 single guide RNA | nucleotide | artificial sequence | | |
| MG35 active effectors sgRNA | 1245 | MG35-550 sg1 single guide RNA | nucleotide | artificial sequence | | |
| MG35 active effectors sgRNA | 1246 | MG35-553 sg1 single guide RNA | nucleotide | artificial sequence | | |
| MG35 active effectors sgRNA | 1247 | MG35-554 sg3 single guide RNA | nucleotide | artificial sequence | | |
| MG35 active effectors sgRNA | 1248 | MG35-554 sg4 single guide RNA | nucleotide | artificial sequence | | |
| MG35 active effectors sgRNA | 1249 | MG35-104_M1 single guide RNA | nucleotide | artificial sequence | | |
| MG35 active effectors sgRNA | 1250 | MG35-104_M2 single guide RNA | nucleotide | artificial sequence | | |
| MG35 active effectors sgRNA | 1251 | MG35-104_M3 single guide RNA | nucleotide | artificial sequence | | |
| MG35 active effectors sgRNA | 1252 | MG35-518_M1 single guide RNA | nucleotide | artificial sequence | | |
| MG35 active effectors sgRNA | 1253 | MG35-518_M2 single guide RNA | nucleotide | artificial sequence | | |
| MG35 active effectors sgRNA | 1254 | MG35-518_M3 single guide RNA | nucleotide | artificial sequence | | |
| MG35 active effectors sgRNA | 1255 | MG35-553_M1 single guide RNA | nucleotide | artificial sequence | | |
| MG35 active effectors sgRNA | 1256 | MG35-553_M2 single guide RNA | nucleotide | artificial sequence | | |
| MG35 active effectors sgRNA | 1257 | MG35-553_M3 single guide RNA | nucleotide | artificial sequence | | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG35 active effectors sgRNA | 1258 | MG35-94_M2 single guide RNA | nucleotide | artificial sequence | | |
| MG35 active effectors sgRNA | 1259 | MG35-94_M3 single guide RNA | nucleotide | artificial sequence | | |
| MG102 effectors | 1260 | MG102-49 effector | protein | unknown | uncultivated organism | |
| MG102 effectors | 1261 | MG102-50 effector | protein | unknown | uncultivated organism | |
| MG102 effectors | 1262 | MG102-51 effector | protein | unknown | uncultivated organism | |
| MG102 effectors | 1263 | MG102-52 effector | protein | unknown | uncultivated organism | |
| MG102 effectors | 1264 | MG102-53 effector | protein | unknown | uncultivated organism | |
| MG102 effectors | 1265 | MG102-54 effector | protein | unknown | uncultivated organism | |
| MG102 effectors | 1266 | MG102-55 effector | protein | unknown | uncultivated organism | |
| MG102 effectors | 1267 | MG102-56 effector | protein | unknown | uncultivated organism | |
| MG102 effectors | 1268 | MG102-57 effector | protein | unknown | uncultivated organism | |
| MG102 effectors | 1269 | MG102-58 effector | protein | unknown | uncultivated organism | |
| MG102 effectors | 1270 | MG102-59 effector | protein | unknown | uncultivated organism | |
| MG102 effectors | 1271 | MG102-60 effector | protein | unknown | uncultivated organism | |
| MG102 effectors | 1272 | MG102-61 effector | protein | unknown | uncultivated organism | |
| MG102 effectors | 1273 | MG102-62 effector | protein | unknown | uncultivated organism | |
| MG144 effectors | 1274 | MG144-5 effector | protein | unknown | uncultivated organism | |
| MG144 effectors | 1275 | MG144-6 effector | protein | unknown | uncultivated organism | |
| MG144 effectors | 1276 | MG144-7 effector | protein | unknown | uncultivated organism | |
| MG144 effectors | 1277 | MG144-8 effector | protein | unknown | uncultivated organism | |
| MG144 effectors | 1278 | MG144-9 effector | protein | unknown | uncultivated organism | |
| MG144 effectors | 1279 | MG144-10 effector | protein | unknown | uncultivated organism | |
| MG144 effectors | 1280 | MG144-11 effector | protein | unknown | uncultivated organism | |
| MG144 effectors | 1281 | MG144-12 effector | protein | unknown | uncultivated organism | |
| MG144 effectors | 1282 | MG144-13 effector | protein | unknown | uncultivated organism | |
| MG144 effectors | 1283 | MG144-14 effector | protein | unknown | uncultivated organism | |
| MG144 effectors | 1284 | MG144-15 effector | protein | unknown | uncultivated organism | |
| MG144 effectors | 1285 | MG144-16 effector | protein | unknown | uncultivated organism | |
| MG144 effectors | 1286 | MG144-17 effector | protein | unknown | uncultivated organism | |
| MG144 effectors | 1287 | MG144-18 effector | protein | unknown | uncultivated organism | |
| MG144 effectors | 1288 | MG144-19 effector | protein | unknown | uncultivated organism | |
| MG33 effectors | 1289 | MG33-36 effector | protein | unknown | uncultivated organism | |
| MG33 effectors | 1290 | MG33-37 effector | protein | unknown | uncultivated organism | |
| MG33 effectors | 1291 | MG33-38 effector | protein | unknown | uncultivated organism | |
| MG33 effectors | 1292 | MG33-39 effector | protein | unknown | uncultivated organism | |

TABLE 8-continued

Listing of additional protein and nucleic acid sequences referred to herein not included in the sequence listing I.

| Category | SEQ ID: | Description | Type | Organism | Other Information | Comments or Sequence |
|---|---|---|---|---|---|---|
| MG33 effectors | 1293 | MG33-40 effector | protein | unknown | uncultivated organism | |
| MG33 effectors | 1294 | MG33-41 effector | protein | unknown | uncultivated organism | |
| MG33 effectors | 1295 | MG33-42 effector | protein | unknown | uncultivated organism | |
| MG33 effectors | 1296 | MG33-43 effector | protein | unknown | uncultivated organism | |
| MG33 effectors | 1297 | MG33-44 effector | protein | unknown | uncultivated organism | |
| MG33 effectors | 1298 | MG33-45 effector | protein | unknown | uncultivated organism | |
| MG33 effectors | 1299 | MG33-46 effector | protein | unknown | uncultivated organism | |
| MG33 effectors | 1300 | MG33-47 effector | protein | unknown | uncultivated organism | |
| MG33 effectors | 1301 | MG33-48 effector | protein | unknown | uncultivated organism | |
| MG33 effectors | 1302 | MG33-49 effector | protein | unknown | uncultivated organism | |
| MG33 effectors | 1303 | MG33-50 effector | protein | unknown | uncultivated organism | |
| MG33 effectors | 1304 | MG33-51 effector | protein | unknown | uncultivated organism | |
| MG33 effectors | 1305 | MG33-52 effector | protein | unknown | uncultivated organism | |
| MG33 effectors | 1306 | MG33-53 effector | protein | unknown | uncultivated organism | |
| MG33 effectors | 1307 | MG33-54 effector | protein | unknown | uncultivated organism | |
| MG33 effectors | 1308 | MG33-55 effector | protein | unknown | uncultivated organism | |
| MG33 effectors | 1309 | MG33-56 effector | protein | unknown | uncultivated organism | |
| MG33 effectors | 1310 | MG33-57 effector | protein | unknown | uncultivated organism | |
| MG33 effectors | 1311 | MG33-58 effector | protein | unknown | uncultivated organism | |
| MG33 effectors | 1312 | MG33-59 effector | protein | unknown | uncultivated organism | |
| MG34 effectors | 1313 | MG34-26 effector | protein | unknown | uncultivated organism | |
| MG34 effectors | 1314 | MG34-27 effector | protein | unknown | uncultivated organism | |
| MG34 effectors | 1315 | MG34-28 effector | protein | unknown | uncultivated organism | |
| MG34 effectors | 1316 | MG34-29 effector | protein | unknown | uncultivated organism | |
| MG34 effectors | 1317 | MG34-30 effector | protein | unknown | uncultivated organism | |
| MG34 effectors | 1318 | MG34-31 effector | protein | unknown | uncultivated organism | |
| MG34 effectors | 1319 | MG34-32 effector | protein | unknown | uncultivated organism | |
| MG34 effectors | 1320 | MG34-33 effector | protein | unknown | uncultivated organism | |
| MG34 effectors | 1321 | MG34-34 effector | protein | unknown | uncultivated organism | |

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

SEQUENCE LISTING

The patent contains a lengthy sequence listing. A copy of the sequence listing is available in electronic form from the USPTO web site (https://seqdata.uspto.gov/?pageRequest=docDetail&DocID=US12410449B2). An electronic copy of the sequence listing will also be available from the USPTO upon request and payment of the fee set forth in 37 CFR 1.19(b)(3).

What is claimed is:

1. An engineered nuclease system comprising:
   (a) an endonuclease or a nucleic acid encoding said endonuclease, wherein said endonuclease comprises a RuvC domain and an HNH domain, wherein said endonuclease comprises a sequence having at least 85% sequence identity to SEQ ID NO: 1316; and
   (b) an engineered guide ribonucleic acid structure or a nucleic acid encoding said engineered guide ribonucleic acid structure, wherein said engineered guide ribonucleic acid structure is configured to form a complex with said endonuclease, wherein said engineered guide ribonucleic acid structure comprises:
      (i) a guide ribonucleic acid sequence configured to hybridize to a target nucleic acid sequence; and
      (ii) a tracr ribonucleic acid sequence configured to bind to said endonuclease.

2. The engineered nuclease system of claim 1, wherein said endonuclease is an archaeal endonuclease.

3. The engineered nuclease system of claim 1, wherein said endonuclease further comprises one or more of: an arginine-rich region comprising an RRxRR motif (SEQ ID NO: 1361), a domain with PF14239 homology, a recognition (REC) domain, a bridge helix (BH) domain, a wedge (WED) domain, or a PAM interacting (PI) domain.

4. The engineered nuclease system of claim 3, wherein said arginine-rich region, said domain with PF14239 homology, said recognition (REC) domain, said bridge helix (BH) domain, said wedge (WED) domain, or said PAM interacting (PI) domain comprises a sequence having at least 85% sequence identity to an arginine-rich region comprising an RRxRR motif (SEQ ID NO: 1361), a domain with PF14239 homology, a recognition (REC) domain, a bridge helix (BH) domain, a wedge (WED) domain, or a PAM interacting (PI) domain, respectively, of SEQ ID NO: 1316.

5. The engineered nuclease system of claim 1, wherein said endonuclease comprises one or more nuclear localization sequences (NLSs) proximal to an N-terminus or a C-terminus of said endonuclease.

6. The engineered nuclease system of claim 1, wherein said endonuclease comprises a sequence having at least 90% sequence identity to SEQ ID NO: 1316.

7. The engineered nuclease system of claim 6, wherein said endonuclease comprises a sequence of SEQ ID NO: 1316.

8. The engineered nuclease system of claim 1, wherein said tracr ribonucleic acid sequence comprises a polynucleotide sequence having at least 80% sequence identity to SEQ ID NO: 200.

9. The engineered nuclease system of claim 8, wherein said tracr ribonucleic acid sequence comprises a polynucleotide sequence having at least 90% sequence identity to SEQ ID NO: 200.

10. The engineered nuclease system of claim 9, wherein said tracr ribonucleic acid sequence comprises a polynucleotide sequence of SEQ ID NO: 200.

11. The engineered nuclease system of claim 1, wherein said engineered guide ribonucleic acid structure comprises a sequence having at least 80% sequence identity to non-degenerate nucleotides of any one of SEQ ID NOs: 613, 615, or 616.

12. The engineered nuclease system of claim 11, wherein said engineered guide ribonucleic acid structure comprises a sequence having at least 90% sequence identity to non-degenerate nucleotides of any one of SEQ ID NOs: 613, 615, or 616.

13. The engineered nuclease system of claim 12, wherein said engineered guide ribonucleic acid structure comprises non-degenerate nucleotides any one of SEQ ID NOs: 613, 615, or 616.

14. The engineered nuclease system of claim 1, wherein said engineered guide ribonucleic acid structure comprises:
   (a) at least two ribonucleic acid polynucleotides; or (b) a single ribonucleic acid polynucleotide comprising said guide ribonucleic acid sequence and said tracr ribonucleic acid sequence.

15. The engineered nuclease system of claim 1, wherein said guide ribonucleic acid sequence is complementary to a eukaryotic, a fungal, a plant, a mammalian, or a human genomic sequence.

16. The engineered nuclease system of claim 1, further comprising a single-stranded or double-stranded deoxyribonucleic acid repair template.

17. The engineered nuclease system of claim 16, wherein said single-stranded or double-stranded deoxyribonucleic acid repair template comprises a transgene donor.

18. The engineered nuclease system of claim 1, wherein said sequence identity is determined by a BLASTP homology search algorithm using parameters of a wordlength (W) of 3, an expectation (E) of 10, and a BLOSUM62 scoring matrix setting gap costs at existence of 11, extension of 1, and using a conditional compositional score matrix adjustment.

19. A method of modifying a target nucleic acid locus, said method comprising contacting said target nucleic acid locus with:
   (a) an endonuclease comprising a RuvC domain and an HNH domain, wherein said endonuclease comprises a sequence having at least 85% sequence identity to SEQ ID NO: 1316; and
   (b) an engineered guide ribonucleic acid structure configured to form a complex with said endonuclease, wherein said engineered guide ribonucleic acid structure comprises:
      (i) a guide ribonucleic acid sequence configured to hybridize to a portion of said target nucleic acid locus; and (ii) a tracr ribonucleic acid sequence configured to bind to said endonuclease, wherein said complex modifies said target nucleic acid locus.

20. The method of claim 19, wherein said endonuclease further comprises one or more of: an arginine-rich region comprising an RRxRR motif (SEQ ID NO: 1361), a domain with PF14239 homology, a recognition (REC) domain, a bridge helix (BH) domain, a wedge (WED) domain, or a PAM interacting (PI) domain.

21. The method of claim 20, wherein said arginine-rich region, said domain with PF14239 homology, said recognition (REC) domain, said bridge helix (BH) domain, said wedge (WED) domain, or said PAM interacting (PI) domain comprises a sequence having at least 85% sequence identity to an arginine-rich region comprising an RRxRR motif (SEQ ID NO: 1361), a domain with PF14239 homology, a recognition (REC) domain, a bridge helix (BH) domain, a wedge (WED) domain, or a PAM interacting (PI) domain, respectively, of SEQ ID NO: 1316.

22. The method of claim 19, wherein said endonuclease comprises a sequence having at least 90% sequence identity to SEQ ID NO: 1316.

23. The method of claim 22, wherein said endonuclease comprises a sequence of SEQ ID NO: 1316.

24. The method of claim 19, wherein said tracr ribonucleic acid sequence comprises a polynucleotide sequence having at least 80% sequence identity to SEQ ID NO: 200.

25. The method of claim 24, wherein said tracr ribonucleic acid sequence comprises a polynucleotide sequence of SEQ ID NO: 200.

26. The method of claim 19, wherein said modifying comprises binding, nicking, cleaving, or marking said target nucleic acid locus.

27. The method of claim 19, wherein said target nucleic acid locus comprises deoxyribonucleic acid (DNA) or ribonucleic acid (RNA).

28. The method of claim 19, wherein said target nucleic acid locus is within a cell.

29. The method of claim 28, wherein said cell is a eukaryotic cell, an animal cell, a mammalian cell, a rodent cell, a primate cell, or a human cell.

* * * * *